(12) United States Patent
Fujino et al.

(10) Patent No.: US 11,725,049 B2
(45) Date of Patent: *Aug. 15, 2023

(54) HUMAN ANTI-IL-33 NEUTRALIZING MONOCLONAL ANTIBODY

(71) Applicant: Mitsubishi Tanabe Pharma Corporation, Osaka (JP)

(72) Inventors: Yasuhiro Fujino, Osaka (JP); Tsutomu Yoshikawa, Osaka (JP); Hiroshi Ochi, Osaka (JP)

(73) Assignee: Mitsubishi Tanabe Pharma Corporation, Osaka (JP)

( * ) Notice: Subject to any disclaimer, the term of this patent is extended or adjusted under 35 U.S.C. 154(b) by 667 days.

This patent is subject to a terminal disclaimer.

(21) Appl. No.: 16/414,602

(22) Filed: May 16, 2019

(65) Prior Publication Data

US 2019/0330329 A1 Oct. 31, 2019

Related U.S. Application Data

(60) Continuation of application No. 15/621,950, filed on Jun. 13, 2017, now abandoned, which is a division of application No. 15/037,998, filed as application No. PCT/JP2014/084695 on Dec. 26, 2014, now Pat. No. 9,758,578.

(30) Foreign Application Priority Data

Dec. 26, 2013 (JP) .................................. 2013-270551
Apr. 4, 2014 (JP) .................................. 2014-078223

(51) Int. Cl.
    *C07K 16/24* (2006.01)
    *A61K 39/395* (2006.01)
    *A61K 39/00* (2006.01)

(52) U.S. Cl.
    CPC ...... *C07K 16/244* (2013.01); *A61K 39/39591* (2013.01); *A61K 2039/505* (2013.01); *C07K 2317/33* (2013.01); *C07K 2317/34* (2013.01); *C07K 2317/55* (2013.01); *C07K 2317/565* (2013.01); *C07K 2317/76* (2013.01); *C07K 2317/92* (2013.01); *C07K 2317/94* (2013.01)

(58) Field of Classification Search
    None
    See application file for complete search history.

(56) References Cited

U.S. PATENT DOCUMENTS

| | | |
|---|---|---|
| 9,758,578 B2 | 9/2017 | Fujino et al. |
| 2008/0063634 A1 | 3/2008 | Salfeld et al. |
| 2014/0099280 A1 | 4/2014 | Girard et al. |
| 2016/0289322 A1 | 10/2016 | Fujino et al. |
| 2020/0190182 A1 | 6/2020 | Tomohiro et al. |
| 2022/0041709 A1 | 2/2022 | Ikemoto et al. |

FOREIGN PATENT DOCUMENTS

| | | |
|---|---|---|
| CN | 101189265 A | 5/2008 |
| EA | 201591331 A1 | 1/2016 |
| EP | 3 277 717 A1 | 2/2018 |
| JP | 2007-523089 A | 8/2007 |
| JP | 2007-537702 A | 12/2007 |
| JP | A 2007-537702 | 12/2007 |
| JP | 2008-520684 A | 6/2008 |
| JP | A 2008-520684 | 6/2008 |
| JP | 2008-543340 A | 12/2008 |
| JP | A 2008-543340 | 12/2008 |
| JP | A 2010-513306 | 4/2010 |
| JP | 2011-526591 A | 10/2011 |
| JP | A 2011-526591 | 10/2011 |
| JP | 2012-010702 A | 1/2012 |
| JP | A 2012-010702 | 1/2012 |
| JP | A 2012-502967 | 2/2012 |
| JP | 2017-008003 A | 1/2017 |
| WO | WO 2005/007699 A2 | 1/2005 |
| WO | WO 2005/079844 A2 | 9/2005 |
| WO | WO 2006/055638 A2 | 5/2006 |
| WO | WO 2006/128690 A1 | 12/2006 |
| WO | WO 2007/002261 A2 | 1/2007 |
| WO | WO 2008/074004 A2 | 6/2008 |
| WO | WO 2008/132709 A1 | 11/2008 |
| WO | WO 2008/144610 A1 | 11/2008 |

(Continued)

OTHER PUBLICATIONS

Lloyd et al. Protein Engineering, Design & Selection 2009, 22:159-168 (Year: 2009).*
Akcay et al., "IL-33 exacerbates acute kidney injury," J. Am. Soc. Nephrol., vol. 22, pp. 2057-2067, 2011.
Guabiraba, R., et al., IL-33 Targeting Attenuates Intestinal Mucositis and Enhances Effective Tumour Chemotherapy in Mice, Mucosal Immunology, vol. 7, No. 5, pp. 1079-1093, 2014.
Hu et al., "Serum IL-33 as a diagnostic and prognostic marker in non-small cell lung cancer," Asian Pacific Journal of Cancer Prevention, vol. 14, No. 4, pp. 2563-2566, 2013.
International Search Report dated Mar. 31, 2015 for International Patent Application No. PCT/JP2014/084695 filed Dec. 26, 2014; 4 pages.

(Continued)

*Primary Examiner* — Daniel C Gamett
(74) *Attorney, Agent, or Firm* — Knobbe, Martens, Olson & Bear, LLP

(57) ABSTRACT

An antibody has an antagonistic effect against IL-33. In particular an isolated human anti-IL-33 neutralizing monoclonal antibody has framework regions with amino acid sequences from a germline, including combinations and fragments of such sequences. The epitopes for a plurality of anti-IL-33 monoclonal antibodies were identified, human anti-IL-33 neutralizing monoclonal antibodies were obtained, and the complementarity-determining regions that achieve high binding ability to IL-33 was specified by introducing mutations in the complementarity-determining regions. The identified complementarity-determining regions were used to produce the foregoing human anti-IL-33 neutralizing monoclonal antibodies having framework regions.

23 Claims, 11 Drawing Sheets

Specification includes a Sequence Listing.

(56) References Cited

FOREIGN PATENT DOCUMENTS

| WO | WO 2010/000721 A1 | 1/2010 |
|---|---|---|
| WO | WO 2010/032061 A1 | 3/2010 |
| WO | WO 2011/031600 A1 | 3/2011 |
| WO | WO 2012/113927 A1 | 8/2012 |
| WO | WO 2014/152195 A1 | 9/2014 |
| WO | WO 2014/164959 A2 | 10/2014 |
| WO | WO 2015/099175 A1 | 7/2015 |
| WO | WO 2015/106080 A2 | 7/2015 |
| WO | WO 2016/031932 A1 | 3/2016 |
| WO | WO 2016/077366 A1 | 5/2016 |
| WO | WO 2016/140921 A1 | 9/2016 |
| WO | WO 2016/140922 A1 | 9/2016 |
| WO | WO 2016/156440 A1 | 10/2016 |
| WO | WO 2017/062456 A2 | 4/2017 |
| WO | WO 2018/158332 A1 | 9/2018 |

OTHER PUBLICATIONS

Lee, H.Y., et al., Blockade of IL-33/ST2 Ameliorates Airway Inflammation in a Murine Model of Allergic Asthma, Experimental Lung Research, vol. 40, No. 2, pp. 66-76, 2014.
Li, P., et al., IL-33 Neutralization Suppresses Lupus Disease in Lupus-Prone Mice, Inflammation, vol. 37, No. 3, pp. 824-832, 2014.
Liu, X., et al., Structural Insights into the Interaction of IL-33 with its Receptors, PNAS, vol. 110, No. 37, pp. 14918-14923, 2013.
Lucchese, G., et al., How a Single Amino Acid Change May Alter the Immunological Information of a Peptide, Frontiers in Bioscience, E4, pp. 1843-1852, Jan. 1, 2012.
Matsuyama et al., "Increased levels of interleukin 33 in sera and synovial fluid from patients with active rheumatoid arthritis," The Journal of Rheumatology, vol. 37, No. 1, pp. 18-25, 2010.
Mchedlidze et al., "Interleukin-33-dependent innate lymphoid cells mediate hepatic fibrosis," Immunity, vol. 39, pp. 357-371, Aug. 22, 2013.
Mitzutani, N., et al., Interleukin-33 and alveolar macrophages contribute to the mechanisms underlying the exacerbation of IgE-mediated airway inflammation and remodeling in mice, Immunology, vol. 139, pp. 205-218, 2013.
Nabe, T., Interleukin (IL)-33: New Therapeutic Target for Atopic Diseases Journal of Pharmacological Sciences, vol. 126, No. 2, pp. 85-91, 2014.
Ohno et al., "Interleukin-33 in allergy," Allergy, vol. 67, pp. 1203-1214, 2012.
Pastorelli et al., "Epithelial-derived IL-33 and its receptor ST2 are dysregulated in ulcerative colitis and in experimental Th1/Th2 driven enteritis," PNAS, vol. 107, No. 17, pp. 8017-8022, Apr. 27, 2010.
Prefontaine et al., "Increased IL-33 expression by epithelial cells in bronchial asthma," J. Allergy Clin. Immunol., Letter to the Editor, vol. 125, No. 3, pp. 752-754, 2010.
Qiu, C., et al., Anti-Interleukin-33 Inhibits Cigarette Smoke-Induced Lung Inflammation in Mice, Immunology, vol. 138, No. 1, pp. 76-82, 2012.
Rankin et al., "IL-33 induces IL-13-dependent cutaneous fibrosis," The Journal of Immunology, pp. 1526-1535, 2010.
Rudikoff, S., et al., Single Amino Acid Substitution Altering Antigen-Binding Specificity, Proc. Natl. Acad. Sci. USA, vol. 79, pp. 1979-1983, Mar. 1982.
Shadie, A.M., et al., Ambient Particulate Matter Includes an Exacerbation of Airway Inflammation in Experimental Asthma: Role of Interleukin-33, Clinical & Experimental Immunology, vol. 177, No. 2, pp. 491-499, 2014.
Suria, "Anaptysbio Announces Development of Novel Anti-IL33 Therapeutic Antibody," AnaptysBio, 1 page, Jan. 10, 2014.
Xu et al., "IL-33 exacerbates autoantibody-induced arthritis," The Journal of Immunology, pp. 2620-2626, 2010.
Xu, Q., et al., Influenza H1N1 A/Solomon Island/3/06 Virus Receptor Binding Specificity Correlates with Virus Pathogenicity, Antigenicity, and Immunogenicity in Ferrets, Journal of Virology, vol. 84, No. 10, pp. 4936-4945, May 2010.
Yanaba et al., "Serum IL-33 levels are raised in patients with systemic sclerosis: association with extent of skin sclerosis and severity of pulmonary figrosis," Clin. Rheumatol., vol. 30, pp. 825-830, 2011.
Choi et al., "Interleukin-33 induces angiogenesis and vascular permeability through ST2/TRAF6-mediated endothelial nitric oxide production", Blood, vol. 114, No. 14, pp. 3117-3126, 2009.
Czajkowsky et al., "Fc-fusion proteins: new developments and future perspectives", EMBO Molecular Medicine, vol. 4, No. 10, pp. 1015-1028, 2012.
Hayakawa et al., "Soluble ST2 Blocks Interleukin-33 Signaling in Allergic Airway Inflammation", The Journal of Biological Chemistry, vol. 282, No. 36, pp. 26369-26380, 2007.
Honda et al., Analytical Tips for Biopharmaceutics Foundation on the Application for Quality Assessment Part 9: Analyzing and engineering protein stabilities, Pharm Tech Japan, vol. 34, No. 5, pp. 885-894, 2018.
Izutsu, K., Lyophilization of Protein Pharmaceuticals, Journal of Pharmaceuticals Science and Technology Japan, vol. 72, No. 6, pp. 353-358, 2012.
Mbarik et al., "Soluble ST2 and IL-33: Potential Markers of Endometriosis in the Tunisian Population", Immunology Letters, vol. 166, pp. 1-5, 2015.
Mei et al., Indoleamine 2,3-dioxygenase-1 (ID01) in human endometrial stromal cells induces macrophage tolerance through interleukin-33 in the progression of endometriosis, International Journal of Clinical and Experimental Pathology, vol. 7, No. 6, pp. 2743-2757, 2014.
Miller et al., "Inter Leukin-33 Modulates Inflammation in Endometriosis", Reproductive Sciences, vol. 25, Supplement 1, pp. 287A-288A, 2018.
Miller et al., "Inter Leukin-33 Modulates Inflammation in Endometriosis", Scientific Reports, vol. 7, No. 17903, pp. 1-11, 2017.
Miller et al., "Pro-inflammatory effects of IL-33 in endometriosis", Reproductive Sciences, vol. 24, Supplement 1, p. 270A, S-113, 2017.
Santulli et al., "Serum and Peritoneal Inter Leukin-33 Levels and Elevated in Deeply Infiltrating Endometriosis", Human Reproduction, vol. 27, No. 7, pp. 2001-2009, 2012.
Uchiyama, U., Analytical Tips for Biopharmaceutics Foundation on the Application for Quality Assessment Part 6: Properties of protein solution, Pharm Tech Japan, vol. 34, No. 1, pp. 109-120, 2018.
International Preliminary Report on Patentability, dated Jul. 31, 2019, in International Application No. PCT/JP2018/032494.
International Search Report & Written Opinion, dated Oct. 9, 2018, in International Application No. PCT/JP2018/032494.
Daugherty et al., "Formulation and delivery issues for monoclonal antibody therapeutics", Advanced Drug Delivery, Elsevier, Amsterdam, NL, vol. 58, No. 5-6, Aug. 7, 2006, pp. 686-706.
Kang et al., "Rapid Formulation Development for Monoclonal Antibodies", Bioprocess International, Informa Life Sciences Group, US, vol. 14,No. 4, Apr. 12, 2016, p. 40, 42, 44, 46.
Shire, "Formulation of proteins and monoclonal antibodies mAbs", Jan. 1, 2015, Monoclonal Antibodies: Meeting the Challenges in Manufacturing, Formulation, Delivery and Stability of Final Drug Product, pp. 93-120.
Wang et al., "Antibody Structure, Instability, and Formulation," Journal of Pharmaceutical Sciences, American Chemical Society and American Pharmaceutical Association, US, vol. 96, No. 1, Jan. 1, 2007, pp. 1-26.
European Search Report and Search Opinion for EP Application No. 19860824.2 dated May 6, 2022.
Notice of Reasons for Rejection dated Jan. 25, 2022 in Patent Application No. P 2020-219204.

* cited by examiner

Almost entire region(S117-T270) of mature human IL-33(S112-T270)

Part of PEP12(S117-N130)

PEP14(D131-L150)

PEP24(E231-I250)

PEP26(K251-T270)

| Peptide ID | Human IL-33 Amino Acid Number N terminus | Human IL-33 Amino Acid Number C terminus | Amino Acid Length | Peptide Sequence | Position in V101-T270 region of human IL-33 |
|---|---|---|---|---|---|
| PEP11 (SEQ ID No.410) | 101 | 120 | 20 | VDKYTRALHDSSITGISPIT | |
| PEP12 (SEQ ID No.411) | 111 | 130 | 20 | SSITGISPITEYLASLSTYN | |
| PEP13 (SEQ ID No.412) | 121 | 140 | 20 | EYLASLSTYNDQSITFALED | |
| PEP14 (SEQ ID No.413) | 131 | 150 | 20 | DQSITFALEDESYEIYVEDL | |
| PEP15 (SEQ ID No.414) | 141 | 160 | 20 | ESYEIYVEDLKKDENKDKVL | |
| PEP16 (SEQ ID No.415) | 151 | 170 | 20 | KKDENKDKVLLSYYESQHPS | |
| PEP17 (SEQ ID No.416) | 161 | 180 | 20 | LSYYESQHPSNESGDGVDGK | |
| PEP18 (SEQ ID No.417) | 171 | 190 | 20 | NESGDGVDGKMLMVTLSPTK | |
| PEP19 (SEQ ID No.418) | 181 | 200 | 20 | MLMVTLSPTKDFWLHANNKE | |
| PEP20 (SEQ ID No.419) | 191 | 210 | 20 | DFWLHANNKEHSVELHKCEK | |
| PEP21 (SEQ ID No.420) | 201 | 220 | 20 | HSVELHKCEKPLPDQAFFVL | |
| PEP22 (SEQ ID No.421) | 211 | 230 | 20 | PLPDQAFFVLHNMHSNCVSF | |
| PEP23 (SEQ ID No.422) | 221 | 240 | 20 | HNMHSNCVSFECKTDPGVFI | |
| PEP24 (SEQ ID No.423) | 231 | 250 | 20 | ECKTDPGVFIGVKDNHLRAL | |
| PEP25 (SEQ ID No.424) | 241 | 260 | 20 | GVKDNHLRALIKVDSSENLC T | |
| PEP26 (SEQ ID No.425) | 251 | 270 | 20 | KVDSSENLCTENILFKLSET | |

FIG. 12

HUMAN ANTI-IL-33 NEUTRALIZING MONOCLONAL ANTIBODY

CROSS REFERENCE TO RELATED APPLICATIONS

This application is a Continuation Application of U.S. application Ser. No. 15/621,950, filed Jun. 13, 2017, which is a Divisional Application of U.S. application Ser. No. 15/037,998, filed May 19, 2016, which issued as U.S. Pat. No. 9,758,578 on Sep. 12, 2017, which is the U.S. National Stage Application under 35 U.S.C. § 371 of International Application No. PCT/JP2014/084695, filed Dec. 26, 2014, designating the U.S. and published as WO 2015/099175 A1 on Jul. 2, 2015, which claims the benefit of Japanese Patent Application Nos. JP 2013-270551, filed Dec. 26, 2013, and JP 2014-078223, filed Apr. 4, 2014. Any and all applications for which a foreign or a domestic priority is claimed is/are identified in the Application Data Sheet filed herewith and is/are hereby incorporated by reference in their entirety under 37 C.F.R. § 1.57.

REFERENCE TO ELECTRONIC SEQUENCE LISTING

The present application is being filed along with an Electronic Sequence Listing in electronic format. The Electronic Sequence Listing is provided as a file entitled SWA018001C1SEQLIST.txt which is 262,898 bytes in size, created and last modified on May 16, 2019. The information in the Electronic Sequence Listing is incorporated herein by reference in its entirety.

TECHNICAL FIELD

The present invention relates to a human anti-IL-33 neutralizing monoclonal antibody and an antibody which competes therewith; and a cytokine expression inhibitor containing any of such antibodies; and a pharmaceutical composition containing any of such antibodies for treatment, prevention, or alleviation of diseases associated with IL-33.

BACKGROUND ART

Interleukin-33 (hereinafter, referred to as IL-33) is a cytokine of the interleukin-1 family, which is believed to be involved in inflammatory conditions. IL-33 is constitutively expressed in the nuclei of epithelial cells and vascular endothelial cells, is released during cell destruction following tissue injury caused by infections or physical or chemical stress, and then acts as alarmin. It is also believed that IL-33 expression and secretion are increased by stimulation with lipopolysaccharide or the like in some mechanisms. The extracellularly released IL-33 binds to IL-33 receptors expressed on cells, thereby being capable of activating intracellular signal transduction. IL-33 receptors are expressed on various immune cells and epithelial cells, where IL-33-induced intracellular signal transduction occurs.

IL-33 is believed to induce allergic inflammation (for example, asthma, atopic dermatitis, pollinosis, and anaphylactic shock) by inducing production of Th2 cytokines (for example, IL-4, IL-5, IL-6, and IL-13) from Th2 cells, mast cells, eosinophils, basophils, natural killer T (NKT) cells, and Group 2 innate lymphocytes, among immune cells expressing IL-33 receptors (NPL 1: Tatsukuni Ohno et al., Allergy, 2012, Vol. 67, p. 1203). In mast cells and macrophages among the immune cells expressing IL-33 receptors, stimulation with IL-33 induces production of IL-1β, IL-6, and tumor necrosis factor α (TNF-α), which is suggested to be involved in the development of autoantibody-induced arthritis (model of rheumatoid arthritis) (NPL 2: Damo Xu et al., Journal of Immunology, 2010, Vol. 184, p. 2620). IL-33 antagonists are suggested to be effective against acute kidney injury (NPL 3: Ali Akcay et al., Journal of American Society Nephrology, 2011, Vol. 22, p. 2057). Increased IL-33 expression is observed in various human inflammatory diseases (for example, rheumatoid arthritis, asthma, systemic sclerosis, fibrosis such as hepatic fibrosis and pulmonary fibrosis, psoriasis, ulcerative colitis, Crohn's disease, multiple sclerosis, and ankylosing spondylitis), and IL-33 is believed to be involved in the development and maintenance of various diseases (NPL 4: Yasushi Matsuyama et al., Journal of Rheumatology, 2010, Vol. 37, p. 18; NPL 5: David Prefontaine et al., Journal of Allergy and Clinical Immunology, 2010, Vol. 125, p. 752; NPL 6: Koichi Yanaba et al., Clinical Rheumatology, 2011, Vol. 30, p. 825; NPL 7: A. L. Rankin et al., Journal of Immunology, 2010, Vol. 184, p. 1526; NPL 8: Tamar Mchedlidze et al., Immunity, 2013, Vol. 39, p. 357; NPL 9: Liang-An Hu et al., Asian Pacific Journal of Cancer Prevention, 2013, Vol. 14, p. 2563; NPL 10: Luca Pastorelli et al., Proceedings of the National Academy of Sciences of the United States of America, 2010, vol. 107, p. 8017).

Based on the knowledge on the association of IL-33 with various diseases, in particular inflammatory diseases, IL-33 agonists and antagonists have been developed (PTLs 1 to 4). Among the IL-33 agonists and antagonists, antibodies to IL-33 have been attracting attention, in view of their specificity and potency. Several antibodies which have been developed are directed to a murine antibody which fails to specify the epitope for the antibody (PTL 1); an antibody which recognizes a region including the caspase cleavage site of IL-33 residues 155 to 198 of SEQ ID NO:226 in the Sequence Listing) as epitope, based on the findings of the specific caspase cleavage site of IL-33 and the findings that the uncleaved form of IL-33 is the active form (PTL2); and several goat polyclonal antibodies which are commercially available. An article dated Jan. 10, 2014 on the website of AnaptysBio, Inc. reports their successful preparation of ANB020, the candidate for development of anti-IL-33 therapeutic antibody, using their proprietary somatic hypermutation technology (SHM-XEL) platform (NPL 11: Hamza Suria, 'AnaptysBio announces development of novel anti-IL-33 therapeutic antibody', [on line], 2014, [retrieved on 11 Jan. 2014], Retrieved from Internet:<URL: http://www.anaptysbio.com/anti-il-33/>). Murphy et al. disclose that they prepared 20 types of human anti-IL-33 monoclonal antibodies using VelocImmune mouse, that is, mouse transgenic for variable regions of a human antibody gene (PTL 5), but fail to disclose the epitope for the antibodies. In addition, the amino acid sequences of the framework regions of the 20 types of human anti-IL-33 monoclonal antibodies are different from human germline sequences in two or more amino acid residues. Due to such a difference, administration of these antibodies to human causes immune reaction to them to induce human anti-human immunoglobulin antibody (HAHA), which undesirably reduces the effects of the antibodies and induces inflammation or other side effects.

CITATION LIST

Patent Literature

PTL 1: WO 2005/079844
PTL 2: WO 2008/132709

PTL 3: WO 2011/031600
PTL 4: WO 2008/144610
PTL 5: WO 2014/164959

Non Patent Literature

NPL 1: Tatsukuni Ohno et al., Allergy, 2012, Vol. 67, p. 120
NPL 2: Damo Xu et al., Journal of Immunology, 2010, Vol. 184, p. 2620
NPL 3: Ali Akcay et al., Journal of American Society Nephrology, 2011, Vol. 22, p. 2057
NPL 4: Yasushi Matsuyama et al., Journal of Rheumatology, 2010, Vol. 37, p. 18
NPL 5: David Prefontaine et al., Journal of Allergy and Clinical Immunology, 2010, Vol. 125, p. 752
NPL 6: Koichi Yanaba et al., Clinical Rheumatology, 2011, Vol. 30, p. 825
NPL 7: A. L. Rankin et al., Journal of Immunology, 2010, Vol. 184, p. 1526
NPL 8: Tamar Mchedlidze et al., Immunity, 2013, Vol. 39, p. 357
NPL 9: Liang-An Hu et al., Asian Pacific Journal of Cancer Prevention, 2013, Vol. 14, p. 2563
NPL 10: Luca Pastorelli et al., Proceedings of the National Academy of Sciences of the United States of America, 2010, vol. 107, p. 8017
NPL 11: Hamza Suria, 'AnaptysBio announces development of novel anti-IL-33 therapeutic antibody', [on line], 2014, [retrieved on 11 Jan. 2014], Retrieved from Internet: <URL: http://www.anaptysbio.com/anti-il-33/>

SUMMARY OF INVENTION

Technical Problem

The association of IL-33 with some diseases has been clarified and development of an anti-IL-33 neutralizing monoclonal antibody having antagonistic effect against IL-33 has been required in recent years. The action of the anti-IL-33 neutralizing monoclonal antibody is closely related to the region of an epitope to which the antibody is to bind. Since IL-33 is extracellularly released during cell destruction, IL-33 is likely to be cleaved by lysosomal proteolytic enzymes, which may produce so-called mature IL-33 and many fragments derived from the mature IL-33 and having the activity of IL-33. If the fragments include an epitope consisting of a continuous amino acid sequence, a monoclonal antibody that is capable of binding to the epitope consisting of a continuous amino acid sequence of IL-33 is more advantageous than a monoclonal antibody that is capable of binding to an epitope consisting of a discontinuous amino acid sequence, because the former is capable of binding firmly to the continuous amino acid sequence of one of the fragments and inhibits the binding between the fragment and IL-33 receptors. However, it has remained difficult to identify such an epitope consisting of a continuous amino acid sequence for production of an anti-IL-33 monoclonal antibody having a desired antagonistic effect.

The anti-IL-33 neutralizing monoclonal antibody that is capable of binding to an epitope consisting of a continuous amino acid sequence of IL-33 preferably exhibits low antigenicity when it is administered to a human or the like. A human antibody preferably exhibits low antigenicity when it is administered to a human and has framework regions comprising amino acid sequences framework regions from a human germline or amino acid sequences consisting of a combination thereof. However, when the SHM-XEL platform or the like is applied to a human antibody contained in a human antibody gene library, amino acid sequence mutation occurs not only in the complementarity-determining regions but also in the framework regions. Furthermore, if a transgenic mouse induced with a gene of a human antibody is immunized with a human IL-33 protein to prepare a human anti-IL-33 neutralizing monoclonal antibody, mutation cannot be avoided in the amino acid sequences of the framework regions of the anti-IL-33 neutralizing monoclonal antibody. Accordingly, it has remained difficult to prepare an isolated anti-IL-33 human monoclonal antibody that includes framework regions comprising amino acid sequences of framework regions from a human germline or amino acid sequences consisting of the combination thereof.

Solution to Problem

The inventors, who have made extensive studies to solve the problems, found that an antibody that is capable of firmly binding to the epitope traditionally believed as preferred epitope, i.e. epitope present in a sequence spanning positions 155 to 198 of IL-33, has little antagonistic effect and that an epitope consisting of a continuous amino acid sequence present in a sequence spanning positions 101 to 154 or 199 to 270 of IL-33, in particular positions 111 to 130, 131 to 150, 231 to 250, or 251 to 270, is significant in view of the antagonistic effect of an antibody that is capable of binding to the epitope, and arrived at the present invention.

The inventors have also isolated a human anti-IL-33 neutralizing monoclonal antibody from a human antibody library, and have introduced mutations only in its complementarity-determining regions to identify the complementarity-determining regions that achieve excellent binding ability and physical properties. As a result, the inventors have successfully obtained a human antibody that has framework regions consisting of amino acid sequences without any mutation as compared to the amino acid sequences of the framework regions of the germline and is capable of binding to human IL-33 to neutralize its functions. The present invention involves the following aspects:

[1]. A monoclonal antibody that is capable of binding to an epitope consisting of a continuous amino acid sequence included in positions 101 to 154 or 199 to 270 of SEQ ID NO:226 in the Sequence Listing.

[2]. The antibody according to Aspect 1, wherein the epitope consisting of a continuous amino acid sequence included in positions 101 to 154 or 199 to 270 of SEQ ID NO:226 in the Sequence Listing consists of a continuous amino acid sequence included in positions 111 to 130, 131 to 150, 231 to 250, or 251 to 270 of SEQ ID NO:226 in the Sequence Listing.

[3]. The antibody according to Aspect 1 or 2, wherein the epitope consisting of a continuous amino acid sequence included in positions 101 to 154 or 199 to 270 of SEQ ID NO:226 in the Sequence Listing consists of an amino acid sequence including an amino acid selected from P118, I119, T120, Y122, L123, R124, S125, L126, S127, Y129, N130, D131, Q132, S133, T135, A137, L138, E139, S142, Y143, E144, I145, Y146, E148, D149, L150, D244, N245, H246, K266, L267, S268, and E269.

[4]. The antibody according to any one of Aspects 1 to 3, wherein the epitope consisting of a continuous amino acid sequence included in positions 101 to 154 or 199 to 270 of SEQ ID NO:226 in the Sequence Listing consists of a continuous amino acid of positions 111 to 130, 131 to 150, 231 to 250, or 251 to 270 of SEQ ID NO:226 in the Sequence Listing.

[5]. The antibody according to any one of Aspects 1 to 4, wherein the epitope consisting of a continuous amino acid sequence included in the sequence spanning positions 101 to 154 or 199 to 270 of SEQ ID NO:226 in the Sequence Listing consists of a continuous amino acid sequence of positions 138 to 147 or 139 to 147 of SEQ ID NO:226 in the Sequence Listing.

[6]. The antibody according to any one of Aspects 1 to 5, wherein the monoclonal antibody that is capable of binding to the epitope consisting of a continuous amino acid sequence included in positions 101 to 154 or 199 to 270 of SEQ ID NO:226 in the Sequence Listing is an IL-33 antagonist.

[7]. The antibody according to any one of Aspects 1 to 6, wherein the monoclonal antibody that is capable of binding to the epitope consisting of a continuous amino acid sequence included in positions 101 to 154 or 199 to 270 of SEQ ID NO:226 in the Sequence Listing inhibits binding between IL-33 receptors and IL-33.

[8]. A pharmaceutical composition for treatment, prevention, or alleviation of a disease associated with IL-33, comprising the antibody according to any one of Aspects 1 to 7.

[9]. A cytokine expression inhibitor comprising the antibody according to any one of Aspects 1 to 7.

[10]. The inhibitor according to Aspect 9, wherein the inhibitor inhibits expression of TNF-α, IFN-γ, IL-1β, IL-4, IL-5, IL-6, or IL-13.

[11]. The inhibitor according to Aspect 9 or 10, wherein the inhibitor inhibits expression of IFN-γ, IL-5, IL-6, or IL-13.

[12]. An epitope selected from the group consisting of:
1) the epitope according to any one of Aspects 1 to 5;
2) an epitope consisting of an amino acid sequence, wherein one or several amino acid are substituted, deleted, or added to the continuous amino acid sequence of the epitope of item 1; and
3) an epitope consisting of an amino acid sequence with at least 90% sequence identity to the continuous amino acid sequence of the epitope.

[13]. An antibody generated or screened using the epitope according to Aspect 12.

[14]. The antibody according to any one of Aspects 1 to 7, wherein the monoclonal antibody that is capable of binding to the epitope consisting of a continuous amino acid sequence included in positions 101 to 154 or 199 to 270 of SEQ ID NO:226 in the Sequence Listing is a chimeric, a humanized, or a human antibody.

[15]. The antibody according to Aspect 14, wherein the amino acid sequence of the framework regions is the amino acid sequences of framework regions from a human germline or a combination of the amino acid sequences thereof.

[16]. The antibody according to Aspect 15, wherein the amino acid sequence of the light-chain framework region 1 is residues 1 to 22 of SEQ ID NO:317 in the Sequence Listing; the amino acid sequence of the light-chain framework region 2 is residues 36 to 50 of SEQ ID NO:317 in the Sequence Listing; the amino acid sequence of the light-chain framework region 3 is residues 58 to 89 of SEQ ID NO:317 in the Sequence Listing; the amino acid sequence of the light-chain framework region 4 is residues 3 to 12 of SEQ ID NO:401 in the Sequence Listing; the amino acid sequence of the heavy-chain framework region 1 is residues 1 to 30 of SEQ ID NO:367 or residues 1 to 30 of SEQ ID NO:368 in the Sequence Listing; the amino acid sequence of the heavy-chain framework region 2 is residues 36 to 49 of SEQ ID NO:367 or residues 36 to 49 of SEQ ID NO:368 in the Sequence Listing; the amino acid sequence of the heavy-chain framework region 3 is residues 67 to 98 of SEQ ID NO:367 or residues 67 to 98 of SEQ ID NO:368 in the Sequence Listing; and the amino acid sequence of the heavy-chain framework region 4 is residues 5 to 15 of SEQ ID NO:407 in the Sequence Listing.

[17]. The antibody according to Aspect 15 or 16, wherein the amino acid sequence of the light-chain framework region 1 is residues 1 to 22 of SEQ ID NO:317 in the Sequence Listing; the amino acid sequence of the light-chain framework region 2 is residues 36 to 50 of SEQ ID NO:317 in the Sequence Listing; the amino acid sequence of the light-chain framework region 3 is residues 58 to 89 of SEQ ID NO:317 in the Sequence Listing; the amino acid sequence of the light-chain framework region 4 is residues 3 to 12 of SEQ ID NO:401 in the Sequence Listing; the amino acid sequence of the heavy-chain framework region 1 is residues 1 to 30 of SEQ ID NO:367 in the Sequence Listing; the amino acid sequence of the heavy-chain framework region 2 is residues 36 to 49 of SEQ ID NO:367 in the Sequence Listing; the amino acid sequence of the heavy-chain framework region 3 is residues 67 to 98 of SEQ ID NO:368 in the Sequence Listing; and the amino acid sequence of the heavy-chain framework region 4 is residues 5 to 15 of SEQ ID NO:407 in the Sequence Listing.

[18]. An isolated human anti-IL-33 neutralizing, wherein a combination of the amino acid sequences of the light-chain complementarity-determining region 1 (LCDR1), the light-chain complementarity-determining region 2 (LCDR2), the light-chain complementarity-determining region 3 (LCDR3), the heavy-chain complementarity-determining region 1 (HCDR1), the heavy-chain complementarity-determining region 2 (HCDR2), and the heavy-chain complementarity-determining region 3 (HCDR3) is selected from the combinations represented by C1 to C30 in Table 1:

TABLE 1

The following SEQ ID Nos. show the SEQ ID Nos. in the Sequence Listing

|  | LCDR1 | LCDR2 | LCDR3 | HCDR1 | HCDR2 | HCDR3 |
| --- | --- | --- | --- | --- | --- | --- |
| C1 | SEQ ID No. 1 | SEQ ID No. 11 | SEQ ID No. 22 | SEQ ID No. 43 | SEQ ID No. 51 | SEQ ID No. 65 |
| C2 | SEQ ID No. 1 | SEQ ID No. 11 | SEQ ID No. 23 | SEQ ID No. 43 | SEQ ID No. 52 | SEQ ID No. 65 |
| C3 | SEQ ID No. 2 | SEQ ID No. 11 | SEQ ID No. 23 | SEQ ID No. 44 | SEQ ID No. 52 | SEQ ID No. 65 |
| C4 | SEQ ID No. 2 | SEQ ID No. 11 | SEQ ID No. 23 | SEQ ID No. 44 | SEQ ID No. 53 | SEQ ID No. 65 |
| C5 | SEQ ID No. 2 | SEQ ID No. 11 | SEQ ID No. 23 | SEQ ID No. 43 | SEQ ID No. 54 | SEQ ID No. 65 |
| C6 | SEQ ID No. 2 | SEQ ID No. 11 | SEQ ID No. 24 | SEQ ID No. 45 | SEQ ID No. 52 | SEQ ID No. 65 |
| C7 | SEQ ID No. 2 | SEQ ID No. 11 | SEQ ID No. 23 | SEQ ID No. 46 | SEQ ID No. 52 | SEQ ID No. 65 |
| C8 | SEQ ID No. 3 | SEQ ID No. 12 | SEQ ID No. 25 | SEQ ID No. 47 | SEQ ID No. 55 | SEQ ID No. 66 |
| C9 | SEQ ID No. 4 | SEQ ID No. 12 | SEQ ID No. 26 | SEQ ID No. 47 | SEQ ID No. 56 | SEQ ID No. 67 |

TABLE 1-continued

The following SEQ ID Nos. show the SEQ ID Nos. in the Sequence Listing

| | LCDR1 | LCDR2 | LCDR3 | HCDR1 | HCDR2 | HCDR3 |
|---|---|---|---|---|---|---|
| C10 | SEQ ID No. 4 | SEQ ID No. 13 | SEQ ID No. 27 | SEQ ID No. 47 | SEQ ID No. 56 | SEQ ID No. 67 |
| C11 | SEQ ID No. 5 | SEQ ID No. 12 | SEQ ID No. 28 | SEQ ID No. 47 | SEQ ID No. 56 | SEQ ID No. 67 |
| C12 | SEQ ID No. 4 | SEQ ID No. 12 | SEQ ID No. 29 | SEQ ID No. 47 | SEQ ID No. 56 | SEQ ID No. 67 |
| C13 | SEQ ID No. 6 | SEQ ID No. 14 | SEQ ID No. 30 | SEQ ID No. 47 | SEQ ID No. 56 | SEQ ID No. 67 |
| C14 | SEQ ID No. 7 | SEQ ID No. 14 | SEQ ID No. 31 | SEQ ID No. 47 | SEQ ID No. 56 | SEQ ID No. 67 |
| C15 | SEQ ID No. 4 | SEQ ID No. 15 | SEQ ID No. 32 | SEQ ID No. 47 | SEQ ID No. 56 | SEQ ID No. 67 |
| C16 | SEQ ID No. 6 | SEQ ID No. 16 | SEQ ID No. 33 | SEQ ID No. 48 | SEQ ID No. 57 | SEQ ID No. 68 |
| C17 | SEQ ID No. 4 | SEQ ID No. 17 | SEQ ID No. 34 | SEQ ID No. 49 | SEQ ID No. 58 | SEQ ID No. 69 |
| C18 | SEQ ID No. 6 | SEQ ID No. 18 | SEQ ID No. 35 | SEQ ID No. 47 | SEQ ID No. 59 | SEQ ID No. 70 |
| C19 | SEQ ID No. 6 | SEQ ID No. 19 | SEQ ID No. 36 | SEQ ID No. 47 | SEQ ID No. 56 | SEQ ID No. 71 |
| C20 | SEQ ID No. 6 | SEQ ID No. 20 | SEQ ID No. 26 | SEQ ID No. 47 | SEQ ID No. 56 | SEQ ID No. 66 |
| C21 | SEQ ID No. 6 | SEQ ID No. 18 | SEQ ID No. 37 | SEQ ID No. 47 | SEQ ID No. 60 | SEQ ID No. 72 |
| C22 | SEQ ID No. 6 | SEQ ID No. 20 | SEQ ID No. 38 | SEQ ID No. 47 | SEQ ID No. 56 | SEQ ID No. 73 |
| C23 | SEQ ID No. 8 | SEQ ID No. 20 | SEQ ID No. 27 | SEQ ID No. 49 | SEQ ID No. 56 | SEQ ID No. 68 |
| C24 | SEQ ID No. 9 | SEQ ID No. 20 | SEQ ID No. 39 | SEQ ID No. 47 | SEQ ID No. 60 | SEQ ID No. 73 |
| C25 | SEQ ID No. 4 | SEQ ID No. 21 | SEQ ID No. 34 | SEQ ID No. 47 | SEQ ID No. 61 | SEQ ID No. 74 |
| C26 | SEQ ID No. 10 | SEQ ID No. 19 | SEQ ID No. 40 | SEQ ID No. 47 | SEQ ID No. 62 | SEQ ID No. 75 |
| C27 | SEQ ID No. 4 | SEQ ID No. 18 | SEQ ID No. 41 | SEQ ID No. 50 | SEQ ID No. 56 | SEQ ID No. 76 |
| C28 | SEQ ID No. 6 | SEQ ID No. 20 | SEQ ID No. 42 | SEQ ID No. 47 | SEQ ID No. 63 | SEQ ID No. 77 |
| C29 | SEQ ID No. 2 | SEQ ID No. 11 | SEQ ID No. 23 | SEQ ID No. 43 | SEQ ID No. 64 | SEQ ID No. 65 |
| C30 | SEQ ID No. 6 | SEQ ID No. 20 | SEQ ID No. 40 | SEQ ID No. 47 | SEQ ID No. 64 | SEQ ID No. 78 |

[19]. The human anti-IL-33 neutralizing monoclonal antibody according to Aspect 18, wherein the combination of the amino acid sequences of the light-chain complementarity-determining region 1 (LCDR1), the light-chain complementarity-determining region 2 (LCDR2), the light-chain complementarity-determining region 3 (LCDR3), the heavy-chain complementarity-determining region 1 (HCDR1), the heavy-chain complementarity-determining region 2 (HCDR2), and the heavy-chain complementarity-determining region 3 (HCDR3) is selected from the combinations represented by C1 to C28 in Table 1.

[20]. The human anti-IL-33 neutralizing monoclonal antibody according to Aspect 18 or 19, wherein the combination of the amino acid sequences of the light-chain complementarity-determining region 1 (LCDR1), the light-chain complementarity-determining region 2 (LCDR2), the light-chain complementarity-determining region 3 (LCDR3), the heavy-chain complementarity-determining region 1 (HCDR1), the heavy-chain complementarity-determining region 2 (HCDR2), and the heavy-chain complementarity-determining region 3 (HCDR3) is selected from the combinations represented by C1, C8, C15, C17, and C18 in Table 1.

[21]. The human anti-IL-33 neutralizing monoclonal antibody according to any one of Aspects 18 to 20, wherein the amino acid sequence of the framework region of the antibody is the amino acid sequences of framework regions from a human germline or a combination of the amino acid sequences thereof.

[22]. The human anti-IL-33 neutralizing monoclonal antibody according to any one of Aspects 18 to 21, wherein the amino acid sequence of the light-chain framework region 1 is residues 1 to 22 of SEQ ID NO:317 in the Sequence Listing; the amino acid sequence of the light-chain framework region 2 is residues 36 to 50 of SEQ ID NO:317 in the Sequence Listing; the amino acid sequence of the light-chain framework region 3 is residues 58 to 89 of SEQ ID NO:317 in the Sequence Listing; the amino acid sequence of the light-chain framework region 4 is residues 3 to 12 of SEQ ID NO:401 in the Sequence Listing; the amino acid sequence of the heavy-chain framework region 1 is residues 1 to 30 of SEQ ID NO:367 or residues 1 to 30 of SEQ ID NO:368 in the Sequence Listing; the amino acid sequence of the heavy-chain framework region 2 is residues 36 to 49 of SEQ ID NO:367 or residues 36 to 49 of SEQ ID NO:368 in the Sequence Listing; the amino acid sequence of the heavy-chain framework region 3 is residues 67 to 98 of SEQ ID NO:367 or residues 67 to 98 of SEQ ID NO:368 in the Sequence Listing; and the amino acid sequence of the heavy-chain framework region 4 is residues 5 to 15 of SEQ ID NO:407 in the Sequence Listing.

[23]. The human anti-IL-33 neutralizing monoclonal antibody according to any one of Aspects 18 to 22, wherein the combination of respective amino acid sequences of light-chain and heavy-chain variable regions is selected from the combinations represented by V1 to V30 in Table 2:

TABLE 2

The following SEQ ID Nos. show the SEQ ID Nos. in the Sequence Listing

| Combination | Light Chain Variable Region | Heavy Chain Variable Region |
|---|---|---|
| V1 | SEQ ID No. 79 | SEQ ID No. 105 |
| V2 | SEQ ID No. 80 | SEQ ID No. 106 |
| V3 | SEQ ID No. 81 | SEQ ID No. 107 |
| V4 | SEQ ID No. 81 | SEQ ID No. 108 |
| V5 | SEQ ID No. 81 | SEQ ID No. 109 |
| V6 | SEQ ID No. 82 | SEQ ID No. 110 |
| V7 | SEQ ID No. 81 | SEQ ID No. 111 |
| V8 | SEQ ID No. 83 | SEQ ID No. 112 |
| V9 | SEQ ID No. 84 | SEQ ID No. 113 |
| V10 | SEQ ID No. 85 | SEQ ID No. 113 |
| V11 | SEQ ID No. 86 | SEQ ID No. 113 |
| V12 | SEQ ID No. 87 | SEQ ID No. 113 |
| V13 | SEQ ID No. 88 | SEQ ID No. 113 |
| V14 | SEQ ID No. 89 | SEQ ID No. 113 |
| V15 | SEQ ID No. 90 | SEQ ID No. 113 |
| V16 | SEQ ID No. 91 | SEQ ID No. 114 |
| V17 | SEQ ID No. 92 | SEQ ID No. 115 |
| V18 | SEQ ID No. 93 | SEQ ID No. 116 |
| V19 | SEQ ID No. 94 | SEQ ID No. 117 |
| V20 | SEQ ID No. 95 | SEQ ID No. 118 |
| V21 | SEQ ID No. 96 | SEQ ID No. 119 |
| V22 | SEQ ID No. 97 | SEQ ID No. 120 |
| V23 | SEQ ID No. 98 | SEQ ID No. 121 |
| V24 | SEQ ID No. 99 | SEQ ID No. 122 |

TABLE 2-continued

The following SEQ ID Nos. show the SEQ ID Nos. in the Sequence Listing

| Combination | Light Chain Variable Region | Heavy Chain Variable Region |
|---|---|---|
| V25 | SEQ ID No. 100 | SEQ ID No. 123 |
| V26 | SEQ ID No. 101 | SEQ ID No. 124 |
| V27 | SEQ ID No. 102 | SEQ ID No. 125 |
| V28 | SEQ ID No. 103 | SEQ ID No. 126 |
| V29 | SEQ ID No. 81 | SEQ ID No. 127 |
| V30 | SEQ ID No. 104 | SEQ ID No. 128 |

[24]. The human anti-IL-33 neutralizing monoclonal antibody according to Aspect 23, wherein the combination of respective amino acid sequences of the light-chain and heavy-chain variable regions is selected from the combinations represented by V1 to V28 in Table 2.

[25]. The human anti-IL-33 neutralizing monoclonal antibody according to Aspect 23 or 24, wherein the combination of the respective amino acid sequences of the light-chain and heavy-chain variable regions is selected from the combinations represented by V1, V8, V15, V17, and V18 in Table 2.

[26]. The human anti-IL-33 neutralizing monoclonal antibody according to any one of Aspects 18 to 25, wherein the light chain is a λ chain.

[27]. The human anti-IL-33 neutralizing monoclonal antibody according to any one of Aspects 18 to 26, wherein the human anti-IL-33 neutralizing monoclonal antibody is IgG.

[28]. The human anti-IL-33 neutralizing monoclonal antibody according to any one of Aspects 18 to 27, wherein the antigen is human IL-33 and monkey IL-33.

[29]. A nucleic acid molecule encoding a protein portion of the human anti-IL-33 neutralizing monoclonal antibody according to any one of Aspects 18 to 28.

[30]. The nucleic acid molecule according to Aspect 29, wherein a combination of nucleic acid sequences respectively encoding the amino acid sequences of the light-chain complementarity-determining region 1 (LCDR1), light-chain complementarity-determining region 2 (LCDR2), light-chain complementarity-determining region 3 (LCDR3), heavy-chain complementarity-determining region 1 (HCDR1), heavy-chain complementarity-determining region 2 (HCDR2) and heavy-chain complementarity-determining region 3 (HCDR3) is selected from the combinations represented by CN1 to CN30 in Table 3:

TABLE 3

The following SEQ ID Nos. show the SEQ ID Nos. in the Sequence Listing

| Combination | LCDR1 | LCDR2 | LCDR3 | HCDR1 | HCDR2 | HCDR3 |
|---|---|---|---|---|---|---|
| CN1 | SEQ ID No. 129 | SEQ ID No. 140 | SEQ ID No. 156 | SEQ ID No. 181 | SEQ ID No. 191 | SEQ ID No. 209 |
| CN2 | SEQ ID No. 129 | SEQ ID No. 140 | SEQ ID No. 157 | SEQ ID No. 181 | SEQ ID No. 192 | SEQ ID No. 209 |
| CN3 | SEQ ID No. 130 | SEQ ID No. 140 | SEQ ID No. 157 | SEQ ID No. 182 | SEQ ID No. 192 | SEQ ID No. 209 |
| CN4 | SEQ ID No. 130 | SEQ ID No. 140 | SEQ ID No. 157 | SEQ ID No. 182 | SEQ ID No. 193 | SEQ ID No. 209 |
| CN5 | SEQ ID No. 130 | SEQ ID No. 140 | SEQ ID No. 157 | SEQ ID No. 181 | SEQ ID No. 194 | SEQ ID No. 209 |
| CN6 | SEQ ID No. 130 | SEQ ID No. 140 | SEQ ID No. 158 | SEQ ID No. 183 | SEQ ID No. 192 | SEQ ID No. 209 |
| CN7 | SEQ ID No. 130 | SEQ ID No. 140 | SEQ ID No. 157 | SEQ ID No. 184 | SEQ ID No. 192 | SEQ ID No. 209 |
| CN8 | SEQ ID No. 131 | SEQ ID No. 141 | SEQ ID No. 159 | SEQ ID No. 185 | SEQ ID No. 195 | SEQ ID No. 210 |
| CN9 | SEQ ID No. 132 | SEQ ID No. 141 | SEQ ID No. 160 | SEQ ID No. 185 | SEQ ID No. 196 | SEQ ID No. 211 |
| CN10 | SEQ ID No. 132 | SEQ ID No. 142 | SEQ ID No. 161 | SEQ ID No. 185 | SEQ ID No. 196 | SEQ ID No. 211 |
| CN11 | SEQ ID No. 133 | SEQ ID No. 143 | SEQ ID No. 162 | SEQ ID No. 185 | SEQ ID No. 196 | SEQ ID No. 211 |
| CN12 | SEQ ID No. 132 | SEQ ID No. 141 | SEQ ID No. 163 | SEQ ID No. 185 | SEQ ID No. 196 | SEQ ID No. 211 |
| CN13 | SEQ ID No. 134 | SEQ ID No. 144 | SEQ ID No. 164 | SEQ ID No. 185 | SEQ ID No. 196 | SEQ ID No. 211 |
| CN14 | SEQ ID No. 135 | SEQ ID No. 144 | SEQ ID No. 165 | SEQ ID No. 185 | SEQ ID No. 196 | SEQ ID No. 211 |
| CN15 | SEQ ID No. 132 | SEQ ID No. 145 | SEQ ID No. 166 | SEQ ID No. 185 | SEQ ID No. 196 | SEQ ID No. 211 |
| CN16 | SEQ ID No. 134 | SEQ ID No. 146 | SEQ ID No. 167 | SEQ ID No. 186 | SEQ ID No. 197 | SEQ ID No. 212 |
| CN17 | SEQ ID No. 132 | SEQ ID No. 147 | SEQ ID No. 168 | SEQ ID No. 187 | SEQ ID No. 198 | SEQ ID No. 213 |
| CN18 | SEQ ID No. 134 | SEQ ID No. 148 | SEQ ID No. 169 | SEQ ID No. 185 | SEQ ID No. 199 | SEQ ID No. 214 |
| CN19 | SEQ ID No. 134 | SEQ ID No. 149 | SEQ ID No. 170 | SEQ ID No. 185 | SEQ ID No. 200 | SEQ ID No. 215 |
| CN20 | SEQ ID No. 134 | SEQ ID No. 150 | SEQ ID No. 171 | SEQ ID No. 185 | SEQ ID No. 200 | SEQ ID No. 216 |
| CN21 | SEQ ID No. 134 | SEQ ID No. 148 | SEQ ID No. 172 | SEQ ID No. 185 | SEQ ID No. 201 | SEQ ID No. 217 |
| CN22 | SEQ ID No. 134 | SEQ ID No. 150 | SEQ ID No. 173 | SEQ ID No. 185 | SEQ ID No. 200 | SEQ ID No. 218 |
| CN23 | SEQ ID No. 136 | SEQ ID No. 151 | SEQ ID No. 174 | SEQ ID No. 188 | SEQ ID No. 202 | SEQ ID No. 219 |
| CN24 | SEQ ID No. 137 | SEQ ID No. 151 | SEQ ID No. 175 | SEQ ID No. 189 | SEQ ID No. 203 | SEQ ID No. 220 |
| CN25 | SEQ ID No. 138 | SEQ ID No. 152 | SEQ ID No. 176 | SEQ ID No. 189 | SEQ ID No. 204 | SEQ ID No. 221 |
| CN26 | SEQ ID No. 139 | SEQ ID No. 153 | SEQ ID No. 177 | SEQ ID No. 189 | SEQ ID No. 205 | SEQ ID No. 222 |
| CN27 | SEQ ID No. 138 | SEQ ID No. 154 | SEQ ID No. 178 | SEQ ID No. 190 | SEQ ID No. 206 | SEQ ID No. 223 |
| CN28 | SEQ ID No. 134 | SEQ ID No. 155 | SEQ ID No. 179 | SEQ ID No. 185 | SEQ ID No. 207 | SEQ ID No. 224 |
| CN29 | SEQ ID No. 130 | SEQ ID No. 140 | SEQ ID No. 157 | SEQ ID No. 181 | SEQ ID No. 208 | SEQ ID No. 209 |
| CN30 | SEQ ID No. 134 | SEQ ID No. 155 | SEQ ID No. 180 | SEQ ID No. 185 | SEQ ID No. 208 | SEQ ID No. 225 |

[31]. A vector comprising the nucleic acid molecule according to Aspect 29 or 30.

[32]. A host cell comprising the vector according to Aspect 31.

[33]. A method of producing the human anti-IL-33 neutralizing monoclonal antibody according to any one of Aspects 18 to 28, comprising culturing the host cell according to Aspect 32.

[34]. A cytokine expression inhibitor comprising the human anti-IL-33 neutralizing monoclonal antibody according to any one of Aspects 18 to 28.

[35]. The inhibitor according to Aspect 34, wherein the inhibitor inhibits expression of TNF-α, IFN-γ, IL-1β, IL-4, IL-5, IL-6, or IL-13.

[36]. The inhibitor according to Aspect 34 or 35, wherein the inhibitor inhibits expression of IFN-γ, IL-5, IL-6, or IL-13.

[37]. A pharmaceutical composition comprising the human anti-IL-33 neutralizing monoclonal antibody according to any one of Aspects 18 to 28.

[38]. The pharmaceutical composition according to Aspect 37 for treatment, prevention, or alleviation of a disease associated with IL-33.

[39]. The pharmaceutical composition according to Aspect 38, wherein the disease associated with IL-33 is selected from the group consisting of asthma, atopic dermatitis, pollinosis, anaphylactic shock, sinusitis (including eosinophilic sinusitis), Crohn's disease, ulcerative colitis, arthritis, systemic lupus erythematosus, pemphigus, pemphigoid, scleroderma, ankylosing spondylitis, hepatic fibrosis (including primary biliary cirrhosis), pulmonary fibrosis, chronic obstructive pulmonary disease (COPD), acute kidney injury, vasculitis, and cancer.

[40]. An anti-IL-33 neutralizing monoclonal antibody which competes with the antibody according to Aspect 20 or 25 in binding to IL-33.

[41]. A method for treatment, prevention, or alleviation of symptom in a patient with a disease associated with IL-33, the method comprising administering the antibody according to any one of Aspects 1 to 7 and 18 to 28 to the patient.

[42]. The method according to Aspect 41, wherein the disease associated with IL-33 is selected from the group consisting of asthma, atopic dermatitis, pollinosis, anaphylactic shock, sinusitis (including eosinophilic sinusitis), Crohn's disease, ulcerative colitis, arthritis, systemic lupus erythematosus, pemphigus, pemphigoid, scleroderma, ankylosing spondylitis, hepatic fibrosis (including primary biliary cirrhosis), pulmonary fibrosis, chronic obstructive pulmonary disease (COPD), acute kidney injury, vasculitis, and cancer.

[43]. Use of the antibody according to any one of Aspects 1 to 7 and 18 to 28 for the manufacture of amedicament to treat, prevent, or alleviate a disease associated with IL-33.

[44]. The use according to Aspect 43, wherein the disease associated with IL-33 is selected from the group consisting of asthma, atopic dermatitis, pollinosis, anaphylactic shock, sinusitis (including eosinophilic sinusitis), Crohn's disease, ulcerative colitis, arthritis, systemic lupus erythematosus, pemphigus, pemphigoid, scleroderma, ankylosing spondylitis, hepatic fibrosis (including primary biliary cirrhosis), pulmonary fibrosis, chronic obstructive pulmonary disease (COPD), acute kidney injury, vasculitis, and cancer.

[45]. Use of the antibody according to any one of Aspects 1 to 7 and 18 to 28 for the treatment, prevention, or alleviation of a disease associated with IL-33.

[46]. The use according to Aspect 45, wherein the disease associated with IL-33 is selected from the group consisting of asthma, atopic dermatitis, pollinosis, anaphylactic shock, sinusitis (including eosinophilic sinusitis), Crohn's disease, ulcerative colitis, arthritis, systemic lupus erythematosus, pemphigus, pemphigoid, scleroderma, ankylosing spondylitis, hepatic fibrosis (including primary biliary cirrhosis), pulmonary fibrosis, chronic obstructive pulmonary disease (COPD), acute kidney injury, vasculitis, and cancer.

[47]. A method for treating, preventing, or alleviating a symptom in a patient in need of inhibition of cytokine expression, the method comprising administering the antibody according to any one of Aspects 1 to 7 and 18 to 28 to the patient.

[48]. The method according to Aspect 47, wherein the cytokine is TNF-α, IFN-γ, IL-1β, IL-4, IL-5, IL-6, or IL-13.

[49]. Use of the antibody according to any one of Aspects 1 to 7 and 18 to 28 for the manufacture of a cytokine expression inhibitor.

[50]. The use according to Aspect 49, wherein the cytokine is TNF-α, IFN-γ, IL-1β, IL-4, IL-5, IL-6, or IL-13.

Advantageous Effects of Invention

Since the monoclonal antibody of the present invention is capable of binding to an epitope consisting of a continuous amino acid sequence, the monoclonal antibody readily exhibits its neutralizing effect by binding to a continuous amino acid sequence, even in the case where IL-33 is cleaved into fragments The monoclonal antibody of the present invention is less likely to induce human anti-human immunoglobulin antibody (HAHA) to its framework regions and/or complementarity-determining regions when it is administered to a human subject. Antibodies can exert a prolonged IL-33 neutralizing effect in vivo, unless they are inhibited by HAHA. In addition, antibodies are safely used, unless inflammation is caused by binding with HAHA. The monoclonal antibody of the present invention is capable of binding to human IL-33 to neutralize its functions, and thus is applicable to novel pharmaceuticals for diagnosis, prevention, treatment, or alleviation of diseases associated with IL-33.

BRIEF DESCRIPTION OF DRAWINGS

FIG. 12 shows the sequence and position of peptides PEP11 to PEP26.

DETAILED DESCRIPTION

Definitions

Figure 1:
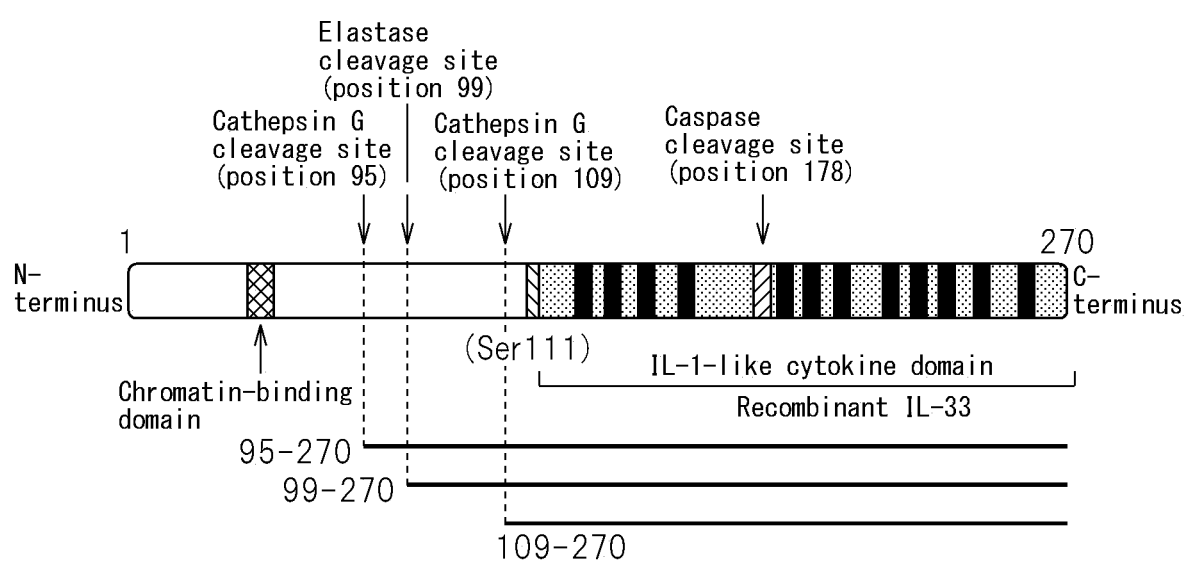
FIG. 1 shows each domain and cleavage site of the IL-33 protein.

The definitions of terms used herein are provided below for better understanding of the invention.

[Epitope]

As used herein, the term "epitope" refers to the part of an antigen recognized by an antibody. As used herein, the term "epitope" relates to a continuous amino acid sequence necessary for the recognition of the antibody.

[Binding]

As used herein, "binding" of a monoclonal antibody to an epitope refers to formation of a complex via binding between the antibody and the peptide which is an epitope. Examples of the binding between a monoclonal antibody and the epitope includes, but are not limited to, ionic, hydrogen, hydrophobic, and van der Waals bonds. Binding ability of a monoclonal antibody to an epitope can be analyzed, for example, by using peptide array scanning or KinExA technology described in the specification.

[Antibody]

The term "antibody" herein is used in the broadest sense, and includes monoclonal antibodies and polyclonal antibodies which exhibit desired binding specificity. The antibody of the present invention may be an antibody from any animal, and may be for example, a mouse antibody, a human antibody, a rat antibody, a rabbit antibody, a goat antibody, or a camel antibody.

[Monoclonal Antibody]

Among the antibodies of the present invention, "monoclonal antibody" refers to a population of antibodies produced from a single clone (i.e. the population includes substantially single molecular species) with respect to a designed amino acid sequence. Monoclonal antibodies include chimeric antibodies, humanized antibodies, human antibodies, multispecific antibodies, and artificial antibody, and functionally modified forms thereof, and conjugated antibodies containing any of such antibodies, and fragments of such antibodies. The monoclonal antibody of the present invention can be produced by any known method including, for example, hybridoma, phage display, and genetic engineering techniques.

[Chimeric Antibody]

The term "chimeric antibody" refers to an antibody containing light chains and/or heavy chains that are composed of variable regions of a non-human animal and constant regions of human.

[Humanized Antibody]

The term "humanized antibody" refers to an antibody which is composed of variable regions consisting of complementarity-determining regions of a non-human antibody and framework regions of a human antibody; and constant regions of a human antibody.

[Human Antibody]

The term "human antibody" refers to an antibody, wherein both light and heavy chains are derived from human. Human antibody includes the following isotypes with different heavy-chain constant regions: IgG (including IgG1, IgG2, IgG3, and IgG4) having γ heavy chains; IgM having μ heavy chains; IgA having α heavy chains (including IgA1 and IgA2); IgD having δ heavy chains; and IgE having ε heavy chains. In principle, each human antibody molecule has either κ or λ light chains.

[Multispecific Antibody]

The term "multispecific antibody" refers to an asymmetric antibody that has two or more independent antigen recognition sites and has specificity for two or more different antigens. Examples of the multispecific antibody include bispecific antibodies with specificity for two antigens, and trispecific antibodies with specificity for three antigens. One or more of the antigens recognized by the multispecific antibody of the present invention are an IL-33 molecule.

[Artificial Antibody]

"Artificial antibody" refers to, for example, protein scaffolds, which do not have a structure of an antibody, but have a function like an antibody. Examples of the applicable protein scaffolds include Kunitz domains of human serine protease inhibitors; extracellular domains of human fibronectin; ankyrin; and lipocalin. A protein scaffold that is capable of binding to the epitope of the present invention can be produced by modifying the sequence of the target-biding site on the scaffold (Clifford Mintz et. al., BioProcess International, 2013, Vol. 11(2), pp. 40-48).

[Functionally Modified Antibody]

As used herein, the term "functionally modified antibody" refers to an antibody which is regulated for its functions or properties, except for the antigen-binding function, such as cytotoxic function, complement activation function, and half-life in blood by mainly modifying amino acids or sugar chains in Fc regions of an antibody.

[Conjugated Antibody]

As used herein, the term "conjugated antibody" refers to an antibody which is conjugated with a non-antibody functional molecule, such as non-peptidic polymers, e.g., poly (ethylene glycol) (PEG); radioactive materials; toxins; low-molecular-weight compounds; cytokines; albumin; and enzymes through any chemical or genetic engineering process.

[Fragment]

As used herein, the term "antibody fragment" refers to a protein which comprises a part of an antibody and can bind to an antigen. Examples of the antibody fragment include Fab fragments, Fv fragments, F(ab')$_2$ fragments, Fab' fragments, and scFv fragments.

These antibody fragments may be conjugated with non-antibody functional molecules, such as non-peptidic polymers, e.g., poly(ethylene glycol) (PEG); radioactive materials; toxins; low-molecular-weight compounds; cytokines; albumin; and enzymes through any chemical or genetic engineering process.

[IL-33]

IL-33 is a cytokine of the IL-1 family. Human IL-33 consists of 270 amino acids as shown in SEQ ID NO:226 in the Sequence Listing. IL-33 comprises an N-terminal chromatin-binding domain, a C-terminal IL-1-like cytokine domain having 12 β-strands and having a molecular weight of 18 kDa, cathepsin G cleavage sites located at positions 95 and 109, an elastase cleavage site located at position 99, and a caspase cleavage site located at position 178 (FIG. 1). It is believed that, during cell necrosis, IL-33 is cleaved by enzymes, such as elastase, cathepsin G and proteinase 3, which are derived from loysosome etc., into various fragments including mature IL-33, such as IL-33 (residues 95 to 270) ("IL-33 (residues 95 to 270)" represents the IL-33 fragment represented by the amino acid sequence at positions 95 to 270 from N-terminus of SEQ ID NO:226 in the Sequence Listing; other fragments are represented in the same way), IL-33 (residues 99 to 270), IL-33 (resides 109 to 270), and IL-33 (residues 112 to 270)), and functions as a cytokine. In the case of apoptotic cell death, IL-33 is cleaved at position 178, by caspase activated during the apoptosis, into inactivated forms of IL-33, such as IL-33 (residues 179 to 270).

Once IL-33 is extracellularly released as a cytokine, it binds to IL-33 receptors and functions as an inducer of intracellular signal transduction in the cells expressing the IL-33 receptor. The IL-33-induced signal transduction occurs through pathways including, but not limited to, NF-κB and MAPKKs pathways, and eventually induces production of various cytokines, chemokines, and inflammatory mediators. Examples of the IL-33-induced cytokines include TNF-α, IL-1β, IFN-γ, IL-3, IL-4, IL-5, IL-6, and IL-13. In particular, production of IFN-γ, IL-5, IL-6, and IL-13 is induced. Examples of the IL-33-induced chemokines include CXCL2, CCL2, CCL3, CCL6, CCL17, and CCL24. Examples of the IL-33-induced inflammatory mediators include PGD2 and LTB4. The IL-33-induced cytokines, chemokines, and inflammatory mediators are involved in migration, cytokine production, and degranulation of immune cells, and cause inflammation. In the present invention, IL-33 may be either full-length IL-33 or any active fragment of IL-33, and may also be any derivative or variant thereof, as long as they are capable of binding to an IL-33 receptor described below and attain its effect. IL-33 may be either human IL-33 or IL-33 derived from any other organism. Among IL-33, human IL-33 represented by the amino acid sequence of SEQ ID NO:226 in the Sequence Listing is preferred.

The IL-33 receptor to which IL-33 binds is a heterodimeric complex composed of ST2 and IL-1RAcP (IL-1 receptor accessory protein). The IL-33 receptor contains the binding site that specifically recognizes IL-33 in the extracellular domain of ST2. The IL-33 receptor is expressed in cells including, but not limited to, various immune cells (such as Th2 cells, mast cells, eosinophils, basophils, macrophages, dendritic cells, NK cells, NKT cells, Group 2 innate lymphocytes (natural helper cells), nuocytes, and Ih2 (innate helper type 2) cells) and epithelial cells.

[Diseases Associated with IL-33]

As used herein, the term "disease associated with IL-33" refers to diseases caused by excessive extracellular release of IL-33. The diseases associated with IL-33 can be prevented, treated, or alleviated with an agent capable of inhibiting the functions of IL-33. The diseases associated with IL-33 include, for example, asthma, atopic dermatitis, pollinosis, anaphylactic shock, sinusitis (including eosinophilic sinusitis), Crohn's disease, ulcerative colitis, arthritis, systemic lupus erythematosus, pemphigus, pemphigoid, scleroderma, ankylosing spondylitis, hepatic fibrosis (including primary biliary cirrhosis), pulmonary fibrosis, chronic obstructive pulmonary disease (COPD), acute kidney injury, vasculitis, and cancer.

[Framework Region]

The term "framework region" refers to the part in variable regions of an immunoglobulin molecule other than complementarity-determining regions. Each light and heavy chain has four framework regions (framework regions 1, 2, 3, and 4). Herein, framework regions of immunoglobulin molecules are numbered in accordance with the Kabat numbering system (Kabat et al., 1987, Sequences of Proteins of Immunological Interest, US Department of Health and Human Services, NIH, USA).

[Germline]

The term "germline" refers to a group of germ cells such as spermatozoa and ovum, and refers to human germline, unless otherwise indicated. Immunoglobulin genes of germ cells contain no mutation, unlike those of B cells expressing antibodies. Accordingly, the term "amino acid sequence(s) of framework region(s) from germline" refers to amino acid sequence(s) without any mutation as compared to the amino acid sequence(s) of the framework region(s) of immunoglobulin. The term "a combination of amino acid sequences of framework regions from germlines" indicates that one or more of the four framework regions have an amino acid sequence of framework region from different germline. Gene that encode light-chain variable regions of human immune globulin is divided into Vκ segment and Jκ segment in κ chain; and Vλ segment and Jλ segment in λ chain. Framework regions 1 to 3 are present on the Vκ and Vλ segments, and framework region 4 is present on the Jκ and Jλ segments. The gene of the heavy-chain variable regions of human immunoglobulin is divided into VH segment, DH segment, and JH segment. Framework regions 1 to 3 are present on the VH segment, and framework region 4 is present on the JH segment. The germline amino acid sequences of each Vκ, Vλ, VH, Jκ, Jλ, and JH segment of human immunoglobulin are shown in Table 4.

TABLE 4

The following SEQ ID Nos. show the SEQ ID Nos. in the Sequence Listing

| Segment | germline name | SEQ ID No. |
| --- | --- | --- |
| Vκ | Vκ1-5 | SEQ ID No. 278 |
| Vκ | Vκ1-6 | SEQ ID No. 279 |
| Vκ | Vκ1-8 | SEQ ID No. 280 |
| Vκ | Vκ1-9 | SEQ ID No. 281 |
| Vκ | Vκ1-12, Vκ1D-12 | SEQ ID No. 282 |
| Vκ | Vκ1-16 | SEQ ID No. 283 |
| Vκ | Vκ1-17 | SEQ ID No. 284 |
| Vκ | Vκ1-27 | SEQ ID No. 285 |
| Vκ | Vκ1-33, Vκ1D-33 | SEQ ID No. 286 |
| Vκ | Vκ1-39, Vκ1D-39 | SEQ ID No. 287 |
| Vκ | Vκ1D-8 | SEQ ID No. 288 |
| Vκ | Vκ1D-13 | SEQ ID No. 289 |
| Vκ | Vκ1D-16 | SEQ ID No. 290 |
| Vκ | Vκ1D-17 | SEQ ID No. 291 |
| Vκ | Vκ1D-43 | SEQ ID No. 292 |
| Vκ | Vκ1-NL1 | SEQ ID No. 293 |
| Vκ | Vκ2-24 | SEQ ID No. 294 |
| Vκ | Vκ2-28, Vκ2D-28 | SEQ ID No. 295 |
| Vκ | Vκ2-30 | SEQ ID No. 296 |
| Vκ | Vκ2-40, Vκ2D-40 | SEQ ID No. 297 |
| Vκ | Vκ2D-26 | SEQ ID No. 298 |
| Vκ | Vκ2D-29 | SEQ ID No. 299 |
| Vκ | Vκ2D-30 | SEQ ID No. 300 |
| Vκ | Vκ3-11 | SEQ ID No. 301 |
| Vκ | Vκ3-15, Vκ3D-15 | SEQ ID No. 302 |
| Vκ | Vκ3-20 | SEQ ID No. 303 |
| Vκ | Vκ3D-7 | SEQ ID No. 304 |
| Vκ | Vκ3D-11 | SEQ ID No. 305 |
| Vκ | Vκ3D-20 | SEQ ID No. 306 |
| Vκ | Vκ3-NL1 | SEQ ID No. 307 |
| Vκ | Vκ3-NL2 | SEQ ID No. 308 |
| Vκ | Vκ3-NL3 | SEQ ID No. 309 |
| Vκ | Vκ3-NL4 | SEQ ID No. 310 |
| Vκ | Vκ3-NL5 | SEQ ID No. 311 |
| Vκ | Vκ4-1 | SEQ ID No. 312 |
| Vκ | Vκ5-2 | SEQ ID No. 313 |
| Vλ | Vλ1-36 | SEQ ID No. 314 |
| Vλ | Vλ1-40 | SEQ ID No. 315 |
| Vλ | Vλ1-44 | SEQ ID No. 316 |
| Vλ | Vλ1-47 | SEQ ID No. 317 |
| Vλ | Vλ1-51 | SEQ ID No. 318 |
| Vλ | Vλ2-8 | SEQ ID No. 319 |
| Vλ | Vλ2-11 | SEQ ID No. 320 |
| Vλ | Vλ2-14 | SEQ ID No. 321 |
| Vλ | Vλ2-18 | SEQ ID No. 322 |
| Vλ | Vλ2-23 | SEQ ID No. 323 |
| Vλ | Vλ3-1 | SEQ ID No. 324 |
| Vλ | Vλ3-9 | SEQ ID No. 325 |
| Vλ | Vλ3-10 | SEQ ID No. 326 |
| Vλ | Vλ3-12 | SEQ ID No. 327 |
| Vλ | Vλ3-16 | SEQ ID No. 328 |
| Vλ | Vλ3-19 | SEQ ID No. 329 |

TABLE 4-continued

The following SEQ ID Nos. show the SEQ ID Nos. in the Sequence Listing

| Segment | germline name | SEQ ID No. |
|---|---|---|
| Vλ | Vλ3-21 | SEQ ID No. 330 |
| Vλ | Vλ3-22 | SEQ ID No. 331 |
| Vλ | Vλ3-25 | SEQ ID No. 332 |
| Vλ | Vλ3-27 | SEQ ID No. 333 |
| Vλ | Vλ4-3 | SEQ ID No. 334 |
| Vλ | Vλ4-60 | SEQ ID No. 335 |
| Vλ | Vλ4-69 | SEQ ID No. 336 |
| Vλ | Vλ5-37 | SEQ ID No. 337 |
| Vλ | Vλ5-39 | SEQ ID No. 338 |
| Vλ | Vλ5-45 | SEQ ID No. 339 |
| Vλ | Vλ5-52 | SEQ ID No. 340 |
| Vλ | Vλ6-57 | SEQ ID No. 341 |
| Vλ | Vλ7-43 | SEQ ID No. 342 |
| Vλ | Vλ7-46 | SEQ ID No. 343 |
| Vλ | Vλ8-61 | SEQ ID No. 344 |
| Vλ | Vλ9-49 | SEQ ID No. 345 |
| Vλ | Vλ10-54 | SEQ ID No. 346 |
| VH | VH1-2 | SEQ ID No. 347 |
| VH | VH1-3 | SEQ ID No. 348 |
| VH | VH1-8 | SEQ ID No. 349 |
| VH | VH1-18 | SEQ ID No. 350 |
| VH | VH1-24 | SEQ ID No. 351 |
| VH | VH1-45 | SEQ ID No. 352 |
| VH | VH1-46 | SEQ ID No. 353 |
| VH | VH1-58 | SEQ ID No. 354 |
| VH | VH1-f | SEQ ID No. 355 |
| VH | VH1-69 | SEQ ID No. 356 |
| VH | VH2-5 | SEQ ID No. 357 |
| VH | VH2-26 | SEQ ID No. 358 |
| VH | VH2-70 | SEQ ID No. 359 |
| VH | VH3-7 | SEQ ID No. 360 |
| VH | VH3-9 | SEQ ID No. 361 |
| VH | VH3-11 | SEQ ID No. 362 |
| VH | VH3-13 | SEQ ID No. 363 |
| VH | VH3-15 | SEQ ID No. 364 |
| VH | VH3-20 | SEQ ID No. 365 |
| VH | VH3-21 | SEQ ID No. 366 |
| VH | VH3-23 | SEQ ID No. 367 |
| VH | VH3-30, VH3-30-3 | SEQ ID No. 368 |
| VH | VH3-33 | SEQ ID No. 369 |
| VH | VH3-43 | SEQ ID No. 370 |
| VH | VH3-48 | SEQ ID No. 371 |
| VH | VH3-49 | SEQ ID No. 372 |
| VH | VH3-53 | SEQ ID No. 373 |
| VH | VH3-64 | SEQ ID No. 374 |
| VH | VH3-66 | SEQ ID No. 375 |
| VH | VH3-72 | SEQ ID No. 376 |
| VH | VH3-73 | SEQ ID No. 377 |
| VH | VH3-74 | SEQ ID No. 378 |
| VH | VH3-d | SEQ ID No. 379 |
| VH | VH3-NL1 | SEQ ID No. 380 |
| VH | VH4-4 | SEQ ID No. 381 |
| VH | VH4-28 | SEQ ID No. 382 |
| VH | VH4-30-2 | SEQ ID No. 383 |
| VH | VH4-30-4 | SEQ ID No. 384 |
| VH | VH4-31 | SEQ ID No. 385 |
| VH | VH4-34 | SEQ ID No. 386 |
| VH | VH4-39 | SEQ ID No. 387 |
| VH | VH4-59 | SEQ ID No. 388 |
| VH | VH4-b | SEQ ID No. 389 |
| VH | VH4-61 | SEQ ID No. 390 |
| VH | VH5-a | SEQ ID No. 391 |
| VH | VH5-51 | SEQ ID No. 392 |
| VH | VH6-1 | SEQ ID No. 393 |
| VH | VH7-4-1 | SEQ ID No. 394 |
| Jκ | Jκ1 | SEQ ID No. 395 |
| Jκ | Jκ2 | SEQ ID No. 396 |
| Jκ | Jκ3 | SEQ ID No. 397 |
| Jκ | Jκ4 | SEQ ID No. 398 |
| Jκ | Jκ5 | SEQ ID No. 399 |
| Jλ | Jλ1 | SEQ ID No. 400 |
| Jλ | Jλ2, Jλ3 | SEQ ID No. 401 |
| Jλ | Jλ6 | SEQ ID No. 402 |
| Jλ | Jλ7 | SEQ ID No. 403 |
| JH | JH1 | SEQ ID No. 404 |
| JH | JH2 | SEQ ID No. 405 |
| JH | JH3 | SEQ ID No. 406 |
| JH | JH4 | SEQ ID No. 407 |
| JH | JH5 | SEQ ID No. 408 |
| JH | JH6 | SEQ ID No. 409 |

[Human Monoclonal Antibody]

The term "human monoclonal antibody" refers to a monoclonal antibody containing variable and constant regions of human germline immunoglobulin sequence. In the present invention, the human monoclonal antibody may be a recombinant generated by replacing its variable regions partially or entirely with variable regions of any other human monoclonal antibody. The recombinant may be generated by recombination at boundaries between the framework regions and the complementarity-determining regions, in order to avoid undesired influences on the binding ability of the antibody. The recombinant may also be generated by recombination of framework regions 1 to 4 respectively with framework regions 1 to 4 of any other human monoclonal antibody, in order to avoid undesired increase in immunogenicity. The human monoclonal antibody of the present invention may be a variant of a human monoclonal antibody. In order to reduce immunogenicity while maintaining or improving its binding ability with the antigen, the human monoclonal antibody preferably includes amino acid sequences of complementarity-determining region with mutation and amino acid sequences of germline framework region without mutation.

[Isolated]

The term "isolated" antibody refers to an antibody identified and separated and/or recovered from a component in its natural environment. Contaminant components in its natural environments are materials that would interfere with diagnostic or therapeutic uses of the antibody, and include enzymes, hormones, and other proteinaceous or non-proteinaceous solutes. In general, an isolated antibody may be obtained by at least one purification step, and an antibody purified by such at least one purification step is referred to as "isolated antibody."

[Neutralization]

As used herein, the term "neutralization" refers to an action of binding to a target of interest and inhibiting one of its functions. Specifically, the term "anti-IL-33 neutralizing monoclonal antibody" refers to a monoclonal antibody which inhibits biological activity induced by the IL-33 polypeptide via binding with IL-33. The biological activity to be inhibited of IL-33 includes, but is not limited to, production of IL-33-induced cytokines such as IL-6. Indicators of the biological activity of IL-33 can be evaluated by one or more of the in vitro or in vivo analyses known in the art. The term "human anti-IL-33 neutralizing monoclonal antibody" refers to a human monoclonal antibody that is capable of binding to IL-33 to inhibit one of its functions.

[Antagonist]

As used herein, the term "antagonist" is a generic term for materials having a neutralizing effect on a target of interest. Specifically, "IL-33 antagonist" refers to a material capable of binding to IL-33 to inhibit one of its functions, for example anti-IL-33 neutralizing monoclonal antibodies.

[Complementarity-Determining Region]

The term "complementarity-determining regions" refers to the regions which form the antigen-binding site in variable regions of an immunoglobulin molecule. It is also referred to as "hypervariable regions" indicating the parts with particularly great variability in the amino acid sequences among different immunoglobulin molecules. Light and heavy chains respectively contain three complementarity-determining regions (complementarity-determining regions 1, 2, and 3). In the present invention, the complementarity-determining regions of immunoglobulin molecules are numbered in accordance with the Kabat numbering system (Kabat et al., 1987, Sequences of Proteins of Immunological Interest, US Department of Health and Human Services, NIH, USA).

[Competition]

As used herein, an antibody which "competes" with a monoclonal antibody indicates that the presence of the monoclonal antibody significantly decreases the binding of an antibody with IL-33, as measured by surface plasmon resonance (SPR) as described in the specification.

As used herein, the term "anti-IL-33 neutralizing monoclonal antibody which competes" encompasses chimeric antibodies, humanized antibodies, human antibodies, multispecific antibodies, and artificial antibody, and functionally modified forms thereof, conjugated antibodies containing any of such antibodies, and fragments of such antibodies.

The embodiments of the present invention are explained below. The following embodiments is illustrative, and should not be construed to limit the present invention.

The present invention relates to a monoclonal antibody that is capable of binding to an epitope of IL-33. Since the monoclonal antibody that is capable of binding to the epitope can neutralize the activity of human IL-33, the epitope preferably has an amino acid sequence of positions 101 to 154 or 199 to 270, more preferably 111 to 130 (PEP12), 131 to 150 (PEP14), 231 to 250 (PEP24), or 251 to 270 (PEP26), of SEQ ID NO:226 in the Sequence Listing. IL-33 is often cleaved during extracellular release. If an epitope is formed from amino acid residues being separate on the primary sequence of IL-33 based on protein folding, cleavage of IL-33 affects the protein folding and deletes the separated amino acid residues of the epitope, which may result in significant decrease of the affinity of the antibody with the resulting fragments. For this reason, the epitope to which the anti-IL-33 monoclonal antibody binds is preferably a continuous amino acid sequence.

In order to attain the neutralizing effect of the monoclonal antibody that is capable of binding to an epitope, it is required, for example, to inhibit binding of IL-33 with IL-33 receptors. Thus, the epitope in the present invention is preferably present not only on the surface of the IL-33 protein but also in close proximity to the IL-33 receptors. The inventors have performed conformational modeling based on the crystallographic structure data in NPL 11, to identify the amino acids containing the atom of IL-33 located at the atomic distance of 5 Å or less from a component atom of the IL-33 receptor, when the two atoms are in the closest proximity (i.e. interfacial atom), as described below in the Examples. Examples of the amino acid containing the interfacial atom include P118 ("P118" represents the proline residue at position 118 of SEQ ID NO:226 in the Sequence Listing; hereinafter, amino acid residues are represented in the same way), I119, T120, Y122, L123, R124, S125, L126, S127, Y129, and N130 of PEP12; D131, Q132, S133, T135, A137, L138, E139, S142, Y143, E144, I145, Y146, E148, D149, and L150 of PEP14; D244, N245, and H246 of PEP24; and K266, L267, S268, and E269 of PEP26. A functional epitope to specifically bind to a monoclonal antibody that can neutralize IL-33 preferably includes the amino acid containing the interfacial atom. The neutralizing effect of a monoclonal antibody that is capable of specifically binding to a functional epitope is believed to depend on the number and the conformational position of the interfacial atoms contained in the functional epitope, but it is not intended to be bound by the theory.

A preferred embodiment of the present invention is directed to a monoclonal antibody wherein the epitope consisting of a continuous amino acid sequence included in positions 101 to 154 or 199 to 270 of SEQ ID NO:226 in the Sequence Listing consists of a continuous amino acid sequence of positions 111 to 130 (PEP12), 131 to 150 (PEP14), 231 to 250 (PEP24), or 251 to 270 (PEP26) of SEQ ID NO:226 in the Sequence Listing. A more preferred embodiment of the present invention is the monoclonal antibody wherein the epitope consists of a continuous amino acid sequence of positions 138 to 147 or 139 to 147 of SEQ ID NO:226 in the Sequence Listing.

The inventors have studied the minimal amino acid sequence required for the epitope, using two different monoclonal antibodies that bind to PEP14, and have determined the continuous amino acid sequences of positions 138 to 147 and 139 to 147 of SEQ ID NO:226 in the Sequence Listing as the minimal sequence for the epitope of IL-33. Accordingly, the present invention relates to an epitope consisting of a continuous amino acid sequence of positions 138 to 147 or 139 to 147 of SEQ ID NO:226 in the Sequence Listing.

The binding of a monoclonal antibody to the epitope of the present invention can be confirmed by a method generally practiced in the art, such as ELISA, immunoprecipitation, surface plasmon resonance (SPR), and KinExA technology. For example, if a monoclonal antibody is tested using the epitope peptides of the present invention in peptide array scanning based on the SPR process, as described in the Examples in the specification, the binding of the monoclonal antibody to the epitope can be determined based on significant increases in RU values. The analysis by KinExA technology described in the specification in the Examples can determine a dissociation constant (Kd). The dissociation constant against an epitope peptide is preferably low, and is preferably 10 μM or lower, 1 μM or lower, 100 nM or lower, 10 nM or lower, 1 nM or lower, 100 pM or lower, or 10 pM or lower.

Another embodiment of the present invention relates to a pharmaceutical composition comprising the monoclonal antibody of the present invention that is capable of binding to an epitope consisting of a continuous amino acid sequence included in positions 101 to 154 or 199 to 270 of SEQ ID NO:226 in the Sequence Listing. The invention also relates to a method for diagnosis, treatment, prevention, or alleviation of a disease associated with IL-33, the method comprising administering the monoclonal antibody of the invention, and to use of the monoclonal antibody of the invention for the manufacture of a amedicament to diagnosing, treating, preventing, or alleviating a disease associated with IL-33.

Non-limiting examples of the disease associated with IL-33 include asthma, atopic dermatitis, urticaria, pollinosis, anaphylactic shock, sinusitis (including eosinophilic sinusitis), allergic encephalomyelitis, hypereosinophilic syndrome, polymyalgia rheumatica, rheumatic heart diseases, multiple sclerosis, arthritis (for example, rheumatoid arthritis, juvenile arthritis, psoriatic arthritis, arthrosis deformans, and Reiter's syndrome), systemic lupus erythematosus (including discoid lupus), pemphigus, pemphigoid, psoriasis, ankylosing spondylitis, hepatitis (for example, autoimmune hepatitis and chronic active hepatitis), inflammatory bowel diseases (for example, ulcerative colitis, Crohn's disease, and gluten-sensitive enteropathy), Sjogren's syndrome, autoimmune hemolytic anemia, autoimmune inflammatory eye diseases, autoimmune neonatal thrombocytopenia, autoimmune neutropenia, autoimmune oophoritis and orchitis, autoimmune thrombocytopenia, autoimmune thyroiditis, multiple myositis, dermatomyositis, myasthenia gravis, adrenergic agonist resistance, alopecia areata (alopecia greata), antiphospholipid syndrome, adrenal autoimmune diseases (for example, autoimmune Addison's disease), celiac sprue-dermatitis, chronic fatigue and immune dysfunction syndrome (CFIDS), cold agglutinin disease, essential mixed cryoglobulinemia, fibromyalgia-fibromyositis, glomerulonephritis (for example, IgA nephropathy), Graves' disease, hyperthyroidism (that is, Hashimoto's thyroiditis), idiopathic thrombocytopenic purpura (ITP), mixed connective tissue disease, Type 1 or immune-mediated diabetes mellitus, pernicious anemia, polychondritis, polyglandular syndrome, stiff-man syndrome, vitiligo, sarcoidosis, polyendocrinopathy, other endocrinopathy, arteriosclerosis, hepatic fibrosis (for example, primary biliary cirrhosis), pulmonary fibrosis (for example, idiopathic pulmonary fibrosis), chronic obstructive pulmonary disease (COPD), scleroderma (including CREST syndrome and Raynaud's phenomenon), tubulointerstitial nephritis, dense deposit disease, acute kidney injury, myocarditis, cardiomyopathy, neuritis (for example, Guillain-Barre syndrome), polyarteritis nodosa, cardiotomy syndrome, chronic inflammatory demyelinating polyneuropathy, IgA neuropathy, lichen planus, Meniere's disease, post-myocardial infarction (post-MI) syndrome, uveitis, uveitis ophthalmia, vasculitis, primary agammaglobulinemia, cancer (for example, brain tumor, laryngeal cancer, lip and oral cancer, hypopharyngeal cancer, thyroid cancer, esophageal cancer, breast cancer, lung cancer, gastric cancer, adrenocortical carcinoma, cancer of the bile duct, gallbladder cancer, liver cancer, pancreatic cancer, bladder cancer, colon cancer, uterine cancer, ovarian cancer, prostate cancer, testicular cancer, chronic lymphocytic leukemia, chronic myelogenous leukemia, Ewing's tumor, Hodgkin's disease, non-Hodgkin lymphoma, melanoma, mesothelioma, and multiple myeloma), infections resistant to clearance by the immune system (for example, severe acute respiratory syndrome (SARS)), lethal cytokine storm associated with virulent influenza infection, and sepsis. The disease associated with IL-33 is preferably asthma, atopic dermatitis, pollinosis, anaphylactic shock, sinusitis (including eosinophilic sinusitis), Crohn's disease, ulcerative colitis, arthritis, systemic lupus erythematosus, pemphigus, pemphigoid, scleroderma, ankylosing spondylitis, hepatic fibrosis (including primary biliary cirrhosis), pulmonary fibrosis, chronic obstructive pulmonary disease (COPD), acute kidney injury, vasculitis, and cancer.

A further embodiment of the present invention relates to an expression inhibitor against a cytokine, chemokine, or an inflammatory mediator, comprising the monoclonal antibody that is capable of binding to an epitope consisting of a continuous amino acid sequence included in positions 101 to 154 or 199 to 270 of SEQ ID NO:226 in the Sequence Listing.

The cytokine to be inhibited by the expression inhibitor for cytokines, chemokines, or inflammatory mediators according to the present invention is one of the IL-33 induced cytokines, including TNF-α, IFN-γ, IL-1β, IL-3, IL-4, IL-5, IL-6, and IL-13. The chemokine to be inhibited with the inhibitor is one of IL-33-induced chemokines, including CXCL2, CCL2, CCL3, CCL6, CCL17, and CCL24. The inflammatory mediator to be inhibited with the inhibitor is one of IL-33-induced inflammatory mediators, including PGD2 and LTB4. A particularly preferred embodiment of the present invention is an expression inhibitor containing an anti-IL-33 monoclonal antibody to inhibit expression of IFN-γ, IL-5, IL-6, or IL-13. More preferably, the inhibitor is an IL-6 expression inhibitor.

In a further embodiment of the present invention, the invention relates to an epitope to which an anti-IL-33 monoclonal antibody binds. In the present invention, the epitope is directed to a sequence consisting of six to twenty amino acids necessary for recognition by the antibody. In another embodiment, the epitope may further contain amino acids in close proximity, either in the sequence or in the three-dimensional structure, to amino acids in the determined sequence, thereby a further epitope may be formed. However, the epitope preferably does not contain discontinuous amino acids.

The continuous amino acid sequence of the epitope of the present invention consists of at least five, preferably at least six, more preferably at least seven, more preferably at least eight, yet more preferably at least nine amino acids. The continuous amino acid sequence consists of at least 10, more preferably 15, yet more preferably at least 20 amino acids, so as to achieve more sufficient antigenicity. On the other hand, if the epitope contains an excessively long sequence, however, it may contain two or more sites recognized by an antibody, which may interfere with production or screening of antibodies having a desired neutralizing effect. For this reason, the sequence of the epitope is preferably 30 amino acids or less, more preferably 20 amino acids or less, yet more preferably 15 amino acids or less, in length, for ensuring exhibition of the desired neutralizing effect by the antibody that is capable of binding to the epitope of the present invention. The number of amino acid residues in the continuous amino acid sequence included in the epitope is selected from, for example, 5, 6, 7, 8, 9, 10, 11, 12, 13, 14, 15, 16, 17, 18, 19, and 20.

The epitope may have one or several amino acid mutations, i.e. amino acid substitutions, deletions, or insertions, unless the mutations change the antigenicity. The number of introduced mutations is preferably five or less, more preferably three or less, most preferably one. The epitope may also be modified, for example, with sugar chains of the original protein, and terminal modification. In another embodiment, the epitope may consist of an amino acid sequence with sequence identity of at least 90%, more preferably at least 95%, more preferably at least 97%, yet more preferably at least 98%, most preferably 99%, to the continuous amino acid sequence specified in the present invention, unless the antigenicity is affected. The epitope peptide may be tagged with histidine or biotin, etc., when it is used as bait, and may be linked to a carrier protein such as KLH, when it is used as vaccine.

"Percent (%) sequence identity" related to a reference polypeptide sequence identified herein is defined as the percentage of amino acid residues that are included in a candidate sequence and are identical with the amino acid residues in a specific reference polypeptide sequence, after aligning the sequences and introducing gaps, if necessary, to achieve the maximum percent sequence identity, and not considering any conservative substitutions as part of the sequence identity. Alignment for the purpose of determining percent amino acid sequence identity can be achieved by using various methods within the skill in the art, for example, a publicly available computer software, such as BLAST, BLAST-2, ALIGN, or Megalign (DNASTAR, Inc.) software. Those skilled in the art can determine appropriate parameters for measuring alignment, including any algorithm necessary for achieving maximal alignment on the full-length sequences to be compared. For the purposes described herein, however, percent amino acid sequence identity values are determined by pairwise comparison using the sequence comparison computer program BLAST. In a circumstance where the program BLAST is used for comparison of amino acid sequences, the percent amino acid sequence identity of a given amino acid sequence A to a given amino acid sequence B is calculated as follows:

Fraction X/Y×100 where X is the number of amino acid residues scored as identical matches by the sequence alignment program BLAST in its alignment of the sequences A and B, and Y is the total number of amino acid residues in the sequence B. It will be appreciated that difference in length between the amino acid sequences A and B results in difference in the percent amino acid sequence identity of the sequence A to the sequence B and that of the sequence B to the sequence A. All the percent amino acid sequence identity values described herein are determined based on the BLAST computer program as just described above, unless otherwise indicated.

The epitope found in the present invention is directed to a functional epitope to which an anti-IL-33 neutralizing antibody binds specifically. Thus, a novel antibody having an antagonistic effect against IL-33 can be obtained efficiently by means of the functional epitope of the present invention. Specifically, a monoclonal antibody having the antagonistic effect can be obtained by screening monoclonal antibodies to full-length IL-33 or mature IL-33 to identify those which are capable of binding to the functional epitope of the invention. Accordingly, in a further embodiment, the present invention relates to a method of screening for an antibody having an antagonistic effect using the functional epitope of IL-33. More specifically, if a clone of antibody having an antagonistic effect against IL-33 is concentrated from a naive antibody library by phage display technique, library selection is first performed using a full-length or mature IL-33 protein as bait, the clones of antibodies that bind to one or more of various epitopes on the surface of IL-33 are enriched and then are subjected to the library selection using the functional epitope peptides found in the invention as bait. Such a method provides efficient screening of an antibody capable of specifically binding to the functional epitope and having an antagonistic effect against IL-33.

In the Examples, the inventors tested monoclonal antibodies that had been confirmed to bind to epitopes of 20 amino acid residues in length to analyze their antagonistic activity against IL-33 at different antibody concentrations, to determine epitopes suitable for production or screening of an antibody having the antagonistic effect. The results show that antibodies binding to an epitope selected from the group consisting of positions 111 to 130 (PEP12), 131 to 150 (PEP14), 231 to 250 (PEP24), and 251 to 271 (PEP26) of SEQ ID NO:226 in the Sequence Listing clearly exhibited concentration-dependent increase in their antagonistic effect. The results demonstrate that such epitopes are functional epitopes suitable for production or screening of an antibody having antagonistic effect. Accordingly, in one embodiment, the present invention relates to an epitope comprising a sequence consisting of at least six, preferably at least 10, more preferably at least 15, consecutive amino acids included in a region selected from the group consisting of positions 111 to 130, 131 to 150, 231 to 250, and 251 to 271 of SEQ ID NO:226 in the Sequence Listing. In another embodiment, the present invention relates to an epitope selected from the group consisting of positions 111 to 130, 131 to 150, 231 to 250, and 251 to 270 of SEQ ID NO:226 in the Sequence Listing.

The epitope can be produced by any peptide synthesizing technique ordinarily practiced in the art. A prepared and purified epitope can be used for immunization of animals or for production of antibodies to the epitope. Alternatively, a purified epitope can be applied to phage displaying technique for production or screening of a monoclonal antibody that is capable of binding to the epitope. The epitope can also be used as vaccine when it is used in combination with an adjuvant.

The present invention relates to a monoclonal antibody that is capable of binding to an epitope consisting of a continuous amino acid sequence included in a sequence spanning positions 101 to 154 or 199 to 270 of SEQ ID NO:226 in the Sequence Listing. Examples of the monoclonal antibody include chimeric antibodies, humanized antibodies, human antibodies, multispecific antibodies, and artificial antibody; and functionally modified forms thereof, conjugated antibody thereof, and fragments thereof. The monoclonal antibody of the present invention may be an antibody from any animal, for example, mouse antibody, human antibody, rat antibody, rabbit antibody, goat antibody, or camel antibody. The monoclonal antibody of the present invention can be produced by a variety of known processes including, for example, hybridoma, phage display, and genetic engineering techniques.

In the hybridoma technique, an animal, in particular rat or mouse, is immunized with an immunogen, and B cells are collected from its spleen or lymph node and are then fused with immortalized cells, e.g., myeloma cells, to form hybridoma cells. The hybridoma cells are screened to identify the hybridoma that produces an antibody having the desired binding ability, and the desired antibody can be produced with the screened hybridoma. A human antibody can be obtained from a transgenic mouse induced with a gene for the human antibody. The monoclonal antibody of interest is obtained from the hybridoma cells by, for example, culturing the hybridoma cells in accordance with an ordinary method and then collecting the culture supernatant; or administering the hybridoma cells to a mammal which is compatible with the hybridoma cells for proliferation, and then collecting the ascitic fluid. The former method is suitable for production of antibodies at high purity, and the latter method is suitable for large-scale production of antibodies. Monoclonal antibodies can be prepared by any known technique, for example, in accordance with the description in Current Protocols in Immunology, Wiley and Sons Inc., Chapter 2.

In the phage display technique, phages selected from any phage antibody library are screened using an immunogen of interest to select the phages that have desired binding ability to the immunogen. The sequence contained in the selected phages and corresponding to the antibody is then isolated or determined, and an expression vector including a nucleic acid molecule that encodes a monoclonal antibody is constructed based on the isolated sequence or determined sequence information. The expression vector is then transfected into a cell line and the cell line is cultured to produce the monoclonal antibody. A human antibody with desired binding ability can be produced with a human antibody library as the phage antibody library.

In genetic engineering techniques, a recombinant antibody can be prepared by introducing a mutation in a sequence corresponding to complementarity-determining regions (CDR) or any other sequence within the gene sequence which encodes the antibody, incorporating the resulting sequence into an expression vector, and then transforming the expresion vector into a host cell (see, for example, Borrebaeck C. A. K. and Larrick J. W. THERAPEUTIC MONOCLONAL ANTIBODIES, Published in the United Kingdom by MACMILLAN PUBLISHERS LTD, 1990).

In the present invention, chimeric antibodies, humanized antibodies, multispecific antibodies, and artificial antibody mimetics can also be used, for example, for the purpose of reducing xenoantigenicity to human or adding other function. Such antibodies can be produced by any known method.

A chimeric antibody can be produced by ligating a DNA which encodes variable regions of a non-human antibody to a DNA which encodes constant regions of a human antibody, incorporating the resulting DNA into an expression vector, which is then transformed into a host cell for expression of the antibody of interest (see EP 125023 and WO 92/19759). Chimeric antibodies useful for the present invention can be produced by such a known technique.

A humanized antibody can be produced by ligating a DNA which encodes complementarity-determining regions (CDR) of a non-human antibody to a DNA which encodes the remaining regions of a human antibody, and incorporating the resulting DNA into an expression vector, which is then transformed into a host cell for expression of the antibody of interest.

A multispecific antibody refers to an asymmetric antibody that has two or more independent antigen recognition sites and have specificity for two or more different antigens. A multispecific antibody such as bispecific antibody can be produced by any genetic engineering technique based on antigen-binding regions of two or more monoclonal antibodies. Such genetic engineering techniques have already been established in the art. For example, a desired bispecific antibody can be obtained by linking antigen-binding regions of two different monoclonal antibodies in tandem in accordance with the DVD-Ig method (Wu et al., Nature Biotechnology 25(11), 1290(2007)), or by modifying Fc region of an antibody to combine heavy chains of two different antibodies that are capable of binding to different antigens in accordance with the ART-Ig method (Kitazawa et al., Nature Medicine 18(10), 1570(2012)).

"Artificial antibody" refers to, for example, protein scaffolds, which do not have a structure of an antibody, but have a function like an antibody. Examples of the applicable protein scaffolds include Kunitz domains of human serine protease inhibitors; extracellular domains of human fibronectin; ankyrin; and lipocalin. A protein scaffold that is capable of binding to the epitope of the present invention can be produced by modifying the sequence of the target-biding site on the scaffold (PTL 4; Clifford Mintz et. al BioProcess International, 2013, Vol. 11(2), pp. 40-48).

The monoclonal antibody of the present invention may be modified in its amino acid sequence or sugar chain structure in Fc regions to regulate its functions or properties, except for the antigen-binding function, such as cytotoxic function, complement activation function, and half-life in blood (Strobl, Current Opinion in Biotechnology, 2009, vol. 20, p. 685). Such a functionally modified antibody can be prepared, for example, by a method described below. A monoclonal antibody produced in CHO host cells knocked out for the α1,6-fucosyltransferase (FUT8) gene has a decreased fucose content on the sugar chains, resulting in increased cytotoxic function, while an antibody produced in CHO host cells transfected with the FUT 8 gene has low cytotoxic function (WO 2005/035586, WO 2002/31140, and WO 00/61739). The complement activation function of the antibody can be regulated by modification of its Fc region via change in amino acid residues (U.S. Pat. Nos. 6,737,056, 7,297,775, and 7,317,091). The half-life in blood of the antibody can be prolonged with an Fc region variant having increased binding ability to FcRn, one of Fc receptors (Shuhei Hashiguchi et al., SEIKAGAKU (The Journal of Biochemistry), 2010, Vol. 82(8), p. 710). Such functionally-modified antibodies can be produced by genetic engineering techniques.

The monoclonal antibody used in the present invention may be a conjugated antibody produced by binding an antibody to any of various molecules, such as non-peptidic polymers, e.g., poly(ethylene glycol) (PEG); radioactive materials; and toxins. Such a conjugated antibody can be produced through chemical modification of the obtained antibody. Methods for chemical modification have already been established in the art. Such conjugated antibodies are also encompassed in the monoclonal antibody of the present invention (D. J. King., Applications and Engineering of Monoclonal antibodies., 1998 T. J. International Ltd, Monoclonal Antibody-Based Therapy of Cancer., 1998 Marcel Dekker Inc; Chari et al., Cancer Res., 1992 Vol. 152:127; Liu et al., Proc Natl Acad Sci USA., 1996 Vol 93:8681).

According to the present invention, in addition to the full-length antibodies described above, the antibody also encompasses fragments of monoclonal antibodies and any modified forms thereof, as long as they have binding ability to an epitope of interest and exerts antagonistic activity. Examples of the antibody fragment include Fab fragments, Fv fragments, F(ab')$_2$ fragments, Fab' fragments, and single-chain Fv (scFv) fragments, which contain the Fv regions of the H and L chains connected via a suitable linker. These antibody fragments may be bound to non-antibody functional molecules, such as non-peptidic polymers, e.g., poly(ethylene glycol) (PEG); radioactive materials; toxins; low-molecular-weight compounds; cytokines; albumin; and enzymes.

The production system for preparing monoclonal antibodies may be any of in vitro and in vivo production systems. The in vitro production system includes the production system using eukaryotic cells, e.g., animal cells, plant cells, or fungal cells; and the production system using prokaryotic cells, e.g., bacterial cells such as *Escherichia coli* and *Bacillus subtilis*. Applicable cells include animal cells, in particular mammalian cells, e.g., generally used cells, such as CHO, COS, myeloma, BHK, HeLa, and Vero cells; insect cells; and plant cells. In vivo production system includes production systems in animals or plants. Examples of the production system in animals include those in mammals and insects. Examples of applicable mammals include goats, porcines, ovines, mice, and bovines (Vicki Glaser, SPECTRUM Biotechnology Applications, 1993). Examples of applicable insects include silkworms. Examples of applicable plants include tobacco.

If the monoclonal antibody is produced in an in vitro or in vivo production system as described above, the DNA encoding the heavy chain (H chain) and the DNA encoding the light chain (L chain) may be incorporated into separate expression vectors to co-transform the host, or may be incorporated together into a single expression vector to transform the host (see WO 94/11523).

The monoclonal antibody thus produced can be purified to homogeneity. The monoclonal antibodies can be separated and purified by any method ordinarily used for separation and purification of proteins. For example, the monoclonal antibodies can be separated and purified by appropriately selecting or combining methods and instruments including, but not limited to, chromatographic columns for affinity chromatography, filtration, ultrafiltration, salt precipitation, dialysis, SDS-polyacrylamide gel electrophoresis, and isoelectric focusing (Antibodies: A Laboratory Manual. Ed Harlow and David Lane, Cold Spring Harbor Laboratory, 1988). Columns used in affinity chromatography include protein A columns and protein G columns. Examples of the protein A column include the Hyper D, POROS, and Sepharose F. F. columns (Amersham Biosciences).

The monoclonal antibody that is capable of binding to an epitope consisting of a continuous amino acid sequence included in positions 101 to 154 or 199 to 270 of SEQ ID NO:226 in the Sequence Listing is preferably a chimeric antibody, humanized antibody, or human antibody, most preferably a human antibody, in view of the low antigenicity it may exhibit when it is administered to a human. Among human antibodies, those wherein the amino acid sequences of the framework regions correspond to amino acid sequences of framework regions from a human germline or a combination of amino acid sequences thereof are preferred. Thus, the present invention relates to a human anti-IL-33 neutralizing monoclonal antibody wherein the amino acid sequences of the framework regions correspond to amino acid sequences of framework regions from a human germline or a combination of amino acid sequences thereof.

Since the framework regions of variable region of such a human anti-IL-33 neutralizing monoclonal antibody comprise amino acid sequences of the human germline framework regions or a combination of amino acid sequences thereof, such a human anti-IL-33 neutralizing monoclonal antibody is characterized by no or significantly low immunogenicity caused by these regions, and also by being capable of binding to IL-33 to inhibit its functions. Thus, when the antibody is used as a pharmaceutical, it is unlikely to induce human anti-human immunoglobulin antibody (HAHA), so that it can avoid clearance in vivo. As a result, the antibody of the invention can attain a prolonged IL-33 neutralizing effect, and is safe because it does not cause inflammation induced by binding with HAHA.

The amino acid sequences of the human germline light-chain and heavy-chain framework regions maybe any amino acid sequence of human germline framework region. Examples of applicable sequence include amino acid sequences encoded by the DNA sequences of heavy-chain and light-chain framework regions of human antibody as registered in the database such as NCBI database (http://www.ncbi.nlm.nih.gov/igblast/showGermline.cgi), and the amino acid sequences of germline framework regions as shown in Table 4. The light-chain variable region may be either a λ chain variable region or κ chain variable region. The light-chain and heavy-chain framework regions of human germline are preferably those which frequently emerge in vivo and are often used. Examples of such a human heavy-chain framework region include the framework regions 1, 2, and 3 of the VH3-23, VH3-30, VH4-39, and VH4-34 germlines and the framework region 4 of the JH4 germline. Examples of human light-chain framework regions which frequently emerge in vivo include the framework regions 1, 2, and 3 of Vλ1-47, Vλ2-14, Vκ3-20, and Vκ1-39 germlines, and the framework region 4 of Jλ2 germline. The heavy-chain framework regions may be composed of any combination of any human heavy-chain framework regions. For example, the framework regions 1 and 2 of VH3-23 germline and the framework region 3 of VH3-30 germline can be selected and used in combination as heavy-chain framework regions. The light-chain framework regions may also be composed of any combination of any human light-chain framework regions.

Preferred amino acid sequences of framework regions of germline in the present invention are those of the framework regions of the VH3-23, VH3-30, JH4, Vλ1-47, and Jλ2 germlines. Specifically, the framework regions preferably have the following amino acid sequences: the amino acid sequence of the light-chain framework region 1 is residues 1 to 22 of SEQ ID NO:317 in the Sequence Listing; the amino acid sequence of the light-chain framework region 2 is residues 36 to 50 of SEQ ID NO:317 in the Sequence Listing; the amino acid sequence of the light-chain framework region 3 is residues 58 to 89 of SEQ ID NO:317 in the Sequence Listing; the amino acid sequence of the light-chain framework region 4 is residues 3 to 12 of SEQ ID NO:401 in the Sequence Listing; the amino acid sequence of the heavy-chain framework region 1 is residues 1 to 30 of SEQ ID NO:367 or residues 1 to 30 of SEQ ID NO:368 in the Sequence Listing; the amino acid sequence of the heavy-chain framework region 2 is residues 36 to 49 of SEQ ID NO:367 or residues 36 to 49 of SEQ ID NO:368 in the Sequence Listing; the amino acid sequence of the heavy-chain framework region 3 is residues 67 to 98 of SEQ ID NO:367 or residues 67 to 98 of SEQ ID NO:368 in the Sequence Listing; and the amino acid sequence of the heavy-chain framework region 4 is residues 5 to 15 of SEQ ID NO:407 in the Sequence Listing. More preferably, the framework regions have the following amino acid sequences: the amino acid sequence of the light-chain framework region 1 is residues 1 to 22 of SEQ ID NO:317 in the Sequence Listing; the amino acid sequence of the light-chain framework region 2 is residues 36 to 50 of SEQ ID NO:317 in the Sequence Listing; the amino acid sequence of the light-chain framework region 3 is residues 58 to 89 of SEQ ID NO:317 in the Sequence Listing; the amino acid sequence of the light-chain framework region 4 is residues 3 to 12 of SEQ ID NO:401 in the Sequence Listing; the amino acid sequence of the heavy-chain framework region 1 is residues 1 to 30 of SEQ ID NO:367 in the Sequence Listing; the amino acid sequence of the heavy-chain framework region 2 is residues 36 to 49 of SEQ ID NO:367 in the Sequence Listing; the amino acid sequence of the heavy-chain framework region 3 is residues 67 to 98 of SEQ ID NO:368 in the Sequence Listing; and the amino acid sequence of the heavy-chain framework region 4 is residues 5 to 15 of SEQ ID NO:407 in the Sequence Listing.

In another embodiment, the present invention relates to an isolated human anti-IL-33 neutralizing monoclonal antibody, wherein the amino acid sequences of a light-chain complementarity-determining region 1 (LCDR1), a light-chain complementarity-determining region 2 (LCDR2), a light-chain complementarity-determining region 3 (LCDR3), a heavy-chain complementarity-determining region 1 (HCDR1), a heavy-chain complementarity-determining region 2 (HCDR2), and a heavy-chain complementarity-determining region 3 (HCDR3) correspond to the combination of amino acid sequences of complementarity-determining regions represented by C1 to C30 in Table 1.

In a preferred embodiment, the human anti-IL-33 neutralizing monoclonal antibody having the combination of complementarity-determining regions represented by C1 to C30 shown in Table 1 has binding ability and neutralizing activity, in particular to mature IL-33 that is capable of binding to an IL-33 receptor to exert activity, e.g., IL-33 (residues 95 to 270), IL-33 (residues 99 to 270), IL-33 (residues 109 to 270), and IL-33 (residues 112 to 270), among IL-33. More preferably, the human anti-IL-33 neutralizing monoclonal antibody having the combination of the complementarity-determining regions represented by C1 to C30 shown in Table 1 has a binding ability to IL-33 (residues 131 to 150).

In a preferred embodiment of the present invention, the combination of amino acid sequences of the complementarity-determining regions provides improved binding ability and/or physical properties of the antibody. In a particularly preferred embodiment, the upper limit of the dissociation rate constant (koff) against human IL-33 is about $3.5 \times 10^{-5}$/sec or lower, more preferably about $2.0 \times 10^{-5}$/sec or lower, more preferably $1.5 \times 10^{-5}$/sec or lower, yet more preferably about $1.0 \times 10^{-5}$/sec or lower, and the lower limit of the dissociation rate constant is, but not limited to, $10^{-7}$/sec or higher, more preferably $10^{-6}$/sec or higher, more preferably about $5 \times 10^{-6}$/sec or higher.

Among human anti-IL-33 neutralizing antibodies, more preferred are those which have a low dissociation constant (Kd) against human IL-33. The upper limit of the dissociation constant (Kd) is $10^{-9}$ M or lower, more preferably $10^{-10}$ M or lower, yet more preferably $10^{-12}$ M or lower, for example. The lower limit of the dissociation rate constant is, but not limited to, preferably $10^{-14}$ M or higher, more preferably $10^{-13}$ or higher.

The human anti-IL-33 neutralizing monoclonal antibody of the present invention inhibits IL-6 production from HUVEC stimulated with IL-33. In particular, antibodies with higher inhibitory effect are more preferred. Specifically, in a preferred embodiment of the present invention, the human anti-IL-33 neutralizing monoclonal antibody, which attains about 50% or higher, more preferably about 70% or higher, yet more preferably about 90% or higher rate (inhibiting rate) of inhibiting IL-6 production from HUVEC which is stimulated with 100 ng/mL of IL-33 as described below in Example 10, is preferred.

The human anti-IL-33 neutralizing monoclonal antibody of the present invention inhibits production of IL-5, IL-6, and/or IL-13 by KU-812 cells stimulated with IL-33. In particular, antibodies with higher inhibitory effect are more preferred. Specifically, in a preferred embodiment of the present invention, the human anti-IL-33 neutralizing monoclonal antibody which attains the about 30% or higher, more preferably about 50% or higher, yet more preferably about 70% or higher rate (inhibiting rate) of inhibiting production of IL-5, IL-6, and/or IL-13 by KU-812 cells stimulated with 100 ng/mL of IL-33, as described below in Example 11, is preferred.

The human anti-IL-33 neutralizing monoclonal antibody of the present invention inhibits IFN-γ production by human peripheral blood mononuclear cells stimulated with IL-33. In particular, antibodies with higher inhibitory effect are more preferred. Specifically, in a preferred embodiment of the present invention, the human anti-IL-33 neutralizing monoclonal antibody which attains about 80% or higher, more preferably about 90% or higher, yet more preferably about 95% or higher rate of inhibiting IFN-γ production by human peripheral blood mononuclear cells stimulated with 10 ng/mL of IL-33, as described below in Example 12, is preferred.

The human anti-IL-33 neutralizing monoclonal antibody of the present invention inhibits inflammation induced by administration of human IL-33 to a mouse. In particular, antibodies with higher anti-inflammatory effect are more preferred. Specifically, in a preferred embodiment of the present invention, daily intraperitoneal administration of 10 mg/kg of the human anti-IL-33 neutralizing monoclonal antibody for seven days, which attains the rate of inhibiting increases in spleen weight, serum IgA concentration, serum IgE concentration, blood neutrophil count, blood basophil count, blood eosinophil count, and/or serum IL-5 concentration, induced by continuous administration of human IL-33 for seven days at an amount of 0.4 μg/individual, of about 30% or higher, more preferably about 50% or higher, yet more preferably about 80% or higher, as described below in Example 13, is preferred.

The human anti-IL-33 neutralizing monoclonal antibody of the present invention preferably has excellent physical properties. In particular, the human anti-IL-33 neutralizing monoclonal antibody preferably does not show bimodal particle size distribution and exhibits significantly low aggregation property in evaluation by dynamic light scattering. The human anti-IL-33 neutralizing monoclonal antibody of the invention preferably has high interaction parameter (kD), which is an indicator of colloidal stability. For example, the interaction parameter is preferably −12.4 mL/g or higher, more preferably −10 mL/g or higher, yet more preferably −8.5 mL/g or higher.

The human anti-IL-33 neutralizing monoclonal antibody of the present invention preferably has an excellent thermodynamic stability. For example, a preferred antibody exhibits thermodynamic stability such that the folded state of the immunoglobulin domain disappears at a temperature (Tm) of 65° C. or higher, preferably 68° C. or higher, more preferably 70° C. or higher, yet more preferably 73° C. or higher.

The human anti-IL-33 neutralizing monoclonal antibody of the present invention preferably has high antibody stability. The antibody stability can be measured by any common method, e.g., preservation stability test or forced oxidation test. In a preferred embodiment of the present invention, the antibody molecules have a monomer ratio of 90% or higher, more preferably 95% or higher, and have binding activity to the human IL-33 protein of 95% or higher, more preferably 99% or higher, after the preservation stability test at a temperature of 40° C. for four weeks, as described below in Example 21.

As described in Example 22, the human anti-IL-33 neutralizing monoclonal antibody of the present invention preferably has a binding activity of 80% or higher, more preferably 85% or higher, yet more preferably 90% or higher to the human IL-33 protein, after forced oxidation with 1% hydrogen peroxide solution at a temperature of 37° C. for 24 hours.

In view of the foregoing points, the human anti-IL-33 neutralizing monoclonal antibody selected from the combination of complementarity-determining regions represented by C1 to C28 in Table 1 is a preferred antibody. A more preferred embodiment of the present invention is a human anti-IL-33 neutralizing monoclonal antibody having complementarity-determining regions that respectively have amino acid sequences in accordance with a specific combination (C1, C8, C15, C17, or C18 in Table 1).

The human anti-IL-33 neutralizing monoclonal antibody identified by the combination of the amino acid sequences of the respective complementarity-determining regions may have any amino acid sequences of any framework regions in the variable regions, as long as the antigen-binding ability is assured. The respective amino acid sequences of framework regions preferably are amino acid sequences of framework regions from a human germline or a combination of amino acid sequences thereof. The amino acid sequences of framework regions of any germline that is used frequently in vivo in human are more preferred.

In the present invention, the amino acid sequences of the framework regions preferably have the following amino acid sequences: the amino acid sequence of the light-chain framework region 1 is residues 1 to 22 of SEQ ID NO:317 in the Sequence Listing; the amino acid sequence of the light-chain framework region 2 is residues 36 to 50 of SEQ ID NO:317 in the Sequence Listing; the amino acid sequence of the light-chain framework region 3 is residues 58 to 89 of SEQ ID NO:317 in the Sequence Listing; the amino acid sequence of the light-chain framework region 4 is residues 3 to 12 of SEQ ID NO:401 in the Sequence Listing; the amino acid sequence of the heavy-chain framework region 1 is residues 1 to 30 of SEQ ID NO:367 or residues 1 to 30 of SEQ ID NO:368 in the Sequence Listing; the amino acid sequence of the heavy-chain framework region 2 is residues 36 to 49 of SEQ ID NO:367 or residues 36 to 49 of SEQ ID NO:368 in the Sequence Listing; the amino acid sequence of the heavy-chain framework region 3 is residues 67 to 98 of SEQ ID NO:367 or residues 67 to 98 of SEQ ID NO:368 in the Sequence Listing; and the amino acid sequence of the heavy-chain framework region 4 is residues 5 to 15 of SEQ ID NO:407 in the Sequence Listing. More preferably, the framework regions have the following amino acid sequences: the amino acid sequence of the light-chain framework region 1 is residues 1 to 22 of SEQ ID NO:317 in the Sequence Listing; the amino acid sequence of the light-chain framework region 2 is residues 36 to 50 of SEQ ID NO:317 in the Sequence Listing; the amino acid sequence of the light-chain framework region 3 is residues 58 to 89 of SEQ ID NO:317 in the Sequence Listing; the amino acid sequence of the light-chain framework region 4 is residues 3 to 12 of SEQ ID NO:401 in the Sequence Listing; the amino acid sequence of the heavy-chain framework region 1 is residues 1 to 30 of SEQ ID NO:367 in the Sequence Listing; the amino acid sequence of the heavy-chain framework region 2 is residues 36 to 49 of SEQ ID NO:367 in the Sequence Listing; the amino acid sequence of the heavy-chain framework region 3 is residues 67 to 98 of SEQ ID NO:368 in the Sequence Listing; and the amino acid sequence of the heavy-chain framework region 4 is residues 5 to 15 of SEQ ID NO:407 in the Sequence Listing.

Examples of the preferred combinations of the amino acid sequences of the heavy-chain variable regions and the light-chain variable regions in the present invention are shown in Table 2.

A preferred embodiment of the present invention is a human anti-IL-33 neutralizing monoclonal antibody comprising variable regions that respectively have amino acid sequences in accordance with any one of combinations V1 to V28 shown in Table 2.

A more preferred embodiment of the present invention is a human anti-IL-33 neutralizing monoclonal antibody comprising complementarity-determining regions that respectively have amino acid sequences in accordance with a specific combination (V1, V8, V15, V17, or V18 in Table 2).

Depending on the difference in the heavy chain constant regions, human immunoglobulin molecules are categorized into IgG (including IgG1, IgG2, IgG3, and IgG4) having γ heavy chains; IgM having μ heavy chains; IgA (including IgA1 and IgA2) having α heavy chains; IgD having δ heavy chains; and IgE having ε heavy chains. All these types are encompassed in the constant regions of the human anti-IL-33 neutralizing monoclonal antibody of the present invention. Light chains are categorized into κ and λ light chains that differ in the position on chromosome. The light chain in the present invention encompasses both of the two light chains. In production of an antibody pharmaceutical, an antibody having κ light chains is preferred from the perspective of aggregation, but an antibody having λ light chains is also useful, because the λ light chains have a different amino acid sequence from that of the κ chains and have similar diversity to the κ chains. The human anti-IL-33 neutralizing monoclonal antibody of the present invention is preferably IgG having λ light chains and γ heavy chains, more preferably IgG1 having λ light chains and γ1 light chains, from the perspective of the stability in blood.

Since the amino acid sequence of IL-33 is different among animal species, the amino acid sequence of human IL-33 shown in SEQ ID NO:226 in the Sequence Listing is different from that of monkey IL-33 shown in SEQ ID NO:227 in the Sequence Listing. In general, since monkeys are used as experimental animals in pharmacological tests or safety tests of antibody pharmaceuticals, the human anti-IL-33 neutralizing monoclonal antibody of the present invention is preferably further capable of binding to monkey IL-33, and more preferably capable of binding to monkey IL-33 with a binding affinity similar to that with a human IL-33. In a particularly preferred embodiment, the ratio of the koff against human IL-33 versus the koff against monkey IL-33 is within about 20-fold, more preferably within about 10-fold, yet more preferably within about five-fold.

Illustrative examples of the antibody fragment of the present invention include Fab fragments, Fv fragments, F(ab')$_2$ fragments, Fab' fragments, and scFv fragments. These antibody fragments may be bound to non-antibody functional moleculessuch asnon-peptidic polymers, e.g., poly(ethylene glycol) (PEG); radioactive materials; toxins; low-molecular-weight compounds; cytokines; albumin; and enzymes.

The human anti-IL-33 neutralizing monoclonal antibody of the present invention may be bound to an antibody having binding specificity for an antigen other than IL-33, to produce a multispecific antibody such as bispecific antibody. Non-limiting examples of the antigen other than IL-33 include TNF-α, IL-6 receptors, CD3, CD20, α4 integrin, BLys, Thymic Stromal Lymphopoietin, IgE, IL-1, IL-2, IL-4, IL-5, IL-6, IL-13, IL-17, IL-23, and IL-25.

The human anti-IL-33 neutralizing monoclonal antibody and fragments thereof of the present invention may be modified in its amino acid sequence or sugar chain structure in Fc regions, to produce a functionally modified antibody having regulated functions or properties, such as cytotoxic function, complement activation function, and half-life in blood (Kenya Shitara, Journal of the Pharmaceutical Society of Japan, 2009, Vol. 129(1), p. 3; Akiko Ishii et al., Folia Pharmacologica Japonica, 2010, Vol. 136(5), p. 280; Shuhei Hashiguchi et al., SEIKAGAKU (The Journal of Biochemistry), 2010, Vol. 82(8), p. 710; Strohl, Current Opinion in Biotechnology, 2009, vol. 20, p. 685).

The human anti-IL-33 neutralizing monoclonal antibody and antibody fragments thereof in the present invention may be bound to other functional molecule to form a conjugated antibody. For example, novel function can be added by binding a functional molecule, such as non-peptidic polymer, e.g., poly(ethylene glycol) (PEG); radioactive materials; toxins; low-molecular-weight compounds; albumin; cytokines; and enzymes to the antibody.

Other embodiments of the present invention relate to a nucleic acid molecule encoding a protein portion of a human anti-IL-33 neutralizing monoclonal antibody comprising framework regions that have amino acid sequences from germline(s); a vector including the nucleic acid molecule; a host cell including the vector; and a method for production of a human anti-IL-33 neutralizing monoclonal antibody including culturing the host cell.

In a yet another embodiment, the present invention relates to a composition comprising the human anti-IL-33 neutralizing monoclonal antibody described above. Since IL-33 induces inflammation and the like, the human anti-IL-33 neutralizing monoclonal antibody is expected to be applicable to diagnosis, treatment, prevention, or alleviation of a disease associated with IL-33.

Accordingly, in one embodiment, the invention relates to a pharmaceutical composition comprising the human anti-IL-33 neutralizing monoclonal antibody for diagnosis, treatment, prevention, or alleviation of a disease associated with IL-33. In a yet another embodiment, since IL-33 induces cytokines, chemokines, and inflammatory mediators, the present invention relates to an expression inhibitor of the expression for cytokines, chemokines, or inflammatory mediators, comprising the human anti-IL-33 neutralizing monoclonal antibody.

The cytokine to be inhibited by the expression inhibitor for cytokines, chemokines, or inflammatory mediators according to the present invention is one of the IL-33-induced cytokines, including TNF-α, IFN-γ, IL-1β, IL-3, IL-4, IL-5, IL-6, and IL-13 etc. The chemokine to be inhibited with the inhibitor is one of IL-33-induced chemokines, including CXCL2, CCL2, CCL3, CCL6, CCL17, and CCL24, etc. The inflammatory mediator to be inhibited with the inhibitor is one of IL-33-induced inflammatory mediators, including PGD2 and LTB4 etc. A particularly preferred embodiment of the present invention is an expression inhibitor containing a human anti-IL-33 neutralizing monoclonal antibody to inhibit expression of IFN-γ, IL-5, IL-6, or IL-13. More preferably, the inhibitor is an IL-6 production inhibitor.

In another embodiment, the present invention relates to a pharmaceutical composition containing the monoclonal antibody of the present invention. The present invention also relates to a method for diagnosis, treatment, prevention, or alleviation of a disease associated with IL-33, the method comprising administering the monoclonal antibody of the invention; and to use of the monoclonal antibody of the invention for manufacture of a medicament for diagnosis, treatment, prevention, or alleviation of a disease associated with IL-33.

The disease associated with IL-33 include, but not limited to, asthma, atopic dermatitis, urticaria, pollinosis, anaphylactic shock, sinusitis (including eosinophilic sinusitis), allergic encephalomyelitis, hypereosinophilic syndrome, polymyalgia rheumatica, rheumatic heart diseases, multiple sclerosis, arthritis (for example, rheumatoid arthritis, juvenile arthritis, psoriatic arthritis, arthrosis deformans, and Reiter's syndrome), systemic lupus erythematosus (including discoid lupus), pemphigus, pemphigoid, psoriasis, ankylosing spondylitis, hepatitis (for example, autoimmune hepatitis and chronic active hepatitis), inflammatory bowel diseases (for example, ulcerative colitis, Crohn's disease, and gluten-sensitive enteropathy), Sjogren's syndrome, autoimmune hemolytic anemia, autoimmune inflammatory eye diseases, autoimmune neonatal thrombocytopenia, autoimmune neutropenia, autoimmune oophoritis and orchitis, autoimmune thrombocytopenia, autoimmune thyroiditis, multiple myositis, dermatomyositis, myasthenia gravis, adrenergic agonist resistance, alopecia areata (alopecia greata), antiphospholipid syndrome, adrenal autoimmune diseases (for example, autoimmune Addison's disease), celiac sprue-dermatitis, chronic fatigue and immune dysfunction syndrome (CFIDS), cold agglutinin disease, essential mixed cryoglobulinemia, fibromyalgia-fibromyositis, glomerulonephritis (for example, IgA nephropathy), Graves' disease, hyperthyroidism (that is, Hashimoto's thyroiditis), idiopathic thrombocytopenic purpura (ITP), mixed connective tissue disease, Type 1 or immune-mediated diabetes mellitus, pernicious anemia, polychondritis, polyglandular syndrome, stiff-man syndrome, vitiligo, sarcoidosis, polyendocrinopathy, other endocrinopathy, arteriosclerosis, hepatic fibrosis (for example, primary biliary cirrhosis), pulmonary fibrosis (for example, idiopathic pulmonary fibrosis), chronic obstructive pulmonary disease (COPD), scleroderma (including CREST syndrome and Raynaud's phenomenon), tubulointerstitial nephritis, dense deposit disease, acute kidney injury, myocarditis, cardiomyopathy, neuritis (for example, Guillain-Barre syndrome), polyarteritis nodosa, cardiotomy syndrome, chronic inflammatory demyelinating polyneuropathy, IgA neuropathy, lichen planus, Meniere's disease, post-myocardial infarction (post-MI) syndrome, uveitis, uveitis ophthalmia, vasculitis, primary agammaglobulinemia, cancer (for example, brain tumor, laryngeal cancer, lip and oral cancer, hypopharyngeal cancer, thyroid cancer, esophageal cancer, breast cancer, lung cancer, gastric cancer, adrenocortical carcinoma, cancer of the bile duct, gallbladder cancer, liver cancer, pancreatic cancer, bladder cancer, colon cancer, uterine cancer, ovarian cancer, prostate cancer, testicular cancer, chronic lymphocytic leukemia, chronic myelogenous leukemia, Ewing's tumor, Hodgkin's disease, non-Hodgkin lymphoma, melanoma, mesothelioma, and multiple myeloma), infections resistant to clearance by the immune system (for example, severe acute respiratory syndrome (SARS)), lethal cytokine storm associated with virulent influenza infection, and sepsis. The disease associated with IL-33 is preferably asthma, atopic dermatitis, pollinosis, anaphylactic shock, sinusitis (including eosinophilic sinusitis), Crohn's disease, ulcerative colitis, arthritis, systemic lupus erythematosus, pemphigus, pemphigoid, scleroderma, ankylosing spondylitis, hepatic fibrosis (including primary biliary cirrhosis), pulmonary fibrosis, chronic obstructive pulmonary disease (COPD), acute kidney injury, vasculitis, and cancer.

A pharmaceutical composition comprising the human anti-IL-33 neutralizing monoclonal antibody of the present invention may further contain a pharmacologically acceptable carrier, diluent, or excipient, in addition to the human anti-IL-33 neutralizing monoclonal antibody or a salt thereof as the active ingredient. The pharmaceutical composition may further contain an additional active ingredient other than the human anti-IL-33 neutralizing monoclonal antibody of the present invention, for example, an anti-inflammatory agent or immunosuppressive agent. Such a composition is provided in a dosage form suitable for parenteral or oral administration. From the perspective of the use as an antibody pharmaceutical, parenteral administration is preferred. Examples of the parenteral administration include, but are not limited to, intravenous, intraarterial, subcutaneous, topical, intraperitoneal, intramuscular, nasal, ophthalmic, transdermal, transmucosal, intrathecal, rectal, intramuscular, and intracerebral administration.

The pharmaceutical composition may be provided in any dosage form depending on the administration route. Examples of the dosage form include injection, powder, infusion, granule, tablet, and suppository. From the perspective of parenteral administration, the dosage form is preferably injection, infusion, or powder to be dissolved before use. These preparations may further contain any of various adjuvants used in pharmaceuticals. Specific examples of the adjuvant include carriers and other additives, such as stabilizer, preservative, analgesic, and emulsifier.

The human anti-IL-33 neutralizing monoclonal antibody of the present invention may be provided by continuous infusion at intervals of, for example, once per day, week, or month, or one to seven times per year, or by dosing. The dosing may be provided by intravenous, subcutaneous, topical, oral, nasal, rectal, intramuscular, or intraventricular administration, or by inhalation. A preferred dose protocol involves the maximum dose or administration frequency to avoid serious adverse side effects. The total weekly dose is generally at least about 0.05 µg/kg (body weight), more generally at least about 0.2 µg/kg, most generally at least about 0.5 µg/kg, typically at least about 1 µg/kg, more typically at least about 10 µg/kg, most typically at least about 100 µg/kg, preferably at least about 0.2 mg/kg, more preferably at least about 1.0 mg/kg, most preferably at least about 2.0 mg/kg, optimally at least about 10 mg/kg, more optimally at least about 25 mg/kg, most optimally at least about 50 mg/kg.

The human anti-IL-33 neutralizing monoclonal antibody of the present invention is useful in, for example, a diagnostic assay for detection of IL-33 expression in specific cells or tissues, or in blood serum, of a patient with a disease associated with IL-33. For diagnostic application, typically, the human anti-IL-33 neutralizing monoclonal antibody is preferably a conjugated antibody labeled with a detectable moiety.

In another embodiment, the present invention relates to an anti-IL-33 neutralizing monoclonal antibody which competes in binding to IL-33 with an anti-IL-33 neutralizing monoclonal antibody comprising amino acid sequences in accordance with a combination of specific complementarity-determining regions amino acid sequences (C1, C8, C15, C17, or C18 in Table 1) or in accordance with a combination of specific variable region amino acid sequences (V1, V8, V15, V17, or V18 in Table 2).

The anti-IL-33 neutralizing monoclonal antibody which competes in binding to IL-33 with an anti-IL-33 neutralizing monoclonal antibody comprising amino acid sequences in accordance with a combination of specific complementarity-determining regions amino acid sequences or in accordance with a combination of specific variable regions amino acid sequences can be obtained as follows: anti-IL-33 antibodies are produced by a genetic engineering technique, e.g., phage display, or the hybridoma technique; and the produced anti-IL-33 antibodies are screened by the surface plasmon resonance (SPR) technique as described below, for example.

Biotinylated human IL-33 protein (4 µg/mL) as ligand is loaded on an avidin-immobilized sensor chip to be immobilized thereon at an amount equivalent to 1300 to 1600 RU. Any anti-IL-33 antibody (15 µg/mL) is then loaded as an analyte thereon, so as to bind to the human IL-33 protein immobilized on the sensor chip. The process is repeated for several times until all the human IL-33 protein molecules immobilized on the sensor chip is bound by the anti-IL-33 antibody (saturation). Then the binding level at saturation (saturation binding level 1) is determined.

The same experiment is carried out with a human anti-IL-33 neutralizing monoclonal antibody comprising complementarity-determining regions that respectively have amino acid sequences in accordance with a specific combination or a human anti-IL-33 neutralizing monoclonal antibody comprising variable regions that respectively have amino acid sequences in accordance with a specific combination according to the invention, and the binding level at saturation (saturation binding level 2) is determined.

After the saturation of the human IL-33 protein on the sensor chip with the human anti-IL-33 neutralizing monoclonal antibody comprising complementarity-determining regions that respectively have amino acid sequences in accordance with a specific combination or the human anti-IL-33 neutralizing monoclonal antibody comprising variable regions that respectively have amino acid sequences in accordance with a specific combination according to the invention, any anti-IL-33 antibody (15 µg/mL) is loaded as an analyte. It is confirmed whether the analyte exhibits additional binding with the human IL-33 protein that has been saturated with the human anti-IL-33 neutralizing monoclonal antibody comprising complementarity-determining regions that respectively have amino acid sequences in accordance with a specific combination or the human anti-IL-33 neutralizing monoclonal antibody comprising variable regions that respectively have amino acid sequences in accordance with a specific combination according to the invention.

If any anti-IL-33 antibody can exhibit additional binding with the human IL-33 protein that has been saturated with the human anti-IL-33 neutralizing monoclonal antibody comprising complementarity-determining regions that respectively have amino acid sequences in accordance with a specific combination or the human anti-IL-33 neutralizing monoclonal antibody comprising variable regions that respectively have amino acid sequences in accordance with a specific combination according to the invention, while maintaining its saturation binding level 1 calculated above, then the anti-IL-33 antibody is determined to be "not competitive." If the anti-IL-33 antibody cannot exhibit additional binding with the human IL-33 protein that has been saturated with the human anti-IL-33 neutralizing monoclonal antibody comprising complementarity-determining regions that respectively have amino acid sequences in accordance with a specific combination or the anti-IL-33 neutralizing monoclonal antibody comprising variable regions that respectively have amino acid sequences in accordance with a specific combination according to the invention, then the anti-IL-33 antibody is determined to be "competitive." If the anti-IL-33 antibody can exhibit additional binding with the human IL-33 protein that has been saturated with the human anti-IL-33 neutralizing monoclonal antibody comprising complementarity-determining regions that respectively have amino acid sequences in accordance with a specific combination or the anti-IL-33 neutralizing monoclonal antibody comprising variable regions that respectively have amino acid sequences in accordance with a specific combination according to the invention but the additional binding level is lower than the saturation binding level 1 with a significant difference, then the antibody is determined to be "competitive." The significant difference can be determined by a common statistical method (for example, Student's t-test). The level of significance is set to equal to or less than 5% or 1%.

The anti-IL-33 neutralizing monoclonal antibody which competes in binding to IL-33 with a human anti-IL-33 neutralizing monoclonal antibody comprising amino acid sequences in accordance with a combination of specific complementarity-determining regions amino acid sequences or in accordance with a combination of specific variable regions amino acid sequences may be an antibody from any animal, for example, mouse, human, rat, rabbit, goat, or camel, and may also be a chimeric antibody or humanized antibody produced by combining such antibodies.

The anti-IL-33 neutralizing monoclonal antibody which competes in binding to IL-33 with the human anti-IL-33 neutralizing monoclonal antibody comprising amino acid sequences in accordance with a combination of specific complementarity-determining regions amino acid sequences or in accordance with a combination of specific variable regions is preferably a chimeric antibody, humanized antibody, or human antibody, most preferably human antibody.

The anti-IL-33 neutralizing monoclonal antibody which competes in binding to IL-33 with the human anti-IL-33 neutralizing monoclonal antibody comprising amino acid sequences according to a combination of specific complementarity-determining regions amino acid sequences or a combination of specific variable regions amino acid sequence includes antibody fragments. Examples of the antibody fragment include Fab fragments, Fv fragments, F(ab')$_2$ fragments, Fab' fragments, and scFv fragments. Antibody fragments bound with PEG or the like are preferred.

The method for production of the anti-IL-33 neutralizing monoclonal antibody and the like of the present invention will be now described. The human anti-IL-33 neutralizing monoclonal antibody can be prepared through a genetic engineering technique, through incorporation of a DNA sequence which contains sequences encoding a desired combination of complementarity-determining regions and a combination of framework regions and encodes light-chain and heavy-chain variable regions into an expression vector; transformation of the expression vector into a host cell; and then culture of the host cell (see, for example, Borrebaeck C. A. K. and Larrick J. W. THERAPEUTIC MONOCLONAL ANTIBODIES, Published in the United Kingdom by MACMILLAN PUBLISHERS LTD, 1990). Alternatively, DNA sequences which respectively encode full-length heavy chain and full-length light chain can be produced through linkage of a DNA sequence encoding light-chain constant region to a DNA sequence encoding light-chain variable region and linkage of a DNA sequence encoding heavy-chain constant region to a DNA sequence encoding heavy-chain variable region. The combination of DNA sequences respectively encoding the full-length heavy chain and full-length light chain of a preferred human anti-IL-33 neutralizing antibody of the present invention include, for example, that of IgG1 having λ light chain as shown in Table 5. If the antibody is produced with an animal cell through a genetic engineering technique, the C-terminal lysine residue may be deleted. For this reason, the three nucleotides "aag" in the 3' terminus of the nucleic acid sequence of the heavy chain shown in Table 5 (SEQ ID NOS:254 to 277 in the Sequence Listing) may be deleted from each heavy-chain nucleic acid sequence.

TABLE 5

The following SEQ ID Nos. show the SEQ ID Nos. in the Sequence Listing

| Combination | Light Chain | Heavy Chain |
|---|---|---|
| IGN1 | SEQ ID No. 228 | SEQ ID No. 254 |
| IGN2 | SEQ ID No. 229 | SEQ ID No. 255 |
| IGN3 | SEQ ID No. 230 | SEQ ID No. 256 |
| IGN4 | SEQ ID No. 230 | SEQ ID No. 257 |
| IGN5 | SEQ ID No. 230 | SEQ ID No. 258 |
| IGN6 | SEQ ID No. 231 | SEQ ID No. 259 |
| IGN7 | SEQ ID No. 230 | SEQ ID No. 260 |
| IGN8 | SEQ ID No. 232 | SEQ ID No. 261 |
| IGN9 | SEQ ID No. 233 | SEQ ID No. 262 |
| IGN10 | SEQ ID No. 234 | SEQ ID No. 262 |
| IGN11 | SEQ ID No. 235 | SEQ ID No. 262 |
| IGN12 | SEQ ID No. 236 | SEQ ID No. 262 |
| IGN13 | SEQ ID No. 237 | SEQ ID No. 262 |
| IGN14 | SEQ ID No. 238 | SEQ ID No. 262 |
| IGN15 | SEQ ID No. 239 | SEQ ID No. 262 |
| IGN16 | SEQ ID No. 240 | SEQ ID No. 263 |
| IGN17 | SEQ ID No. 241 | SEQ ID No. 264 |
| IGN18 | SEQ ID No. 242 | SEQ ID No. 265 |
| IGN19 | SEQ ID No. 243 | SEQ ID No. 266 |
| IGN20 | SEQ ID No. 244 | SEQ ID No. 267 |
| IGN21 | SEQ ID No. 245 | SEQ ID No. 268 |
| IGN22 | SEQ ID No. 246 | SEQ ID No. 269 |
| IGN23 | SEQ ID No. 247 | SEQ ID No. 270 |
| IGN24 | SEQ ID No. 248 | SEQ ID No. 271 |
| IGN25 | SEQ ID No. 249 | SEQ ID No. 272 |
| IGN26 | SEQ ID No. 250 | SEQ ID No. 273 |
| IGN27 | SEQ ID No. 251 | SEQ ID No. 274 |
| IGN28 | SEQ ID No. 252 | SEQ ID No. 275 |
| IGN29 | SEQ ID No. 230 | SEQ ID No. 276 |
| IGN30 | SEQ ID No. 253 | SEQ ID No. 277 |

The production system for preparing antibodies may be any of in vitro production systems. Examples of the in vitro production system include eukaryotic cells, e.g., animal cells, plant cells, or fungal cells; and prokaryotic cells, e.g., bacterial cells such as *Escherichia coli* and *Bacillus subtilis*. Examples of the applicable animal cells include mammalian cells, e.g., generally used cells, such as CHO, COS, myeloma, BHK, HeLa, Vero, 293, NS0, Namalwa, and YB2/0 cells; and insect cells and plant cells can also be used. The 293 and CHO cells are preferred.

If the monoclonal antibody is produced in an in vitro production system as described above, the DNA encoding the heavy chain and the DNA encoding the light chain may be incorporated into separate expression vectors to co-transform the host, or may be incorporated together into a single expression vector to transform the host (see WO 94/11523). Examples of the preferred vector applicable to animal cells include, but are not limited to, pConPlus, pcDM8, pcDNA I/Amp, pcDNA3.1, and pREP4.

The antibody thus produced can be purified to homogeneity. The antibodies can be separated and purified by any ordinary method used for separation and purification of proteins. For example, the antibodies can be separated and purified by appropriately selecting or combining methods and instruments including, but not limited to, chromatographic columns for affinity chromatography, filtration, ultrafiltration, salt precipitation, dialysis, SDS-polyacrylamide gel electrophoresis, and isoelectric focusing (Antibodies: A Laboratory Manual. Ed Harlow and David Lane, Cold Spring Harbor Laboratory, 1988). Columns used in affinity chromatography include protein A columns and protein G columns. Examples of the protein A column include the Hyper D, POROS, and Sepharose F. F. columns (Amersham Biosciences).

The human anti-IL-33 neutralizing monoclonal antibody of the present invention can be bound to any antibody that have binding specificity for other antigen than IL-33 to produce a multispecific antibody, such as bispecific antibody. Several chemical methods of producing the bispecific antibody have been already known well (Nisonoff, A. et al., Archives of biochemistry and biophysics., 1961, Vol. 90, p. 460-462, Brennan, M. et al., Science, 1985, Vol. 299, pp. 81-83). In such methods, two different antibodies are each hydrolyzed with an enzyme, and then disulfide bonds in the heavy chains of the antibody are cleaved with a reducing agent, followed by mixing of the two heterologous antibodies and re-oxidization of the mixture. A bivalent antibody is thereby produced. Preparation of antibodies using a cross-linker, such as glutaraldehyde or carbodiimide, has also been recently disclosed (Japanese Patent Application Laid-Open Publication No. 2-1556). Several genetic engineering techniques for producing multispecific antibodies such as bispecific antibodies have already been established in the art. A desired bispecific antibody can be prepared by linking antigen-binding regions of two different monoclonal antibodies in tandem in accordance with a DVD-Ig method (Wu et al., Nature Biotechnology 25(11), 1290(2007)), or by modifying Fc region of an antibody to combine heavy chains of two different antibodies that are capable of binding to different antigens in accordance with the ART-Ig method (Kitazawa et al., Nature Medicine 18(10), 1570(2012)), for example.

A functionally modified form of the human anti-IL-33 neutralizing monoclonal antibody of the present invention or a conjugated antibody containing the antibody of the invention can be prepared by a method described below, for example. If the human anti-IL-33 neutralizing monoclonal antibody of the invention is produced in CHO host cells knocked out for the α1,6-fucosyltransferase (FUT8) gene, the antibody has a decreased fucose content on the sugar chains, resulting in an increased cytotoxic function, while an antibody produced in CHO host cells transfected with the FUT 8 gene has a low cytotoxic function (WO 2005/035586, WO 2002/31140, and WO 00/61739). The complement activation function of the antibody can be regulated by modification of its Fc region via a modification in amino acid residues (U.S. Pat. Nos. 6,737,056, 7,297,775, and 7,317,091). The half-life of the antibody in blood can be prolonged with an Fc region variant having increased binding ability to FcRn, one of Fc receptors (Shuhei Hashiguchi et al., SEIKAGAKU (The Journal of Biochemistry), 2010, Vol. 82(8), p. 710). Such functionally-modified antibodies can be produced by genetic engineering techniques.

The human anti-IL-33 neutralizing monoclonal antibody of the present invention can be bound to other functional molecules to produce a conjugated antibody. For example, if PEG is bound as a functional molecule to an antibody, non-limiting examples of the PEG include PEG with a molecular weight of 2000 to 100000 Da, more preferably 10000 to 50000 Da. The PEG may be either linear or branched. PEG can be bound to an N-terminal amino group of an amino acid in the antibody by using NHS active group. Examples of radioactive materials used as a functional molecule include $^{131}I$, $^{125}I$, $^{90}Yr$, $^{64}Cu$, $^{99}Tc$, $^{77}Lu$, $^{211}At$ and the like. Radioactive materials can be directly bound to the antibody by any method such as chloramine T method. Examples of toxins used as a functional molecule include bacterial toxins (for example, diphtheria toxin), phytotoxins (for example, ricin), low-molecular-weight toxins (for example, geldanamycin), maytansinoid, and calicheamicin. Examples of the low-molecular-weight compound used as a functional molecule include daunomycin, doxorubicin, methotrexate, mitomycin, neocarzonostatin, vindesine, and fluorescent dyes such as FITC. Examples of enzymes used as a functional molecule include luciferase (for example, firefly luciferase and bacterial luciferase; U.S. Pat. No. 4,737,456), malate dehydrogenase, urease, peroxidase (for example, horseradish peroxidase (HRPO)), alkaline phosphatase, β-galactosidase, glucoamylase, lysozyme, saccharide oxidase (for example, glucose oxidase, galactose oxidase, and glucose-6-phosphate dehydrogenase), heterocyclic oxidase (for example, uricase and xanthine oxidase), lactoperoxidase, and microperoxidase. Examples of the linker used in chemical binding of toxin, low-molecular weight compound or enzyme include divalent radicals (for example, alkylene, arylene, and heteroarylene), linkers represented by —$(CR_2)_nO(CR_2)_n$— (where R is any substituent group), repeating units of alkoxy (for example, polyethyleneoxy, PEG, and polymethyleneoxy), alkylamino (for example, polyethyleneamino and Jeffamine™), and diacid esters and amides (including succinates, succinamides, diglycollates, malonates, and capramides). Several methods for chemical modification to bind the functional molecule have been already established in the art (D. J. King., Applications and Engineering of Monoclonal antibodies., 1998 T. J. International Ltd, Monoclonal Antibody-Based Therapy of Cancer., 1998 Marcel Dekker Inc; Chari et al., Cancer Res., 1992 Vol. 152:127; Liu et al., Proc Natl Acad Sci USA., 1996 Vol. 93:8681).

The anti-IL-33 neutralizing monoclonal antibody which competes in binding to IL-33 with a human anti-IL-33 neutralizing monoclonal antibody comprising a combination of specific complementarity-determining regions amino acid sequences (C1, C8, C15, C17, or C18 in Table 1) or a combination of specific variable regions amino acid sequences (V1, V8, V15, V17, or V18 in Table 2) may be an antibody from any animal, for example, mouse antibody, human antibody, rat antibody, rabbit antibody, goat antibody, or camel antibody, and may also be a chimeric antibody or humanized antibody produced by combining such antibodies. Such anti-IL-33 neutralizing monoclonal antibodies can be produced by any known method including, for example, hybridoma technique, phage display technique, and genetic engineering techniques. In particular, the antibody is preferably produced by a genetic engineering method.

A chimeric antibody can be produced by ligating a DNA which encodes variable regions of a non-human antibody to a DNA which encodes constant regions of a human antibody, incorporating the resulting DNA into an expression vector, which is then transformed into a host cell for expression of the antibody of interest (see EP 125023 and WO 92/19759).

A humanized antibody can be produced by ligating a DNA which encodes complementarity-determining regions (CDR) of a non-human antibody to a DNA which encodes the remaining regions of a human antibody, and incorporating the resulting DNA into an expression vector, which is then transformed into a host cell A human antibody can be prepared through the process described in the Examples below. The human antibody can also be prepared by any technique such as trioma technique, human B CELLS hybridoma technique (Kozbor et al., 1983 Immunol Today 4: p. 72) and EBV hybridoma technique for producing a human monoclonal antibody (Cole et al., 1985, MONOCLONAL ANTIBODIES AND CANCER THERAPY, Alan R. Liss, Inc., p. 77). The human antibody may also be produced by immunizing a transgenic mouse introduced a human antibody gene with an antigen protein to produce a hybridoma. Examples of the transgenic mouse include HuMab (registered trademark) mouse (Medarex), KM™ mouse (Kirin Pharma), KM (FCγRIIb-KO) mouse, and VelocImmune mouse (Regeneron Pharmaceuticals, Inc.).

In another embodiment, the present invention relates to an artificial antibody which competes in binding to IL-33 with the anti-IL-33 neutralizing monoclonal antibody comprising amino acid sequences in accordance with a combination of a specific complementarity-determining regions amino acid sequences (C1, C8, C15, C17, or C18 in Table 1) or a specific variable regions amino acid sequences (V1, V8, V15, V17, or V18 in Table 2). As the artificial antibody, for example, the tenth unit in the human fibronectin type III domain (FNfn10) can be used. An artificial antibody capable of binding to a desired target can be produced by introducing mutation in the BC, DE, and/or FG loops of the unit. Besides the extracellular domain of fibronectin, Kunitz domain of serine protease inhibitor and peptides such as ankyrin and lipocalin can be used as the artificial antibody. These artificial antibodies can be produced by a genetic engineering technique involving introduction of a vector containing a nucleic acid molecule which encodes the peptide into *Escherichia coli*, yeast, or animal cells, culture of the host cells, and then recovery and purification of the culture supernatant.

The artificial antibody can be selected by searching a random sequence library including random combinations of amino acids for a low-molecular-weight peptide molecules which are capable of binding specifically to the epitope of the present invention, such as an antibody, instead of use of the amino acid sequence of a specific protein or a part thereof as described above (for example, Hipolito et al., Current Opinion in Chemical Biology, 2012 Vol. 16: 196; Yamagishi et al., Chemistry & Biology, 2011 Vol. 18: 1562). Such a peptide can also be produced by any chemical synthetic method such as a fluorenylmethyloxycarbonyl technique or t-butyloxycarbonyl technique, instead of a genetic engineering technique.

[Combination of Sequences of Antibody]

The combinations C1 to C30 shown in Table 1, i.e. combinations of amino acid sequences for complementarity-determining regions; the combinations V1 to V30 shown in Table 2, i.e. combinations of amino acid sequences for variable regions; the combinations CN1 to CN30 shown in Table 5, i.e. the combinations of nucleic acid sequences for complementarity-determining regions; and the combinations IGN1 to IGN30 shown in Table 5, i.e. combinations of nucleic acid sequences, of the human anti-IL-33 neutralizing monoclonal antibody described in the specification respectively correspond to identical clone sequences. The correspondence between the sequences is shown in Table 6. For example, the complementarity-determining regions of the clone A10-1C04 respectively correspond to the six amino acid sequences of complementarity-determining regions represented by the combination C1, and the combination of amino acid sequences of the complementarity-determining regions may be respectively encoded by the six nucleic acid sequences of the combination CN1. The clone comprises heavy-chain and light-chain variable regions respectively corresponding to the two amino acid sequences of the combination V1. The amino acid sequences of λ light chain and γ heavy chain, including the variable regions, of the combination V1 are respectively encoded by the two nucleic acid sequences of the combination IGN1.

TABLE 6

| Clone name | CDR (Amino Acids Sequence) | Variable Region (Amino Acids Sequence) | CDR (Nucleic Acids Sequence) | Heavy Chain/Light Chain (Nucleic Acid Sequence) |
|---|---|---|---|---|
| A10-1C04 | C1 | V1 | CN1 | IGN1 |
| A12-1E04 | C2 | V2 | CN2 | IGN2 |
| A12-1H04 | C3 | V3 | CN3 | IGN3 |
| A12-1H08 | C4 | V4 | CN4 | IGN4 |
| A13-1F05 | C5 | V5 | CN5 | IGN5 |
| A13-1F07 | C6 | V6 | CN6 | IGN6 |
| A13-1G05 | C7 | V7 | CN7 | IGN7 |
| A23-1A05 | C8 | V8 | CN8 | IGN8 |
| A25-2D01 | C9 | V9 | CN9 | IGN9 |
| A25-2B02 | C10 | V10 | CN10 | IGN10 |
| A25-2E04 | C11 | V11 | CN11 | IGN11 |
| A25-2C06 | C12 | V12 | CN12 | IGN12 |
| A25-2C07 | C13 | V13 | CN13 | IGN13 |
| A25-2H11 | C14 | V14 | CN14 | IGN14 |
| A25-2C02 | C15 | V15 | CN15 | IGN15 |
| A25-3G05 | C16 | V16 | CN16 | IGN16 |
| A25-3H04 | C17 | V17 | CN17 | IGN17 |
| A26-1F02 | C18 | V18 | CN18 | IGN18 |
| A26-2A05 | C19 | V19 | CN19 | IGN19 |
| A26-2B01 | C20 | V20 | CN20 | IGN20 |
| A27-1A06 | C21 | V21 | CN21 | IGN21 |
| A27-1C06 | C22 | V22 | CN22 | IGN22 |
| A28-1C08 | C23 | V23 | CN23 | IGN23 |
| A28-1G07 | C24 | V24 | CN24 | IGN24 |
| A28-2C06 | C25 | V25 | CN25 | IGN25 |
| A28-2F01 | C26 | V26 | CN26 | IGN26 |
| A28-2G07 | C27 | V27 | CN27 | IGN27 |
| A28-2H06 | C28 | V28 | CN28 | IGN28 |
| A00-0070 | C29 | V29 | CN29 | IGN29 |
| A00-0036 | C30 | V30 | CN30 | IGN30 |

EXAMPLES

The present invention will now be described in more details by way of Examples, which should not be construed to limit the invention, unless otherwise indicated.

Example 1: Preparation of Anti-IL-33 Antibodies and Identification of Epitope Peptides

[Preparation of Antibodies]

A human IL-33 protein was immunized to an animal to produce a hybridoma from the splenic cells of the immunized animal, and the monoclonal antibody was thereby prepared. The RNA was extracted from the splenic cells of the immunized animal to produce a library of antibodies of the animal. Antibodies capable of binding to the human IL-33 protein were cloned from such a library and the human naive antibody library by phage display technique. Eight anti-IL-33 monoclonal antibodies (Antibodies A to H) were thereby prepared.

[Peptide Array Scanning]

In order to identify the epitope for the resulting IL-33 antibodies, peptide array scanning was carried out to confirm the binding of each antibody to each of the partial peptides (20 residues in length) of human IL-33. Peptides consisting of 20 amino acids were synthesized, each shifted by 10 amino acids within the sequence spanning valine at N-terminal position 101 (V101) and threonine at N-terminal position 270 (T270) to cover the major part of mature human IL-33 molecules. Sixteen peptides (PEP11 to PEP26) in total were thereby synthesized. The sequence and position of each of these peptides are shown in FIG. 12.

Figure 2:
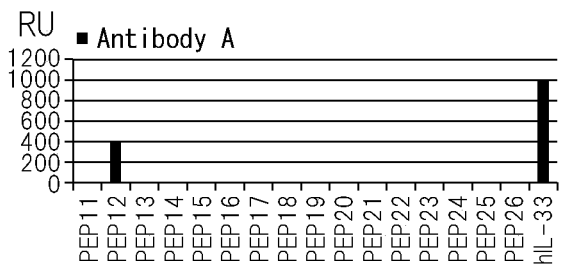
FIG. 2 shows a binding activity of each of antibodies to a human IL-33 protein (residues 112 to 270) and each partial peptide fragments thereof (PEP11 to PEP26).
Figure 2:
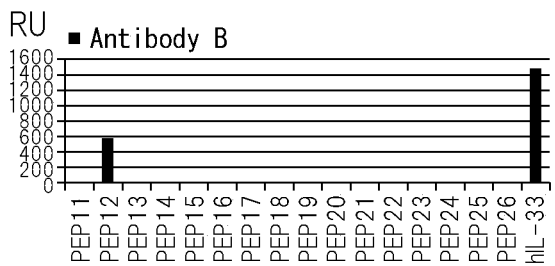
Figure 2:
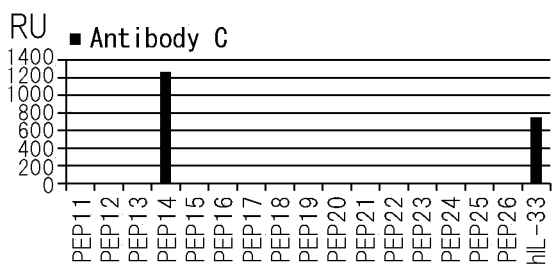
Figure 2:
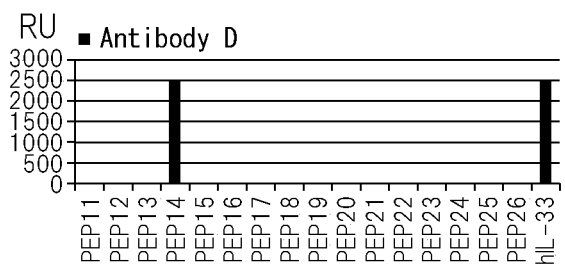
Figure 2:
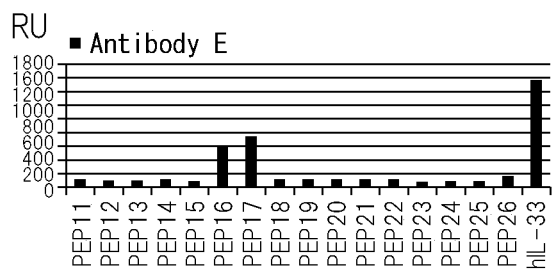
Figure 2:
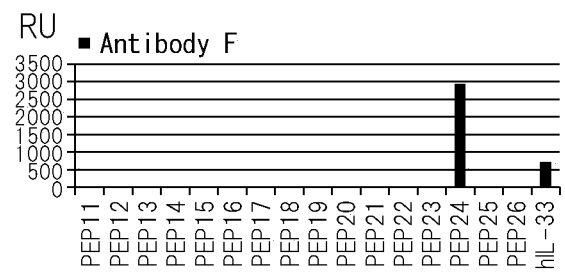
Figure 2:
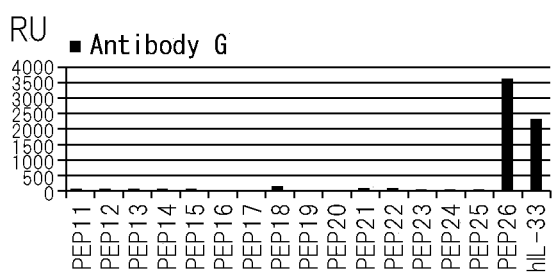
Figure 2:
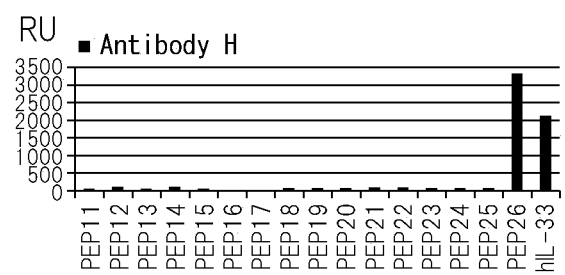

Each peptide was N-terminally biotinylated, and was immobilized as ligand onto a NeutrAvidin sensor chip of a surface plasmon resonance (SPR) system (ProteOn XPR36, available from Bio-Rad Laboratories, Inc.). As positive control, the mature human IL-33 (residues 112 to 270) was N-terminally linked with the Avitag sequence, and was biotinylated by biotin ligase reaction specific for the AviTag sequence. The resulting protein (hIL-33) as a ligand was immobilized onto the SPR sensor chip. Each test antibody, the human IL-33 receptor protein (recombinant human ST2 Fc chimera) (ALX-201-367-0050, available from Enzo Life Science, Inc.), or buffer (0.05% Tween20/PBS) alone was then loaded as an analyte onto the sensor chip containing the ligand immobilized thereon (antibody concentration: 10 µg/ml; flow rate: 100 µl/min), to allow them to bind to the ligand. After washing, the amount of analyte (amount of antibody) bound to the ligand on the sensor chip was measured as RU value. The results are shown in FIG. 2.

The antibodies were designated, in sequence, in accordance with the position of epitope in the human IL-33 protein: the antibody to the epitope located at the most N-terminal portion was designated "Antibody A". The Antibodies A and B bound to PEP12, the Antibodies C and D bound to PEP14, the Antibody E bound to both PEP16 and PEP17, the Antibody F bound to PEP24, and the Antibodies G and H bound to PEP26. A commercially available anti-human IL-33 polyclonal antibody (AF3625, available from R&D Systems, Inc.) bound to most of the 16 human IL-33 peptides studied. The human IL-33 receptor (ST2) bound to the human IL-33 protein, but substantially did not bind to the human IL-33 peptides (PEP11 to PEP26). The experiment failed to identify what portion of the IL-33 was significant for the binding with ST2. No binding with the ligand was observed in the buffer alone or murine IgG (MAB002, available from R&D Systems, Inc.). The tested antibodies were compared for the binding ability to hIL-33 (residues 112 to 270). The descending order of the binding ability of the antibody to hIL-33 (residues 112 to 270) was Antibody G, Antibody H, Antibody D, Antibody E, Antibody B, Antibody A, Antibody C, and Antibody F.

Example 2: Evaluation of IL-33 Neutralizing Activity of Anti-IL-33 Monoclonal Antibodies-1

The Antibodies A, B, E, and F were measured for the IL-33 neutralizing activity, based on the inhibitory effect on the binding between immobilized human ST2 and humanIL-33 as indicator. Recombinant human ST2 Fc chimera (ALX-201-367-0050, available from Enzo Life Science, Inc.) diluted with phosphate buffered saline (PBS) was dispensed into a 96-well microplate (Nunc™, #442404) (1 µg/mL, 50 µL/well), and was left to stand overnight at a temperature of 4° C. The following day, the microplate was washed once with 1% BSA-containing PBS (PBS-B), and PBS-B was added to the microplate (250 µL/well) for blocking at a room temperature for two hours. After the blocking, a mixed solution of each test antibody diluted with PBS-B (final concentration: 10 µg/mL) and a recombinant human IL-33 protein (ILC0701, available from ATGen Co. Ltd) (final concentration: 1 µg/mL) was added to the microplate (50 µL/well), and the solution was incubated at a room temperature for two hours. After the microplate was washed with 0.1% Tween 20-containing PBS (PBS-T) for five times, goat anti-human IL-33 antibody (AF3625, available from R&D Systems, Inc.; final concentration: 1 µg/mL; 50 µL/well) diluted with PBS-B was subsequently added to the microplate, and the solution was then incubated at a room temperature for one hour. After the microplate was washed with PBS-T for five times, the HRP-labeled rabbit anti-goat IgG antibody (Invitrogen:61-1620, 50 µL/well) diluted to 2000-fold with PBS-B was added, and the solution was incubated at a room temperature for one hour. After the microplate was washed with PBS-T for five times, SureBlue™ TMB Microwell Peroxidase Substrate (KPL:52-00-01, 50 µL/well) was added. The solution was allowed to react at a room temperature for 20 minutes, and then the reaction was stopped with TMB Stop Solution (KPL: 50-85-05, 50 µL/well). The difference between the absorbance at wavelength of 450 nm and that at wavelength of 620 nm was measured with a microplate reader (SpectraMax 190, available from Molecular Devices, LLC.). A sample was prepared by replacing the human IL-33 with human IL-1β (Pepro-Tech, 200-01B) (final concentration: 1 µg/mL), and the results observed in this sample was set as background. The inhibitory effect of each antibody on the binding of ST2 and IL-33 (competitive inhibition percentage in IL-33/ST2 binding system) was determined by calculating the percentage of inhibition (%) of binding by each antibody relative to the binding observed in a sample containing the human IL-33 alone (final concentration: 1 µg/mL). According to the results, the Antibody A (epitope: PEP12) exhibited 66% inhibition, the Antibody B (epitope: PEP12) exhibited 55% inhibition, the Antibody E (epitopes: PEP16 and PEP17) exhibited 0% inhibition, and the Antibody F (epitope: PEP24) exhibited 39% inhibition. All of the four antibodies tested, except for the Antibody E, (i.e. Antibodies A, B and F) exhibited inhibition percentage of 30% or higher at final concentration of 10 µg/mL.

TABLE 8

| | Epitope | Competitive Inhibition Percentage in IL-33/ST2 binding system [%] |
|---|---|---|
| Antibody A | PEP12 | 66 |
| Antibody B | PEP12 | 55 |
| Antibody E | PEP16-17 | <0 |
| Antibody F | PEP24 | 39 |

Example 3: Evaluation of the IL-33 Neutralizing Effect of Anti-IL-33 Monoclonal Antibody-2

Each of the test antibodies (Antibodies A to H) was measured for the IL-33 neutralizing activity based on the inhibitory effect on human IL-33-induced IL-6 production in normal human umbilical vein endothelial cells (HUVEC) (CLC2517A, available from LONZA Group Ltd.) as indicator. The HUVEC cells were inoculated in a 96-well microplate (IWAKI, MT4940-010) ($6 \times 10^3$/0.1 mL/well), and cell confluence was confirmed. Each anti-IL-33 antibody (final concentration: 10 µg/mL) and recombinant human IL-33 (ILC0701, available from ATGen Co. Ltd; final concentration: 100 ng/mL) were added (0.2 mL/well) to a medium (EGM-2 medium (CLCC-3156 and CLCC-4176, available from LONZA Group Ltd.)), and the solution was incubated at a temperature of 37° C. for 24 hours. After 24 hours, the IL-6 concentration in the medium was measured with a commercially available ELISA kit (EH2IL6, available from Thermo Scientific). After collection of the medium, cell viability was measured with a cell counting kit (345-06463, available from Dojindo Molecular Technologies, Inc.), so as to confirm that the inhibitory effect on IL-6 production was not caused by a decrease in the viable cell count. In order to determine the IL-33 neutralizing activity of each test antibody (inhibition % of IL-6 production in HUVEC system), the percentage of inhibition (%) of IL-6 production relative to the IL-6 production caused by the treatment with recombinant human IL-33 alone was calculated. According to the results, the Antibody A (epitope: PEP12) exhibited 51% inhibition, the Antibody B (epitope: PEP12) exhibited 48% inhibition, the Antibody C (epitope: PEP14) exhibited 33% inhibition, the Antibody D (epitope: PEP14) exhibited 38% inhibition, the Antibody E (epitope: PEP16 to PEP17) exhibited 0% inhibition, the Antibody F (epitope: PEP24) exhibited 38% inhibition, the Antibody G (epitope: PEP26) exhibited 48% inhibition, and the Antibody H (epitope: PEP26) exhibited 56% inhibition. All of the eight antibodies tested, except for the Antibody E, exhibited inhibition percentage of 30% or higher (Table 9). Among these antibodies, those that were capable of binding to an epitope consisting of a sequence selected from the group consisting of positions 111 to 130, 131 to 150, 231 to 250, and 251 to 270 of SEQ ID NO:1 in the Sequence Listing exhibited significant increases in the neutralizing activity, at the antibody concentration of 3, 10, and 30 µg/mL (for example, the Antibody D exhibited inhibition of 23%, 42%, and 61%, respectively); the results demonstrate that such epitopes are suitable for producing an antibody having an antagonistic action.

TABLE 9

|  | Epitope | Inhibition Percentage of IL-6 production in HUVEC system [%] |
| --- | --- | --- |
| Antibody A | PEP12 | 51 |
| Antibody B | PEP12 | 48 |
| Antibody C | PEP14 | 33 |
| Antibody D | PEP14 | 38 |
| Antibody E | PEP16-17 | <0 |
| Antibody F | PEP24 | 38 |
| Antibody G | PEP26 | 48 |
| Antibody H | PEP26 | 56 |

The Antibody E bound to hIL-33 (FIG. 2), but did not exhibit functional neutralizing ability (Tables 8 and 9). PTL 2 (WO 2008/132709) discloses three epitopes: epitope 1 (positions 155 to 198), epitope 2 (positions 165 to 188), and epitope 3 (positions 175 to 178). The present experiments revealed that these epitopes had a sequence overlapping with the epitope peptides for the Antibody E (positions 151 to 180) which was confirmed not to have IL-33 neutralizing activity. These results suggest that antibodies to the epitopes disclosed in PTL 2 cannot sufficiently inhibit the binding of IL-33 with ST2, its receptor, and has no or very low IL-33 neutralizing activity.

Theoretically, possible causes for the absence of IL-33 neutralizing activity in the Antibody E would be inferiority of the epitope and insufficiency of affinity. The Antibodies D, G, and H tended to have lower avidity with hIL-33, as compared to the Antibody E, but clearly exhibited IL-33 neutralizing activity. In view of the existence of such clones, it is believed that the absence of the neutralizing activity is probably not caused by insufficiency of affinity. Based on such findings, the four epitopes currently found by the inventors (PEP12, PEP14, PEP24, and PEP26) are believed to be functional epitopes when the purpose is neutralization of IL-33 cytokine, in that the avidity between IL-33 and antibodies for the epitopes is relevant to the IL-33 neutralizing activity of the antibodies, unlike the epitopes disclosed in PTL 2. An antibody that is capable of binding to a functional epitope has high antagonistic effect on IL-33, while an antibody that is capable of binding to a non-functional epitope has a low or no antagonistic effect on IL-33.

Example 4: Mapping of Epitope Peptides to the Conformation of Human IL-33

Figure 3:
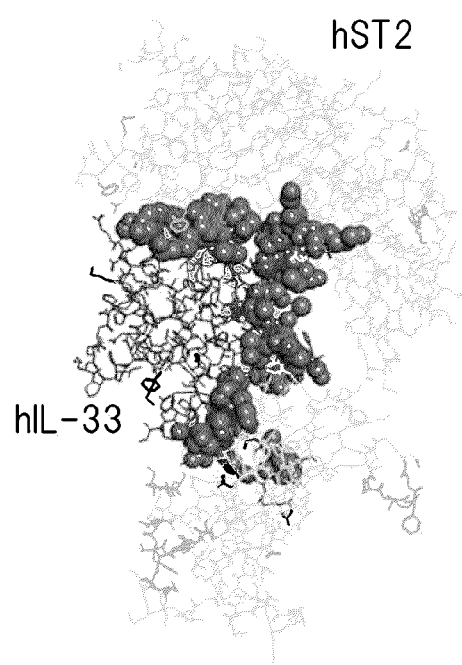
FIG. 3 shows conformational model of a complex of mature human IL-33 (residues 117 to 270) (shown as "S117-T270" in FIG. 3) and human ST2 (hST2).
Figure 4:
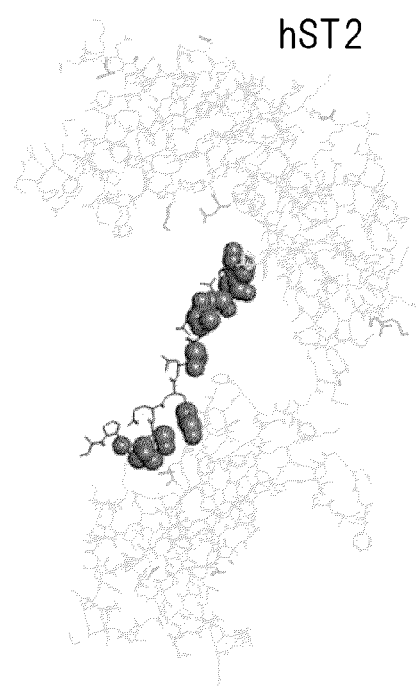
FIG. 4 shows a part of the conformational model in FIG. 3 illustrating human ST2 and a partial conformation of PEP12 epitope of human IL-33 (corresponding to positions 117 to 130 of SEQ ID NO:226 in the Sequence Listing and is represented by "5117-N130" in FIG. 4; hereinafter, other epitopes are represented in the same way).
Figure 5:
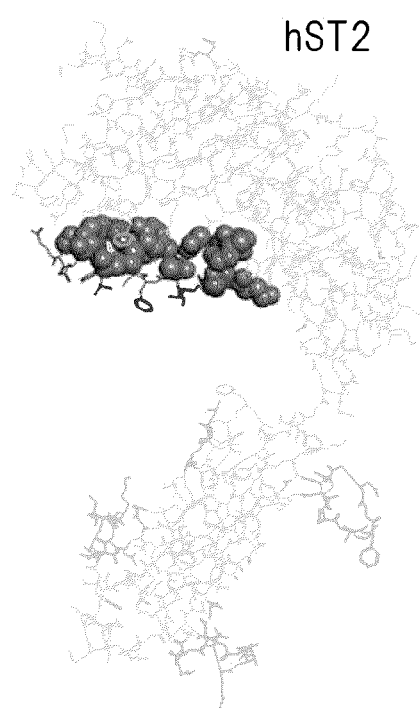
FIG. 5 shows a part of the conformational model in FIG. 3 illustrating only PEP 14 epitope of human IL-33 and human ST2.
Figure 6:
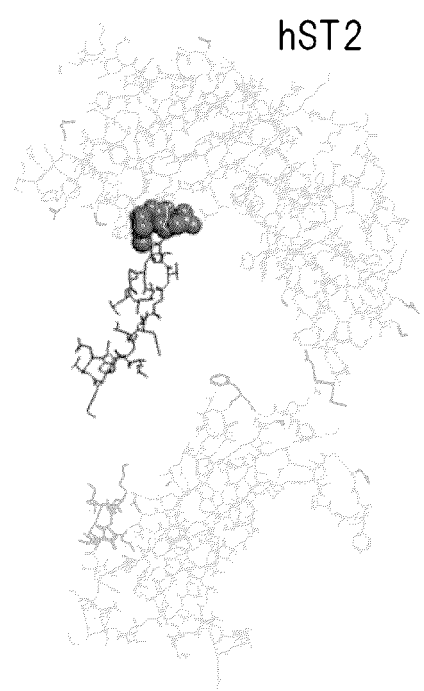
FIG. 6 shows a part of the conformational model in FIG. 3 illustrating only PEP24 epitope of human IL-33, d and human ST2.
Figure 7:
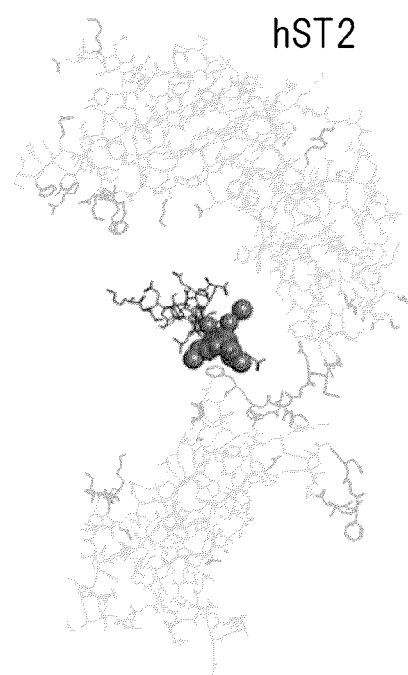
FIG. 7 shows a part of the conformational model in FIG. 3 illustrating only PEP26 epitope of human IL-33, and human ST2.

In order to identify the interfacial atoms (the atom of IL-33 located at the atomic distance of 5 Å or less from a component atom of ST2, when the two atoms are in the closest proximity) which would be a preferred epitope for production of an antibody with antagonistic effect, the four epitope peptides were mapped on the conformation of the human IL-33/human ST2 complex. The X-ray crystallographic structure of the human IL-33/human ST2 complex (Research Collaboratory for Structural Bioinformatics: PDB ID 4KC3) lacked a partial structure of the IL-33 protein, and thus it was impossible to show the positions of all the epitope peptides identified in the invention. The inventors thus created homology model based on the X-ray crystallographic structure (4KC3) as template (FIG. 3; Discovery Studio 3.5 (available from Accelrys) was used), and the epitope peptides (PEP12, PEP14, PEP24, and PEP26) corresponding to the antibodies which exhibited neutralizing activity in the present experiments were mapped on the model (FIG. 4 to FIG. 7). In FIG. 4 to FIG. 7, human IL-33 and epitope peptides are shown in dark grey, and ST2 bound to the IL-33 or epitope peptides are shown in light grey. The interfacial atoms are highlighted by indicating them with larger spheres in order to clearly show the position of interface between the IL-33 protein and IL-33 receptors on the IL-33 protein surface. The results demonstrated that these epitope peptides (PEP12, PEP14, PEP24, and PEP26) each have amino acids containing interfacial atoms. Examples of amino acids containing the interfacial atoms include P118, I119, T120, Y122, L123, R124, S125, L126, S127, Y129, and N130 of PEP12; D131, Q132, S133, T135, A137, L138, E139, S142, Y143, E144, I145, Y146, E148, D149, and L150 of PEP14; D244, N245, and H246 of PEP24; and K266, L267, S268, and E269 of PEP26. A preferred epitope to which an antibody with antagonistic effect is to bind specifically is believed to have amino acids containing the interfacial atoms.

Example 5: Preparation of Human Anti-IL-33 Antibodies (Parental Clones)

Using a human scFv phage display library (n-CoDeR, available from BioInvent International AB) (Soderlind et al., Nature biotechnology, 2000 Vol. 18(8), p. 852), two different parental clones (scFv) (it indicates that the molecular form is scFv; hereinafter, represented in the same way) were prepared (clones designated A00-0070 and A00-0036), which were capable of binding to mature IL-33 (residues 112 to 270) to inhibit the binding of IL-33 to ST2 and inhibit IL-33 activity, when they were analyzed based on the IL-33-dependent IL-6 production in normal human umbilical vein endothelial cells (HUVEC) as described below. The antibodies were sequenced to obtain their base sequences and amino acid sequences of light-chain and heavy-chain variable regions. A00-0070 and A00-0036 respectively had amino acid sequences of light-chain and heavy-chain variable regions in accordance with the combinations V29 and V30, respectively, shown in Table 2.

Example 6: Determination of Amino Acid Substitution for Improving Complementarity-Determining Regions The complementarity-determining regions of two parental clones were modified by Fab ribosome display and Fab phage display techniques, for increased affinity with IL-33 and improved physical properties (i.e. reduced surface hydrophobicity and consequent decreased aggregation and increased solubility) of the clones. The complementarity-determining regions were modified in the following two steps: the first step of determination of single-amino acid substitutions for improving the affinity with IL-33 and the physical properties; and the second step of determination of combinations of such single-amino acid substitutions (Fujino et al., Biochem. Biophys. Res. Commun., 2012 Vol. 428(3), p. 395).

A Fab ribosome display vector was constructed based on the light-chain and heavy-chain variable regions of the two parental clones, and was then subjected to multistep PCR reactions involving site-directed mutagenesis PCR and overlap extension PCR, to construct a comprehensive library of single-amino acid substitution variants covering all single-amino acid substitutions within the six complementarity-determining regions (LCDR1, LCDR2, LCDR3, HCDR1, HCDR2, and HCDR3) of the antibody. Amino acid residues respectively were replaced with 20 natural amino acids in total. The Fab ribosome display process (Fujino et al., Biochem. Biophys. Res. Commun., 2012 Vol. 428(3), p. 395) was performed in a reconstituted cell-free translation system, PURE system (PUREfrex, available from Gene-Frontier Corporation) (Shimizu et al., Nature Biotechnology, 2001, Vol. 19(8), p. 751) over the comprehensive library of single-amino acid substitution variants. Library selection was repeated several rounds using a recombinant human IL-33 protein (ILC0701, available from ATGen Co. Ltd) as bait, to enrich the library. Each of the clones (Fab) ("clone (Fab)" indicates that the clone has a molecular form of Fab; hereinafter, the same representation is used) contained in the library before the enrichment (i.e. just after construction) and after the enrichment was sequenced with a next-generation sequencer (Roche, 454) to determine the base sequences of the light-chain and heavy-chain variable regions. Sequence data with several thousands of reads of the library before and after the enrichment was obtained to calculate the frequency of each of all variants having single-amino acid substitution in the complementarity-determining regions. The ratio of change between the frequencies in the library before and after the enrichment (i.e. enrichment ratio) was calculated for each of all single-amino acid substitution variants. The magnitude of the enrichment ratio in the library enrichment was used as an indicator to determine some single-amino acid substitutions assumed to be useful for improving affinity with the human IL-33 protein. Based on the total number of the single-amino acid substitutions and the distribution on the amino acid sequence, positions where the amino acid substitutions were to be introduced were determined for construction of the custom library in the second step.

In the parental clone A00-0070, introduction of amino acid substitutions in the following positions was determined: asparagine at position 12 of LCDR1 (SEQ ID NO:2 in the Sequence Listing); glutamine at position 4 of LCDR2 (SEQ ID NO:11 in the Sequence Listing); serine at position 2, tyrosine at position 3, and serine at position 6 of LCDR3 (SEQ ID NO:23 in the Sequence Listing); aspartic acid at position 1 and asparagine at position 5 of HCDR1 (SEQ ID NO:43 in the Sequence Listing), serine at position 4, serine at position 5, serine at position 7, and isoleucine at position 9 of HCDR2 (SEQ ID NO:64 in the Sequence Listing). In the parental clone A00-0036, introduction of amino acid substitutions in the following positions was determined: asparagine at position 9 and asparagine at position 13 of LCDR1 (SEQ ID NO:6 in the Sequence Listing); arginine at position 6 and leucine at position 7 of LCDR2 (SEQ ID NO:20 in the Sequence Listing); alanine at position 1, alanine at position 9, and valine at position 10 of LCDR3 (SEQ ID NO:40 in the Sequence Listing); asparagine at position 1 of HCDR1 (SEQ ID NO:47 in the Sequence Listing); serine at position 4, serine at position 5, serine at position 6, serine at position 7, tyrosine at position 8, isoleucine at position 9, tyrosine at position 10, tyrosine at position 11, aspartic acid at position 13, and lysine at position 16 of HCDR2 (SEQ ID NO:64 in the Sequence Listing); and glycine at position 2, histidine at position 5, and aspartic acid at position 6 of HCDR3 (SEQ ID NO:78 in the Sequence Listing).

For improving physical properties of the clones, homology models of the two parental clones were generated with a protein structure analysis program (Discovery Studio, available from Accelrys) to predict regions with high surface hydrophobicity within the complementarity-determining regions, and then to determine positions to be substituted for reducing the surface hydrophobicity of the predicted regions. In the parental clone A00-0070, introduction of amino acid substitutions in the following positions was determined: tyrosine at position 3 of LCDR3 (SEQ ID NO:23 in the Sequence Listing); and serine at position 7 and isoleucine at position 9 of HCDR2 (SEQ ID NO:64 in the Sequence Listing). In the parental clone A00-0036, introduction of amino acid substitutions in the following positions was determined: arginine at position 6 and leucine at position 7 of LCDR2 (SEQ ID NO:20 in the Sequence Listing); and serine at position 7, tyrosine at position 8, and isoleucine at position 9 of HCDR2 (SEQ ID NO:64 in the Sequence Listing). Based on the data on enrichment ratio obtained in the analysis of mutation using the comprehensive library of single-amino acid substitution variants, the amino acid substitutions assumed to be useful for reducing the surface hydrophobicity without affecting the binding ability to the human IL-33 protein was determined among these sites.

Example 7: Production of a Human Anti-IL-33 Antibody with Modified Complementarity-Determining Regions Two or more of the useful amino acid substitutions for improvements in affinity and physical properties as described above were combined to design a full-scale custom library for modifying the complementarity-determining regions. Vectors for Fab ribosome display and Fab phage display processes were constructed. The Fab ribosome display vector was then subjected to multistep PCR reactions involving site-directed mutagenesis PCR and overlap extension PCR, and the Fab phage display vector was used as a template to perform site-specific mutagenesis by Kunkel mutagenesis method (Fellouse et al., J. Mol. Biol. 2007 Vol. 373, p. 924), to construct a custom library for improvement of complementarity-determining regions, in which the positions in the complementarity-determining regions were randomized based on the design described above. The Fab ribosome display and Fab phage display processes were performed. Library selection was repeated for several rounds using Human IL-33 protein and cynomolgus monkey IL-33 protein (GenBank: EHH57404; spanning from Ser residue 112 to Glu residue 269 in SEQ ID NO:227 in the Sequence Listing) as bait, to enrich the library. In the latter half of the rounds, negative selection was performed with hydrophobic column carriers such as octyl sepharose (GE Healthcare) or phenyl sepharose (GE Healthcare) before allowing the binding with the IL-33 proteins, so as to enrich the Fab having high affinity with the IL-33 protein and low surface hydrophobicity.

The recombinant proteins used as bait were prepared by the following process. A gene sequence encoding the mature humanIL-33 (residues 112 to 270) and mature cynomolgus monkey IL-33 (residues 112 to 269 of SEQ ID NO:227 in the Sequence Listing) was N-terminally linked with 6His tag-AviTag, and the resulting sequence was inserted into pET30a(−) to construct an expression vector to prepare the recombinant protein. *Escherichia coli* BL21 (DE3) strain including the expression vector was pre-cultured in 5 mL of LB medium, and then 1 mL of the pre-culture solution was inoculated into 50 mL of expression medium (Overnight Express, available from Merck Millipore Corporation; supplemented with kanamycin). The bacterial cells were cultured for protein expression for 18 hours at 200 rpm and at a temperature of 30° C. The bacterial cells were collected and washed, and then were bacteriolyzed with BagBuster (Novagen), and the supernatant was recovered. The 6His-AviTag-linked cynomolgus monkey IL 33 (residues 112 to 269) contained in the supernatant was purified with Ni-NTA Agarose (available from QIAGEN), and was biotinylated. The biotin modification specific for the AviTag portion was introduced with a commercially available biotin ligase (BirA, available from Avidity LLC).

The library after the enrichment was used to construct a library of *Escherichia coli* secreting and expressing Fab. The culture supernatants of several hundreds of clones of *Escherichia coli* were subjected to measurement of dissociation rate constant (koff) by surface plasmon resonance (SPR) (ProteOn XPR36, available from Bio-Rad Laboratories, Inc.). The biotinylated human IL-33 protein (4 µg/mL) and cynomolgus monkey IL-33 protein (4 µg/mL) were loaded as ligands on a sensor chip (NLC sensor chip, available from Bio-Rad Laboratories, Inc.), to immobilize the human IL-33 protein at an amount equivalent to 1300 to 1600 RU, and the cynomolgus monkeyIL-33 protein at an amount equivalent to 1100 to 1500 RU. The culture supernatant of *Escherichia coli* was then loaded thereon as analyte to obtain a sensorgram with association phase of one minute and dissociation phase of 10 to 30 minutes. The sensorgram was subjected to interspot correction and blank correction using an SPR data analysis program (ProteOn Manager v3.1.0, available from Bio-Rad Laboratories, Inc.), and then values of koff were determined by off-rate analysis of Langmuir model.

Among the clones (Fab) with modified complementarity-determining regions, 28 clones (corresponding to V1 to V28 in Table 2) that had an increased affinity with human IL-33 protein and had binding ability to cynomolgus monkey IL-33 protein were selected to be analyzed in higher-level tests in Example 8 and following Examples. As shown in Table 10, the selected clones (Fab) had higher affinity (i.e. low koff value) with the human and cynomolgus monkey IL-33 proteins, as compared to their parental clones (Fab). These clones had no amino acid substitution within the framework regions in the variable regions. Even two variants have an identical single-amino acid substitution in the complementarity-determining regions, the effect of improving affinity is different between a single-amino acid substitution variant and a variant with two or more amino acid substitutions. For such a reason, some amino acid substitutions were frequent in the sequences of the 28 clones for higher-level evaluation, although the enrichment ratio of single-amino acid substitution variants containing such substitutions was low in the first step in the comprehensive library of single-amino acid substitution variants, and vice versa.

TABLE 10

| Clone Name | Combination of Variable Region | Human IL-33 koff (/sec) | Human IL-33 Binding Amount (RU) | Cynomolgus Monkey IL-33 koff (/sec) | Cynomolgus Monkey IL-33 Binding Amount (RU) |
| --- | --- | --- | --- | --- | --- |
| A10-1C04 | V1 | 1.00E−05 | 26 | 1.65E−04 | 20 |
| A12-1E04 | V2 | 2.19E−05 | 414 | 5.58E−05 | 512 |
| A12-1H04 | V3 | 1.94E−05 | 94 | 4.83E−05 | 131 |
| A12-1H08 | V4 | 1.00E−05 | 77 | 7.51E−05 | 102 |
| A13-1F05 | V5 | 1.32E−05 | 127 | 5.79E−05 | 171 |
| A13-1F07 | V6 | 1.00E−05 | 112 | 3.48E−05 | 151 |
| A13-1G05 | V7 | 1.00E−05 | 59 | 5.45E−05 | 80 |
| A23-1A05 | V8 | 1.58E−05 | 52 | 2.61E−05 | 54 |
| A25-2D01 | V9 | 1.00E−05 | 950 | 1.00E−05 | 832 |
| A25-2B02 | V10 | 1.00E−05 | 256 | 1.00E−05 | 237 |
| A25-2E04 | V11 | 1.27E−05 | 195 | 1.00E−05 | 199 |
| A25-2C06 | V12 | 1.36E−05 | 480 | 1.59E−05 | 501 |
| A25-2C07 | V13 | 3.41E−05 | 334 | 7.37E−05 | 330 |
| A25-2H11 | V14 | 1.22E−05 | 534 | 2.57E−05 | 492 |
| A25-2C02 | V15 | 1.00E−05 | 930 | 1.00E−05 | 839 |
| A25-3G05 | V16 | 1.34E−05 | 135 | 2.02E−05 | 143 |
| A25-3H04 | V17 | 1.00E−05 | 162 | 1.00E−05 | 179 |
| A26-1F02 | V18 | 1.00E−05 | 96 | 1.00E−05 | 100 |
| A26-2A05 | V19 | 1.00E−05 | 153 | 1.00E−05 | 147 |
| A26-2B01 | V20 | 1.00E−05 | 364 | 1.00E−05 | 363 |
| A27-1A06 | V21 | 1.00E−05 | 306 | 1.00E−05 | 320 |
| A27-1C06 | V22 | 1.00E−05 | 294 | 1.14E−05 | 304 |
| A28-1C08 | V23 | 1.00E−05 | 156 | 1.00E−05 | 144 |
| A28-1G07 | V24 | 1.00E−05 | 165 | 1.05E−05 | 173 |

TABLE 10-continued

| Clone Name | Combination of Variable Region | Human IL-33 koff (/sec) | Human IL-33 Binding Amount (RU) | Cynomolgus Monkey IL-33 koff (/sec) | Cynomolgus Monkey IL-33 Binding Amount (RU) |
|---|---|---|---|---|---|
| A28-2C06 | V25 | 1.00E−05 | 123 | 1.00E−05 | 134 |
| A28-2F01 | V26 | 1.00E−05 | 289 | 1.00E−05 | 258 |
| A28-2G07 | V27 | 1.00E−05 | 289 | 1.14E−05 | 259 |
| A28-2H06 | V28 | 1.00E−05 | 349 | 1.00E−05 | 317 |
| A00-0070 | V29 | 4.27E−03 | 571 | 5.22E−03 | 270 |
| A00-0036 | V30 | 1.52E−02 | 78 | 3.47E−02 | 59 |

Example 8: Preparation of IgG Antibodies

DNAs which respectively encode amino acid sequences of light and heavy chains of the seven human anti-IL-33 antibody clones prepared above (A10-1C04, A23-1A05, A25-2C02, A25-3H04, A26-1F02, A00-0070, and A00-0036) were each inserted downstream of a CMV promoter to construct an expression vector for mammalian cells for expression of IgG. The DNA sequences of the light chain of the clones were those shown in SEQ ID NOs:228, 232, 239, 241, 242, 230, and 253, respectively, in the Sequence Listing. The DNA sequences of the heavy chain of the clones were those shown in SEQ ID NOs:254, 261, 262, 264, 265, 276, and 277, respectively, in the Sequence Listing. Each of the expression vectors was transfected into FreeStyle 293-F cells (Life Technologies) using a transfection reagent Neo-Fection-293-1 (available from Astec Co., Ltd.). After the transfection, the cells were cultured for five days, and then the culture supernatant was collected. Stable cell lines of CHO cells were established with GS system (available from LONZA Group Ltd.) using a pConPlus vector and CHO K1SV cells. The stable cell lines of CHO cells were cultured, starting from a concentration of $0.3 \times 10^6$ cells/mL using WAVE Bioreactor SYSTEM 20/50 EHT (GE Healthcare), and the culture solution containing secreted IgG was collected. IgG was purified from the culture supernatant by affinity chromatography using AKTA explorer 100 (GE Healthcare) and a Protein A resin (HiTrap MabSelect SuRe, available from GE Healthcare). IgG bound to the protein A resin was eluted with an elution buffer with a pH of 3.2, and then the eluate was immediately neutralized to have an approximately neutral pH, and then was dialyzed with PBS (with a pH of 7.2). IgG after the purification with the protein A column was further purified with CHT (ceramic hydroxyapatite Type I resin, available from Bio-Rad Laboratories, Inc.) to increase the purity. IgG bound to CHT was eluted with NaCl concentration gradient. Fractions of interest were collected and then were dialyzed with PBS (with pH of 7.2). The antibodies obtained by this purification process are referred to as "neutral-purified antibodies".

Another purification process was also performed, which further involves the step of washing with six-column volume of 100 mM sodium carbonate buffer (with a pH of 11.0) for six minutes prior to the step of elution of IgG from the protein A resin in the purification process described above. The antibodies obtained from this purification process are referred to as "alkaline-purified antibodies". Recovery rates of the individual alkaline-purified antibodies after each step are shown in Table 11. The alkaline-purified antibodies after purification were concentrated by centrifugal ultrafiltration with VIVASPIN Turbo15 30000 MWCO (Sartorius AG).

TABLE 11

| Clone Name | Collection Rate by Protein A Purification (%) | Collection Rate by CHT Purification (%) | Collection Rate by condensation (%) |
|---|---|---|---|
| A10-1C04 | 87 | 90 | 79 |
| A23-1A05 | 64 | 86 | 72 |
| A25-3H04 | 91 | 91 | 101 |
| A25-2C02 | 64 | 80 | 65 |
| A26-1F02 | 93 | 82 | 108 |

Example 9: Affinity with IL-33 Protein

Each test antibody (IgG) ("antibody (IgG)" indicates an antibody having a molecular form of IgG; hereinafter, the same representation is used) was analyzed to confirm the affinity with the human IL-33 protein by measuring dissociation constant (Kd) between each test antibody and the human IL-33 protein in PBS by kinetic exclusion assay (KinExA) (KinExA3200, available from Sapidyne Instruments, Inc.). Mixture samples of a test antibody and a human IL-33 protein (ILC0701, available from ATGen Co. Ltd) were prepared. The human IL-33 protein was titrated to a constant concentration of test antibody (final concentration: several tens of pM to several hundreds of pM) over a wide concentration range of the human IL-33 protein (so that it covered the concentrations of the human IL-33 protein resulting from 12-step serial doubling dilutions, i.e. one- to 2048-fold, with the upper limit of final concentration set to several nM to several tens of nM). The mixture samples were incubated at a room temperature until the antigen-antibody reaction reached equilibrium. After the reaction reached equilibrium, the percentage of free anti-IL-33 antibody in each sample was analyzed using KinExA3200. The values of Kd were calculated by fitting the plot of percentages of anti-IL-33 antibody not bound to the human IL-33 protein (vertical axis) and concentrations of antigen (horizontal axis) to a theoretical formula, using a KinExA data analysis program (KinExA Pro Software v3.5.3, available from Sapidyne Instruments, Inc.). Beads for capturing the anti-IL-33 antibody were prepared by suspending 50 mg of Azlactone beads (Sapidyne) in 1 mL of coating solution (10 µg/mL human IL-33 protein (ILC0701, available from ATGen Co. Ltd), 50 mM sodium carbonate at pH of 9.6) and incubating the solution at a room temperature for one hour. The antibody for detection used was anti-human F(ab)'2-DyLight649 (Jackson, 309-495-006). As shown in Table 12, the antibodies with modified complementarity-determining regions (A10-1C04, A23-1A05, A25-2C02, A25-3H04, A26-1F02) exhibited affinity with the human IL-33 protein of Kd=231 pM at the lowest (A23-1A05) and Kd=720 fM at the highest (A25-2C02), in the case where they were evaluated in the form of neutral-purified antibodies.

Each of the alkaline-purified antibodies was analyzed to confirm the affinity with the human IL-33 protein (residues 112 to 270) (ILC0701, available from ATGen Co. Ltd) or full-length human IL-33 protein with KinExA instrument (Table 12), as in the evaluation described above. The affinity with the human IL-33 protein (residues 112 to 270) was as follows: A10-1C04 exhibited affinity of Kd=100.3 pM; A23-1A05 exhibited affinity of Kd=195.3 pM; A25-2C02 exhibited affinity of Kd=700 fM; A25-3H04 exhibited affinity of Kd=7.7 pM; and A26-1F02 exhibited affinity of Kd=5.3 pM. The affinity with the full-length human IL-33 protein was as follows: A10-1C04 exhibited Kd=179.8 pM, and A26-1F02 exhibited affinity of Kd=10.4 pM.

The recombinant protein used as ligand was prepared by the following process. The gene sequence encoding the full-length human IL-33 protein was N-terminally linked with NusA tag-6His tag-TEV Protease cleaving sequence, and the resulting sequence was inserted into pET30a(+) to construct an expression vector to prepare the recombinant protein. *Escherichia coli* BL21 (DE3) strain including the expression vector was pre-cultured, and the bacterial cells were inoculated into 50 mL of LB medium at a density of OD=0.5, and were cultured with shaking for four hours at a temperature of 37° C. After four hours, the culturing temperature was changed to 13° C., and the cells were cultured with shaking for 30 minutes. IPTG was added to a final concentration of 0.1 mM, and the cells were further cultured with shaking for 72 hours at a temperature of 13° C. The *Escherichia coli* expressing the full-length IL-33 was thereby obtained. The *Escherichia coli* expressing the full-length IL-33 was bacteriolyzed with BugBuster Master Mix (Novagen), and then the supernatant fraction was collected by centrifugal separation. The supernatant fraction was then subjected to IMAC purification with HisTrap FF Crude column (GE Healthcare) and then to anion exchange purification with CaptoQ Impress column (GE Healthcare), to increase the protein purity. Each sample after the anion exchange was concentrated by centrifugal ultrafiltration using VIVASPIN6 (5,000 MWCO). To 1750 µL of the concentrate, 100 µL of Turbo TEV protease (Nacalai Tesque, Inc.) and 4.5 µL of 1M DTT were added. The resulting solution was incubated at a temperature of 4° C. to cleave the NusTag and HisTag. After the cleavage of the tags, the solution was passed through a Ni Sepharose Excel column (GE Healthcare) in order to remove the NusTag and Turbo TEV protease (fused with HisTag) in the solution, and the flow-through fraction was collected. DTT was added to the flow-through fraction to a final concentration of 3.3 mM, and the resultant was used as the full-length human IL-33 protein in the measurement with KinExA.

TABLE 12

| | Purification Method | | |
|---|---|---|---|
| | Neutral-Purified Antibody | Alkaline-Purified Antibody | |
| Ligand | Human IL-33 (Residues 112-270) | Human IL-33 (Residues 112-270) | Human IL-33 (Full-Length) |
| A10-1C04 | 166* | 100.3 | 179.8 |
| A23-1A05 | 231 | 195.3 | NCW |
| A25-3H04 | 5.38 | 7.7 | NCW |

TABLE 12-continued

| | Purification Method | | |
|---|---|---|---|
| | Neutral-Purified Antibody | Alkaline-Purified Antibody | |
| Ligand | Human IL-33 (Residues 112-270) | Human IL-33 (Residues 112-270) | Human IL-33 (Full-Length) |
| A25-2C02 | 0.72 | 0.7 | NCW |
| A26-1F02 | 10.8 | 5.3 | 10.4 |

*The numerical value in the table means dissociation constant of anti IL-33 monoclonal antibody (IgG) purified by a specific method for each ligand Example 10: Evaluation of In Vitro Neutralizing Activity Against Human IL-33 in HUVEC Each test antibody (IgG) was evaluated for in vitro neutralizing activity against human IL-33, based on IL-33-dependent IL-6 production by HUVEC as indicator. A commercially available polyclonal anti-IL-33 antibody (AF3625, available from R&D Systems, Inc.) was used as a positive control. HUVECs (CLC2517A, available from LONZA Group Ltd.) were suspended in an EGM-2 medium (CLCC-3156 and CLCC-4176, available from LONZA Group Ltd.), and were inoculated in a 96-well microplate (IWAKI) ($6\times10^3$/well), and the cell density was confirmed to be confluent. A mixed solution of each anti-IL-33 antibody (final concentration: 1 µg/mL (about 6.7 nM)) and a recombinant human IL-33 protein (ILC0701, available from ATGen Co. Ltd) (final concentration: 100 ng/mL (about 5 nM)) was added to the medium, and the resulting solution was incubated at a temperature of 37° C. for 24 hours. The medium was then collected, and the IL-6 concentration in the culture supernatant was measured with a commercially available ELISA kit (EH2IL6, available from Thermo Scientific). Cell viability after the collection of the medium was also measured with a cell counting kit (345-06463, available from Dojindo Molecular Technologies, Inc.), to confirm that the inhibitory effect on IL-6 production was not caused by a decrease in the viable cell count. The percentage of inhibition (%) of IL-6 production relative to the IL-6 production caused by the treatment with IL-33 alone was calculated to determine the IL-33 neutralizing activity of each test antibody. In the evaluation of neutral-purified form, A10-1C04 exhibited 67% inhibition, A23-1A05 exhibited 74% inhibition, A25-2C02 exhibited 96% inhibition, A25-3H04 exhibited 97% inhibition, A26-1F02 exhibited 96% inhibition, A00-0070 exhibited 4% inhibition, and A00-0036 exhibited −2% inhibition. The results demonstrate that the clones exhibited strong neutralizing activity, while the parental clones exhibited very low neutralizing activity. When the concentration was increased to 10 µg/mL, the parental clones exhibited moderate neutralizing activity: A00-0070 exhibited 42% inhibition, and A00-0036 exhibited 38% inhibition. The commercially available polyclonal antibody (AF3625, available from R&D Systems, Inc.) exhibited 30% inhibition, indicating moderate neutralizing activity, when it was added to a final concentration of 1 µg/mL.

As well as the evaluation above, a mixed solution of each alkaline-purified test antibody (final concentration: 0.1 to 10 µg/mL (about 0.67 to 67 nM)) and the recombinant human IL-33 (ILC0701, available from ATGen Co. Ltd) (final concentration: 100 ng/mL (about 5 nM)) was added to the HUVECs. The inhibitory effect on IL6 production relative to the IL-6 production caused by the treatment with IL-33 alone was calculated ($IC_{50}$ value) to determine the neutralizing activity of the antibody. The results were as follows: A10-1C04 had $IC_{50}$=0.35 µg/mL; A23-1A05 had $IC_{50}$=0.27

µg/mL; A25-2C02 had IC$_{50}$=0.19 µg/mL; A25-3H04 had IC$_{50}$=0.21 µg/mL; and A26-1F02 had IC$_{50}$=0.23 µg/mL.

Further, a mixture solution of each alkaline-purified antibody (final concentration: 0.1 to 3 µg/mL) and recombinant cynomolgus monkey IL-33 (prepared as in Example 7 and was used without biotinylation) (final concentration: 100 ng/mL) was added to the HUVECs. The inhibitory effect on IL6 production relative to the IL-6 production caused by the treatment with IL-33 alone was calculated (IC$_{50}$ value) to determine the neutralizing activity of the antibody. A10-1C04 had IC$_{50}$=0.43 µg/mL, and was confirmed to neutralize human IL-33 and cynomolgus monkey IL-33 at a similar level.

Example 11: Evaluation of In Vitro Neutralizing Activity Against Human IL-33 in KU-812 Cells Each test antibody (IgG) was evaluated for in vitro neutralizing activity against human IL-33, based on IL-33-dependent production of IL-5, IL-6, and IL-13 by KU-812 cells as indicator. A commercially available polyclonal anti-IL-33 antibody (AF3625, available from R&D Systems, Inc.) was used as a positive control. Human basophil cell line, KU-812 cells (ECACC, EC90071807) were inoculated in a 96-well microplate (Falcon) (1×10$^4$/well). A mixed solution of each test antibody (final concentration: 3 µg/mL (about 20 nM)) and a recombinant human IL-33 protein (ILC0701, available from ATGen Co. Ltd) (final concentration: 100 ng/mL (about 5 nM)) was added to the medium, and the resulting solution was incubated at a temperature of 37° C. for 24 hours. The concentrations of IL-5, IL-6, and IL-13 in the RPMI-1640 medium containing 10% FBS were measured using Human IL-5 Flex set, Human IL-6 Flex set, and Human IL-13 Flex set of BD™ Cytometric Bead Array (BD Biosciences). Cell viability after the collection of the medium was also measured with a cell counting kit (345-06463, available from Dojindo Molecular Technologies, Inc.), so as to confirm that the inhibitory effect on the production of IL-5, IL-6, and IL-13 was not caused by a decrease in the viable cell count. In the evaluation of neutral-purified form, A26-1F02 inhibited production of IL-5, IL-6, and IL-13 by 70%, 82%, and 72%, respectively, in this evaluation system. The results indicate that A26-1F02 exhibited stronger neutralizing activity on production of all the cytokines, as compared to the commercially available polyclonal antibody (it exhibited 47%, 51%, and 41% inhibition, respectively).

As in the evaluation above, a mixed solution of each alkaline-purified test antibody (final concentration: 100 to 0.01 µg/mL (about 667 to 0.067 nM)) and the recombinant human IL-33 (ILC0701, available from ATGen Co. Ltd) (final concentration: 3 ng/mL (about 0.15 nM)), human IL-3 (PeproTech, 200-03; final concentration: 10 ng/mL (about 0.67 nM)), and human complement C5a (C5788, available from Sigma-Aldrich Co. LLC.) (final concentration: 1 nM) was added to the KU-812 cells. The resulting solution was incubated at a temperature of 37° C. for 24 hours. The concentrations of IL-5 and IL-13 in the RPMI-1640 medium containing 10% FBS were measured. Cell viability after the collection of the medium was also measured with a cell counting kit, so as to confirm that the inhibitory effect on the production of IL-5 and IL-13 was not caused by a decrease in the viable cell count. In this evaluation system, alkaline-purified test antibodies (A10-1C04, A23-1A05, A25-2C02, A25-3H04, and A26-1F02) each exhibited an inhibitory effect of 50% or higher inhibition against production of IL-5 and IL-13 at a final concentration of 1 µg/mL.

Example 12: Evaluation of In Vitro Neutralizing Activity Against Human IL-33 in Human Peripheral Blood Mononuclear Cells Each test antibody (IgG) was evaluated for in vitro neutralizing activity against human IL-33, based on IL-33-dependent IFN-γ production by human peripheral blood mononuclear cell (PBMC) as indicator. A commercially available polyclonal anti-IL-33 antibody (AF3625, available from R&D Systems, Inc.) was used as a positive control. PBMCs were prepared and were inoculated in a 96-well microplate (2×10$^5$/well), and a recombinant human IL-12 (Wako Pure Chemical Industries, Inc.) was added (final concentration: 10 ng/mL) to the microplate. A mixture of each test antibody and a recombinant human IL-33 protein (10 ng/mL) was added to the microplate, and the resulting solution was incubated at a temperature of 37° C. for 48 hours. The culture supernatant was then collected, and the IFN-γ production level in the medium was measured with AlfaLISA™ human IFN-γ immunoassay kit (PerkinElmer Inc.) to evaluate IL-33 neutralizing activity. In this evaluation system, when the alkaline-purified antibodies were allowed to act at a final concentration of 10 µg/mL, the inhibition percentages were as follows: A10-1C04 exhibited 96.9% inhibition, A23-1A05 shows 97.5% inhibition, A25-2C02 exhibited 98.75% inhibition, A25-3H04 exhibited 97.9% inhibition, and A26-1F02 exhibited 98.25% inhibition.

Example 13: Evaluation of Effects on Inflammation Induced by Intraperitoneal Administration of Human IL-33

Intraperitoneal administration of human IL-33 to mice induced various inflammatory changes, i.e. increases in blood IgE, IgA, and IL-5, and blood neutrophil count, blood eosinophil count, and blood basophil count, and an increase in splenic cells (an increase in spleen weight), and pathological changes in various mucosal organs. Based on these changes as indicators, anti-inflammatory action in vivo of test antibody (IgG) was evaluated.

Human IL-33 protein (R&D Systems, 3625-IL-010) was intraperitoneally administered to male C57BL6 (six- to eight-weeks-old) (Charles River Laboratories International, Inc.) at a dose of 0.4 µg/individual for seven days (day 0 to day 6). The test antibody (IgG) was also administered intraperitoneally for seven days (day 0 to day 6). Seven days after initiation of the administration (day 7), the animals administered with PBS instead of human IL-33 protein (represented as "vehicle" in the figures) had a mean spleen weight of 76±4 mg, while the animals administered with IL-33 protein had a mean spleen weight of 90±7 mg. The animals intraperitoneally administered with 10 mg/kg (represented as "mpk" in the figures) of human control IgG (MP Biomedicals, 55908) in addition to the IL-33 protein had a mean spleen weight of 93±4 mg, while the animals intraperitoneally administered with 10 mg/kg of the neutral-purified antibody A26-1F02 in addition to the IL-33 protein had a mean spleen weight of 66±3 mg.

Figure 8:
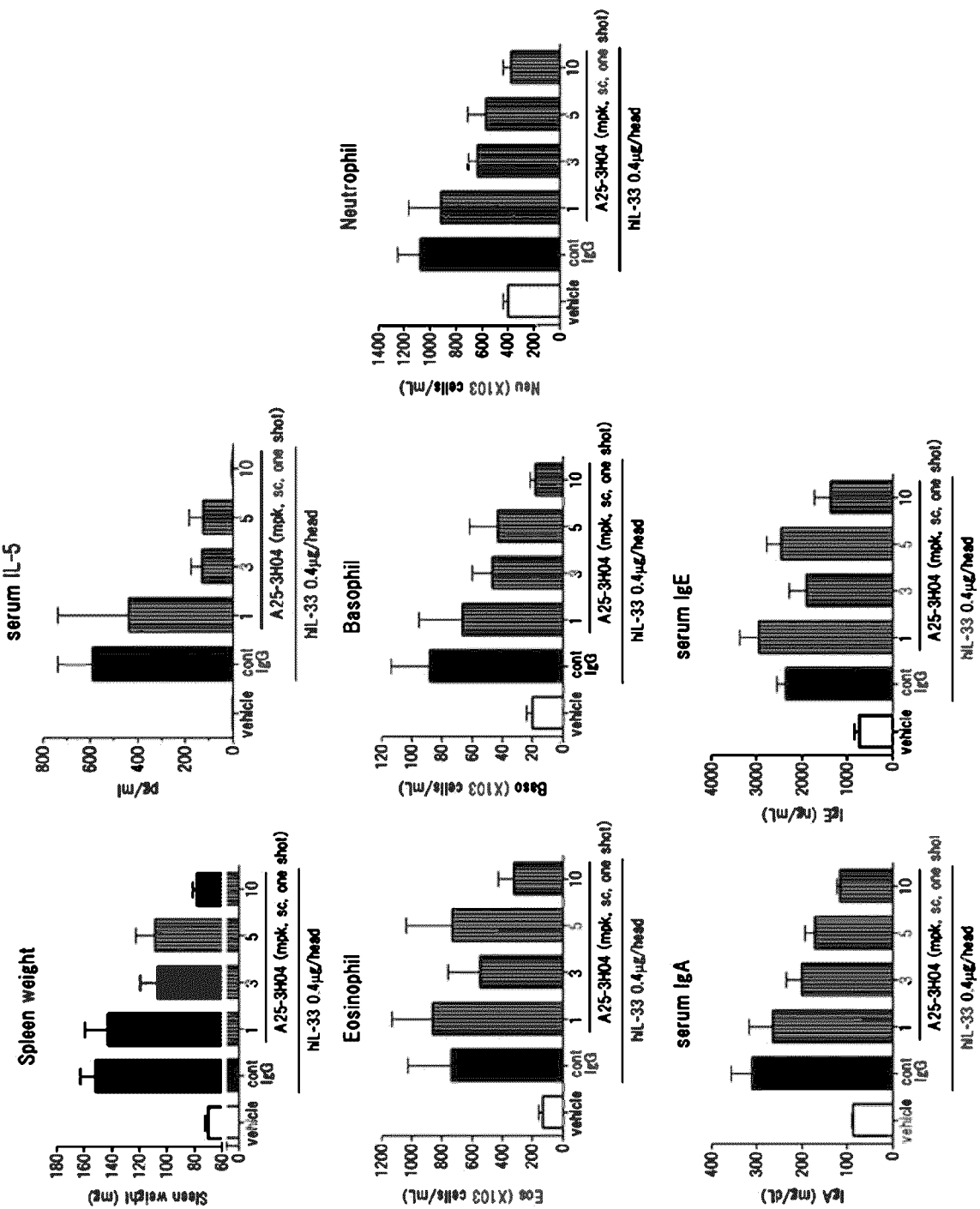
FIG. 8 shows effects of a human anti-IL-33 neutralizing monoclonal antibody designated A25-3H04 on inflammation induced by intraperitoneal administration of human IL-33, based on inflammatory markers (spleen weight, serum IL-5 concentration, blood eosinophil count, blood basophil count, blood neutrophil count, serum IgA concentration, and serum IgE concentration).

The alkaline-purified antibody was then evaluated. The alkaline-purified antibody was subcutaneously administered only once (sc, one shot), on the day before the administration of the human IL-33 protein (Day −1) and the evaluation was performed. Seven days after initiation of the administration (day 7), the animals administered with PBS instead of human IL-33 protein had a mean spleen weight of 70 mg, while the animals subcutaneously administered only once with the human control IgG (10 mg/kg) in addition to the IL-33 protein had a mean spleen weight of 152 mg. Contrarily, the animals subcutaneously administered with A25-3H04 (1, 3, 5, and 10 mg/kg) in addition to the IL-33 protein had spleen weights of 143, 106, 109, and 78 mg, respectively, as shown in FIG. 8. The results indicated that A25-3H04 exhibited dose-dependent inhibition of increase in spleen weight caused by inflammation. In addition to the anti-inflammatory effects on the spleen weight, A25-3H04 was confirmed to have anti-inflammatory effects on increases in serum IgA concentration, serum IgE concentration, blood neutrophil count, blood basophil count, and blood eosinophil count, and serum IL-5 concentration, which had been caused by administration of human IL-33 (FIG. 8). These results confirm that A25-3H04 exhibits inhibitory effect on the inflammatory response induced in vivo by IL-33. The blood A25-3H04 concentration in mice was measured seven days after the initiation of the administration (day 7). The measured concentrations in the animals administered with the antibody at doses of 1, 3, 5, and 10 mg/kg, respectively, were 0.6, 3.7, 6.5, and 20.3 µg/ml.

Figure 9:
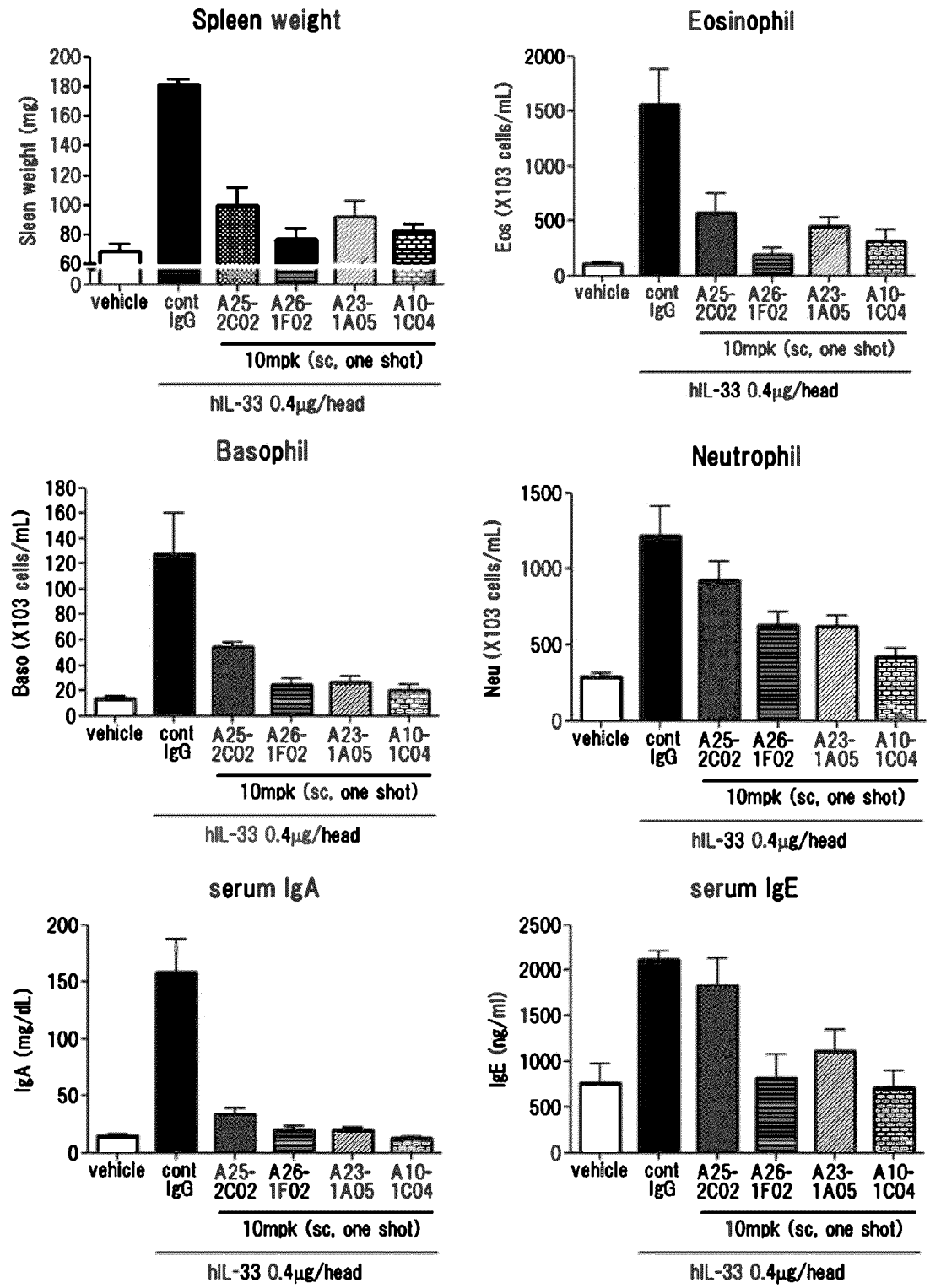
FIG. 9 shows effects of human anti-IL-33 neutralizing monoclonal antibodies designated A10-1C04, A23-1A05, A25-2C02, and A26-1F02 on inflammation induced by intraperitoneal administration of human IL-33, based on inflammatory markers (spleen weight, blood eosinophil count, blood basophil count, blood neutrophil count, serum IgA concentration, and serum IgE concentration).

Other test antibodies (IgG) were also evaluated for in vivo anti-inflammatory effects by subcutaneous administration in accordance with the same protocol (10 mg/kg). As a result, the animals subcutaneously administered with human control IgG had a mean spleen weight of 181 mg, the animals subcutaneously administered with alkaline-purified antibody (A10-1C04, A23-1A05, A25-2C02, or A26-1F02) in addition to administration of IL-33 protein had mean spleen weights of 82 mg, 92 mg, 100 mg, and 77 mg, respectively, as shown in FIG. 9. The results indicate that each antibody inhibited increase in spleen weight caused by inflammation. In addition to the anti-inflammatory effects on the spleen weight, each alkaline-purified antibody (A10-1C04, A23-1A05, A25-2C02, and A26-1F02) was confirmed to have anti-inflammatory effects on increases in serum IgA concentration, serum IgE concentration, blood neutrophil count, blood basophil count, and blood eosinophil count, which had been caused by administration of human IL-33 protein (FIG. 9). These results confirm that these antibodies (A10-1C04, A23-1A05, A25-2C02, and A26-1F02), in addition to A25-3H04, also exhibit inhibitory effects on the inflammatory response induced in vivo by IL-33.

Example 14: Evaluation of Effects on Pulmonary Disorders Induced by Intratracheal Administration of Human IL-33

Mice are intratracheally administered with human IL-33 protein, and then the bronchoalveolar lavage fluid (BALF) is collected from the mice. Increases in the total cell count, eosinophil count, and neutrophil count are observed in the BALF, and mucosal hyperplasia in the tracheal epithelium is observed. Production of cytokines, such as IL-4, IL-5, IL-6, and IL-13, is also observed in the BALF. Effects of each test antibody on the pulmonary disorders can be evaluated by intraperitoneal, subcutaneous, or intravenous administration of the test antibody (IgG) to the system.

Example 15: Evaluation of Effects on Airway Hyperresponsiveness Induced by Intranasal Administration of Human IL-33

Intranasal administration of an IL-33 protein induces airway hyperresponsiveness to subsequently inhaled methacholine. Effects of the test antibody on airway hyperresponsiveness can be evaluated by intraperitoneal, subcutaneous, or intravenous administration of the test antibody (IgG) to the evaluation system.

Example 16: Evaluation of Effects of IL-33 on Human IL-33-Knockin Mice

Administration of *Dermatophagoides* antigen or papain to human IL-33-knockin mice by nasal dripping or intratracheal administration induces airway inflammation. The BALF collected from the mice exhibits an increased total cell count in the BALF. Regarding airway inflammation induced by *Dermatophagoides* antigen or papain, it is known that protease activity of *Dermatophagoides* antigen or papain causes release of IL-33 from the airway epithelial cells (Oboki et al., Proceedings of the National Academy of Sciences of the United States of America, 2010, vol. 107, p 18581). Effects of each test antibody on the protease-induced airway inflammation and on IL-33-induced in vivo can be evaluated by intraperitoneal, subcutaneous, or intravenous administration of the test antibody (IgG) to the evaluation system.

Example 17: Evaluation of Anti-Inflammatory Effects on Sepsis Model Intraperitoneally Administered with LPS Intraperitoneal administration of LPS to human IL-33-knockin mice induces sepsis (Oboki et al., Proceedings of the National Academy of Sciences of the United States of America, 2010, vol. 107, p 18581). Intraperitoneal, subcutaneous, or intravenous administration of the test antibody (IgG) prior to the administration of LPS allows evaluation of effects of the test antibody on subsequent mortality of the mice. Inflammatory cytokines, such as IL-6 and TNF-α, are detected in blood at high concentrations within several hours after the administration of LPS. Anti-inflammatory effects of the test antibody can be evaluated by measuring concentrations of such inflammatory cytokines.

Example 18: Evaluation of In Vivo Effects on Cancer in Cancer-Bearing Mice

Murine or human cancer cell line cells are subcutaneously or intravenously transferred into mice, and are then administered with human IL-33. The number of cells to be transferred is appropriately determined depending on the cancer cell line, and the site of transfer is the same among animals. The mice are administered intraperitoneally, subcutaneously or intravenously with each test antibody (IgG), and are analyzed to confirm the number of cancer cells in the primary cancer site and in the metastatic lesion in other organ after the transfer of the cancer cell line cells on the basis of volume or cell count. The effects of each test antibody on cancer can be thereby evaluated.

Example 19: Evaluation of Colloidal Stability of Antibodies

Each test antibody (IgG) was analyzed to confirm colloidal stability by dynamic light scattering based on the presence of aggregates. Each alkaline-purified antibody was concentrated to a level of approximately 50 mg/mL with VIVASPIN or VIVASPIN TURBO (available from Sartorius AG; 10000 to 50000 MWCO). The centrifugation was performed at a temperature of 4° C., while the revolutions per minute and the duration were appropriately changed. The solution of each test antibody was sequentially diluted, and 200 to 250 μL of each sample was subjected to measurement of dynamic light scattering (Nanotrac UPA UT-151, available from NIKKISO CO., LTD.), to obtain data within a concentration range covering approximately 1 mg/mL to approximately 50 mg/mL. The particle size distribution of each antibody protein was calculated based on the data accumulated over 200 seconds, to evaluate the presence of aggregates. The particle size distribution of the test antibodies (A10-1C04, A23-1A05, A25-2C02, A25-3H04, and A26-1F02) showed a very slight peak shift from approximately 10 nm towards larger particle sizes along with the increase of antibody concentration, and did not have peak at particle size exceeding several tens of nanometers, i.e. it did not have a peak assumed not to be dependent on the antibody concentration but to be caused by irreversible aggregation. These results confirm that the test antibodies have excellent colloidal stability.

In order to quantitatively evaluate the colloidal stability, the interaction parameter ($k_D$) was calculated. The interaction parameter indicates concentration dependence of the diffusion coefficient (inversely proportional to the particle size), and is an important indicator used in formulation design of high-concentration protein formulations, such as antibodies. It is reported that an interaction parameter greater than −12.4 mL/g indicates high colloidal stability and low self-association due to repulsive interaction (Saito et al., Pharm. Res., 2013. Vol. 30 p. 1263). Each test antibody solution dissolved in PBS (at pH of 7.2) was concentrated by ultrafiltration to a concentration of several tens of mg/mL, and was subjected to serial doubling dilutions with the same solvent to prepare samples. Each sample was analyzed to confirm the particle size with a dynamic light scattering analyzer (Nanotrac UPA UT 151, available from NIKKISO CO., LTD.). Based on the measured particle size, the diffusion coefficient was calculated by the following Stokes-Einstein equation:
[Mathematical Formula 1]
where D is the diffusion coefficient (cm²/sec); $K_B$ is the Boltzmann's constant (J/K); T is the thermodynamic temperature (K); π is the constant Pi; η is the viscosity P (poise) of the diluted solution; and d is the particle size (nm).

The concentration dependence of the diffusion coefficient was plotted, and the plot was fit to the following equation to determine the interaction parameter.
[Mathematical Formula 2]
where D is the diffusion coefficient calculated by the Stokes-Einstein equation; Do is the diffusion coefficient in the infinite dilution; and c is the measured concentration of each test antibody (g/mL). Based on the equation, the interaction parameter ($k_B$) representing the inclination of the fitting line was calculated. The results are as follows: A10-1C04 had an interaction parameter $k_D$=−8.1 mL/g (analytical range: 0.41-63.7 mg/mL); A23-1A05 had an interaction parameter $k_D$=−5.6 mL/g (analytical range: 0.40-61.8 mg/mL); A25-2C02 had an interaction parameter $k_D$=−6.2 mL/g (analytical range: 0.43-66.3 mg/mL); A25-3H04 had an interaction parameter $k_D$=−7.5 mL/g (analytical range of 0.34-56.5 mg/mL); A26-1F02 had an interaction parameter $k_D$=−6.7 mL/g (analytical range: 0.35-62.7 mg/mL). The results demonstrate that all the test antibodies had an interaction parameter exceeding −12.4 mL/g, indicating excellent colloidal stability.

Example 20: Evaluation of Thermodynamic Stability of Antibodies

Each test antibody (IgG) was analyzed to confirm thermodynamic stability at a temperature where the folding of immunoglobulin domain disappeared (Tm). Protein Thermal Shift Dye (Life Technologies) was added to each test antibody solution at a concentration of several tens of μg/mL in accordance with the instruction manual. The fluorescence intensity of the diluted solution was measured with Real-Time PCR 7500 Fast (Life Technologies) while the temperature was increased at a rate of about 1° C./min. The obtained data was analyzed with Protein Thermal Shift (Life Technologies) to determine the temperature Tm. If two or more temperatures Tm were observed, the lowest temperature was defined as Tm1, the second lowest temperature as Tm2, and so on. The results of evaluation of neutral-purified antibodies were as follows: A10-1C04 had Tm=73.9° C.; A23-1A05 had Tm1=69.3° C. and Tm2=77.6° C.; A25-2C02 had Tm1=69.3° C. and Tm2=80.3° C.; A25-3H04 had Tm1=70.0° C. and Tm2=76.4° C.; and A26-1F02 had Tm=74.5° C. The results of evaluation of alkaline-purified antibodies were as follows: A10-1C04 had Tm=73.7° C.; A23-1A05 had Tm1=69.5° C. and Tm2=77.5° C.; A25-2C02 had Tm1=69.5° C. and Tm2=80.4° C.; A25-3H04 had Tm1=70.1° C. and Tm2=76.4° C.; and A26-1F02 had Tm=74.4° C. The results indicate that all antibodies had a temperature Tm exceeding 65° C., demonstrating excellent thermodynamic stability.

Example 21: Evaluation of Preservation Stability of Antibodies

Each alkaline-purified antibody was dissolved in a citrate buffer (50 mM citric acid; 150 mM NaCl (pH: 6.3)) at a concentration of about 10 mg/mL, and was preserved at a temperature of 40° C. for four weeks, to evaluate the preservation stability of each test antibody (IgG). For evaluation of the monomer purity of each antibody after the preservation, monomer purity was measured by size exclusion chromatography analysis (SEC) and microchip capillary SDS electrophoresis (mCE-SDS), and antigen-binding activity was measured by surface plasmon resonance.

Two TSKgel G3000SWXL columns (available from Tosoh Bioscience LLC) were linked together and were mounted on an HPLC system (Beckman System Gold (126 solvent manager, 166 detector, and 508 auto sampler)) and gel filtration analysis was performed. The mobile phase solvent was 0.1 M phosphate buffer (at pH of 6.7) containing 0.1 M sodium sulfate. Each sample was separated at a flow rate of 0.5 mL/min, and was detected at absorbance of UV 215 nm. The sample for analysis was prepared by diluting about 10 mg/mL of the preserved antibody solution to 100-fold, and 50 μL of the sample for analysis was injected to the columns. Monomer purity determined by the size exclusion chromatography is shown in Table 13. The results indicate that all the test antibodies (A10-1C04, A23-1A05, A25-2C02, A25-3H04, and A26-1F02) retained a monomer purity exceeding 90% after preservation at a temperature of 40° C. for four weeks, demonstrating excellent preservation stability.

Capillary SDS electrophoresis was performed using Lab Chip GX II (available from PerkinElmer Inc.). Each sample was reduced with the reagent kit dedicated for the system, HT Protein Express Reagent (available from PerkinElmer Inc.), in accordance with the manufacturer's standard protocol, under denaturing conditions. As an analytical sample, 2 μL of preserved antibody solution with a concentration of about 10 mg/mL was added. The reagent used for the electrophoresis was taken from the kit and was added to a dedicated chip, HT Protein Express Lab Chip, version 2 (available from PerkinElmer Inc.), and the sample was measured in accordance with the built-in protocol for analysis of antibodies, HT Antibody 200. As shown in Table 13, under denaturing and reducing conditions, all the test antibodies (A10-1C04, A23-1A05, A25-2C02, A25-3H04, and A26-1F02) retained a monomer purity exceeding 90% after preservation at a temperature of 40° C. for four weeks, demonstrating excellent preservation stability.

In order to confirm the presence or absence of irreversible aggregation not dependent on the antibody concentration after the preservation, the particle size of each test antibody was measured. Each sample for analysis was prepared by diluting each preserved antibody solution to 10-fold with a citrate buffer (50 mM citric acid, 150 mM NaCl (pH: 6.3)) (final concentration: about 1 mg/mL), and was analyzed by dynamic light scattering technique (Nanotrac UPA UT-151, available from NIKKISO CO., LTD.) to measure the particle size of each test antibody. The accumulation time was 200 seconds. No aggregate was detected in the analysis of the test antibodies (A10-1C04, A23-1A05, A25-2C02, A25-3H04, A26-1F02, A00-0070, A00-0036) after preservation at a temperature of 40° C. for four weeks, demonstrating excellent preservation stability.

In order to confirm the presence of the antigen-binding ability after the preservation, the antigen-binding activity was measured with a surface plasmon resonance system, Biacore T200 (available from GE Healthcare). A human IL-33 protein (ILC0701, available from ATGen Co. Ltd) was immobilized onto a Sensor Chip CM5 (GE Healthcare) (the amount of immobilized protein was about 3000 to 6000 RU) with Amine Coupling Kit (GE Healthcare). Each preserved antibody solution was then diluted to 10-fold with a citric buffer (50 mM citric acid, 150 mM NaCl (pH: 6.3)), and the resulting solution was analyzed to measure the total protein concentration in the solution, using a microvolume spectrophotometer, Astragene II (Astranet Systems, Ltd.) (protein concentration: about 1 mg/mL). The antibody solution after the measurement of the total protein concentration was diluted to 1000-fold with HBS-EP buffer (10 mM HEPES, 150 mM NaCl, 3 mM EDTA, 0.05% (v/v) Surfactant P20 (at pH of 7.4)). The analyte was thereby prepared. The measurement temperature was 25° C. Each analyte was added for 36 seconds at two flow rates of 5 µL/min and 100 µL/min to obtain sensorgrams of the association phase. The sensorgrams were then analyzed by Calibration Free Concentration Analysis using a data analysis program (GE Healthcare, Biacore T200 Evaluation Software v1.0) to determine the concentration of the antibody having antigen-binding activity. As control, each test antibody after preservation at a temperature of 4° C. for four weeks was also analyzed to confirm the antigen-binding activity, to calculate the ratio of antigen-binding activity of each test antibody after the preservation at a temperature of 40° C. for four weeks. As shown in Table 13, all the test antibodies (A10-1C04, A23-1A05, A25-2C02, A25-3H04, and A26-1F02) retained antigen-binding activity exceeding 90% even after preservation at a temperature of 40° C. for four weeks, demonstrating excellent preservation stability.

TABLE 13

| | Preservation Stability at 40° C. for 4 W | | |
|---|---|---|---|
| Antibody | SEC % monomer | mCE-SDS % monomer | Antigen Binding Activity % Active IgG |
| A23-1A05 | 95.8 | 97.7 | 101.8 |
| A10-1C04 | 96.5 | 97.4 | 99.3 |
| A26-1F02 | 95.9 | 98.2 | 101.1 |
| A25-2C02 | 95.7 | 97.9 | 100.4 |
| A25-3H04 | 95.8 | 98.0 | 101.8 |

Example 22: Evaluation of Stability of Antibodies by Forced Oxidation

Each test antibody (IgG) was analyzed to confirm influences of oxidation on its antigen-binding activity. To each alkaline-purified antibody with a final concentration of about 1 mg/mL, a hydrogen peroxide solution (final concentration: 1%) was added, and the resulting solution was oxidized at a temperature of 37° C. for 24 hours. To the resulting solution, 80 mM methionine solution was then added to stop oxidation. Each test antibody solution was then replaced with PBS with a desalting column, Zebaspin (available from Thermo Scientific). The oxidized test antibodies were each analyzed with a surface plasmon resonance system Biacore T200 (GE Healthcare) to confirm antigen-binding activity, as in Example 21. The ratio of antigen-binding activity of the oxidized antibody to that of untreated test antibody was calculated. The results are as follows: A10-1C04 retained 83% binding activity, A23-1A05 retained 95% binding activity, A25-2C02 retained 100.5% binding activity, A25-3H04 retained 98.7% binding activity, and A26-1F02 retained 89.5% binding activity. These results indicate that all the test antibodies (A10-1C04, A23-1A05, A25-2C02, A25-3H04, and A26-1F02) exhibited stability such that they retained antigen-binding activity exceeding 80% even after forced oxidation by treatment with 1% hydrogen peroxide solution.

Example 23: Evaluation of Aggregation Caused by Physical Stress (Stirring)

Each test antibody (IgG) was diluted with PBS to a concentration of 0.2 mg/mL, and the diluted solution was stirred in a batch cell placed on the Aggregates Sizer (available from Shimadzu Corporation) to apply physical stress. Each solution was stirred by vertical motion of stirring plate at a room temperature for 30 minutes (190 vibrations/min), and then was analyzed to confirm concentrations of aggregates having a particle size of 40 nm to 20 µm with the Aggregates Sizer. In the evaluation of each alkaline-purified antibody, the concentrations of aggregates produced by stirring were as follows: 17.2 µg/mL in A10-1C04; 16.4 µg/mL in A23-1A05; 13.3 µg/mL in A25-2C02; 23.4 µg/mL in A25-3H04; and 17.0 µg/mL in A26-1F02. The results indicate that all the antibodies exhibited 15% or less aggregation induced by physical stress, demonstrating that all the test antibodies were stable against physical stress.

Example 24: Evaluation of Plasma Concentration of the Antibodies in Mice

Figure 10:
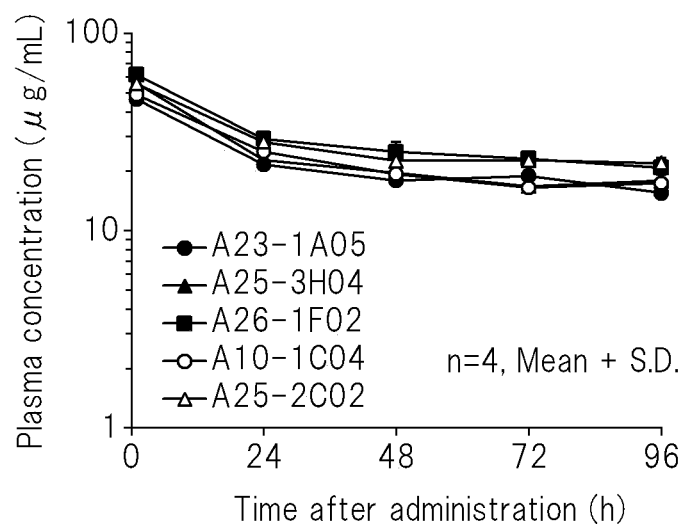
FIG. 10 shows variations in plasma concentration of each of the human anti-IL-33 neutralizing monoclonal antibodies (A23-1A05, A25-3H04, A26-1F02, A10-1C04, and A25-2C02) in mice.

Each test antibody (IgG) was fluorescent-labeled, and was intravenously administered (3 mg/kg) to male C57BL6 mice (eight- to ten-weeks-old) (Charles River Laboratories International, Inc.). The concentration of the test antibody was measured by detecting the fluorescence in the plasma. As shown in FIG. 10, in the evaluation of each alkaline-purified antibody, all the test antibodies (A10-1C04, A23-1A05, A25-2C02, A25-3H04, and A26-1F02) had an elimination half-life of 100 hours or more, indicating good pharmacokinetic profile.

Example 25: Evaluation of Serum Concentration of the Antibodies in Monkeys

Figure 11:
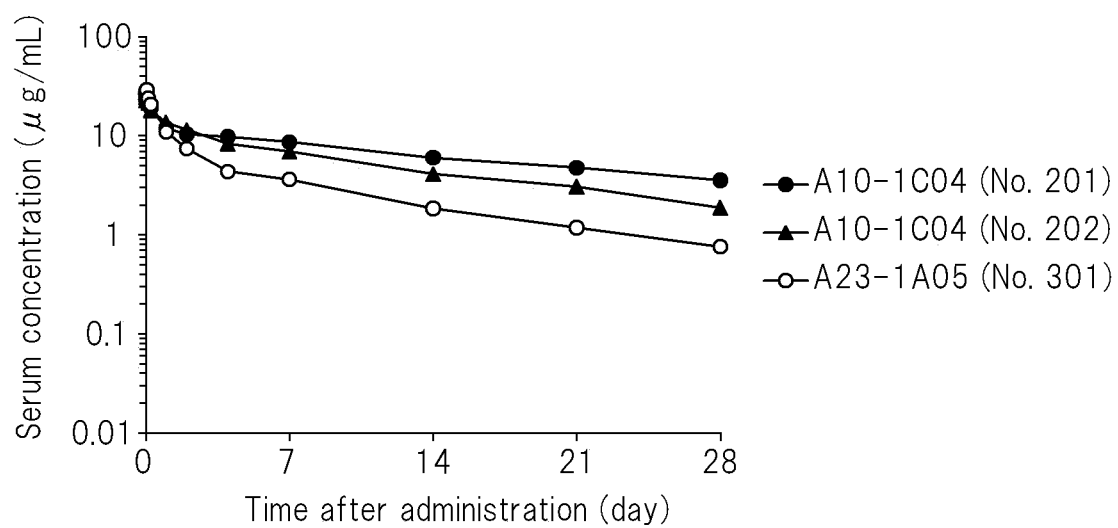
FIG. 11 shows variations in serum concentration of each of the human anti-IL-33 neutralizing monoclonal antibodies (A10-1C04 and A23-1A05) in monkeys.

Each test antibody (IgG) (1 mg/kg) was intravenously administered to male cynomolgus monkeys (two- to three-years old) (Hamri Co., Ltd.), and then the serum concentration of the test antibody was measured with Human Therapeutic IgG1 EIA Kit (500910, available from Cayman Chemical). The alkaline-purified antibody A10-1C04 was administered to two cynomolgus monkeys (Nos. 201 and 202), and the alkaline-purified antibody A23-1A05 was administered to one cynomolgus monkey (No. 301). As shown in FIG. 11, the elimination half-life of A10-1C04 was 16.56 days (No. 201) and 11.40 days (No. 202), and the clearance was 3.598 mL/day/kg (No. 201) and 5.451 mL/day/kg (No. 202). A23-1A05 had an elimination half-life of 10.87 days, and a clearance of 10.07 mL/day/kg. Both test antibodies exhibited good pharmacokinetic profiles in cynomolgus monkeys.

Example 26: Evaluation of Immunogenicity of Antibodies

Each test antibody (IgG) was evaluated for immunogenicity potential by in vitro T-cell assay (LONZA Group Ltd.). Samples were collected from 50 donors to represent the target population, and 50 µg/mL of each alkaline-purified antibody was added to dendritic cells of human peripheral blood collected from the donors, so that the antibody was taken in the dendritic cells. CD4-positive T-cells of human peripheral blood collected from an identical donor were isolated. Subsequently, both cells, that is, the dendritic cells which had taken the test antibody and the CD4-positive T-cells, were co-cultured, to determine the reaction (proliferation) of the CD4-positive T-cells. As a negative control, a buffer (PBS) not containing any test antibody was used in the same reaction of CD4-positive T-cells, and the results were compared to evaluate the immunogenicity potential of each antibody. The results indicate that none of the test antibodies (A10-1C04, A25-2C02, A25-3H04, and A26-1F02) showed immunogenicity potential in the test condition Example 27: Evaluation of Human Tissue Cross-Reactivity Each test antibody (IgG) was evaluated for cross-reactivity to human tissues (frozen specimen of 35 tissues which satisfy the FDA and EMA guidelines, from one donor) by immunohistochemical staining (Covance Laboratories Ltd.). The 35 tissues include adrenal gland, bladder, blood cells, bone marrow, mammary gland, cerebellum, cerebral cortex, colon, endothelial cells (blood vessel), eyeball, oviduct, gastrointestinal tract (including smooth muscle), heart, kidney (glomerulus and renal tubule), liver, lung, lymph node, ovary, pancreas, parathyroid gland, parotid gland, peripheral nerve, pituitary gland, placenta, prostate gland, skin, spinal cord, spleen, striated muscle, testis, thymus, thyroid, tonsil, ureter, and uterus (cervical region and, endometrium). As a result, in the evaluation of alkaline-purified antibodies, all the test antibodies (A10-1C04, A23-1A05, A26-1F02, and A25-2C02) intensively stained vascular endothelial cells (positive control). IL-33 is known to be broadly expressed in the vascular endothelial cells. In various tissues such as epithelium, interstitial cells, neural tissues, muscular tissues, and hemocytes, cross-reactivity to the cytoplasm or nucleus was confirmed, but cross-reactivity to the cytoplasmic membrane was not observed in any tissue. According to the ICH S6(R1) guidelines and other articles (Toxicologic Pathology 2010, 38(7):1138-1166), cross-reactivity to the cytoplasm or nucleus, where an antibody is less likely to reach in vivo, has less toxicological significance. Therefore, none of the test antibodies (A10-1C04, A23-1A05, A26-1F02, and A25-2C02) exhibited toxicological concern.

Example 28: Narrowing of the Epitope Regions of A10-1C04 and A25-3H04

The anti-IL-33 monoclonal antibodies A10-1C04 and A25-3H04 bound to the epitope PEP14 as described in the Example 1. Experiments were performed with a phage display library of continuous amino acid sequences that are included in PEP14 consisting of 20 amino acids and are shorter than PEP14, and two different epitopes (LEDESYEIYV (SEQ ID NO:426 in the Sequence Listing) and EDESYEIYV (SEQ ID NO:427 in the Sequence Listing)) were found. The peptide LEDESYEIYV corresponds to the sequence spanning residues 138 to 147 of human IL-33 shown in SEQ ID NO:226 in the Sequence Listing, and the peptide EDESYEIYV corresponds to the sequence spanning residues 139 to 147 of human IL-33 shown in SEQ ID NO:226 in the Sequence Listing. These peptides were synthesized, and the affinity with the alkali-purified antibodies was calculated as Kd by the KinExA experiment as in Example 9 (Table 14).

TABLE 14

| Peptide | Kd | |
| --- | --- | --- |
| | A10-1C04 | A25-3H04 |
| DQSITFALEDESYEIYVEDL (PEP14) | 9.0 nM | 1.5 pM |
| LEDESYEIYV | 386.2 nM | 11.0 nM |
| EDESYEIYV | 2070.0 nM | 301.3 nM |

INDUSTRIAL APPLICABILITY

The antibody with neutralizing effect of the present invention can be used as a pharmaceutical composition for diagnosis, treatment, prevention, or alleviation of diseases associated with IL-33.

What is claimed is:

1. A monoclonal antibody,
wherein the monoclonal antibody is capable of binding to an epitope consisting of a continuous amino acid sequence included in positions 131 to 150 of SEQ ID NO:226 in the Sequence Listing,
wherein the monoclonal antibody comprises either:
(a) a light-chain complementarity-determining region 1 (LCDR1) comprises a sequence selected from the group consisting of SEQ ID NO:1 and SEQ ID NO:2, a light-chain complementarity-determining region 2 (LCDR2) comprises a sequence of SEQ ID NO: 11, a light-chain complementarity-determining region 3 (LCDR3) comprises a sequence selected from the group consisting of SEQ ID NOs:22-24, a heavy-chain complementarity-determining region 1 (HCDR1) comprises a sequence selected from the group consisting of SEQ ID NOs:43-46, a heavy-chain complementarity-determining region 2 (HCDR2) comprises a sequence selected from the group consisting of SEQ ID NO:51-54 and 64, and a heavy-chain complementarity-determining region 3 (HCDR3) comprises a sequence of SEQ ID NO:65; or
(b) a light-chain complementarity-determining region 1 (LCDR1) comprises a sequence selected from the group consisting of SEQ ID NOs:3-10, a light-chain complementarity-determining region 2 (LCDR2) comprises a sequence selected from the group consisting of SEQ ID NOs:12-21, a light-chain complementarity-determining region 3 (LCDR3) comprises a sequence selected from the group consisting of SEQ ID NOs: 25-42, a heavy-chain complementarity-determining region 1 (HCDR1) comprises a sequence selected from the group consisting of SEQ ID NOs:47-50, a heavy-chain complementarity-determining region 2 (HCDR2) comprises a sequence selected from the group consisting of SEQ ID NO:55-64, and a heavy-chain complementarity-determining region 3 (HCDR3) comprises a sequence of SEQ ID NO:66-78.

2. The antibody according to claim 1, wherein the epitope consists of at least 6 amino acids.

3. The antibody according to claim 2, wherein the dissociation constant against human IL-33 is not more than 231 pM.

4. The antibody according to claim 1, wherein the epitope consists of a continuous amino acid sequence of positions 138 to 147 or positions 139-147 of SEQ ID NO:226 in the Sequence Listing.

5. The antibody according to claim 4, wherein the dissociation constant against human IL-33 is not more than 231 pM.

6. The antibody according to claim 1, wherein the epitope consists of a continuous amino acid sequence of positions 131 to 150 of SEQ ID NO:226 in the Sequence Listing.

7. The antibody according to claim 6, wherein the dissociation constant against human IL-33 is not more than 231 pM.

8. A method for treatment, prevention, or alleviation of a disease associated with IL-33 in a subject, the method comprising administering to the subject the antibody according to claim 1.

9. The method according to claim 8, wherein the disease associated with IL-33 is selected from the group consisting of asthma, atopic dermatitis, pollinosis, anaphylactic shock, sinusitis (including eosinophilic sinusitis), Crohn's disease, ulcerative colitis, arthritis, systemic lupus erythematosus, pemphigus, pemphigoid, scleroderma, ankylosing spondylitis, hepatic fibrosis (including primary biliary cirrhosis), pulmonary fibrosis, chronic obstructive pulmonary disease (COPD), acute kidney injury, vasculitis, Sjogren's syndrome, and cancer.

10. A cytokine expression inhibitor comprising the antibody according to claim 1.

11. The inhibitor according to claim 10, wherein the inhibitor inhibits expression of TNF-α, IFN-γ, IL-1β, IL-4, IL-5, IL-6, or IL-13.

12. The inhibitor according to claim 10, wherein the inhibitor inhibits expression of IFN-γ, IL-5, IL-6, or IL-13.

13. The antibody according to claim 1, wherein the monoclonal antibody that is capable of binding to the epitope consisting of a continuous amino acid sequence included in positions 131 to 150 of SEQ ID NO:226 in the Sequence Listing is a chimeric, a humanized, or a human antibody.

14. The antibody according to claim 13, wherein the amino acid sequences of the framework regions are amino acid sequences of framework regions from a human germline or a combination of amino acid sequences thereof.

15. The antibody according to claim 14, wherein the amino acid sequence of the light-chain framework region 1 is residues 1 to 22 of SEQ ID NO:317 in the Sequence Listing; the amino acid sequence of the light-chain framework region 2 is residues 36 to 50 of SEQ ID NO:317 in the Sequence Listing; the amino acid sequence of the light-chain framework region 3 is residues 58 to 89 of SEQ ID NO:317 in the Sequence Listing; the amino acid sequence of the light-chain framework region 4 is residues 3 to 12 of SEQ ID NO:401 in the Sequence Listing; the amino acid sequence of the heavy-chain framework region I is residues 1 to 30 of SEQ ID NO:367 or residues 1 to 30 of SEQ ID NO:368 in the Sequence Listing; the amino acid sequence of the heavy-chain framework region 2 is residues 36 to 49 of SEQ ID NO:367 or residues 36 to 49 of SEQ ID NO:368 in the Sequence Listing; the amino acid sequence of the heavy-chain framework region 3 is residues 67 to 98 of SEQ ID NO:367 or residues 67 to 98 of SEQ ID NO:368 in the Sequence Listing; and the amino acid sequence of the heavy-chain framework region 4 is residues 5 to 15 of SEQ ID NO:407 in the Sequence Listing.

16. The antibody according to claim 14, wherein the amino acid sequence of the light-chain framework region 1 is residues 1 to 22 of SEQ ID NO:317 in the Sequence Listing; the amino acid sequence of the light-chain framework region 2 is residues 36 to 50 of SEQ ID NO:317 in the Sequence Listing; the amino acid sequence of the light-chain framework region 3 is residues 58 to 89 of SEQ ID NO:317 in the Sequence Listing; the amino acid sequence of the light-chain framework region 4 is residues 3 to 12 of SEQ ID NO:401 in the Sequence Listing; the amino acid sequence of the heavy-chain framework region 1 is residues 1 to 30 of SEQ ID NO:367 in the Sequence Listing; the amino acid sequence of the heavy-chain framework region 2 is residues 36 to 49 of SEQ ID NO:367 in the Sequence Listing; the amino acid sequence of the heavy-chain framework region 3 is residues 67 to 98 of SEQ ID NO:368 in the Sequence Listing; and the amino acid sequence of the heavy-chain framework region 4 is residues 5 to 15 of SEQ ID NO:407 in the Sequence Listing.

17. The antibody according to claim 1, wherein the dissociation constant against human IL-33 is not more than 231 pM.

18. The monoclonal antibody according to claim 1, wherein a combination of the light-chain variable regions, LCDR1, LCDR2 and LCDR3 and the heavy-chain variable regions, HDCR1, HDCR2 and HDCR3 of the monoclonal antibody are selected from those set forth in Table 1:

|  | LCDR1 | LCDR2 | LCDR3 | HCDR1 | HCDR2 | HCDR3 |
|---|---|---|---|---|---|---|
| C1 | SEQ ID No. 1 | SEQ ID No. 11 | SEQ ID No. 22 | SEQ ID No. 43 | SEQ ID No. 51 | SEQ ID No. 65 |
| C2 | SEQ ID No. 1 | SEQ ID No. 11 | SEQ ID No. 23 | SEQ ID No. 43 | SEQ ID No. 52 | SEQ ID No. 65 |
| C3 | SEQ ID No. 2 | SEQ ID No. 11 | SEQ ID No. 23 | SEQ ID No. 44 | SEQ ID No. 52 | SEQ ID No. 65 |
| C4 | SEQ ID No. 2 | SEQ ID No. 11 | SEQ ID No. 23 | SEQ ID No. 44 | SEQ ID No. 53 | SEQ ID No. 65 |
| C5 | SEQ ID No. 2 | SEQ ID No. 11 | SEQ ID No. 23 | SEQ ID No. 43 | SEQ ID No. 54 | SEQ ID No. 65 |
| C6 | SEQ ID No. 2 | SEQ ID No. 11 | SEQ ID No. 24 | SEQ ID No. 45 | SEQ ID No. 52 | SEQ ID No. 65 |
| C7 | SEQ ID No. 2 | SEQ ID No. 11 | SEQ ID No. 23 | SEQ ID No. 46 | SEQ ID No. 52 | SEQ ID No. 65 |
| C8 | SEQ ID No. 3 | SEQ ID No. 12 | SEQ ID No. 25 | SEQ ID No. 47 | SEQ ID No. 55 | SEQ ID No. 66 |
| C9 | SEQ ID No. 4 | SEQ ID No. 12 | SEQ ID No. 26 | SEQ ID No. 47 | SEQ ID No. 56 | SEQ ID No. 67 |
| C10 | SEQ ID No. 4 | SEQ ID No. 13 | SEQ ID No. 27 | SEQ ID No. 47 | SEQ ID No. 56 | SEQ ID No. 67 |
| C11 | SEQ ID No. 5 | SEQ ID No. 12 | SEQ ID No. 28 | SEQ ID No. 47 | SEQ ID No. 56 | SEQ ID No. 67 |
| C12 | SEQ ID No. 4 | SEQ ID No. 12 | SEQ ID No. 29 | SEQ ID No. 47 | SEQ ID No. 56 | SEQ ID No. 67 |
| C13 | SEQ ID No. 6 | SEQ ID No. 14 | SEQ ID No. 30 | SEQ ID No. 47 | SEQ ID No. 56 | SEQ ID No. 67 |
| C14 | SEQ ID No. 7 | SEQ ID No. 14 | SEQ ID No. 31 | SEQ ID No. 47 | SEQ ID No. 56 | SEQ ID No. 67 |
| C15 | SEQ ID No. 4 | SEQ ID No. 15 | SEQ ID No. 32 | SEQ ID No. 47 | SEQ ID No. 56 | SEQ ID No. 67 |
| C16 | SEQ ID No. 6 | SEQ ID No. 16 | SEQ ID No. 33 | SEQ ID No. 48 | SEQ ID No. 57 | SEQ ID No. 68 |
| C17 | SEQ ID No. 4 | SEQ ID No. 17 | SEQ ID No. 34 | SEQ ID No. 49 | SEQ ID No. 58 | SEQ ID No. 69 |
| C18 | SEQ ID No. 6 | SEQ ID No. 18 | SEQ ID No. 35 | SEQ ID No. 47 | SEQ ID No. 59 | SEQ ID No. 70 |
| C19 | SEQ ID No. 6 | SEQ ID No. 19 | SEQ ID No. 36 | SEQ ID No. 47 | SEQ ID No. 56 | SEQ ID No. 71 |
| C20 | SEQ ID No. 6 | SEQ ID No. 20 | SEQ ID No. 26 | SEQ ID No. 47 | SEQ ID No. 56 | SEQ ID No. 66 |
| C21 | SEQ ID No. 6 | SEQ ID No. 18 | SEQ ID No. 37 | SEQ ID No. 47 | SEQ ID No. 60 | SEQ ID No. 72 |
| C22 | SEQ ID No. 6 | SEQ ID No. 20 | SEQ ID No. 38 | SEQ ID No. 47 | SEQ ID No. 56 | SEQ ID No. 73 |
| C23 | SEQ ID No. 8 | SEQ ID No. 20 | SEQ ID No. 27 | SEQ ID No. 49 | SEQ ID No. 56 | SEQ ID No. 68 |
| C24 | SEQ ID No. 9 | SEQ ID No. 20 | SEQ ID No. 29 | SEQ ID No. 47 | SEQ ID No. 60 | SEQ ID No. 73 |
| C25 | SEQ ID No. 4 | SEQ ID No. 21 | SEQ ID No. 34 | SEQ ID No. 47 | SEQ ID No. 61 | SEQ ID No. 74 |
| C26 | SEQ ID No. 10 | SEQ ID No. 19 | SEQ ID No. 40 | SEQ ID No. 47 | SEQ ID No. 62 | SEQ ID No. 75 |
| C27 | SEQ ID No. 4 | SEQ ID No. 18 | SEQ ID No. 41 | SEQ ID No. 50 | SEQ ID No. 56 | SEQ ID No. 76 |
| C28 | SEQ ID No. 6 | SEQ ID No. 20 | SEQ ID No. 42 | SEQ ID No. 47 | SEQ ID No. 63 | SEQ ID No. 77 |
| C29 | SEQ ID No. 2 | SEQ ID No. 11 | SEQ ID No. 23 | SEQ ID No. 43 | SEQ ID No. 64 | SEQ ID No. 65 |
| C30 | SEQ ID No. 6 | SEQ ID No. 20 | SEQ ID No. 40 | SEQ ID No. 47 | SEQ ID No. 64 | SEQ ID No. 78 |

19. The monoclonal antibody according to claim 18, wherein the light-chain complementarity-determining region 1 (LCDR1), the light-chain complementarity-determining region 2 (LCDR2), the light-chain complementarity-determining region 3 (LCDR3), the heavy-chain complementarity-determining region 1 (HCDR1), the heavy-chain complementarity-determining region 2 (HCDR2), and the heavy-chain complementarity-determining region 3 (HCDR3) of the monoclonal antibody are selected from C1, C8, C15, C17, C18 in said Table 1.

20. An antibody generated or screened using an isolated and purified epitope selected from the group consisting of:
   an isolated and purified epitope consisting of an amino acid sequence including one or several amino acid substitutions, deletions, or additions as compared to the continuous amino acid sequence included in positions 131 to 150 of SEQ ID NO:226; and
   an isolated and purified epitope consisting of an amino acid sequence with at least 90% sequence identity, but not 100% identity to the continuous amino acid sequence included in positions 131 to 150 of SEQ ID NO:226,
   wherein the antibody comprises either:
   (a) a light-chain complementarity-determining region 1 (LCDR1) comprises a sequence selected from the group consisting of SEQ ID NO:1 and SEQ ID NO:2, a light-chain complementarity-determining region 2 (LCDR2) comprises a sequence of SEQ ID NO: 11, a light-chain complementarity-determining region 3 (LCDR3) comprises a sequence selected from the group consisting of SEQ ID NOs:22-24, a heavy-chain complementarity-determining region 1 (HCDR1) comprises a sequence selected from the group consisting of SEQ ID NOs:43-46, a heavy-chain complementarity-determining region 2 (HCDR2) comprises a sequence selected from the group consisting of SEQ ID NO:51-54 and 64, and a heavy-chain complementarity-determining region 3 (HCDR3) comprises a sequence of SEQ ID NO:65; or
   (b) light-chain complementarity-determining region 1 (LCDR1) comprises a sequence selected from the group consisting of SEQ ID NOs:3-10, a light-chain complementarity-determining region 2 (LCDR2) comprises a sequence selected from the group consisting of SEQ ID NOs:12-21, alight-chain complementarity-determining region 3 (LCDR3) comprises a sequence selected from the group consisting of SEQ ID NOs: 25-42, a heavy-chain complementarity-determining region 1 (HCDRJ) comprises a sequence selected from the group consisting of SEQ ID NOs:47-50, a heavy-chain complementarity-determining region 2 (HCDR2) comprises a sequence selected from the group consisting of SEQ ID NO:55-64, and a heavy-chain complementarity-determining region 3 (HCDR3) comprises a sequence of SEQ ID NO:66-78.

21. A monoclonal antibody,
   wherein the monoclonal antibody is capable of binding to an epitope consisting of a continuous amino acid sequence included in positions 131 to 150 of SEQ ID NO:226 in the Sequence Listing,
   wherein the monoclonal antibody comprises either:
   (a) a light-chain variable region comprising a sequence selected from the group consisting of SEQ ID NOs: 79-82 and a heavy chain variable region comprising a sequence selected from the group consisting of SEQ ID NOs:105-111 and SEQ ID NO: 127; or
   (b) a light-chain variable region comprising a sequence selected from the group consisting of SEQ ID NOs: 83-104 and a heavy chain variable region comprising a sequence selected from the group consisting of SEQ ID NOs:112-126 and SEQ ID NO:128.

22. The monoclonal antibody according to claim 21, wherein a combination of the light-chain variable region and the heavy-chain variable region of the monoclonal antibody are selected from those set forth in Table 2:

| Combination | Light Chain Variable Region | Heavy Chain Variable Region |
| --- | --- | --- |
| V1 | SEQ ID No. 79 | SEQ ID No. 105 |
| V2 | SEQ ID No. 80 | SEQ ID No. 106 |
| V3 | SEQ ID No. 81 | SEQ ID No. 107 |
| V4 | SEQ ID No. 81 | SEQ ID No. 108 |
| V5 | SEQ ID No. 81 | SEQ ID No. 109 |
| V6 | SEQ ID No. 82 | SEQ ID No. 110 |
| V7 | SEQ ID No. 81 | SEQ ID No. 111 |
| V8 | SEQ ID No. 83 | SEQ ID No. 112 |
| V9 | SEQ ID No. 84 | SEQ ID No. 113 |
| V10 | SEQ ID No. 85 | SEQ ID No. 113 |
| V11 | SEQ ID No. 86 | SEQ ID No. 113 |
| V12 | SEQ ID No. 87 | SEQ ID No. 113 |
| V13 | SEQ ID No. 88 | SEQ ID No. 113 |
| V14 | SEQ ID No. 89 | SEQ ID No. 113 |
| V15 | SEQ ID No. 90 | SEQ ID No. 113 |
| V16 | SEQ ID No. 91 | SEQ ID No. 114 |
| V17 | SEQ ID No. 92 | SEQ ID No. 115 |
| V18 | SEQ ID No. 93 | SEQ ID No. 116 |
| V19 | SEQ ID No. 94 | SEQ ID No. 117 |
| V20 | SEQ ID No. 95 | SEQ ID No. 118 |
| V21 | SEQ ID No. 96 | SEQ ID No. 119 |
| V22 | SEQ ID No. 97 | SEQ ID No. 120 |
| V23 | SEQ ID No. 98 | SEQ ID No. 121 |
| V24 | SEQ ID No. 99 | SEQ ID No. 122 |
| V25 | SEQ ID No. 100 | SEQ ID No. 123 |
| V26 | SEQ ID No. 101 | SEQ ID No. 124 |
| V27 | SEQ ID No. 102 | SEQ ID No. 125 |
| V28 | SEQ ID No. 103 | SEQ ID No. 126 |
| V29 | SEQ ID No. 81 | SEQ ID No. 127 |
| V30 | SEQ ID No. 104 | SEQ ID No. 128 |

23. The monoclonal antibody according to claim 22, wherein the combination of the light-chain variable region and the heavy-chain variable region of the monoclonal antibody are selected from the group consisting of V1, V8, V15, V17, and V18 in said Table 2.

* * * * *

UNITED STATES PATENT AND TRADEMARK OFFICE
CERTIFICATE OF CORRECTION

PATENT NO. : 11,725,049 B2
APPLICATION NO. : 16/414602
DATED : August 15, 2023
INVENTOR(S) : Yasuhiro Fujino It is certified that error appears in the above-identified patent and that said Letters Patent is hereby corrected as shown below:

On the Title Page

Page 2, Column 2 (Item (56) Other Publications), Line 7, delete "figrosis," and insert -- fibrosis," --.

Page 2, Column 2 (Item (56) Other Publications), Line 28, delete "(ID01)" and insert -- (IDO1) --.

Page 2, Column 2 (Item (56) Other Publications), Line 33, delete "Inter Leukin-33" and insert -- Interleukin-33 --.

In the Specification

Column 2, Line 50, delete "Veloclmmune" and insert -- VelocImmune --.

Column 11, Line 27, delete "amedicament" and insert -- a medicament --.

Column 12, Line 3, delete "fragments" and insert -- fragments. --.

Column 12, Line 33 (approx.), delete ""5117" and insert -- "S117 --.

Column 12, Line 37 (approx.), delete "PEP 14" and insert -- PEP14 --.

Column 14, Line 56, delete "loysosome" and insert -- lysosome --.

Column 19, Line 64, delete "1119," and insert -- I119, --.

Column 19, Line 67, delete "1145," and insert -- I145, --.

Column 20, Line 57, delete "amedicament" and insert -- medicament --.

Signed and Sealed this
Twenty-seventh Day of February, 2024

Katherine Kelly Vidal
*Director of the United States Patent and Trademark Office*

CERTIFICATE OF CORRECTION (continued)
U.S. Pat. No. 11,725,049 B2

Column 21, Line 11-12, delete "(alopecia greata),".

Column 25, Line 9, delete "expresion" and insert -- expression --.

Column 25, Line 66, delete "(Strobl," and insert -- (Strohl, --.

Column 32, Line 41, delete "moleculessuch asnon" and insert -- molecules such as non --.

Column 39, Line 60, delete "$^{90}$Yr," and insert -- $^{90}$Y, --.

Column 40, Line 2, delete "neocarzonostatin," and insert -- neocarzinostatin, --.

Column 40, Line 20-21, delete "succinamides," and insert -- succinimides, --.

Column 40, Line 56, delete "cell" and insert -- cell. --.

Column 41, Line 3, delete "VeloclmmuneImmune" and insert -- VelocImmune --.

Column 43, Line 11, delete "0050," and insert -- C050, --.

Column 43, Line 47-48, delete "humanIL-33" and insert -- human IL-33 --.

Column 43, Line 49, delete "0050," and insert -- C050, --.

Column 46, Line 54, delete "BioInvent" and insert -- BioInvent --.

Column 49, Line 16, delete "humanIL-33" and insert -- human IL-33 --.

Column 49, Line 29, delete "BagBuster" and insert -- BugBuster --.

Column 49, Line 30, delete "6His-AviTag-" and insert -- 6His tag-AviTag --.

Column 50, Line 8, delete "monkeyIL-33" and insert -- monkey IL-33 --.

Column 53, Line 40, delete "CaptoQ Impress" and insert -- Capto Q ImpRes --.

Column 53, Line 58 (approx.), below "TABLE 12" delete "Purification Method".

Column 53, Line 62 (approx.), above "Ligand" insert -- Purification Method --.

Column 54, Line 2 (approx.), below "TABLE 12-continued" delete "Purification Method".

Column 54, Line 7 (approx.), above "Ligand" insert -- Purification Method --.

Column 54, Line 12 (approx.), delete "anti IL-33" and insert -- anti-IL-33 --.

Column 54, Line 13 (approx.), delete "ligand" and insert -- ligand. --.

Column 56, Line 23, delete "AlfaLISA™" and insert -- AlphaLISA™ --.

Column 56, Line 46, delete "C57BL6" and insert -- C57BL/6 --.

Column 59, Line 47 (approx.), delete "Do" and insert -- $D_0$ --.

Column 59, Line 49 (approx.), delete "($k_B$)" and insert -- ($k_D$) --.

Column 62, Line 23, delete "Zebaspin" and insert -- Zeba Spin --.

Column 62, Line 65, delete "C57BL6" and insert -- C57BL/6 --.

Column 63, Line 46-47, delete "condition" and insert -- condition. --.

In the Claims

Column 311, Line 55, Claim 1, delete "NO:51" and insert -- NOs:51 --.

Column 312, Line 40, Claim 1, delete "NO:55" and insert -- NOs:55 --.

Column 312, Line 42, Claim 1, delete "NO:66" and insert -- NOs:66 --.

Column 312, Line 63-64, Claim 8, delete "administering to the subject the antibody according to Claim 1" and insert -- administering an antibody of Claim 1 to the subject --.

Column 313, Line 35, Claim 15, delete "region I" and insert -- region 1 --.

Column 314, Line 35, Claim 18, delete "HDCR1, HDCR2 and HDCR3" and insert -- HCDR1, HCDR2 and HCDR3 --.

Column 313-314, Line 37 (approx.), Claim 18, below "Table 1:" insert -- [Table 1] --.

Column 313-314, Line 63 (approx.), Claim 18, delete "No. 29" and insert -- No. 39 --.

Column 313-314, Line 69 (approx.), Claim 18, after "SEQ ID No. 78" insert -- . --.

Column 315, Line 11 (approx.), Claim 19, delete "C18" and insert -- and C18 --.

Column 315, Line 37, Claim 20, delete "NO:51" and insert -- NOs:51 --.

Column 315, Line 46, Claim 20, delete "alight-chain" and insert -- a light-chain --.

Column 315, Line 49 (approx.), Claim 20, delete "(HCDRJ)" and insert -- (HCDR1) --.

CERTIFICATE OF CORRECTION (continued)
U.S. Pat. No. 11,725,049 B2

Column 315, Line 54 (approx.), Claim 20, delete "NO:55" and insert -- NOs:55 --.

Column 315, Line 56 (approx.), Claim 20, delete "NO:66" and insert -- NOs:66 --.

Column 316, Line 20 (approx.), Claim 22, below "Table 2:" insert -- [Table 2] --.

Column 316, Line 48 (approx.), Claim 22, after "SEQ ID No. 128" insert -- . --.

SEQUENCE LISTING

<160> NUMBER OF SEQ ID NOS: 427

<210> SEQ ID NO 1
<211> LENGTH: 14
<212> TYPE: PRT

```
<213> ORGANISM: Artificial Sequence
<220> FEATURE:
<223> OTHER INFORMATION: LCDR1-1

<400> SEQUENCE: 1

Thr Gly Ser Ser Ser Asn Ile Gly Ala Val Tyr Asp Val His
1               5                   10

<210> SEQ ID NO 2
<211> LENGTH: 14
<212> TYPE: PRT
<213> ORGANISM: Artificial Sequence
<220> FEATURE:
<223> OTHER INFORMATION: LCDR1-2

<400> SEQUENCE: 2

Thr Gly Ser Ser Ser Asn Ile Gly Ala Val Tyr Asn Val His
1               5                   10

<210> SEQ ID NO 3
<211> LENGTH: 13
<212> TYPE: PRT
<213> ORGANISM: Artificial Sequence
<220> FEATURE:
<223> OTHER INFORMATION: LCDR1-3

<400> SEQUENCE: 3

Ser Gly Ser Ser Ser Asn Ile Gly Asn Asn Ala Val Ser
1               5                   10

<210> SEQ ID NO 4
<211> LENGTH: 13
<212> TYPE: PRT
<213> ORGANISM: Artificial Sequence
<220> FEATURE:
<223> OTHER INFORMATION: LCDR1-4

<400> SEQUENCE: 4

Ser Gly Ser Ser Ser Asn Ile Gly Arg Asn Ala Val Asn
1               5                   10

<210> SEQ ID NO 5
<211> LENGTH: 13
<212> TYPE: PRT
<213> ORGANISM: Artificial Sequence
<220> FEATURE:
<223> OTHER INFORMATION: LCDR1-5

<400> SEQUENCE: 5

Ser Gly Ser Cys Ser Asn Ile Gly Arg Asn Ala Val Asn
1               5                   10

<210> SEQ ID NO 6
<211> LENGTH: 13
<212> TYPE: PRT
<213> ORGANISM: Artificial Sequence
<220> FEATURE:
<223> OTHER INFORMATION: LCDR1-6

<400> SEQUENCE: 6

Ser Gly Ser Ser Ser Asn Ile Gly Asn Asn Ala Val Asn
1               5                   10

<210> SEQ ID NO 7
<211> LENGTH: 13
<212> TYPE: PRT
<213> ORGANISM: Artificial Sequence
```

```
<220> FEATURE:
<223> OTHER INFORMATION: LCDR1-7

<400> SEQUENCE: 7

Ser Gly Ser Ser Ser Asn Ile Gly Ser Asn Ala Val Ser
1               5                   10

<210> SEQ ID NO 8
<211> LENGTH: 13
<212> TYPE: PRT
<213> ORGANISM: Artificial Sequence
<220> FEATURE:
<223> OTHER INFORMATION: LCDR1-8

<400> SEQUENCE: 8

Ser Gly Ser Ser Ser Asn Ile Gly Arg Asn Ala Val Ser
1               5                   10

<210> SEQ ID NO 9
<211> LENGTH: 13
<212> TYPE: PRT
<213> ORGANISM: Artificial Sequence
<220> FEATURE:
<223> OTHER INFORMATION: LCDR1-9

<400> SEQUENCE: 9

Ser Gly Ser Ser Ser Asn Ile Gly His Asn Ala Val Ser
1               5                   10

<210> SEQ ID NO 10
<211> LENGTH: 13
<212> TYPE: PRT
<213> ORGANISM: Artificial Sequence
<220> FEATURE:
<223> OTHER INFORMATION: LCDR1-10

<400> SEQUENCE: 10

Ser Gly Ser Ser Ser Asn Ile Gly His Asn Ala Val Trp
1               5                   10

<210> SEQ ID NO 11
<211> LENGTH: 7
<212> TYPE: PRT
<213> ORGANISM: Artificial Sequence
<220> FEATURE:
<223> OTHER INFORMATION: LCDR2-1

<400> SEQUENCE: 11

Arg Asn Asn Gln Arg Pro Ser
1               5

<210> SEQ ID NO 12
<211> LENGTH: 7
<212> TYPE: PRT
<213> ORGANISM: Artificial Sequence
<220> FEATURE:
<223> OTHER INFORMATION: LCDR2-2

<400> SEQUENCE: 12

Ala Ser Asn Met Arg Val Ile
1               5

<210> SEQ ID NO 13
<211> LENGTH: 7
<212> TYPE: PRT
<213> ORGANISM: Artificial Sequence
<220> FEATURE:
```

<223> OTHER INFORMATION: LCDR2-3

<400> SEQUENCE: 13

Ala Ser Asn Met Arg Val Leu
1               5

<210> SEQ ID NO 14
<211> LENGTH: 7
<212> TYPE: PRT
<213> ORGANISM: Artificial Sequence
<220> FEATURE:
<223> OTHER INFORMATION: LCDR2-4

<400> SEQUENCE: 14

Ala Ser Asn Met Arg Gly Ser
1               5

<210> SEQ ID NO 15
<211> LENGTH: 7
<212> TYPE: PRT
<213> ORGANISM: Artificial Sequence
<220> FEATURE:
<223> OTHER INFORMATION: LCDR2-5

<400> SEQUENCE: 15

Ala Ser Asn Met Arg Val Ser
1               5

<210> SEQ ID NO 16
<211> LENGTH: 7
<212> TYPE: PRT
<213> ORGANISM: Artificial Sequence
<220> FEATURE:
<223> OTHER INFORMATION: LCDR2-6

<400> SEQUENCE: 16

Ala Ser Asn Met Arg Gly Leu
1               5

<210> SEQ ID NO 17
<211> LENGTH: 7
<212> TYPE: PRT
<213> ORGANISM: Artificial Sequence
<220> FEATURE:
<223> OTHER INFORMATION: LCDR2-7

<400> SEQUENCE: 17

Ala Ser Asn Met Arg Arg Ser
1               5

<210> SEQ ID NO 18
<211> LENGTH: 7
<212> TYPE: PRT
<213> ORGANISM: Artificial Sequence
<220> FEATURE:
<223> OTHER INFORMATION: LCDR2-8

<400> SEQUENCE: 18

Ala Ser Asn Met Arg Arg Pro
1               5

<210> SEQ ID NO 19
<211> LENGTH: 7
<212> TYPE: PRT
<213> ORGANISM: Artificial Sequence
<220> FEATURE:
<223> OTHER INFORMATION: LCDR2-9

```
<400> SEQUENCE: 19

Ala Ser Asn Met Arg Arg Met
1               5

<210> SEQ ID NO 20
<211> LENGTH: 7
<212> TYPE: PRT
<213> ORGANISM: Artificial Sequence
<220> FEATURE:
<223> OTHER INFORMATION: LCDR2-10

<400> SEQUENCE: 20

Ala Ser Asn Met Arg Arg Leu
1               5

<210> SEQ ID NO 21
<211> LENGTH: 7
<212> TYPE: PRT
<213> ORGANISM: Artificial Sequence
<220> FEATURE:
<223> OTHER INFORMATION: LCDR2-11

<400> SEQUENCE: 21

Ala Ser Asn Met Arg Gly Met
1               5

<210> SEQ ID NO 22
<211> LENGTH: 9
<212> TYPE: PRT
<213> ORGANISM: Artificial Sequence
<220> FEATURE:
<223> OTHER INFORMATION: LCDR3-1

<400> SEQUENCE: 22

Gln Thr Tyr Asp Ser Ser Arg Trp Val
1               5

<210> SEQ ID NO 23
<211> LENGTH: 9
<212> TYPE: PRT
<213> ORGANISM: Artificial Sequence
<220> FEATURE:
<223> OTHER INFORMATION: LCDR3-2

<400> SEQUENCE: 23

Gln Ser Tyr Asp Ser Ser Arg Trp Val
1               5

<210> SEQ ID NO 24
<211> LENGTH: 9
<212> TYPE: PRT
<213> ORGANISM: Artificial Sequence
<220> FEATURE:
<223> OTHER INFORMATION: LCDR3-3

<400> SEQUENCE: 24

Gln Ser Tyr Asp Ser Arg Arg Trp Val
1               5

<210> SEQ ID NO 25
<211> LENGTH: 11
<212> TYPE: PRT
<213> ORGANISM: Artificial Sequence
<220> FEATURE:
<223> OTHER INFORMATION: LCDR3-4
```

```
<400> SEQUENCE: 25

Gly Ala Trp Asp Asp Ser Gln Lys Ala Leu Val
1               5                   10

<210> SEQ ID NO 26
<211> LENGTH: 11
<212> TYPE: PRT
<213> ORGANISM: Artificial Sequence
<220> FEATURE:
<223> OTHER INFORMATION: LCDR3-5

<400> SEQUENCE: 26

Ala Ala Trp Asp Asp Ser Gln Lys Ala Trp Val
1               5                   10

<210> SEQ ID NO 27
<211> LENGTH: 11
<212> TYPE: PRT
<213> ORGANISM: Artificial Sequence
<220> FEATURE:
<223> OTHER INFORMATION: LCDR3-6

<400> SEQUENCE: 27

Trp Ala Trp Asp Asp Ser Gln Lys Ala Val Val
1               5                   10

<210> SEQ ID NO 28
<211> LENGTH: 11
<212> TYPE: PRT
<213> ORGANISM: Artificial Sequence
<220> FEATURE:
<223> OTHER INFORMATION: LCDR3-7

<400> SEQUENCE: 28

Glu Ala Trp Asp Asp Ser Gln Lys Gly Val Val
1               5                   10

<210> SEQ ID NO 29
<211> LENGTH: 11
<212> TYPE: PRT
<213> ORGANISM: Artificial Sequence
<220> FEATURE:
<223> OTHER INFORMATION: LCDR3-8

<400> SEQUENCE: 29

Gly Ala Trp Asp Asp Ser Gln Lys Arg Tyr Val
1               5                   10

<210> SEQ ID NO 30
<211> LENGTH: 11
<212> TYPE: PRT
<213> ORGANISM: Artificial Sequence
<220> FEATURE:
<223> OTHER INFORMATION: LCDR3-9

<400> SEQUENCE: 30

Ala Ala Trp Asp Asp Ser Gln Lys Gly Gln Val
1               5                   10

<210> SEQ ID NO 31
<211> LENGTH: 11
<212> TYPE: PRT
<213> ORGANISM: Artificial Sequence
<220> FEATURE:
<223> OTHER INFORMATION: LCDR3-10

<400> SEQUENCE: 31
```

Ala Ala Trp Asp Asp Ser Gln Lys Val Val Val
1               5                   10

<210> SEQ ID NO 32
<211> LENGTH: 11
<212> TYPE: PRT
<213> ORGANISM: Artificial Sequence
<220> FEATURE:
<223> OTHER INFORMATION: LCDR3-11

<400> SEQUENCE: 32

Trp Ala Trp Asp Asp Ser Gln Lys Val Gly Val
1               5                   10

<210> SEQ ID NO 33
<211> LENGTH: 11
<212> TYPE: PRT
<213> ORGANISM: Artificial Sequence
<220> FEATURE:
<223> OTHER INFORMATION: LCDR3-12

<400> SEQUENCE: 33

Gly Ala Trp Asp Asp Ser Gln Lys Val Phe Val
1               5                   10

<210> SEQ ID NO 34
<211> LENGTH: 11
<212> TYPE: PRT
<213> ORGANISM: Artificial Sequence
<220> FEATURE:
<223> OTHER INFORMATION: LCDR3-13

<400> SEQUENCE: 34

Ser Ala Trp Asp Asp Ser Gln Lys Val Val Val
1               5                   10

<210> SEQ ID NO 35
<211> LENGTH: 11
<212> TYPE: PRT
<213> ORGANISM: Artificial Sequence
<220> FEATURE:
<223> OTHER INFORMATION: LCDR3-14

<400> SEQUENCE: 35

Glu Ala Trp Asp Asp Ser Gln Lys Ala Val Val
1               5                   10

<210> SEQ ID NO 36
<211> LENGTH: 11
<212> TYPE: PRT
<213> ORGANISM: Artificial Sequence
<220> FEATURE:
<223> OTHER INFORMATION: LCDR3-15

<400> SEQUENCE: 36

Ala Ala Trp Asp Asp Ser Gln Lys Ala Phe Val
1               5                   10

<210> SEQ ID NO 37
<211> LENGTH: 11
<212> TYPE: PRT
<213> ORGANISM: Artificial Sequence
<220> FEATURE:
<223> OTHER INFORMATION: LCDR3-16

<400> SEQUENCE: 37

```
Ala Ala Trp Asp Asp Ser Gln Lys Val Phe Val
1               5                   10
```

<210> SEQ ID NO 38
<211> LENGTH: 11
<212> TYPE: PRT
<213> ORGANISM: Artificial Sequence
<220> FEATURE:
<223> OTHER INFORMATION: LCDR3-17

<400> SEQUENCE: 38

```
Gly Ala Trp Asp Asp Ser Gln Lys Ala Phe Val
1               5                   10
```

<210> SEQ ID NO 39
<211> LENGTH: 11
<212> TYPE: PRT
<213> ORGANISM: Artificial Sequence
<220> FEATURE:
<223> OTHER INFORMATION: LCDR3-18

<400> SEQUENCE: 39

```
Gly Ala Trp Asp Asp Ser Gln Lys Val Val Val
1               5                   10
```

<210> SEQ ID NO 40
<211> LENGTH: 11
<212> TYPE: PRT
<213> ORGANISM: Artificial Sequence
<220> FEATURE:
<223> OTHER INFORMATION: LCDR3-19

<400> SEQUENCE: 40

```
Ala Ala Trp Asp Asp Ser Gln Lys Ala Val Val
1               5                   10
```

<210> SEQ ID NO 41
<211> LENGTH: 11
<212> TYPE: PRT
<213> ORGANISM: Artificial Sequence
<220> FEATURE:
<223> OTHER INFORMATION: LCDR3-20

<400> SEQUENCE: 41

```
Ser Ala Trp Asp Asp Ser Gln Lys Ala Gly Val
1               5                   10
```

<210> SEQ ID NO 42
<211> LENGTH: 11
<212> TYPE: PRT
<213> ORGANISM: Artificial Sequence
<220> FEATURE:
<223> OTHER INFORMATION: LCDR3-21

<400> SEQUENCE: 42

```
Ala Ala Trp Asp Asp Ser Gln Lys Ala Leu Val
1               5                   10
```

<210> SEQ ID NO 43
<211> LENGTH: 5
<212> TYPE: PRT
<213> ORGANISM: Artificial Sequence
<220> FEATURE:
<223> OTHER INFORMATION: HCDR1-1

<400> SEQUENCE: 43

```
Asp Tyr Tyr Met Asn
```

```
1               5

<210> SEQ ID NO 44
<211> LENGTH: 5
<212> TYPE: PRT
<213> ORGANISM: Artificial Sequence
<220> FEATURE:
<223> OTHER INFORMATION: HCDR1-2

<400> SEQUENCE: 44

Asp Tyr Tyr Met Asp
1               5

<210> SEQ ID NO 45
<211> LENGTH: 5
<212> TYPE: PRT
<213> ORGANISM: Artificial Sequence
<220> FEATURE:
<223> OTHER INFORMATION: HCDR1-3

<400> SEQUENCE: 45

Val Tyr Tyr Met Asn
1               5

<210> SEQ ID NO 46
<211> LENGTH: 5
<212> TYPE: PRT
<213> ORGANISM: Artificial Sequence
<220> FEATURE:
<223> OTHER INFORMATION: HCDR1-4

<400> SEQUENCE: 46

Asp Tyr Tyr Val Asn
1               5

<210> SEQ ID NO 47
<211> LENGTH: 5
<212> TYPE: PRT
<213> ORGANISM: Artificial Sequence
<220> FEATURE:
<223> OTHER INFORMATION: HCDR1-5

<400> SEQUENCE: 47

Asn Tyr Tyr Met His
1               5

<210> SEQ ID NO 48
<211> LENGTH: 5
<212> TYPE: PRT
<213> ORGANISM: Artificial Sequence
<220> FEATURE:
<223> OTHER INFORMATION: HCDR1-6

<400> SEQUENCE: 48

His Tyr Tyr Met His
1               5

<210> SEQ ID NO 49
<211> LENGTH: 5
<212> TYPE: PRT
<213> ORGANISM: Artificial Sequence
<220> FEATURE:
<223> OTHER INFORMATION: HCDR1-7

<400> SEQUENCE: 49

Arg Tyr Tyr Met His
1               5
```

```
<210> SEQ ID NO 50
<211> LENGTH: 5
<212> TYPE: PRT
<213> ORGANISM: Artificial Sequence
<220> FEATURE:
<223> OTHER INFORMATION: HCDR1-8

<400> SEQUENCE: 50

Ser Tyr Tyr Met His
1               5

<210> SEQ ID NO 51
<211> LENGTH: 17
<212> TYPE: PRT
<213> ORGANISM: Artificial Sequence
<220> FEATURE:
<223> OTHER INFORMATION: HCDR2-1

<400> SEQUENCE: 51

Ser Ile Ser Arg Tyr Ser Ser Tyr Ile Tyr Tyr Ala Asp Ser Val Lys
1               5                   10                  15

Gly

<210> SEQ ID NO 52
<211> LENGTH: 17
<212> TYPE: PRT
<213> ORGANISM: Artificial Sequence
<220> FEATURE:
<223> OTHER INFORMATION: HCDR2-2

<400> SEQUENCE: 52

Ser Ile Ser Arg Tyr Ser Gly Tyr Val Tyr Tyr Ala Asp Ser Val Lys
1               5                   10                  15

Gly

<210> SEQ ID NO 53
<211> LENGTH: 17
<212> TYPE: PRT
<213> ORGANISM: Artificial Sequence
<220> FEATURE:
<223> OTHER INFORMATION: HCDR2-3

<400> SEQUENCE: 53

Ser Ile Ser Arg Ala Ser Ser Tyr Val Tyr Tyr Ala Asp Ser Val Lys
1               5                   10                  15

Gly

<210> SEQ ID NO 54
<211> LENGTH: 17
<212> TYPE: PRT
<213> ORGANISM: Artificial Sequence
<220> FEATURE:
<223> OTHER INFORMATION: HCDR2-4

<400> SEQUENCE: 54

Ser Ile Ser Arg Tyr Ser Gly Tyr Ile Tyr Tyr Ala Asp Ser Val Lys
1               5                   10                  15

Gly

<210> SEQ ID NO 55
<211> LENGTH: 17
<212> TYPE: PRT
<213> ORGANISM: Artificial Sequence
```

<220> FEATURE:
<223> OTHER INFORMATION: HCDR2-5

<400> SEQUENCE: 55

Ser Ile Ser Ala Arg Ser Arg Tyr His Tyr Tyr Ala Asp Ser Val Lys
1               5                   10                  15

Gly

<210> SEQ ID NO 56
<211> LENGTH: 17
<212> TYPE: PRT
<213> ORGANISM: Artificial Sequence
<220> FEATURE:
<223> OTHER INFORMATION: HCDR2-6

<400> SEQUENCE: 56

Ser Ile Ser Ala Arg Ser Ser Tyr Ile Tyr Tyr Ala Asp Ser Val Lys
1               5                   10                  15

Gly

<210> SEQ ID NO 57
<211> LENGTH: 17
<212> TYPE: PRT
<213> ORGANISM: Artificial Sequence
<220> FEATURE:
<223> OTHER INFORMATION: HCDR2-7

<400> SEQUENCE: 57

Ser Ile Ser Ala Leu Ser Ser Tyr Ile Tyr Tyr Ala Asp Ser Val Arg
1               5                   10                  15

Gly

<210> SEQ ID NO 58
<211> LENGTH: 17
<212> TYPE: PRT
<213> ORGANISM: Artificial Sequence
<220> FEATURE:
<223> OTHER INFORMATION: HCDR2-8

<400> SEQUENCE: 58

Ser Ile Ser Ala Gln Ser Ser His Ile Tyr Tyr Ala Asp Ser Val Glu
1               5                   10                  15

Gly

<210> SEQ ID NO 59
<211> LENGTH: 17
<212> TYPE: PRT
<213> ORGANISM: Artificial Sequence
<220> FEATURE:
<223> OTHER INFORMATION: HCDR2-9

<400> SEQUENCE: 59

Ser Ile Ser Ala Arg Ser Ser Tyr Leu Tyr Tyr Ala Asp Ser Val Lys
1               5                   10                  15

Gly

<210> SEQ ID NO 60
<211> LENGTH: 17
<212> TYPE: PRT
<213> ORGANISM: Artificial Sequence
<220> FEATURE:
<223> OTHER INFORMATION: HCDR2-10

<400> SEQUENCE: 60

```
Ser Ile Ser Ala Arg Ser Ser Tyr Arg Tyr Tyr Ala Asp Ser Val Lys
1               5                   10                  15
Gly
```

<210> SEQ ID NO 61
<211> LENGTH: 17
<212> TYPE: PRT
<213> ORGANISM: Artificial Sequence
<220> FEATURE:
<223> OTHER INFORMATION: HCDR2-11

<400> SEQUENCE: 61

```
Ser Ile Ser Ala Arg Ser Ser Tyr Ile Tyr Tyr Ala Gly Ser Val Lys
1               5                   10                  15
Gly
```

<210> SEQ ID NO 62
<211> LENGTH: 17
<212> TYPE: PRT
<213> ORGANISM: Artificial Sequence
<220> FEATURE:
<223> OTHER INFORMATION: HCDR2-12

<400> SEQUENCE: 62

```
Ser Ile Ser Ser Arg Ser Ser His Gln Tyr Tyr Ala Gly Ser Val Lys
1               5                   10                  15
Gly
```

<210> SEQ ID NO 63
<211> LENGTH: 17
<212> TYPE: PRT
<213> ORGANISM: Artificial Sequence
<220> FEATURE:
<223> OTHER INFORMATION: HCDR2-13

<400> SEQUENCE: 63

```
Ser Ile Ser Ala Leu Ser Ser Tyr Arg Tyr Tyr Ala Asp Ser Val Lys
1               5                   10                  15
Gly
```

<210> SEQ ID NO 64
<211> LENGTH: 17
<212> TYPE: PRT
<213> ORGANISM: Artificial Sequence
<220> FEATURE:
<223> OTHER INFORMATION: HCDR2-14

<400> SEQUENCE: 64

```
Ser Ile Ser Ser Ser Ser Ser Tyr Ile Tyr Tyr Ala Asp Ser Val Lys
1               5                   10                  15
Gly
```

<210> SEQ ID NO 65
<211> LENGTH: 7
<212> TYPE: PRT
<213> ORGANISM: Artificial Sequence
<220> FEATURE:
<223> OTHER INFORMATION: HCDR3-1

<400> SEQUENCE: 65

```
Asp Ile Gly Gly Met Asp Val
1               5
```

```
<210> SEQ ID NO 66
<211> LENGTH: 10
<212> TYPE: PRT
<213> ORGANISM: Artificial Sequence
<220> FEATURE:
<223> OTHER INFORMATION: HCDR3-2

<400> SEQUENCE: 66

Leu Ala Thr Arg His Asn Ala Phe Asp Ile
1               5                   10

<210> SEQ ID NO 67
<211> LENGTH: 10
<212> TYPE: PRT
<213> ORGANISM: Artificial Sequence
<220> FEATURE:
<223> OTHER INFORMATION: HCDR3-3

<400> SEQUENCE: 67

Leu Ala Thr Arg Asn Asn Ala Phe Asp Ile
1               5                   10

<210> SEQ ID NO 68
<211> LENGTH: 10
<212> TYPE: PRT
<213> ORGANISM: Artificial Sequence
<220> FEATURE:
<223> OTHER INFORMATION: HCDR3-4

<400> SEQUENCE: 68

Leu Ala Thr Arg Arg Asp Ala Phe Asp Ile
1               5                   10

<210> SEQ ID NO 69
<211> LENGTH: 10
<212> TYPE: PRT
<213> ORGANISM: Artificial Sequence
<220> FEATURE:
<223> OTHER INFORMATION: HCDR3-5

<400> SEQUENCE: 69

Leu Ala Thr Arg Gln Asn Ala Phe Asp Ile
1               5                   10

<210> SEQ ID NO 70
<211> LENGTH: 10
<212> TYPE: PRT
<213> ORGANISM: Artificial Sequence
<220> FEATURE:
<223> OTHER INFORMATION: HCDR3-6

<400> SEQUENCE: 70

Leu Ala Thr Arg His Val Ala Phe Asp Ile
1               5                   10

<210> SEQ ID NO 71
<211> LENGTH: 10
<212> TYPE: PRT
<213> ORGANISM: Artificial Sequence
<220> FEATURE:
<223> OTHER INFORMATION: HCDR3-7

<400> SEQUENCE: 71

Leu Ala Thr Arg His Gly Ala Phe Asp Ile
1               5                   10
```

```
<210> SEQ ID NO 72
<211> LENGTH: 10
<212> TYPE: PRT
<213> ORGANISM: Artificial Sequence
<220> FEATURE:
<223> OTHER INFORMATION: HCDR3-8

<400> SEQUENCE: 72

Leu Ala Thr Arg His Leu Ala Phe Asp Ile
1               5                   10

<210> SEQ ID NO 73
<211> LENGTH: 10
<212> TYPE: PRT
<213> ORGANISM: Artificial Sequence
<220> FEATURE:
<223> OTHER INFORMATION: HCDR3-9

<400> SEQUENCE: 73

Leu Ala Thr Arg His Ser Ala Phe Asp Ile
1               5                   10

<210> SEQ ID NO 74
<211> LENGTH: 10
<212> TYPE: PRT
<213> ORGANISM: Artificial Sequence
<220> FEATURE:
<223> OTHER INFORMATION: HCDR3-10

<400> SEQUENCE: 74

Leu Gly Thr Arg Arg Val Ala Phe Asp Ile
1               5                   10

<210> SEQ ID NO 75
<211> LENGTH: 10
<212> TYPE: PRT
<213> ORGANISM: Artificial Sequence
<220> FEATURE:
<223> OTHER INFORMATION: HCDR3-11

<400> SEQUENCE: 75

Leu Gly Leu Arg His Asp Ala Phe Asp Ile
1               5                   10

<210> SEQ ID NO 76
<211> LENGTH: 10
<212> TYPE: PRT
<213> ORGANISM: Artificial Sequence
<220> FEATURE:
<223> OTHER INFORMATION: HCDR3-12

<400> SEQUENCE: 76

Leu Ala Thr Arg Arg Ile Ala Phe Asp Ile
1               5                   10

<210> SEQ ID NO 77
<211> LENGTH: 10
<212> TYPE: PRT
<213> ORGANISM: Artificial Sequence
<220> FEATURE:
<223> OTHER INFORMATION: HCDR3-13

<400> SEQUENCE: 77

Leu Ala Thr Arg Arg Val Ala Phe Asp Ile
1               5                   10

<210> SEQ ID NO 78
```

<211> LENGTH: 10
<212> TYPE: PRT
<213> ORGANISM: Artificial Sequence
<220> FEATURE:
<223> OTHER INFORMATION: HCDR3-14

<400> SEQUENCE: 78

Leu Gly Thr Arg His Asp Ala Phe Asp Ile
1               5                   10

<210> SEQ ID NO 79
<211> LENGTH: 109
<212> TYPE: PRT
<213> ORGANISM: Artificial Sequence
<220> FEATURE:
<223> OTHER INFORMATION: VL-1

<400> SEQUENCE: 79

Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Ala Val
            20                  25                  30

Tyr Asp Val His Trp Tyr Gln Gln Leu Pro Gly Thr Ala Pro Lys Leu
        35                  40                  45

Leu Ile Tyr Arg Asn Asn Gln Arg Pro Ser Gly Val Pro Asp Arg Phe
    50                  55                  60

Ser Gly Ser Lys Ser Gly Thr Ser Ala Ser Leu Ala Ile Ser Gly Leu
65                  70                  75                  80

Arg Ser Glu Asp Glu Ala Asp Tyr Tyr Cys Gln Thr Tyr Asp Ser Ser
                85                  90                  95

Arg Trp Val Phe Gly Gly Gly Thr Lys Leu Thr Val Leu
            100                 105

<210> SEQ ID NO 80
<211> LENGTH: 109
<212> TYPE: PRT
<213> ORGANISM: Artificial Sequence
<220> FEATURE:
<223> OTHER INFORMATION: VL-2

<400> SEQUENCE: 80

Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Ala Val
            20                  25                  30

Tyr Asp Val His Trp Tyr Gln Gln Leu Pro Gly Thr Ala Pro Lys Leu
        35                  40                  45

Leu Ile Tyr Arg Asn Asn Gln Arg Pro Ser Gly Val Pro Asp Arg Phe
    50                  55                  60

Ser Gly Ser Lys Ser Gly Thr Ser Ala Ser Leu Ala Ile Ser Gly Leu
65                  70                  75                  80

Arg Ser Glu Asp Glu Ala Asp Tyr Tyr Cys Gln Ser Tyr Asp Ser Ser
                85                  90                  95

Arg Trp Val Phe Gly Gly Gly Thr Lys Leu Thr Val Leu
            100                 105

<210> SEQ ID NO 81
<211> LENGTH: 109
<212> TYPE: PRT
<213> ORGANISM: Artificial Sequence
<220> FEATURE:

<223> OTHER INFORMATION: VL-3

<400> SEQUENCE: 81

Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Ala Val
            20                  25                  30

Tyr Asn Val His Trp Tyr Gln Gln Leu Pro Gly Thr Ala Pro Lys Leu
        35                  40                  45

Leu Ile Tyr Arg Asn Asn Gln Arg Pro Ser Gly Val Pro Asp Arg Phe
    50                  55                  60

Ser Gly Ser Lys Ser Gly Thr Ser Ala Ser Leu Ala Ile Ser Gly Leu
65                  70                  75                  80

Arg Ser Glu Asp Glu Ala Asp Tyr Tyr Cys Gln Ser Tyr Asp Ser Ser
                85                  90                  95

Arg Trp Val Phe Gly Gly Gly Thr Lys Leu Thr Val Leu
            100                 105

<210> SEQ ID NO 82
<211> LENGTH: 109
<212> TYPE: PRT
<213> ORGANISM: Artificial Sequence
<220> FEATURE:
<223> OTHER INFORMATION: VL-4

<400> SEQUENCE: 82

Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Ala Val
            20                  25                  30

Tyr Asn Val His Trp Tyr Gln Gln Leu Pro Gly Thr Ala Pro Lys Leu
        35                  40                  45

Leu Ile Tyr Arg Asn Asn Gln Arg Pro Ser Gly Val Pro Asp Arg Phe
    50                  55                  60

Ser Gly Ser Lys Ser Gly Thr Ser Ala Ser Leu Ala Ile Ser Gly Leu
65                  70                  75                  80

Arg Ser Glu Asp Glu Ala Asp Tyr Tyr Cys Gln Ser Tyr Asp Ser Arg
                85                  90                  95

Arg Trp Val Phe Gly Gly Gly Thr Lys Leu Thr Val Leu
            100                 105

<210> SEQ ID NO 83
<211> LENGTH: 110
<212> TYPE: PRT
<213> ORGANISM: Artificial Sequence
<220> FEATURE:
<223> OTHER INFORMATION: VL-5

<400> SEQUENCE: 83

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Asn Asn
            20                  25                  30

Ala Val Ser Trp Tyr Gln Gln Leu Pro Gly Thr Ala Pro Lys Leu Leu
        35                  40                  45

Ile Tyr Ala Ser Asn Met Arg Val Ile Gly Val Pro Asp Arg Phe Ser
    50                  55                  60

Gly Ser Lys Ser Gly Thr Ser Ala Ser Leu Ala Ile Ser Gly Leu Arg

```
                65                  70                  75                  80
Ser Glu Asp Glu Ala Asp Tyr Tyr Cys Gly Ala Trp Asp Ser Gln
                    85                  90                  95

Lys Ala Leu Val Phe Gly Gly Thr Lys Leu Thr Val Leu
                100                 105                 110
```

<210> SEQ ID NO 84
<211> LENGTH: 110
<212> TYPE: PRT
<213> ORGANISM: Artificial Sequence
<220> FEATURE:
<223> OTHER INFORMATION: VL-6

<400> SEQUENCE: 84

```
Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Arg Asn
                20                  25                  30

Ala Val Asn Trp Tyr Gln Gln Leu Pro Gly Thr Ala Pro Lys Leu Leu
            35                  40                  45

Ile Tyr Ala Ser Asn Met Arg Val Ile Gly Val Pro Asp Arg Phe Ser
50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Ser Gln
                    85                  90                  95

Lys Ala Trp Val Phe Gly Gly Thr Lys Leu Thr Val Leu
                100                 105                 110
```

<210> SEQ ID NO 85
<211> LENGTH: 110
<212> TYPE: PRT
<213> ORGANISM: Artificial Sequence
<220> FEATURE:
<223> OTHER INFORMATION: VL-7

<400> SEQUENCE: 85

```
Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Arg Asn
                20                  25                  30

Ala Val Asn Trp Tyr Gln Gln Leu Pro Gly Thr Ala Pro Lys Leu Leu
            35                  40                  45

Ile Tyr Ala Ser Asn Met Arg Val Leu Gly Val Pro Asp Arg Phe Ser
50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Trp Ala Trp Asp Ser Gln
                    85                  90                  95

Lys Ala Val Val Phe Gly Gly Thr Lys Leu Thr Val Leu
                100                 105                 110
```

<210> SEQ ID NO 86
<211> LENGTH: 110
<212> TYPE: PRT
<213> ORGANISM: Artificial Sequence
<220> FEATURE:
<223> OTHER INFORMATION: VL-8

<400> SEQUENCE: 86

Gln Ser Val Leu Thr Gln Pro Pro Ser Ala Ser Gly Thr Pro Gly Gln
1               5                   10                  15

Arg Val Thr Ile Ser Cys Ser Gly Ser Cys Ser Asn Ile Gly Arg Asn
                20                  25                  30

Ala Val Asn Trp Tyr Gln Gln Leu Pro Gly Thr Ala Pro Lys Leu Leu
            35                  40                  45

Ile Tyr Ala Ser Asn Met Arg Val Ile Gly Val Pro Asp Arg Phe Ser
        50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Glu Ala Trp Asp Asp Ser Gln
                85                  90                  95

Lys Gly Val Val Phe Gly Gly Gly Thr Lys Leu Thr Val Leu
                100                 105                 110

<210> SEQ ID NO 87
<211> LENGTH: 110
<212> TYPE: PRT
<213> ORGANISM: Artificial Sequence
<220> FEATURE:
<223> OTHER INFORMATION: VL-9

<400> SEQUENCE: 87

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Arg Asn
                20                  25                  30

Ala Val Asn Trp Tyr Gln Gln Leu Pro Gly Thr Ala Pro Lys Leu Leu
            35                  40                  45

Ile Tyr Ala Ser Asn Met Arg Val Ile Gly Val Pro Asp Arg Phe Ser
        50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Ala Trp Asp Asp Ser Gln
                85                  90                  95

Lys Arg Tyr Val Phe Gly Gly Gly Thr Lys Leu Thr Val Leu
                100                 105                 110

<210> SEQ ID NO 88
<211> LENGTH: 110
<212> TYPE: PRT
<213> ORGANISM: Artificial Sequence
<220> FEATURE:
<223> OTHER INFORMATION: VL-10

<400> SEQUENCE: 88

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Asn Asn
                20                  25                  30

Ala Val Asn Trp Tyr Gln Gln Leu Pro Gly Thr Ala Pro Lys Leu Leu
            35                  40                  45

Ile Tyr Ala Ser Asn Met Arg Gly Ser Gly Val Pro Asp Arg Phe Ser
        50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Gln

```
                    85                  90                  95

Lys Gly Gln Val Phe Gly Gly Gly Thr Lys Leu Thr Val Leu
                100                 105                 110

<210> SEQ ID NO 89
<211> LENGTH: 110
<212> TYPE: PRT
<213> ORGANISM: Artificial Sequence
<220> FEATURE:
<223> OTHER INFORMATION: VL-11

<400> SEQUENCE: 89

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
                20                  25                  30

Ala Val Ser Trp Tyr Gln Gln Leu Pro Gly Thr Ala Pro Lys Leu Leu
            35                  40                  45

Ile Tyr Ala Ser Asn Met Arg Gly Ser Gly Val Pro Asp Arg Phe Ser
        50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Gln
                85                  90                  95

Lys Val Val Val Phe Gly Gly Gly Thr Lys Leu Thr Val Leu
                100                 105                 110

<210> SEQ ID NO 90
<211> LENGTH: 110
<212> TYPE: PRT
<213> ORGANISM: Artificial Sequence
<220> FEATURE:
<223> OTHER INFORMATION: VL-12

<400> SEQUENCE: 90

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Arg Asn
                20                  25                  30

Ala Val Asn Trp Tyr Gln Gln Leu Pro Gly Thr Ala Pro Lys Leu Leu
            35                  40                  45

Ile Tyr Ala Ser Asn Met Arg Val Ser Gly Val Pro Asp Arg Phe Ser
        50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Trp Ala Trp Asp Asp Ser Gln
                85                  90                  95

Lys Val Gly Val Phe Gly Gly Gly Thr Lys Leu Thr Val Leu
                100                 105                 110

<210> SEQ ID NO 91
<211> LENGTH: 110
<212> TYPE: PRT
<213> ORGANISM: Artificial Sequence
<220> FEATURE:
<223> OTHER INFORMATION: VL-13

<400> SEQUENCE: 91

Gln Ser Val Leu Thr Gln Pro Pro Ser Ala Ser Gly Thr Pro Gly Gln
1               5                   10                  15
```

```
Arg Val Thr Ile Ser Cys Ser Gly Ser Ser Asn Ile Gly Asn Asn
            20                  25                  30

Ala Val Asn Trp Tyr Gln Gln Leu Pro Gly Thr Ala Pro Lys Leu Leu
        35                  40                  45

Ile Tyr Ala Ser Asn Met Arg Gly Leu Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Ala Trp Asp Asp Ser Gln
                85                  90                  95

Lys Val Phe Val Phe Gly Gly Gly Thr Lys Leu Thr Val Leu
            100                 105                 110

<210> SEQ ID NO 92
<211> LENGTH: 110
<212> TYPE: PRT
<213> ORGANISM: Artificial Sequence
<220> FEATURE:
<223> OTHER INFORMATION: VL-14

<400> SEQUENCE: 92

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Arg Asn
            20                  25                  30

Ala Val Asn Trp Tyr Gln Gln Leu Pro Gly Thr Ala Pro Lys Leu Leu
        35                  40                  45

Ile Tyr Ala Ser Asn Met Arg Arg Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ser Ala Trp Asp Asp Ser Gln
                85                  90                  95

Lys Val Val Val Phe Gly Gly Gly Thr Lys Leu Thr Val Leu
            100                 105                 110

<210> SEQ ID NO 93
<211> LENGTH: 110
<212> TYPE: PRT
<213> ORGANISM: Artificial Sequence
<220> FEATURE:
<223> OTHER INFORMATION: VL-15

<400> SEQUENCE: 93

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Asn Asn
            20                  25                  30

Ala Val Asn Trp Tyr Gln Gln Leu Pro Gly Thr Ala Pro Lys Leu Leu
        35                  40                  45

Ile Tyr Ala Ser Asn Met Arg Arg Pro Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Glu Ala Trp Asp Asp Ser Gln
                85                  90                  95

Lys Ala Val Val Phe Gly Gly Gly Thr Lys Leu Thr Val Leu
```

-continued

```
                100               105                110

<210> SEQ ID NO 94
<211> LENGTH: 110
<212> TYPE: PRT
<213> ORGANISM: Artificial Sequence
<220> FEATURE:
<223> OTHER INFORMATION: VL-16

<400> SEQUENCE: 94

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Asn Asn
            20                  25                  30

Ala Val Asn Trp Tyr Gln Gln Leu Pro Gly Thr Ala Pro Lys Leu Leu
        35                  40                  45

Ile Tyr Ala Ser Asn Met Arg Arg Met Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Gln
                85                  90                  95

Lys Ala Phe Val Phe Gly Gly Gly Thr Lys Leu Thr Val Leu
            100                 105                 110

<210> SEQ ID NO 95
<211> LENGTH: 110
<212> TYPE: PRT
<213> ORGANISM: Artificial Sequence
<220> FEATURE:
<223> OTHER INFORMATION: VL-17

<400> SEQUENCE: 95

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Asn Asn
            20                  25                  30

Ala Val Asn Trp Tyr Gln Gln Leu Pro Gly Thr Ala Pro Lys Leu Leu
        35                  40                  45

Ile Tyr Ala Ser Asn Met Arg Arg Leu Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Gln
                85                  90                  95

Lys Ala Trp Val Phe Gly Gly Gly Thr Lys Leu Thr Val Leu
            100                 105                 110

<210> SEQ ID NO 96
<211> LENGTH: 110
<212> TYPE: PRT
<213> ORGANISM: Artificial Sequence
<220> FEATURE:
<223> OTHER INFORMATION: VL-18

<400> SEQUENCE: 96

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Asn Asn
            20                  25                  30
```

Ala Val Asn Trp Tyr Gln Gln Leu Pro Gly Thr Ala Pro Lys Leu Leu
            35                  40                  45

Ile Tyr Ala Ser Asn Met Arg Arg Pro Gly Val Pro Asp Arg Phe Ser
 50                  55                  60

Gly Ser Lys Ser Gly Thr Ser Ala Ser Leu Ala Ile Ser Gly Leu Arg
 65                  70                  75                  80

Ser Glu Asp Glu Ala Asp Tyr Tyr Cys Ala Ala Trp Asp Asp Ser Gln
                 85                  90                  95

Lys Val Phe Val Phe Gly Gly Gly Thr Lys Leu Thr Val Leu
                100                 105                 110

<210> SEQ ID NO 97
<211> LENGTH: 110
<212> TYPE: PRT
<213> ORGANISM: Artificial Sequence
<220> FEATURE:
<223> OTHER INFORMATION: VL-19

<400> SEQUENCE: 97

Gln Ser Val Leu Thr Gln Pro Pro Ser Ala Ser Gly Thr Pro Gly Gln
 1               5                  10                  15

Arg Val Thr Ile Ser Cys Ser Gly Ser Ser Ser Asn Ile Gly Asn Asn
                20                  25                  30

Ala Val Asn Trp Tyr Gln Gln Leu Pro Gly Thr Ala Pro Lys Leu Leu
            35                  40                  45

Ile Tyr Ala Ser Asn Met Arg Arg Leu Gly Val Pro Asp Arg Phe Ser
 50                  55                  60

Gly Ser Lys Ser Gly Thr Ser Ala Ser Leu Ala Ile Ser Gly Leu Arg
 65                  70                  75                  80

Ser Glu Asp Glu Ala Asp Tyr Tyr Cys Gly Ala Trp Asp Asp Ser Gln
                 85                  90                  95

Lys Ala Phe Val Phe Gly Gly Gly Thr Lys Leu Thr Val Leu
                100                 105                 110

<210> SEQ ID NO 98
<211> LENGTH: 110
<212> TYPE: PRT
<213> ORGANISM: Artificial Sequence
<220> FEATURE:
<223> OTHER INFORMATION: VL-20

<400> SEQUENCE: 98

Gln Ser Val Leu Thr Gln Pro Pro Ser Ala Ser Gly Thr Pro Gly Gln
 1               5                  10                  15

Arg Val Thr Ile Ser Cys Ser Gly Ser Ser Ser Asn Ile Gly Arg Asn
                20                  25                  30

Ala Val Ser Trp Tyr Gln Gln Leu Pro Gly Thr Ala Pro Lys Leu Leu
            35                  40                  45

Ile Tyr Ala Ser Asn Met Arg Arg Leu Gly Val Pro Asp Arg Phe Ser
 50                  55                  60

Gly Ser Lys Ser Gly Thr Ser Ala Ser Leu Ala Ile Ser Gly Leu Arg
 65                  70                  75                  80

Ser Glu Asp Glu Ala Asp Tyr Tyr Cys Trp Ala Trp Asp Asp Ser Gln
                 85                  90                  95

Lys Ala Val Val Phe Gly Gly Gly Thr Lys Leu Thr Val Leu
                100                 105                 110

<210> SEQ ID NO 99
<211> LENGTH: 110
<212> TYPE: PRT
<213> ORGANISM: Artificial Sequence
<220> FEATURE:
<223> OTHER INFORMATION: VL-21

<400> SEQUENCE: 99

```
Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly His Asn
            20                  25                  30

Ala Val Ser Trp Tyr Gln Gln Leu Pro Gly Thr Ala Pro Lys Leu Leu
        35                  40                  45

Ile Tyr Ala Ser Asn Met Arg Arg Leu Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Ala Trp Asp Asp Ser Gln
                85                  90                  95

Lys Val Val Val Phe Gly Gly Gly Thr Lys Leu Thr Val Leu
            100                 105                 110
```

<210> SEQ ID NO 100
<211> LENGTH: 110
<212> TYPE: PRT
<213> ORGANISM: Artificial Sequence
<220> FEATURE:
<223> OTHER INFORMATION: VL-22

<400> SEQUENCE: 100

```
Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Arg Asn
            20                  25                  30

Ala Val Asn Trp Tyr Gln Gln Leu Pro Gly Thr Ala Pro Lys Leu Leu
        35                  40                  45

Ile Tyr Ala Ser Asn Met Arg Gly Met Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ser Ala Trp Asp Asp Ser Gln
                85                  90                  95

Lys Val Val Val Phe Gly Gly Gly Thr Lys Leu Thr Val Leu
            100                 105                 110
```

<210> SEQ ID NO 101
<211> LENGTH: 110
<212> TYPE: PRT
<213> ORGANISM: Artificial Sequence
<220> FEATURE:
<223> OTHER INFORMATION: VL-23

<400> SEQUENCE: 101

```
Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly His Asn
            20                  25                  30

Ala Val Trp Trp Tyr Gln Gln Leu Pro Gly Thr Ala Pro Lys Leu Leu
        35                  40                  45
```

```
Ile Tyr Ala Ser Asn Met Arg Arg Met Gly Val Pro Asp Arg Phe Ser
            50                  55                  60

Gly Ser Lys Ser Gly Thr Ser Ala Ser Leu Ala Ile Ser Gly Leu Arg
 65                  70                  75                  80

Ser Glu Asp Glu Ala Asp Tyr Tyr Cys Ala Ala Trp Asp Asp Ser Gln
                85                  90                  95

Lys Ala Val Val Phe Gly Gly Gly Thr Lys Leu Thr Val Leu
                100                 105                 110

<210> SEQ ID NO 102
<211> LENGTH: 110
<212> TYPE: PRT
<213> ORGANISM: Artificial Sequence
<220> FEATURE:
<223> OTHER INFORMATION: VL-24

<400> SEQUENCE: 102

Gln Ser Val Leu Thr Gln Pro Pro Ser Ala Ser Gly Thr Pro Gly Gln
 1               5                  10                  15

Arg Val Thr Ile Ser Cys Ser Gly Ser Ser Asn Ile Gly Arg Asn
                20                  25                  30

Ala Val Asn Trp Tyr Gln Gln Leu Pro Gly Thr Ala Pro Lys Leu Leu
            35                  40                  45

Ile Tyr Ala Ser Asn Met Arg Arg Pro Gly Val Pro Asp Arg Phe Ser
            50                  55                  60

Gly Ser Lys Ser Gly Thr Ser Ala Ser Leu Ala Ile Ser Gly Leu Arg
 65                  70                  75                  80

Ser Glu Asp Glu Ala Asp Tyr Tyr Cys Ser Ala Trp Asp Asp Ser Gln
                85                  90                  95

Lys Ala Gly Val Phe Gly Gly Gly Thr Lys Leu Thr Val Leu
                100                 105                 110

<210> SEQ ID NO 103
<211> LENGTH: 110
<212> TYPE: PRT
<213> ORGANISM: Artificial Sequence
<220> FEATURE:
<223> OTHER INFORMATION: VL-25

<400> SEQUENCE: 103

Gln Ser Val Leu Thr Gln Pro Pro Ser Ala Ser Gly Thr Pro Gly Gln
 1               5                  10                  15

Arg Val Thr Ile Ser Cys Ser Gly Ser Ser Asn Ile Gly Asn Asn
                20                  25                  30

Ala Val Asn Trp Tyr Gln Gln Leu Pro Gly Thr Ala Pro Lys Leu Leu
            35                  40                  45

Ile Tyr Ala Ser Asn Met Arg Arg Leu Gly Val Pro Asp Arg Phe Ser
            50                  55                  60

Gly Ser Lys Ser Gly Thr Ser Ala Ser Leu Ala Ile Ser Gly Leu Arg
 65                  70                  75                  80

Ser Glu Asp Glu Ala Asp Tyr Tyr Cys Ala Ala Trp Asp Asp Ser Gln
                85                  90                  95

Lys Ala Leu Val Phe Gly Gly Gly Thr Lys Leu Thr Val Leu
                100                 105                 110

<210> SEQ ID NO 104
<211> LENGTH: 110
<212> TYPE: PRT
```

<213> ORGANISM: Artificial Sequence
<220> FEATURE:
<223> OTHER INFORMATION: VL-26

<400> SEQUENCE: 104

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Asn Asn
            20                  25                  30

Ala Val Asn Trp Tyr Gln Gln Leu Pro Gly Thr Ala Pro Lys Leu Leu
        35                  40                  45

Ile Tyr Ala Ser Asn Met Arg Arg Leu Gly Val Pro Asp Arg Phe Ser
50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Gln
                85                  90                  95

Lys Ala Val Val Phe Gly Gly Gly Thr Lys Leu Thr Val Leu
            100                 105                 110

<210> SEQ ID NO 105
<211> LENGTH: 116
<212> TYPE: PRT
<213> ORGANISM: Artificial Sequence
<220> FEATURE:
<223> OTHER INFORMATION: VH-1

<400> SEQUENCE: 105

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met Asn Trp Val Arg Gln Ala Pro Gly Lys Gly Leu Glu Trp Val
        35                  40                  45

Ser Ser Ile Ser Arg Tyr Ser Ser Tyr Ile Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Ile Gly Gly Met Asp Val Trp Gly Gln Gly Thr Leu Val
            100                 105                 110

Thr Val Ser Ser
        115

<210> SEQ ID NO 106
<211> LENGTH: 116
<212> TYPE: PRT
<213> ORGANISM: Artificial Sequence
<220> FEATURE:
<223> OTHER INFORMATION: VH-2

<400> SEQUENCE: 106

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met Asn Trp Val Arg Gln Ala Pro Gly Lys Gly Leu Glu Trp Val
        35                  40                  45

```
Ser Ser Ile Ser Arg Tyr Ser Gly Tyr Val Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Ile Gly Gly Met Asp Val Trp Gly Gln Gly Thr Leu Val
                100                 105                 110

Thr Val Ser Ser
        115

<210> SEQ ID NO 107
<211> LENGTH: 116
<212> TYPE: PRT
<213> ORGANISM: Artificial Sequence
<220> FEATURE:
<223> OTHER INFORMATION: VH-3

<400> SEQUENCE: 107

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
                20                  25                  30

Tyr Met Asp Trp Val Arg Gln Ala Pro Gly Lys Gly Leu Glu Trp Val
            35                  40                  45

Ser Ser Ile Ser Arg Tyr Ser Gly Tyr Val Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Ile Gly Gly Met Asp Val Trp Gly Gln Gly Thr Leu Val
                100                 105                 110

Thr Val Ser Ser
        115

<210> SEQ ID NO 108
<211> LENGTH: 116
<212> TYPE: PRT
<213> ORGANISM: Artificial Sequence
<220> FEATURE:
<223> OTHER INFORMATION: VH-4

<400> SEQUENCE: 108

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
                20                  25                  30

Tyr Met Asp Trp Val Arg Gln Ala Pro Gly Lys Gly Leu Glu Trp Val
            35                  40                  45

Ser Ser Ile Ser Arg Ala Ser Ser Tyr Val Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Ile Gly Gly Met Asp Val Trp Gly Gln Gly Thr Leu Val
```

Thr Val Ser Ser
         115

<210> SEQ ID NO 109
<211> LENGTH: 116
<212> TYPE: PRT
<213> ORGANISM: Artificial Sequence
<220> FEATURE:
<223> OTHER INFORMATION: VH-5

<400> SEQUENCE: 109

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met Asn Trp Val Arg Gln Ala Pro Gly Lys Gly Leu Glu Trp Val
        35                  40                  45

Ser Ser Ile Ser Arg Tyr Ser Gly Tyr Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Ile Gly Gly Met Asp Val Trp Gly Gln Gly Thr Leu Val
            100                 105                 110

Thr Val Ser Ser
         115

<210> SEQ ID NO 110
<211> LENGTH: 116
<212> TYPE: PRT
<213> ORGANISM: Artificial Sequence
<220> FEATURE:
<223> OTHER INFORMATION: VH-6

<400> SEQUENCE: 110

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Val Tyr
            20                  25                  30

Tyr Met Asn Trp Val Arg Gln Ala Pro Gly Lys Gly Leu Glu Trp Val
        35                  40                  45

Ser Ser Ile Ser Arg Tyr Ser Gly Tyr Val Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Ile Gly Gly Met Asp Val Trp Gly Gln Gly Thr Leu Val
            100                 105                 110

Thr Val Ser Ser
         115

<210> SEQ ID NO 111
<211> LENGTH: 116
<212> TYPE: PRT
<213> ORGANISM: Artificial Sequence
<220> FEATURE:

-continued

<223> OTHER INFORMATION: VH-7

<400> SEQUENCE: 111

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Val Asn Trp Val Arg Gln Ala Pro Gly Lys Gly Leu Glu Trp Val
        35                  40                  45

Ser Ser Ile Ser Arg Tyr Ser Gly Tyr Val Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Ile Gly Gly Met Asp Val Trp Gly Gln Gly Thr Leu Val
            100                 105                 110

Thr Val Ser Ser
        115

<210> SEQ ID NO 112
<211> LENGTH: 119
<212> TYPE: PRT
<213> ORGANISM: Artificial Sequence
<220> FEATURE:
<223> OTHER INFORMATION: VH-8

<400> SEQUENCE: 112

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Tyr Met His Trp Val Arg Gln Ala Pro Gly Lys Gly Leu Glu Trp Val
        35                  40                  45

Ser Ser Ile Ser Ala Arg Ser Arg Tyr His Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Ala Thr Arg His Asn Ala Phe Asp Ile Trp Gly Gln Gly
            100                 105                 110

Thr Leu Val Thr Val Ser Ser
        115

<210> SEQ ID NO 113
<211> LENGTH: 119
<212> TYPE: PRT
<213> ORGANISM: Artificial Sequence
<220> FEATURE:
<223> OTHER INFORMATION: VH-9

<400> SEQUENCE: 113

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Tyr Met His Trp Val Arg Gln Ala Pro Gly Lys Gly Leu Glu Trp Val

```
                35                  40                  45
Ser Ser Ile Ser Ala Arg Ser Ser Tyr Ile Tyr Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Leu Ala Thr Arg Asn Asn Ala Phe Asp Ile Trp Gly Gln Gly
               100                 105                 110

Thr Leu Val Thr Val Ser Ser
            115

<210> SEQ ID NO 114
<211> LENGTH: 119
<212> TYPE: PRT
<213> ORGANISM: Artificial Sequence
<220> FEATURE:
<223> OTHER INFORMATION: VH-10

<400> SEQUENCE: 114

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser His Tyr
                20                  25                  30

Tyr Met His Trp Val Arg Gln Ala Pro Gly Lys Gly Leu Glu Trp Val
                35                  40                  45

Ser Ser Ile Ser Ala Leu Ser Tyr Ile Tyr Tyr Ala Asp Ser Val
        50                  55                  60

Arg Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Leu Ala Thr Arg Arg Asp Ala Phe Asp Ile Trp Gly Gln Gly
               100                 105                 110

Thr Leu Val Thr Val Ser Ser
            115

<210> SEQ ID NO 115
<211> LENGTH: 119
<212> TYPE: PRT
<213> ORGANISM: Artificial Sequence
<220> FEATURE:
<223> OTHER INFORMATION: VH-11

<400> SEQUENCE: 115

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Arg Tyr
                20                  25                  30

Tyr Met His Trp Val Arg Gln Ala Pro Gly Lys Gly Leu Glu Trp Val
                35                  40                  45

Ser Ser Ile Ser Ala Gln Ser His Ile Tyr Tyr Ala Asp Ser Val
        50                  55                  60

Glu Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95
```

Ala Arg Leu Ala Thr Arg Gln Asn Ala Phe Asp Ile Trp Gly Gln Gly
            100                 105                 110

Thr Leu Val Thr Val Ser Ser
        115

<210> SEQ ID NO 116
<211> LENGTH: 119
<212> TYPE: PRT
<213> ORGANISM: Artificial Sequence
<220> FEATURE:
<223> OTHER INFORMATION: VH-12

<400> SEQUENCE: 116

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Tyr Met His Trp Val Arg Gln Ala Pro Gly Lys Gly Leu Glu Trp Val
            35                  40                  45

Ser Ser Ile Ser Ala Arg Ser Ser Tyr Leu Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Ala Thr Arg His Val Ala Phe Asp Ile Trp Gly Gln Gly
            100                 105                 110

Thr Leu Val Thr Val Ser Ser
        115

<210> SEQ ID NO 117
<211> LENGTH: 119
<212> TYPE: PRT
<213> ORGANISM: Artificial Sequence
<220> FEATURE:
<223> OTHER INFORMATION: VH-13

<400> SEQUENCE: 117

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Tyr Met His Trp Val Arg Gln Ala Pro Gly Lys Gly Leu Glu Trp Val
            35                  40                  45

Ser Ser Ile Ser Ala Arg Ser Ser Tyr Ile Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Ala Thr Arg His Gly Ala Phe Asp Ile Trp Gly Gln Gly
            100                 105                 110

Thr Leu Val Thr Val Ser Ser
        115

<210> SEQ ID NO 118
<211> LENGTH: 119
<212> TYPE: PRT
<213> ORGANISM: Artificial Sequence

```
<220> FEATURE:
<223> OTHER INFORMATION: VH-14

<400> SEQUENCE: 118

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Tyr Met His Trp Val Arg Gln Ala Pro Gly Lys Gly Leu Glu Trp Val
        35                  40                  45

Ser Ser Ile Ser Ala Arg Ser Ser Tyr Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Ala Thr Arg His Asn Ala Phe Asp Ile Trp Gly Gln Gly
            100                 105                 110

Thr Leu Val Thr Val Ser Ser
        115

<210> SEQ ID NO 119
<211> LENGTH: 119
<212> TYPE: PRT
<213> ORGANISM: Artificial Sequence
<220> FEATURE:
<223> OTHER INFORMATION: VH-15

<400> SEQUENCE: 119

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Tyr Met His Trp Val Arg Gln Ala Pro Gly Lys Gly Leu Glu Trp Val
        35                  40                  45

Ser Ser Ile Ser Ala Arg Ser Ser Tyr Arg Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Ala Thr Arg His Leu Ala Phe Asp Ile Trp Gly Gln Gly
            100                 105                 110

Thr Leu Val Thr Val Ser Ser
        115

<210> SEQ ID NO 120
<211> LENGTH: 119
<212> TYPE: PRT
<213> ORGANISM: Artificial Sequence
<220> FEATURE:
<223> OTHER INFORMATION: VH-16

<400> SEQUENCE: 120

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30
```

Tyr Met His Trp Val Arg Gln Ala Pro Gly Lys Gly Leu Glu Trp Val
            35                  40                  45

Ser Ser Ile Ser Ala Arg Ser Ser Tyr Ile Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Leu Ala Thr Arg His Ser Ala Phe Asp Ile Trp Gly Gln Gly
            100                 105                 110

Thr Leu Val Thr Val Ser Ser
            115

<210> SEQ ID NO 121
<211> LENGTH: 119
<212> TYPE: PRT
<213> ORGANISM: Artificial Sequence
<220> FEATURE:
<223> OTHER INFORMATION: VH-17

<400> SEQUENCE: 121

Glu Val Gln Leu Leu Glu Ser Gly Gly Gly Leu Val Gln Pro Gly Gly
 1               5                   10                  15

Ser Leu Arg Leu Ser Cys Ala Ala Ser Gly Phe Thr Phe Ser Arg Tyr
            20                  25                  30

Tyr Met His Trp Val Arg Gln Ala Pro Gly Lys Gly Leu Glu Trp Val
            35                  40                  45

Ser Ser Ile Ser Ala Arg Ser Ser Tyr Ile Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Leu Ala Thr Arg Arg Asp Ala Phe Asp Ile Trp Gly Gln Gly
            100                 105                 110

Thr Leu Val Thr Val Ser Ser
            115

<210> SEQ ID NO 122
<211> LENGTH: 119
<212> TYPE: PRT
<213> ORGANISM: Artificial Sequence
<220> FEATURE:
<223> OTHER INFORMATION: VH-18

<400> SEQUENCE: 122

Glu Val Gln Leu Leu Glu Ser Gly Gly Gly Leu Val Gln Pro Gly Gly
 1               5                   10                  15

Ser Leu Arg Leu Ser Cys Ala Ala Ser Gly Phe Thr Phe Ser Asn Tyr
            20                  25                  30

Tyr Met His Trp Val Arg Gln Ala Pro Gly Lys Gly Leu Glu Trp Val
            35                  40                  45

Ser Ser Ile Ser Ala Arg Ser Ser Tyr Arg Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

```
Ala Arg Leu Ala Thr Arg His Ser Ala Phe Asp Ile Trp Gly Gln Gly
            100                 105                 110

Thr Leu Val Thr Val Ser Ser
        115

<210> SEQ ID NO 123
<211> LENGTH: 119
<212> TYPE: PRT
<213> ORGANISM: Artificial Sequence
<220> FEATURE:
<223> OTHER INFORMATION: VH-19

<400> SEQUENCE: 123

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Tyr Met His Trp Val Arg Gln Ala Pro Gly Lys Gly Leu Glu Trp Val
        35                  40                  45

Ser Ser Ile Ser Ala Arg Ser Ser Tyr Ile Tyr Tyr Ala Gly Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Gly Thr Arg Arg Val Ala Phe Asp Ile Trp Gly Gln Gly
            100                 105                 110

Thr Leu Val Thr Val Ser Ser
        115

<210> SEQ ID NO 124
<211> LENGTH: 119
<212> TYPE: PRT
<213> ORGANISM: Artificial Sequence
<220> FEATURE:
<223> OTHER INFORMATION: VH-20

<400> SEQUENCE: 124

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Tyr Met His Trp Val Arg Gln Ala Pro Gly Lys Gly Leu Glu Trp Val
        35                  40                  45

Ser Ser Ile Ser Ser Arg Ser Ser His Gln Tyr Tyr Ala Gly Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Gly Leu Arg His Asp Ala Phe Asp Ile Trp Gly Gln Gly
            100                 105                 110

Thr Leu Val Thr Val Ser Ser
        115

<210> SEQ ID NO 125
<211> LENGTH: 119
<212> TYPE: PRT
```

<213> ORGANISM: Artificial Sequence
<220> FEATURE:
<223> OTHER INFORMATION: VH-21

<400> SEQUENCE: 125

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Tyr Met His Trp Val Arg Gln Ala Pro Gly Lys Gly Leu Glu Trp Val
        35                  40                  45

Ser Ser Ile Ser Ala Arg Ser Ser Tyr Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Ala Thr Arg Arg Ile Ala Phe Asp Ile Trp Gly Gln Gly
            100                 105                 110

Thr Leu Val Thr Val Ser Ser
        115

<210> SEQ ID NO 126
<211> LENGTH: 119
<212> TYPE: PRT
<213> ORGANISM: Artificial Sequence
<220> FEATURE:
<223> OTHER INFORMATION: VH-22

<400> SEQUENCE: 126

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Tyr Met His Trp Val Arg Gln Ala Pro Gly Lys Gly Leu Glu Trp Val
        35                  40                  45

Ser Ser Ile Ser Ala Leu Ser Ser Tyr Arg Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Ala Thr Arg Arg Val Ala Phe Asp Ile Trp Gly Gln Gly
            100                 105                 110

Thr Leu Val Thr Val Ser Ser
        115

<210> SEQ ID NO 127
<211> LENGTH: 116
<212> TYPE: PRT
<213> ORGANISM: Artificial Sequence
<220> FEATURE:
<223> OTHER INFORMATION: VH-23

<400> SEQUENCE: 127

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met Asn Trp Val Arg Gln Ala Pro Gly Lys Gly Leu Glu Trp Val
        35                  40                  45

Ser Ser Ile Ser Ser Ser Ser Tyr Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Ile Gly Gly Met Asp Val Trp Gly Gln Gly Thr Leu Val
            100                 105                 110

Thr Val Ser Ser
        115

<210> SEQ ID NO 128
<211> LENGTH: 119
<212> TYPE: PRT
<213> ORGANISM: Artificial Sequence
<220> FEATURE:
<223> OTHER INFORMATION: VH-24

<400> SEQUENCE: 128

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Tyr Met His Trp Val Arg Gln Ala Pro Gly Lys Gly Leu Glu Trp Val
        35                  40                  45

Ser Ser Ile Ser Ser Ser Ser Tyr Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Gly Thr Arg His Asp Ala Phe Asp Ile Trp Gly Gln Gly
            100                 105                 110

Thr Leu Val Thr Val Ser Ser
        115

<210> SEQ ID NO 129
<211> LENGTH: 42
<212> TYPE: DNA
<213> ORGANISM: Artificial Sequence
<220> FEATURE:
<223> OTHER INFORMATION: N-LCDR1-1

<400> SEQUENCE: 129
actgggagca gctccaacat cggggcagtt tatgatgtac ac          42

<210> SEQ ID NO 130
<211> LENGTH: 42
<212> TYPE: DNA
<213> ORGANISM: Artificial Sequence
<220> FEATURE:
<223> OTHER INFORMATION: N-LCDR1-2

<400> SEQUENCE: 130
actgggagca gctccaacat cggggcagtt tataatgtac ac          42

<210> SEQ ID NO 131

```
<211> LENGTH: 39
<212> TYPE: DNA
<213> ORGANISM: Artificial Sequence
<220> FEATURE:
<223> OTHER INFORMATION: N-LCDR1-3

<400> SEQUENCE: 131
tctggaagca gctccaacat cggaaataat gctgtaagc                    39

<210> SEQ ID NO 132
<211> LENGTH: 39
<212> TYPE: DNA
<213> ORGANISM: Artificial Sequence
<220> FEATURE:
<223> OTHER INFORMATION: N-LCDR1-4

<400> SEQUENCE: 132
tctggaagca gctccaacat cggacgtaat gctgtaaac                    39

<210> SEQ ID NO 133
<211> LENGTH: 39
<212> TYPE: DNA
<213> ORGANISM: Artificial Sequence
<220> FEATURE:
<223> OTHER INFORMATION: N-LCDR1-5

<400> SEQUENCE: 133
tctggaagct gctccaacat cggacgtaat gctgtaaac                    39

<210> SEQ ID NO 134
<211> LENGTH: 39
<212> TYPE: DNA
<213> ORGANISM: Artificial Sequence
<220> FEATURE:
<223> OTHER INFORMATION: N-LCDR1-6

<400> SEQUENCE: 134
tctggaagca gctccaacat cggaaataat gctgtaaac                    39

<210> SEQ ID NO 135
<211> LENGTH: 39
<212> TYPE: DNA
<213> ORGANISM: Artificial Sequence
<220> FEATURE:
<223> OTHER INFORMATION: N-LCDR1-7

<400> SEQUENCE: 135
tctggaagca gctccaacat cggaagtaat gctgtaagc                    39

<210> SEQ ID NO 136
<211> LENGTH: 39
<212> TYPE: DNA
<213> ORGANISM: Artificial Sequence
<220> FEATURE:
<223> OTHER INFORMATION: N-LCDR1-8

<400> SEQUENCE: 136
tctggaagca gctccaacat cggacgcaat gctgtaagc                    39

<210> SEQ ID NO 137
<211> LENGTH: 39
<212> TYPE: DNA
<213> ORGANISM: Artificial Sequence
<220> FEATURE:
<223> OTHER INFORMATION: N-LCDR1-9

<400> SEQUENCE: 137
```
tctggaagca gctccaacat cggacacaat gctgtaagc                              39

<210> SEQ ID NO 138
<211> LENGTH: 39
<212> TYPE: DNA
<213> ORGANISM: Artificial Sequence
<220> FEATURE:
<223> OTHER INFORMATION: N-LCDR1-10

<400> SEQUENCE: 138
tctggaagca gctccaacat cggacgcaat gctgtaaac                              39

<210> SEQ ID NO 139
<211> LENGTH: 39
<212> TYPE: DNA
<213> ORGANISM: Artificial Sequence
<220> FEATURE:
<223> OTHER INFORMATION: N-LCDR1-11

<400> SEQUENCE: 139
tctggaagca gctccaacat cggacacaat gctgtatgg                              39

<210> SEQ ID NO 140
<211> LENGTH: 21
<212> TYPE: DNA
<213> ORGANISM: Artificial Sequence
<220> FEATURE:
<223> OTHER INFORMATION: N-LCDR1-12

<400> SEQUENCE: 140
aggaataatc agcggccctc a                                                 21

<210> SEQ ID NO 141
<211> LENGTH: 21
<212> TYPE: DNA
<213> ORGANISM: Artificial Sequence
<220> FEATURE:
<223> OTHER INFORMATION: N-LCDR2-1

<400> SEQUENCE: 141
gccagtaaca tgagagtcat t                                                 21

<210> SEQ ID NO 142
<211> LENGTH: 21
<212> TYPE: DNA
<213> ORGANISM: Artificial Sequence
<220> FEATURE:
<223> OTHER INFORMATION: N-LCDR2-2

<400> SEQUENCE: 142
gccagtaaca tgagagtctt a                                                 21

<210> SEQ ID NO 143
<211> LENGTH: 21
<212> TYPE: DNA
<213> ORGANISM: Artificial Sequence
<220> FEATURE:
<223> OTHER INFORMATION: N-LCDR2-3

<400> SEQUENCE: 143
gccagtaaca tgagagtcat a                                                 21

<210> SEQ ID NO 144
<211> LENGTH: 21
<212> TYPE: DNA

<213> ORGANISM: Artificial Sequence
<220> FEATURE:
<223> OTHER INFORMATION: N-LCDR2-4

<400> SEQUENCE: 144
gccagtaaca tgagaggctc t          21

<210> SEQ ID NO 145
<211> LENGTH: 21
<212> TYPE: DNA
<213> ORGANISM: Artificial Sequence
<220> FEATURE:
<223> OTHER INFORMATION: N-LCDR2-5

<400> SEQUENCE: 145
gccagtaaca tgagagtctc t          21

<210> SEQ ID NO 146
<211> LENGTH: 21
<212> TYPE: DNA
<213> ORGANISM: Artificial Sequence
<220> FEATURE:
<223> OTHER INFORMATION: N-LCDR2-6

<400> SEQUENCE: 146
gccagtaaca tgagaggctt a          21

<210> SEQ ID NO 147
<211> LENGTH: 21
<212> TYPE: DNA
<213> ORGANISM: Artificial Sequence
<220> FEATURE:
<223> OTHER INFORMATION: N-LCDR2-7

<400> SEQUENCE: 147
gccagtaaca tgagacgctc t          21

<210> SEQ ID NO 148
<211> LENGTH: 21
<212> TYPE: DNA
<213> ORGANISM: Artificial Sequence
<220> FEATURE:
<223> OTHER INFORMATION: N-LCDR2-8

<400> SEQUENCE: 148
gccagtaaca tgagacgccc g          21

<210> SEQ ID NO 149
<211> LENGTH: 21
<212> TYPE: DNA
<213> ORGANISM: Artificial Sequence
<220> FEATURE:
<223> OTHER INFORMATION: N-LCDR2-9

<400> SEQUENCE: 149
gccagtaaca tgagacgcat g          21

<210> SEQ ID NO 150
<211> LENGTH: 21
<212> TYPE: DNA
<213> ORGANISM: Artificial Sequence
<220> FEATURE:
<223> OTHER INFORMATION: N-LCDR2-10

<400> SEQUENCE: 150
gccagtaaca tgagacgcct g          21

<210> SEQ ID NO 151
<211> LENGTH: 21
<212> TYPE: DNA
<213> ORGANISM: Artificial Sequence
<220> FEATURE:
<223> OTHER INFORMATION: N-LCDR2-11

<400> SEQUENCE: 151
gccagtaaca tgagacgtct g                                             21

<210> SEQ ID NO 152
<211> LENGTH: 21
<212> TYPE: DNA
<213> ORGANISM: Artificial Sequence
<220> FEATURE:
<223> OTHER INFORMATION: N-LCDR2-12

<400> SEQUENCE: 152
gccagtaaca tgagaggtat g                                             21

<210> SEQ ID NO 153
<211> LENGTH: 21
<212> TYPE: DNA
<213> ORGANISM: Artificial Sequence
<220> FEATURE:
<223> OTHER INFORMATION: N-LCDR2-13

<400> SEQUENCE: 153
gccagtaaca tgagacgtat g                                             21

<210> SEQ ID NO 154
<211> LENGTH: 21
<212> TYPE: DNA
<213> ORGANISM: Artificial Sequence
<220> FEATURE:
<223> OTHER INFORMATION: N-LCDR2-14

<400> SEQUENCE: 154
gccagtaaca tgagacgtcc g                                             21

<210> SEQ ID NO 155
<211> LENGTH: 21
<212> TYPE: DNA
<213> ORGANISM: Artificial Sequence
<220> FEATURE:
<223> OTHER INFORMATION: N-LCDR2-15

<400> SEQUENCE: 155
gccagtaaca tgagacgctt a                                             21

<210> SEQ ID NO 156
<211> LENGTH: 27
<212> TYPE: DNA
<213> ORGANISM: Artificial Sequence
<220> FEATURE:
<223> OTHER INFORMATION: N-LCDR3-1

<400> SEQUENCE: 156
cagacttatg acagcagccg ttgggtg                                       27

<210> SEQ ID NO 157
<211> LENGTH: 27
<212> TYPE: DNA
<213> ORGANISM: Artificial Sequence
<220> FEATURE:

<223> OTHER INFORMATION: N-LCDR3-2

<400> SEQUENCE: 157
cagtcctatg acagcagccg ttgggtg                                      27

<210> SEQ ID NO 158
<211> LENGTH: 27
<212> TYPE: DNA
<213> ORGANISM: Artificial Sequence
<220> FEATURE:
<223> OTHER INFORMATION: N-LCDR3-3

<400> SEQUENCE: 158
cagtcctatg acagccgccg ttgggtg                                      27

<210> SEQ ID NO 159
<211> LENGTH: 33
<212> TYPE: DNA
<213> ORGANISM: Artificial Sequence
<220> FEATURE:
<223> OTHER INFORMATION: N-LCDR3-4

<400> SEQUENCE: 159
ggagcatggg atgacagcca gaaggctctt gtt                               33

<210> SEQ ID NO 160
<211> LENGTH: 33
<212> TYPE: DNA
<213> ORGANISM: Artificial Sequence
<220> FEATURE:
<223> OTHER INFORMATION: N-LCDR3-5

<400> SEQUENCE: 160
gcagcatggg atgacagcca gaaggcttgg gtt                               33

<210> SEQ ID NO 161
<211> LENGTH: 33
<212> TYPE: DNA
<213> ORGANISM: Artificial Sequence
<220> FEATURE:
<223> OTHER INFORMATION: N-LCDR3-6

<400> SEQUENCE: 161
tgggcatggg atgacagcca gaaggctgtg gtt                               33

<210> SEQ ID NO 162
<211> LENGTH: 33
<212> TYPE: DNA
<213> ORGANISM: Artificial Sequence
<220> FEATURE:
<223> OTHER INFORMATION: N-LCDR3-7

<400> SEQUENCE: 162
gaggcatggg atgacagcca gaagggtgtg gtt                               33

<210> SEQ ID NO 163
<211> LENGTH: 33
<212> TYPE: DNA
<213> ORGANISM: Artificial Sequence
<220> FEATURE:
<223> OTHER INFORMATION: N-LCDR3-8

<400> SEQUENCE: 163
ggagcatggg atgacagcca gaagcgttat gtt                               33

```
<210> SEQ ID NO 164
<211> LENGTH: 33
<212> TYPE: DNA
<213> ORGANISM: Artificial Sequence
<220> FEATURE:
<223> OTHER INFORMATION: N-LCDR3-9

<400> SEQUENCE: 164
gcggcatggg atgacagcca gaagggtcag gtt                                    33

<210> SEQ ID NO 165
<211> LENGTH: 33
<212> TYPE: DNA
<213> ORGANISM: Artificial Sequence
<220> FEATURE:
<223> OTHER INFORMATION: N-LCDR3-10

<400> SEQUENCE: 165
gcagcatggg atgacagcca gaaggttgtg gtt                                    33

<210> SEQ ID NO 166
<211> LENGTH: 33
<212> TYPE: DNA
<213> ORGANISM: Artificial Sequence
<220> FEATURE:
<223> OTHER INFORMATION: N-LCDR3-11

<400> SEQUENCE: 166
tgggcatggg atgacagcca gaaggttggt gtt                                    33

<210> SEQ ID NO 167
<211> LENGTH: 33
<212> TYPE: DNA
<213> ORGANISM: Artificial Sequence
<220> FEATURE:
<223> OTHER INFORMATION: N-LCDR3-12

<400> SEQUENCE: 167
ggggcatggg atgacagcca gaaggttttt gtt                                    33

<210> SEQ ID NO 168
<211> LENGTH: 33
<212> TYPE: DNA
<213> ORGANISM: Artificial Sequence
<220> FEATURE:
<223> OTHER INFORMATION: N-LCDR3-13

<400> SEQUENCE: 168
tcagcatggg atgacagcca gaaggttgtg gtt                                    33

<210> SEQ ID NO 169
<211> LENGTH: 33
<212> TYPE: DNA
<213> ORGANISM: Artificial Sequence
<220> FEATURE:
<223> OTHER INFORMATION: N-LCDR3-14

<400> SEQUENCE: 169
gaggcatggg atgacagcca gaaggctgtt gtt                                    33

<210> SEQ ID NO 170
<211> LENGTH: 33
<212> TYPE: DNA
<213> ORGANISM: Artificial Sequence
<220> FEATURE:
<223> OTHER INFORMATION: N-LCDR3-15
```

<400> SEQUENCE: 170
gcggcatggg atgacagcca gaaggctttt gtt                          33

<210> SEQ ID NO 171
<211> LENGTH: 33
<212> TYPE: DNA
<213> ORGANISM: Artificial Sequence
<220> FEATURE:
<223> OTHER INFORMATION: N-LCDR3-16

<400> SEQUENCE: 171
gcggcatggg atgacagcca gaaggcttgg gtt                          33

<210> SEQ ID NO 172
<211> LENGTH: 33
<212> TYPE: DNA
<213> ORGANISM: Artificial Sequence
<220> FEATURE:
<223> OTHER INFORMATION: N-LCDR3-17

<400> SEQUENCE: 172
gcggcatggg atgacagcca gaaggttttt gtt                          33

<210> SEQ ID NO 173
<211> LENGTH: 33
<212> TYPE: DNA
<213> ORGANISM: Artificial Sequence
<220> FEATURE:
<223> OTHER INFORMATION: N-LCDR3-18

<400> SEQUENCE: 173
ggggcatggg atgacagcca gaaggctttt gtt                          33

<210> SEQ ID NO 174
<211> LENGTH: 33
<212> TYPE: DNA
<213> ORGANISM: Artificial Sequence
<220> FEATURE:
<223> OTHER INFORMATION: N-LCDR3-19

<400> SEQUENCE: 174
tgggcatggg atgacagcca gaaggctgtt gtt                          33

<210> SEQ ID NO 175
<211> LENGTH: 33
<212> TYPE: DNA
<213> ORGANISM: Artificial Sequence
<220> FEATURE:
<223> OTHER INFORMATION: N-LCDR3-20

<400> SEQUENCE: 175
ggggcatggg atgacagcca gaaggttgtg gtt                          33

<210> SEQ ID NO 176
<211> LENGTH: 33
<212> TYPE: DNA
<213> ORGANISM: Artificial Sequence
<220> FEATURE:
<223> OTHER INFORMATION: N-LCDR3-21

<400> SEQUENCE: 176
tcggcatggg atgacagcca gaaggttgtt gtt                          33

<210> SEQ ID NO 177
<211> LENGTH: 33

```
<212> TYPE: DNA
<213> ORGANISM: Artificial Sequence
<220> FEATURE:
<223> OTHER INFORMATION: N-LCDR3-22

<400> SEQUENCE: 177
gcggcatggg atgacagcca gaaggctgtt gtt                               33

<210> SEQ ID NO 178
<211> LENGTH: 33
<212> TYPE: DNA
<213> ORGANISM: Artificial Sequence
<220> FEATURE:
<223> OTHER INFORMATION: N-LCDR3-23

<400> SEQUENCE: 178
tcggcatggg atgacagcca gaaggctggg gtt                               33

<210> SEQ ID NO 179
<211> LENGTH: 33
<212> TYPE: DNA
<213> ORGANISM: Artificial Sequence
<220> FEATURE:
<223> OTHER INFORMATION: N-LCDR3-24

<400> SEQUENCE: 179
gcggcatggg atgacagcca gaaggctttg gtt                               33

<210> SEQ ID NO 180
<211> LENGTH: 33
<212> TYPE: DNA
<213> ORGANISM: Artificial Sequence
<220> FEATURE:
<223> OTHER INFORMATION: N-LCDR3-25

<400> SEQUENCE: 180
gcagcatggg atgacagcca gaaggctgtt gtt                               33

<210> SEQ ID NO 181
<211> LENGTH: 15
<212> TYPE: DNA
<213> ORGANISM: Artificial Sequence
<220> FEATURE:
<223> OTHER INFORMATION: N-HCDR1-1

<400> SEQUENCE: 181
gactactaca tgaac                                                   15

<210> SEQ ID NO 182
<211> LENGTH: 15
<212> TYPE: DNA
<213> ORGANISM: Artificial Sequence
<220> FEATURE:
<223> OTHER INFORMATION: N-HCDR1-2

<400> SEQUENCE: 182
gactactaca tggac                                                   15

<210> SEQ ID NO 183
<211> LENGTH: 15
<212> TYPE: DNA
<213> ORGANISM: Artificial Sequence
<220> FEATURE:
<223> OTHER INFORMATION: N-HCDR1-3

<400> SEQUENCE: 183
```
gtctactaca tgaac                                                          15

<210> SEQ ID NO 184
<211> LENGTH: 15
<212> TYPE: DNA
<213> ORGANISM: Artificial Sequence
<220> FEATURE:
<223> OTHER INFORMATION: N-HCDR1-4

<400> SEQUENCE: 184
gactactacg tgaac                                                          15

<210> SEQ ID NO 185
<211> LENGTH: 15
<212> TYPE: DNA
<213> ORGANISM: Artificial Sequence
<220> FEATURE:
<223> OTHER INFORMATION: N-HCDR1-5

<400> SEQUENCE: 185
aattactaca tgcac                                                          15

<210> SEQ ID NO 186
<211> LENGTH: 15
<212> TYPE: DNA
<213> ORGANISM: Artificial Sequence
<220> FEATURE:
<223> OTHER INFORMATION: N-HCDR1-6

<400> SEQUENCE: 186
cattactaca tgcac                                                          15

<210> SEQ ID NO 187
<211> LENGTH: 15
<212> TYPE: DNA
<213> ORGANISM: Artificial Sequence
<220> FEATURE:
<223> OTHER INFORMATION: N-HCDR1-7

<400> SEQUENCE: 187
cgttactaca tgcac                                                          15

<210> SEQ ID NO 188
<211> LENGTH: 15
<212> TYPE: DNA
<213> ORGANISM: Artificial Sequence
<220> FEATURE:
<223> OTHER INFORMATION: N-HCDR1-8

<400> SEQUENCE: 188
cgctactaca tgcac                                                          15

<210> SEQ ID NO 189
<211> LENGTH: 15
<212> TYPE: DNA
<213> ORGANISM: Artificial Sequence
<220> FEATURE:
<223> OTHER INFORMATION: N-HCDR1-9

<400> SEQUENCE: 189
aactactaca tgcac                                                          15

<210> SEQ ID NO 190
<211> LENGTH: 15
<212> TYPE: DNA
<213> ORGANISM: Artificial Sequence

<220> FEATURE:
<223> OTHER INFORMATION: N-HCDR1-10

<400> SEQUENCE: 190
agctactaca tgcac                                                        15

<210> SEQ ID NO 191
<211> LENGTH: 51
<212> TYPE: DNA
<213> ORGANISM: Artificial Sequence
<220> FEATURE:
<223> OTHER INFORMATION: N-HCDR2-1

<400> SEQUENCE: 191
tccattagtc ggtatagtag ttacatatac tacgcagact cagtgaaggg c                 51

<210> SEQ ID NO 192
<211> LENGTH: 51
<212> TYPE: DNA
<213> ORGANISM: Artificial Sequence
<220> FEATURE:
<223> OTHER INFORMATION: N-HCDR2-2

<400> SEQUENCE: 192
tccattagtc ggtatagtgg ctacgtttac tacgcagact cagtgaaggg c                 51

<210> SEQ ID NO 193
<211> LENGTH: 51
<212> TYPE: DNA
<213> ORGANISM: Artificial Sequence
<220> FEATURE:
<223> OTHER INFORMATION: N-HCDR2-3

<400> SEQUENCE: 193
tccattagtc gggctagtag ctacgtttac tacgcagact cagtgaaggg c                 51

<210> SEQ ID NO 194
<211> LENGTH: 51
<212> TYPE: DNA
<213> ORGANISM: Artificial Sequence
<220> FEATURE:
<223> OTHER INFORMATION: N-HCDR2-4

<400> SEQUENCE: 194
tccattagtc ggtatagtgg ctacatatac tacgcagact cagtgaaggg c                 51

<210> SEQ ID NO 195
<211> LENGTH: 51
<212> TYPE: DNA
<213> ORGANISM: Artificial Sequence
<220> FEATURE:
<223> OTHER INFORMATION: N-HCDR2-5

<400> SEQUENCE: 195
tccattagtg ctaggagtcg ttaccactac tacgcagact cagtgaaggg c                 51

<210> SEQ ID NO 196
<211> LENGTH: 51
<212> TYPE: DNA
<213> ORGANISM: Artificial Sequence
<220> FEATURE:
<223> OTHER INFORMATION: N-HCDR2-6

<400> SEQUENCE: 196
tccattagtg ctcgtagtag ttacatatac tacgcagact cagtgaaggg c                 51

```
<210> SEQ ID NO 197
<211> LENGTH: 51
<212> TYPE: DNA
<213> ORGANISM: Artificial Sequence
<220> FEATURE:
<223> OTHER INFORMATION: N-HCDR2-7

<400> SEQUENCE: 197
tccattagtg ctcttagtag ttacatatac tacgcagact cagtgagggg c        51

<210> SEQ ID NO 198
<211> LENGTH: 51
<212> TYPE: DNA
<213> ORGANISM: Artificial Sequence
<220> FEATURE:
<223> OTHER INFORMATION: N-HCDR2-8

<400> SEQUENCE: 198
tccattagtg ctcagagtag tcacatatac tacgcagact cagtggaggg c         51

<210> SEQ ID NO 199
<211> LENGTH: 51
<212> TYPE: DNA
<213> ORGANISM: Artificial Sequence
<220> FEATURE:
<223> OTHER INFORMATION: N-HCDR2-9

<400> SEQUENCE: 199
tccattagtg ctcggagtag ctacctatac tacgcagact cagtgaaggg c         51

<210> SEQ ID NO 200
<211> LENGTH: 51
<212> TYPE: DNA
<213> ORGANISM: Artificial Sequence
<220> FEATURE:
<223> OTHER INFORMATION: N-HCDR2-10

<400> SEQUENCE: 200
tccattagtg ctcggagtag ctacatatac tacgcagact cagtgaaggg c         51

<210> SEQ ID NO 201
<211> LENGTH: 51
<212> TYPE: DNA
<213> ORGANISM: Artificial Sequence
<220> FEATURE:
<223> OTHER INFORMATION: N-HCDR2-11

<400> SEQUENCE: 201
tccattagtg ctcgcagtag ctaccgctac tacgcagact cagtgaaggg c         51

<210> SEQ ID NO 202
<211> LENGTH: 51
<212> TYPE: DNA
<213> ORGANISM: Artificial Sequence
<220> FEATURE:
<223> OTHER INFORMATION: N-HCDR2-12

<400> SEQUENCE: 202
tccattagtg ctcggagtag ctacatctac tacgcagatt cagtgaaggg c         51

<210> SEQ ID NO 203
<211> LENGTH: 51
<212> TYPE: DNA
<213> ORGANISM: Artificial Sequence
<220> FEATURE:
<223> OTHER INFORMATION: N-HCDR2-13
```

<400> SEQUENCE: 203
tccattagtg ctcggagtag ctaccgctac tacgcagatt cagtgaaggg c    51

<210> SEQ ID NO 204
<211> LENGTH: 51
<212> TYPE: DNA
<213> ORGANISM: Artificial Sequence
<220> FEATURE:
<223> OTHER INFORMATION: N-HCDR2-14

<400> SEQUENCE: 204
tccattagtg ctcggagtag ctacatctac tacgcaggtt cagtgaaggg c    51

<210> SEQ ID NO 205
<211> LENGTH: 51
<212> TYPE: DNA
<213> ORGANISM: Artificial Sequence
<220> FEATURE:
<223> OTHER INFORMATION: N-HCDR2-15

<400> SEQUENCE: 205
tccattagtt ctaggagtag ccaccaatac tacgcaggtt cagtgaaggg c    51

<210> SEQ ID NO 206
<211> LENGTH: 51
<212> TYPE: DNA
<213> ORGANISM: Artificial Sequence
<220> FEATURE:
<223> OTHER INFORMATION: N-HCDR2-16

<400> SEQUENCE: 206
tccattagtg ctaggagtag ctacatctac tacgcagatt cagtgaaggg c    51

<210> SEQ ID NO 207
<211> LENGTH: 51
<212> TYPE: DNA
<213> ORGANISM: Artificial Sequence
<220> FEATURE:
<223> OTHER INFORMATION: N-HCDR2-17

<400> SEQUENCE: 207
tccattagtg ctctgagtag ctaccgatac tacgcagatt cagtgaaggg c    51

<210> SEQ ID NO 208
<211> LENGTH: 51
<212> TYPE: DNA
<213> ORGANISM: Artificial Sequence
<220> FEATURE:
<223> OTHER INFORMATION: N-HCDR2-18

<400> SEQUENCE: 208
tccattagta gtagtagtag ttacatatac tacgcagact cagtgaaggg c    51

<210> SEQ ID NO 209
<211> LENGTH: 21
<212> TYPE: DNA
<213> ORGANISM: Artificial Sequence
<220> FEATURE:
<223> OTHER INFORMATION: N-HCDR3-1

<400> SEQUENCE: 209
gatattggcg gtatggacgt c    21

<210> SEQ ID NO 210

```
<211> LENGTH: 30
<212> TYPE: DNA
<213> ORGANISM: Artificial Sequence
<220> FEATURE:
<223> OTHER INFORMATION: N-HCDR3-2

<400> SEQUENCE: 210
cttgctacga ggcataatgc ttttgatatc                                      30

<210> SEQ ID NO 211
<211> LENGTH: 30
<212> TYPE: DNA
<213> ORGANISM: Artificial Sequence
<220> FEATURE:
<223> OTHER INFORMATION: N-HCDR3-3

<400> SEQUENCE: 211
cttgctacga ggaataatgc ttttgatatc                                      30

<210> SEQ ID NO 212
<211> LENGTH: 30
<212> TYPE: DNA
<213> ORGANISM: Artificial Sequence
<220> FEATURE:
<223> OTHER INFORMATION: N-HCDR3-4

<400> SEQUENCE: 212
cttgctacga ggcgtgatgc ttttgatatc                                      30

<210> SEQ ID NO 213
<211> LENGTH: 30
<212> TYPE: DNA
<213> ORGANISM: Artificial Sequence
<220> FEATURE:
<223> OTHER INFORMATION: N-HCDR3-5

<400> SEQUENCE: 213
cttgctacga ggcaaaacgc ttttgatatc                                      30

<210> SEQ ID NO 214
<211> LENGTH: 30
<212> TYPE: DNA
<213> ORGANISM: Artificial Sequence
<220> FEATURE:
<223> OTHER INFORMATION: N-HCDR3-6

<400> SEQUENCE: 214
cttgctacca ggcatgtcgc ttttgatatc                                      30

<210> SEQ ID NO 215
<211> LENGTH: 30
<212> TYPE: DNA
<213> ORGANISM: Artificial Sequence
<220> FEATURE:
<223> OTHER INFORMATION: N-HCDR3-7

<400> SEQUENCE: 215
cttgctacca ggcatggcgc ttttgatatc                                      30

<210> SEQ ID NO 216
<211> LENGTH: 30
<212> TYPE: DNA
<213> ORGANISM: Artificial Sequence
<220> FEATURE:
<223> OTHER INFORMATION: N-HCDR3-8

<400> SEQUENCE: 216
```
cttgctacca ggcataacgc ttttgatatc                                    30

<210> SEQ ID NO 217
<211> LENGTH: 30
<212> TYPE: DNA
<213> ORGANISM: Artificial Sequence
<220> FEATURE:
<223> OTHER INFORMATION: N-HCDR3-9

<400> SEQUENCE: 217
cttgctacca ggcatctcgc ttttgatatc                                    30

<210> SEQ ID NO 218
<211> LENGTH: 30
<212> TYPE: DNA
<213> ORGANISM: Artificial Sequence
<220> FEATURE:
<223> OTHER INFORMATION: N-HCDR3-10

<400> SEQUENCE: 218
cttgctacca ggcatagcgc ttttgatatc                                    30

<210> SEQ ID NO 219
<211> LENGTH: 30
<212> TYPE: DNA
<213> ORGANISM: Artificial Sequence
<220> FEATURE:
<223> OTHER INFORMATION: N-HCDR3-11

<400> SEQUENCE: 219
cttgctacca ggcgcgacgc ttttgatatc                                    30

<210> SEQ ID NO 220
<211> LENGTH: 30
<212> TYPE: DNA
<213> ORGANISM: Artificial Sequence
<220> FEATURE:
<223> OTHER INFORMATION: N-HCDR3-12

<400> SEQUENCE: 220
cttgctacca ggcacagcgc ttttgatatc                                    30

<210> SEQ ID NO 221
<211> LENGTH: 30
<212> TYPE: DNA
<213> ORGANISM: Artificial Sequence
<220> FEATURE:
<223> OTHER INFORMATION: N-HCDR3-13

<400> SEQUENCE: 221
cttggtacca ggcgcgtcgc ttttgatatc                                    30

<210> SEQ ID NO 222
<211> LENGTH: 30
<212> TYPE: DNA
<213> ORGANISM: Artificial Sequence
<220> FEATURE:
<223> OTHER INFORMATION: N-HCDR3-14

<400> SEQUENCE: 222
cttggtctca ggcacgacgc ttttgatatc                                    30

<210> SEQ ID NO 223
<211> LENGTH: 30
<212> TYPE: DNA

```
<213> ORGANISM: Artificial Sequence
<220> FEATURE:
<223> OTHER INFORMATION: N-HCDR3-15

<400> SEQUENCE: 223
cttgctacca ggcgcatcgc ttttgatatc                                    30

<210> SEQ ID NO 224
<211> LENGTH: 30
<212> TYPE: DNA
<213> ORGANISM: Artificial Sequence
<220> FEATURE:
<223> OTHER INFORMATION: N-HCDR3-16

<400> SEQUENCE: 224
cttgctacca ggcgcgtcgc ttttgatatc                                    30

<210> SEQ ID NO 225
<211> LENGTH: 30
<212> TYPE: DNA
<213> ORGANISM: Artificial Sequence
<220> FEATURE:
<223> OTHER INFORMATION: N-HCDR3-17

<400> SEQUENCE: 225
cttggtacga ggcatgatgc ttttgatatc                                    30

<210> SEQ ID NO 226
<211> LENGTH: 270
<212> TYPE: PRT
<213> ORGANISM: Homo sapiens

<400> SEQUENCE: 226
```

Met Lys Pro Lys Met Lys Tyr Ser Thr Asn Lys Ile Ser Thr Ala Lys
1               5                   10                  15

Trp Lys Asn Thr Ala Ser Lys Ala Leu Cys Phe Lys Leu Gly Lys Ser
            20                  25                  30

Gln Gln Lys Ala Lys Glu Val Cys Pro Met Tyr Phe Met Lys Leu Arg
        35                  40                  45

Ser Gly Leu Met Ile Lys Lys Glu Ala Cys Tyr Phe Arg Arg Glu Thr
    50                  55                  60

Thr Lys Arg Pro Ser Leu Lys Thr Gly Arg Lys His Lys Arg His Leu
65                  70                  75                  80

Val Leu Ala Ala Cys Gln Gln Gln Ser Thr Val Glu Cys Phe Ala Phe
                85                  90                  95

Gly Ile Ser Gly Val Gln Lys Tyr Thr Arg Ala Leu His Asp Ser Ser
            100                 105                 110

Ile Thr Gly Ile Ser Pro Ile Thr Glu Tyr Leu Ala Ser Leu Ser Thr
        115                 120                 125

Tyr Asn Asp Gln Ser Ile Thr Phe Ala Leu Glu Asp Glu Ser Tyr Glu
    130                 135                 140

Ile Tyr Val Glu Asp Leu Lys Lys Asp Glu Lys Asp Lys Val Leu
145                 150                 155                 160

Leu Ser Tyr Tyr Glu Ser Gln His Pro Ser Asn Glu Ser Gly Asp Gly
                165                 170                 175

Val Asp Gly Lys Met Leu Met Val Thr Leu Ser Pro Thr Lys Asp Phe
            180                 185                 190

Trp Leu His Ala Asn Asn Lys Glu His Ser Val Glu Leu His Lys Cys
        195                 200                 205

```
Glu Lys Pro Leu Pro Asp Gln Ala Phe Phe Val Leu His Asn Met His
    210                 215                 220

Ser Asn Cys Val Ser Phe Glu Cys Lys Thr Asp Pro Gly Val Phe Ile
225                 230                 235                 240

Gly Val Lys Asp Asn His Leu Ala Leu Ile Lys Val Asp Ser Ser Glu
                245                 250                 255

Asn Leu Cys Thr Glu Asn Ile Leu Phe Lys Leu Ser Glu Thr
            260                 265                 270

<210> SEQ ID NO 227
<211> LENGTH: 269
<212> TYPE: PRT
<213> ORGANISM: Macaca fascicularis

<400> SEQUENCE: 227

Met Lys Pro Lys Met Lys Tyr Ser Thr Asn Lys Ile Ser Thr Ala Lys
1               5                   10                  15

Arg Lys Asn Thr Ala Ser Lys Ala Leu Cys Phe Lys Leu Gly Lys Ser
            20                  25                  30

Gln Gln Lys Ala Lys Glu Val Cys His Val Tyr Phe Met Lys Leu Arg
        35                  40                  45

Ser Gly Leu Met Ile Lys Lys Glu Ala Cys Tyr Phe Arg Arg Glu Thr
50                  55                  60

Thr Lys Arg Pro Ser Leu Lys Thr Gly Lys His Lys Gly His Leu
65                  70                  75                  80

Val Leu Ala Ala Cys Gln Gln Gln Ser Thr Val Glu Cys Phe Ala Phe
                85                  90                  95

Gly Ile Ser Gly Val Pro Lys Tyr Thr Arg Ala Leu His Asp Ser Ser
            100                 105                 110

Ile Thr Gly Ile Ser Pro Ile Thr Glu Ser Leu Ala Ser Leu Ser Thr
        115                 120                 125

Tyr Asn Asp Gln Ser Ile Thr Phe Ala Leu Glu Asp Glu Ser Tyr Glu
130                 135                 140

Ile Tyr Val Glu Asp Leu Lys Lys Asp Lys Lys Lys Asp Lys Val Leu
145                 150                 155                 160

Leu Ser Tyr Tyr Glu Ser Gln His Pro Ser Ser Glu Ser Gly Asp Gly
                165                 170                 175

Val Asp Gly Lys Met Leu Met Val Thr Leu Ser Pro Thr Lys Asp Phe
            180                 185                 190

Trp Leu Gln Ala Asn Asn Lys Glu His Ser Val Glu Leu His Lys Cys
        195                 200                 205

Glu Lys Pro Leu Pro Asp Gln Ala Phe Phe Val Leu His Asn Arg Ser
210                 215                 220

Phe Asn Cys Val Ser Phe Glu Cys Lys Thr Asp Pro Gly Val Phe Ile
225                 230                 235                 240

Gly Val Lys Asp Asn His Leu Ala Leu Ile Lys Val Asp Tyr Ser Glu
                245                 250                 255

Asn Leu Gly Ser Glu Asn Ile Leu Phe Lys Leu Ser Glu
            260                 265

<210> SEQ ID NO 228
<211> LENGTH: 645
<212> TYPE: DNA
<213> ORGANISM: Artificial Sequence
<220> FEATURE:
<223> OTHER INFORMATION: N-LC-1
```

<400> SEQUENCE: 228

```
cagtctgtgc tgactcagcc accctcagcg tctgggaccc cggggcagag ggtcaccatc    60
tcctgcactg ggagcagctc caacatcggg gcagtttatg atgtacactg gtatcagcag   120
ctcccaggaa cggcccccaa actcctcatc tataggaata atcagcggcc ctcaggggtc   180
cctgaccgat tctctggctc caagtctggc acctcagcct ccctggccat cagtgggctc   240
cggtccgagg atgaggctga ttattactgc cagacttatg acagcagccg ttgggtgttc   300
ggcggaggaa ccaagctgac ggtcctaggt caacccaagg ccgctcccag cgtgaccctg   360
ttccccccca gcagcgagga gctgcaggcc aacaaggcca cctggtgtg tctgatcagc    420
gacttctacc caggcgccgt gaccgtggcc tggaaggccg acagcagccc cgtgaaggcc   480
ggcgtggaga ccaccacccc cagcaagcag agcaacaaca agtacgccgc cagcagctac   540
ctgagcctga ccccagagca gtggaagagc cacaggagct acagctgcca ggtcacccac   600
gagggcagca ccgtggaaaa gaccgtggcc ccaaccgagt gctcc              645
```

<210> SEQ ID NO 229
<211> LENGTH: 645
<212> TYPE: DNA
<213> ORGANISM: Artificial Sequence
<220> FEATURE:
<223> OTHER INFORMATION: N-LC-2

<400> SEQUENCE: 229

```
cagtctgtgc tgactcagcc accctcagcg tctgggaccc cggggcagag ggtcaccatc    60
tcctgcactg ggagcagctc caacatcggg gcagtttatg atgtacactg gtatcagcag   120
ctcccaggaa cggcccccaa actcctcatc tataggaata atcagcggcc ctcaggggtc   180
cctgaccgat tctctggctc caagtctggc acctcagcct ccctggccat cagtgggctc   240
cggtccgagg atgaggctga ttattactgc cagtcctatg acagcagccg ttgggtgttc   300
ggcggaggaa ccaagctgac ggtcctaggt caacccaagg ccgctcccag cgtgaccctg   360
ttccccccca gcagcgagga gctgcaggcc aacaaggcca cctggtgtg tctgatcagc    420
gacttctacc caggcgccgt gaccgtggcc tggaaggccg acagcagccc cgtgaaggcc   480
ggcgtggaga ccaccacccc cagcaagcag agcaacaaca agtacgccgc cagcagctac   540
ctgagcctga ccccagagca gtggaagagc cacaggagct acagctgcca ggtcacccac   600
gagggcagca ccgtggaaaa gaccgtggcc ccaaccgagt gctcc              645
```

<210> SEQ ID NO 230
<211> LENGTH: 645
<212> TYPE: DNA
<213> ORGANISM: Artificial Sequence
<220> FEATURE:
<223> OTHER INFORMATION: N-LC-3

<400> SEQUENCE: 230

```
cagtctgtgc tgactcagcc accctcagcg tctgggaccc cggggcagag ggtcaccatc    60
tcctgcactg ggagcagctc caacatcggg gcagtttata atgtacactg gtatcagcag   120
ctcccaggaa cggcccccaa actcctcatc tataggaata atcagcggcc ctcaggggtc   180
cctgaccgat tctctggctc caagtctggc acctcagcct ccctggccat cagtgggctc   240
cggtccgagg atgaggctga ttattactgc cagtcctatg acagcagccg ttgggtgttc   300
ggcggaggaa ccaagctgac ggtcctaggt caacccaagg ccgctcccag cgtgaccctg   360
ttccccccca gcagcgagga gctgcaggcc aacaaggcca cctggtgtg tctgatcagc    420
```

```
gacttctacc caggcgccgt gaccgtggcc tggaaggccg acagcagccc cgtgaaggcc    480
ggcgtggaga ccaccacccc cagcaagcag agcaacaaca agtacgccgc cagcagctac    540
ctgagcctga ccccagagca gtggaagagc acaggagct  acagctgcca ggtcacccac    600
gagggcagca ccgtggaaaa gaccgtggcc ccaaccgagt gctcc                    645

<210> SEQ ID NO 231
<211> LENGTH: 645
<212> TYPE: DNA
<213> ORGANISM: Artificial Sequence
<220> FEATURE:
<223> OTHER INFORMATION: N-LC-4

<400> SEQUENCE: 231
cagtctgtgc tgactcagcc accctcagcg tctgggaccc ccgggcagag ggtcaccatc     60
tcctgcactg ggagcagctc caacatcggg gcagtttata atgtacactg gtatcagcag    120
ctcccaggaa cggcccccaa actcctcatc tataggaata tcagcggcc  ctcaggggtc    180 cctgaccgat tctctggctc caagtctggc acctcagcct ccctggccat cagtgggctc    240
cggtccgagg atgaggctga ttattactgc cagtcctatg acagccgccg ttgggtgttc    300
ggcggaggaa ccaagctgac ggtcctaggt caacccaagg ccgctcccag cgtgaccctg    360 ttcccccca  gcagcgagga gctgcaggcc aacaaggcca cc ctggtgtg tctgatcagc    420 gacttctacc caggcgccgt gaccgtggcc tggaaggccg acagcagccc cgtgaaggcc    480
ggcgtggaga ccaccacccc cagcaagcag agcaacaaca agtacgccgc cagcagctac    540
ctgagcctga ccccagagca gtggaagagc acaggagct  acagctgcca ggtcacccac    600
gagggcagca ccgtggaaaa gaccgtggcc ccaaccgagt gctcc                    645

<210> SEQ ID NO 232
<211> LENGTH: 648
<212> TYPE: DNA
<213> ORGANISM: Artificial Sequence
<220> FEATURE:
<223> OTHER INFORMATION: N-LC-5

<400> SEQUENCE: 232
cagtctgtgc tgactcagcc accctcagcg tctgggaccc ccgggcagag ggtcacgata     60
tcctgttctg gaagcagctc caacatcgga aataatgctg taagctggta tcagcagctc    120
ccaggaacgg cccccaaact cctcatctat gccagtaaca tgagagtcat tggggtccct    180
gaccgattct ctggctccaa gtctggcacc tcagcctccc tggccatcag tgggctccgg    240
tccgaggatg aggctgatta ttactgtgga gcatgggatg acagccagaa ggctcttgtt    300
ttcggcggag gaaccaagct tacggtccta ggtcaaccca aggccgctcc cagcgtgacc    360
ctgttccccc ccagcagcga ggagctgcag gccaacaagg ccaccctggt gtgtctgatc    420
agcgacttct acccaggcgc cgtgaccgtg gcctggaagg ccgacagcag ccccgtgaag    480
gccggcgtgg agaccaccac ccccagcaag cagagcaaca acaagtacgc cgccagcagc    540
tacctgagcc tgaccccaga gcagtggaag agcacaggag ctacagctg  ccaggtcacc    600 cacgagggca gcaccgtgga aaagaccgtg gccccaaccg agtgctcc                 648

<210> SEQ ID NO 233
<211> LENGTH: 648
<212> TYPE: DNA
<213> ORGANISM: Artificial Sequence
<220> FEATURE:
```

<223> OTHER INFORMATION: N-LC-6

<400> SEQUENCE: 233

```
cagtctgtgc tgactcagcc accctcagcg tctgggaccc ccgggcagag ggtcacgata    60
tcctgttctg gaagcagctc caacatcgga cgtaatgctg taaactggta tcagcagctc   120
ccaggaacgg cccccaaact cctcatctat gccagtaaca tgagagtcat tggggtccct   180
gaccgattct ctggctccaa gtctggcacc tcagcctccc tggccatcag tgggctccgg   240
tccgaggatg aggctgatta ttactgtgca gcatgggatg acagccagaa ggcttgggtt   300
ttcggcggag gaaccaagct tacggtccta ggtcaaccca aggccgctcc cagcgtgacc   360
ctgttccccc ccagcagcga ggagctgcag gccaacaagg ccaccctggt gtgtctgatc   420
agcgacttct acccaggcgc cgtgaccgtg gcctggaagg ccgacagcag ccccgtgaag   480
gccggcgtgg agaccaccac ccccagcaag cagagcaaca caagtacgc cgccagcagc    540
tacctgagcc tgaccccaga gcagtggaag agccacagga gctacagctg ccaggtcacc   600
cacgagggca gcaccgtgga aaagaccgtg gccccaaccg agtgctcc                648
```

<210> SEQ ID NO 234
<211> LENGTH: 648
<212> TYPE: DNA
<213> ORGANISM: Artificial Sequence
<220> FEATURE:
<223> OTHER INFORMATION: N-LC-7

<400> SEQUENCE: 234

```
cagtctgtgc tgactcagcc accctcagcg tctgggaccc ccgggcagag ggtcacgata    60
tcctgttctg gaagcagctc caacatcgga cgtaatgctg taaactggta tcagcagctc   120
ccaggaacgg cccccaaact cctcatctat gccagtaaca tgagagtctt aggggtccct   180
gaccgattct ctggctccaa gtctggcacc tcagcctccc tggccatcag tgggctccgg   240
tccgaggatg aggctgatta ttactgttgg gcatgggatg acagccagaa ggctgtggtt   300
ttcggcggag gaaccaagct tacggtccta ggtcaaccca aggccgctcc cagcgtgacc   360
ctgttccccc ccagcagcga ggagctgcag gccaacaagg ccaccctggt gtgtctgatc   420
agcgacttct acccaggcgc cgtgaccgtg gcctggaagg ccgacagcag ccccgtgaag   480
gccggcgtgg agaccaccac ccccagcaag cagagcaaca caagtacgc cgccagcagc    540
tacctgagcc tgaccccaga gcagtggaag agccacagga gctacagctg ccaggtcacc   600
cacgagggca gcaccgtgga aaagaccgtg gccccaaccg agtgctcc                648
```

<210> SEQ ID NO 235
<211> LENGTH: 648
<212> TYPE: DNA
<213> ORGANISM: Artificial Sequence
<220> FEATURE:
<223> OTHER INFORMATION: N-LC-8

<400> SEQUENCE: 235

```
cagtctgtgc tgactcagcc accctcagcg tctgggaccc ccgggcagag ggtcacgata    60
tcctgttctg gaagctgctc caacatcgga cgtaatgctg taaactggta tcagcagctc   120
ccaggaacgg cccccaaact cctcatctat gccagtaaca tgagagtcat aggggtccct   180
gaccgattct ctggctccaa gtctggcacc tcagcctccc tggccatcag tgggctccgg   240
tccgaggatg aggctgatta ttactgtgag gcatgggatg acagccagaa gggtgtggtt   300
ttcggcggag gaaccaagct tacggtccta ggtcaaccca aggccgctcc cagcgtgacc   360
```

```
ctgttccccc ccagcagcga ggagctgcag gccaacaagg ccaccctggt gtgtctgatc      420
agcgacttct acccaggcgc cgtgaccgtg gcctggaagg ccgacagcag ccccgtgaag      480
gccggcgtgg agaccaccac ccccagcaag cagagcaaca acaagtacgc cgccagcagc      540
tacctgagcc tgaccccaga gcagtggaag agccacagga gctacagctg ccaggtcacc      600
cacgagggca gcaccgtgga aaagaccgtg gccccaaccg agtgctcc                   648
```

<210> SEQ ID NO 236
<211> LENGTH: 648
<212> TYPE: DNA
<213> ORGANISM: Artificial Sequence
<220> FEATURE:
<223> OTHER INFORMATION: N-LC-9

<400> SEQUENCE: 236

```
cagtctgtgc tgactcagcc accctcagcg tctgggaccc ccgggcagag ggtcacgata       60
tcctgttctg gaagcagctc caacatcgga cgtaatgctg taaactggta tcagcagctc      120
ccaggaacgg cccccaaact cctcatctat gccagtaaca tgagagtcat tggggtccct      180
gaccgattct ctggctccaa gtctggcacc tcagcctccc tggccatcag tgggctccgg      240
tccgaggatg aggctgatta ttactgtgga gcatgggatg acagccagaa gcgttatgtt      300
ttcggcggag gaaccaagct tacggtccta ggtcaaccca aggccgctcc cagcgtgacc      360
ctgttccccc ccagcagcga ggagctgcag gccaacaagg ccaccctggt gtgtctgatc      420
agcgacttct acccaggcgc cgtgaccgtg gcctggaagg ccgacagcag ccccgtgaag      480
gccggcgtgg agaccaccac ccccagcaag cagagcaaca acaagtacgc cgccagcagc      540
tacctgagcc tgaccccaga gcagtggaag agccacagga gctacagctg ccaggtcacc      600
cacgagggca gcaccgtgga aaagaccgtg gccccaaccg agtgctcc                   648
```

<210> SEQ ID NO 237
<211> LENGTH: 648
<212> TYPE: DNA
<213> ORGANISM: Artificial Sequence
<220> FEATURE:
<223> OTHER INFORMATION: N-LC-10

<400> SEQUENCE: 237

```
cagtctgtgc tgactcagcc accctcagcg tctgggaccc ccgggcagag ggtcacgata       60
tcctgttctg gaagcagctc caacatcgga aataatgctg taaactggta tcagcagctc      120
ccaggaacgg cccccaaact cctcatctat gccagtaaca tgagaggctc tggggtccct      180
gaccgattct ctggctccaa gtctggcacc tcagcctccc tggccatcag tgggctccgg      240
tccgaggatg aggctgatta ttactgtgcg gcatgggatg acagccagaa gggtcaggtt      300
ttcggcggag gaaccaagct tacggtccta ggtcaaccca aggccgctcc cagcgtgacc      360
ctgttccccc ccagcagcga ggagctgcag gccaacaagg ccaccctggt gtgtctgatc      420
agcgacttct acccaggcgc cgtgaccgtg gcctggaagg ccgacagcag ccccgtgaag      480
gccggcgtgg agaccaccac ccccagcaag cagagcaaca acaagtacgc cgccagcagc      540
tacctgagct gaccccaga gcagtggaag agccacagga gctacagctg ccaggtcacc      600
cacgagggca gcaccgtgga aaagaccgtg gccccaaccg agtgctcc                   648
```

<210> SEQ ID NO 238
<211> LENGTH: 648
<212> TYPE: DNA

<213> ORGANISM: Artificial Sequence
<220> FEATURE:
<223> OTHER INFORMATION: N-LC-11

<400> SEQUENCE: 238

| | | | | | |
|---|---|---|---|---|---|
| cagtctgtgc | tgactcagcc | accctcagcg | tctgggaccc | cgggcagag | ggtcacgata | 60 |
| tcctgttctg | gaagcagctc | caacatcgga | agtaatgctg | taagctggta | tcagcagctc | 120 |
| ccaggaacgg | cccccaaact | cctcatctat | gccagtaaca | tgagaggctc | tggggtccct | 180 |
| gaccgattct | ctggctccaa | gtctggcacc | tcagcctccc | tggccatcag | tgggctccgg | 240 |
| tccgaggatg | aggctgatta | ttactgtgca | gcatgggatg | acagccagaa | ggttgtggtt | 300 |
| ttcggcggag | gaaccaagct | tacggtccta | ggtcaaccca | aggccgctcc | cagcgtgacc | 360 |
| ctgttccccc | ccagcagcga | ggagctgcag | gccaacaagg | ccaccctggt | gtgtctgatc | 420 |
| agcgacttct | acccaggcgc | cgtgaccgtg | gcctggaagg | ccgacagcag | ccccgtgaag | 480 |
| gccggcgtgg | agaccaccac | ccccagcaag | cagagcaaca | acaagtacgc | cgccagcagc | 540 |
| tacctgagcc | tgaccccaga | gcagtggaag | agccacagga | gctacagctg | ccaggtcacc | 600 |
| cacgagggca | gcaccgtgga | aaagaccgtg | gccccaaccg | agtgctcc | | 648 |

<210> SEQ ID NO 239
<211> LENGTH: 648
<212> TYPE: DNA
<213> ORGANISM: Artificial Sequence
<220> FEATURE:
<223> OTHER INFORMATION: N-LC-12

<400> SEQUENCE: 239

| | | | | | |
|---|---|---|---|---|---|
| cagtctgtgc | tgactcagcc | accctcagcg | tctgggaccc | cgggcagag | ggtcacgata | 60 |
| tcctgttctg | gaagcagctc | caacatcgga | cgtaatgctg | taaactggta | tcagcagctc | 120 |
| ccaggaacgg | cccccaaact | cctcatctat | gccagtaaca | tgagagtctc | tggggtccct | 180 |
| gaccgattct | ctggctccaa | gtctggcacc | tcagcctccc | tggccatcag | tgggctccgg | 240 |
| tccgaggatg | aggctgatta | ttactgttgg | gcatgggatg | acagccagaa | ggttggtgtt | 300 |
| ttcggcggag | gaaccaagct | tacggtccta | ggtcaaccca | aggccgctcc | cagcgtgacc | 360 |
| ctgttccccc | ccagcagcga | ggagctgcag | gccaacaagg | ccaccctggt | gtgtctgatc | 420 |
| agcgacttct | acccaggcgc | cgtgaccgtg | gcctggaagg | ccgacagcag | ccccgtgaag | 480 |
| gccggcgtgg | agaccaccac | ccccagcaag | cagagcaaca | acaagtacgc | cgccagcagc | 540 |
| tacctgagcc | tgaccccaga | gcagtggaag | agccacagga | gctacagctg | ccaggtcacc | 600 |
| cacgagggca | gcaccgtgga | aaagaccgtg | gccccaaccg | agtgctcc | | 648 |

<210> SEQ ID NO 240
<211> LENGTH: 648
<212> TYPE: DNA
<213> ORGANISM: Artificial Sequence
<220> FEATURE:
<223> OTHER INFORMATION: N-LC-13

<400> SEQUENCE: 240

| | | | | | |
|---|---|---|---|---|---|
| cagtctgtgc | tgactcagcc | accctcagcg | tctgggaccc | cgggcagag | ggtcacgata | 60 |
| tcctgttctg | gaagcagctc | caacatcgga | aataatgctg | taaactggta | tcagcagctc | 120 |
| ccaggaacgg | cccccaaact | cctcatctat | gccagtaaca | tgagaggctt | aggggtccct | 180 |
| gaccgattct | ctggctccaa | gtctggcacc | tcagcctccc | tggccatcag | tgggctccgg | 240 |
| tccgaggatg | aggctgatta | ttactgtggg | gcatgggatg | acagccagaa | ggtttttgtt | 300 |

| | |
|---|---|
| ttcggcggag gaaccaagct tacggtccta ggtcaaccca aggccgctcc cagcgtgacc | 360 |
| ctgttccccc ccagcagcga ggagctgcag gccaacaagg ccaccctggt gtgtctgatc | 420 |
| agcgacttct acccaggcgc cgtgaccgtg gcctggaagg ccgacagcag ccccgtgaag | 480 |
| gccggcgtgg agaccaccac ccccagcaag cagagcaaca caagtacgc cgccagcagc | 540 |
| tacctgagcc tgaccccaga gcagtggaag agccacagga gctacagctg ccaggtcacc | 600 |
| cacgagggca gcaccgtgga aaagaccgtg gccccaaccg agtgctcc | 648 |

<210> SEQ ID NO 241
<211> LENGTH: 648
<212> TYPE: DNA
<213> ORGANISM: Artificial Sequence
<220> FEATURE:
<223> OTHER INFORMATION: N-LC-14

<400> SEQUENCE: 241

| | |
|---|---|
| cagtctgtgc tgactcagcc accctcagcg tctgggaccc ccgggcagag ggtcacgata | 60 |
| tcctgttctg gaagcagctc caacatcgga cgtaatgctg taaactggta tcagcagctc | 120 |
| ccaggaacgg ccccccaaact cctcatctat gccagtaaca tgagacgctc tggggtccct | 180 |
| gaccgattct ctggctccaa gtctggcacc tcagcctccc tggccatcag tgggctccgg | 240 |
| tccgaggatg aggctgatta ttactgttca gcatgggatg acagccagaa ggttgtggtt | 300 |
| ttcggcggag gaaccaagct tacggtccta ggtcaaccca aggccgctcc cagcgtgacc | 360 |
| ctgttccccc ccagcagcga ggagctgcag gccaacaagg ccaccctggt gtgtctgatc | 420 |
| agcgacttct acccaggcgc cgtgaccgtg gcctggaagg ccgacagcag ccccgtgaag | 480 |
| gccggcgtgg agaccaccac ccccagcaag cagagcaaca caagtacgc cgccagcagc | 540 |
| tacctgagcc tgaccccaga gcagtggaag agccacagga gctacagctg ccaggtcacc | 600 |
| cacgagggca gcaccgtgga aaagaccgtg gccccaaccg agtgctcc | 648 |

<210> SEQ ID NO 242
<211> LENGTH: 648
<212> TYPE: DNA
<213> ORGANISM: Artificial Sequence
<220> FEATURE:
<223> OTHER INFORMATION: N-LC-15

<400> SEQUENCE: 242

| | |
|---|---|
| cagtctgtgc tgactcagcc accctcagcg tctgggaccc ccgggcagag ggtcacgata | 60 |
| tcctgttctg gaagcagctc caacatcgga aataatgctg taaactggta tcagcagctc | 120 |
| ccaggaacgg ccccccaaact cctcatctat gccagtaaca tgagacgccc ggggatccct | 180 |
| gaccgattct ctggctccaa gtctggcacc tcagcctccc tggccatcag tgggctccgg | 240 |
| tccgaggatg aggctgatta ttactgtgag gcatgggatg acagccagaa ggctgttgtt | 300 |
| ttcggcggag gaaccaagct tacggtccta ggtcaaccca aggccgctcc cagcgtgacc | 360 |
| ctgttccccc ccagcagcga ggagctgcag gccaacaagg ccaccctggt gtgtctgatc | 420 |
| agcgacttct acccaggcgc cgtgaccgtg gcctggaagg ccgacagcag ccccgtgaag | 480 |
| gccggcgtgg agaccaccac ccccagcaag cagagcaaca caagtacgc cgccagcagc | 540 |
| tacctgagcc tgaccccaga gcagtggaag agccacagga gctacagctg ccaggtcacc | 600 |
| cacgagggca gcaccgtgga aaagaccgtg gccccaaccg agtgctcc | 648 |

<210> SEQ ID NO 243

```
<211> LENGTH: 648
<212> TYPE: DNA
<213> ORGANISM: Artificial Sequence
<220> FEATURE:
<223> OTHER INFORMATION: N-LC-16

<400> SEQUENCE: 243
cagtctgtgc tgactcagcc accctcagcg tctgggaccc ccgggcagag ggtcacgata        60
tcctgttctg gaagcagctc caacatcgga aataatgctg taaactggta tcagcagctc       120
ccaggaacgg cccccaaact cctcatctat gccagtaaca tgagacgcat gggggtccct       180
gaccgattct ctggctccaa gtctggcacc tcagcctccc tggccatcag tgggctccgg       240
tccgaggatg aggctgatta ttactgtgcg gcatgggatg acagccagaa ggcttttgtt       300
ttcggcggag gaaccaagct tacggtccta ggtcaaccca aggccgctcc cagcgtgacc       360
ctgttccccc ccagcagcga ggagctgcag gccaacaagg ccaccctggt gtgtctgatc       420
agcgacttct acccaggcgc cgtgaccgtg gcctggaagg ccgacagcag ccccgtgaag       480
gccggcgtgg agaccaccac ccccagcaag cagagcaaca caagtacgc cgccagcagc        540 tacctgagcc tgaccccaga gcagtggaag agccacagga gctacagctg ccaggtcacc       600
cacgagggca gcaccgtgga aaagaccgtg gccccaaccg agtgctcc                    648

<210> SEQ ID NO 244
<211> LENGTH: 648
<212> TYPE: DNA
<213> ORGANISM: Artificial Sequence
<220> FEATURE:
<223> OTHER INFORMATION: N-LC-17

<400> SEQUENCE: 244
cagtctgtgc tgactcagcc accctcagcg tctgggaccc ccgggcagag ggtcacgata        60
tcctgttctg gaagcagctc caacatcgga aataatgctg taaactggta tcagcagctc       120
ccaggaacgg cccccaaact cctcatctat gccagtaaca tgagacgcct ggggtccct        180 gaccgattct ctggctccaa gtctggcacc tcagcctccc tggccatcag tgggctccgg       240
tccgaggatg aggctgatta ttactgtgcg gcatgggatg acagccagaa ggcttgggtt       300
ttcggcggag gaaccaagct tacggtccta ggtcaaccca aggccgctcc cagcgtgacc       360
ctgttccccc ccagcagcga ggagctgcag gccaacaagg ccaccctggt gtgtctgatc       420
agcgacttct acccaggcgc cgtgaccgtg gcctggaagg ccgacagcag ccccgtgaag       480
gccggcgtgg agaccaccac ccccagcaag cagagcaaca caagtacgc cgccagcagc        540 tacctgagcc tgaccccaga gcagtggaag agccacagga gctacagctg ccaggtcacc       600
cacgagggca gcaccgtgga aaagaccgtg gccccaaccg agtgctcc                    648

<210> SEQ ID NO 245
<211> LENGTH: 648
<212> TYPE: DNA
<213> ORGANISM: Artificial Sequence
<220> FEATURE:
<223> OTHER INFORMATION: N-LC-18

<400> SEQUENCE: 245
cagtctgtgc tgactcagcc accctcagcg tctgggaccc ccgggcagag ggtcacgata        60
tcctgttctg gaagcagctc caacatcgga aataatgctg taaactggta tcagcagctc       120
ccaggaacgg cccccaaact cctcatctat gccagtaaca tgagacgcct ggggtccct        180 gaccgattct ctggctccaa gtctggcacc tcagcctccc tggccatcag tgggctccgg       240
```

```
tccgaggatg aggctgatta ttactgtgcg gcatgggatg acagccagaa ggttttgtt      300 ttcggcggag gaaccaagct tacggtccta ggtcaaccca aggccgctcc cagcgtgacc    360
ctgttccccc ccagcagcga ggagctgcag gccaacaagg ccaccctggt gtgtctgatc    420
agcgacttct acccaggcgc cgtgaccgtg gcctggaagg ccgacagcag ccccgtgaag    480
gccggcgtgg agaccaccac ccccagcaag cagagcaaca acaagtacgc cgccagcagc    540
tacctgagcc tgaccccaga gcagtggaag agccacagga gctacagctg ccaggtcacc    600
cacgagggca gcaccgtgga aaagaccgtg gccccaaccg agtgctcc                 648
```

```
<210> SEQ ID NO 246
<211> LENGTH: 648
<212> TYPE: DNA
<213> ORGANISM: Artificial Sequence
<220> FEATURE:
<223> OTHER INFORMATION: N-LC-19

<400> SEQUENCE: 246
```

```
cagtctgtgc tgactcagcc accctcagcg tctgggaccc ccgggcagag ggtcacgata   60
tcctgttctg gaagcagctc caacatcgga aataatgctg taaactggta tcagcagctc   120
ccaggaacgg ccccccaaact cctcatctat gccagtaaca tgagacgcct gggggtccct   180
gaccgattct ctggctccaa gtctggcacc tcagcctccc tggccatcag tgggctccgg   240
tccgaggatg aggctgatta ttactgtggg gcatgggatg acagccagaa ggcttttgtt  300
ttcggcggag gaaccaagct tacggtccta ggtcaaccca aggccgctcc cagcgtgacc  360
ctgttccccc ccagcagcga ggagctgcag gccaacaagg ccaccctggt gtgtctgatc  420
agcgacttct acccaggcgc cgtgaccgtg gcctggaagg ccgacagcag ccccgtgaag  480
gccggcgtgg agaccaccac ccccagcaag cagagcaaca acaagtacgc cgccagcagc  540
tacctgagcc tgaccccaga gcagtggaag agccacagga gctacagctg ccaggtcacc  600
cacgagggca gcaccgtgga aaagaccgtg gccccaaccg agtgctcc                 648
```

```
<210> SEQ ID NO 247
<211> LENGTH: 648
<212> TYPE: DNA
<213> ORGANISM: Artificial Sequence
<220> FEATURE:
<223> OTHER INFORMATION: N-LC-20

<400> SEQUENCE: 247
```

```
cagtctgtgc tgactcagcc accctcagcg tctgggaccc ccgggcagag ggtcacgata   60
tcctgttctg gaagcagctc caacatcgga cgcaatgctg taagctggta tcagcagctc  120
ccaggaacgg ccccccaaact cctcatctat gccagtaaca tgagacgtct gggggtccct  180
gaccgattct ctggctccaa gtctggcacc tcagcctccc tggccatcag tgggctccgg   240
tccgaggatg aggctgatta ttactgttgg gcatgggatg acagccagaa ggctgttgtt  300
ttcggcggag gaaccaagct tacggtccta ggtcaaccca aggccgctcc cagcgtgacc  360
ctgttccccc ccagcagcga ggagctgcag gccaacaagg ccaccctggt gtgtctgatc  420
agcgacttct acccaggcgc cgtgaccgtg gcctggaagg ccgacagcag ccccgtgaag  480
gccggcgtgg agaccaccac ccccagcaag cagagcaaca acaagtacgc cgccagcagc  540
tacctgagcc tgaccccaga gcagtggaag agccacagga gctacagctg ccaggtcacc  600
cacgagggca gcaccgtgga aaagaccgtg gccccaaccg agtgctcc                 648
```

<210> SEQ ID NO 248
<211> LENGTH: 648
<212> TYPE: DNA
<213> ORGANISM: Artificial Sequence
<220> FEATURE:
<223> OTHER INFORMATION: N-LC-21

<400> SEQUENCE: 248

```
cagtctgtgc tgactcagcc accctcagcg tctgggaccc ccgggcagag ggtcacgata      60
tcctgttctg gaagcagctc caacatcgga cacaatgctg taagctggta tcagcagctc     120
ccaggaacgg cccccaaact cctcatctat gccagtaaca tgagacgtct gggggtccct     180
gaccgattct ctggctccaa gtctggcacc tcagcctccc tggccatcag tgggctccgg     240
tccgaggatg aggctgatta ttactgtggg catgggatg acagccagaa ggttgtggtt      300
ttcggcggag gaaccaagct tacggtccta ggtcaaccca aggccgctcc cagcgtgacc     360
ctgttccccc ccagcagcga ggagctgcag gccaacaagg ccaccctggt gtgtctgatc     420
agcgacttct acccaggcgc cgtgaccgtg gcctggaagg ccgacagcag ccccgtgaag     480
gccggcgtgg agaccaccac ccccagcaag cagagcaaca acaagtacgc cgccagcagc     540
tacctgagcc tgaccccaga gcagtggaag agccacagga gctacagctg ccaggtcacc     600
cacgagggca gcaccgtgga aaagaccgtg gccccaaccg agtgctcc                 648
```

<210> SEQ ID NO 249
<211> LENGTH: 648
<212> TYPE: DNA
<213> ORGANISM: Artificial Sequence
<220> FEATURE:
<223> OTHER INFORMATION: N-LC-22

<400> SEQUENCE: 249

```
cagtctgtgc tgactcagcc accctcagcg tctgggaccc ccgggcagag ggtcacgata      60
tcctgttctg gaagcagctc caacatcgga cgcaatgctg taaactggta tcagcagctc     120
ccaggaacgg cccccaaact cctcatctat gccagtaaca tgagaggtat gggggtccct     180
gaccgattct ctggctccaa gtctggcacc tcagcctccc tggccatcag tgggctccgg     240
tccgaggatg aggctgatta ttactgttcg catgggatg acagccagaa ggttgttgtt      300
ttcggcggag gaaccaagct tacggtccta ggtcaaccca aggccgctcc cagcgtgacc     360
ctgttccccc ccagcagcga ggagctgcag gccaacaagg ccaccctggt gtgtctgatc     420
agcgacttct acccaggcgc cgtgaccgtg gcctggaagg ccgacagcag ccccgtgaag     480
gccggcgtgg agaccaccac ccccagcaag cagagcaaca acaagtacgc cgccagcagc     540
tacctgagcc tgaccccaga gcagtggaag agccacagga gctacagctg ccaggtcacc     600
cacgagggca gcaccgtgga aaagaccgtg gccccaaccg agtgctcc                 648
```

<210> SEQ ID NO 250
<211> LENGTH: 648
<212> TYPE: DNA
<213> ORGANISM: Artificial Sequence
<220> FEATURE:
<223> OTHER INFORMATION: N-LC-23

<400> SEQUENCE: 250

```
cagtctgtgc tgactcagcc accctcagcg tctgggaccc ccgggcagag ggtcacgata      60
tcctgttctg gaagcagctc caacatcgga cacaatgctg tatggtggta tcagcagctc     120
ccaggaacgg cccccaaact cctcatctat gccagtaaca tgagacgtat gggggtccct     180
```

```
gaccgattct ctggctccaa gtctggcacc tcagcctccc tggccatcag tgggctccgg      240
tccgaggatg aggctgatta ttactgtgcg gcatgggatg acagccagaa ggctgttgtt      300
ttcggcggag gaaccaagct tacggtccta ggtcaaccca aggccgctcc cagcgtgacc      360
ctgttccccc ccagcagcga ggagctgcag gccaacaagg ccaccctggt gtgtctgatc      420
agcgacttct acccaggcgc cgtgaccgtg gcctggaagg ccgacagcag ccccgtgaag      480
gccggcgtgg agaccaccac ccccagcaag cagagcaaca caagtacgc cgccagcagc       540 tacctgagcc tgaccccaga gcagtggaag agccacagga gctacagctg ccaggtcacc      600
cacgagggca gcaccgtgga aaagaccgtg gccccaaccg agtgctcc                   648

<210> SEQ ID NO 251
<211> LENGTH: 648
<212> TYPE: DNA
<213> ORGANISM: Artificial Sequence
<220> FEATURE:
<223> OTHER INFORMATION: N-LC-24

<400> SEQUENCE: 251
cagtctgtgc tgactcagcc accctcagcg tctgggaccc ccgggcagag ggtcacgata       60
tcctgttctg gaagcagctc caacatcgga cgcaatgctg taaactggta tcagcagctc      120
ccaggaacgg cccccaaact cctcatctat gccagtaaca tgagacgtcc ggggtccct      180 gaccgattct ctggctccaa gtctggcacc tcagcctccc tggccatcag tgggctccgg      240
tccgaggatg aggctgatta ttactgttcg gcatgggatg acagccagaa ggctggggtt      300
ttcggcggag gaaccaagct tacggtccta ggtcaaccca aggccgctcc cagcgtgacc      360
ctgttccccc ccagcagcga ggagctgcag gccaacaagg ccaccctggt gtgtctgatc      420
agcgacttct acccaggcgc cgtgaccgtg gcctggaagg ccgacagcag ccccgtgaag      480
gccggcgtgg agaccaccac ccccagcaag cagagcaaca caagtacgc cgccagcagc       540 tacctgagcc tgaccccaga gcagtggaag agccacagga gctacagctg ccaggtcacc      600
cacgagggca gcaccgtgga aaagaccgtg gccccaaccg agtgctcc                   648

<210> SEQ ID NO 252
<211> LENGTH: 648
<212> TYPE: DNA
<213> ORGANISM: Artificial Sequence
<220> FEATURE:
<223> OTHER INFORMATION: N-LC-25

<400> SEQUENCE: 252
cagtctgtgc tgactcagcc accctcagcg tctgggaccc ccgggcagag ggtcacgata       60
tcctgttctg gaagcagctc caacatcgga aataatgctg taaactggta tcagcagctc      120
ccaggaacgg cccccaaact cctcatctat gccagtaaca tgagacgctt aggggtccct      180
gaccgattct ctggctccaa gtctggcacc tcagcctccc tggccatcag tgggctccgg      240
tccgaggatg aggctgatta ttactgtgcg gcatgggatg acagccagaa ggctttggtt      300
ttcggcggag gaaccaagct tacggtccta ggtcaaccca aggccgctcc cagcgtgacc      360
ctgttccccc ccagcagcga ggagctgcag gccaacaagg ccaccctggt gtgtctgatc      420
agcgacttct acccaggcgc cgtgaccgtg gcctggaagg ccgacagcag ccccgtgaag      480
gccggcgtgg agaccaccac ccccagcaag cagagcaaca caagtacgc cgccagcagc       540 tacctgagcc tgaccccaga gcagtggaag agccacagga gctacagctg ccaggtcacc      600
```
cacgagggca gcaccgtgga aaagaccgtg gccccaaccg agtgctcc        648

<210> SEQ ID NO 253
<211> LENGTH: 648
<212> TYPE: DNA
<213> ORGANISM: Artificial Sequence
<220> FEATURE:
<223> OTHER INFORMATION: N-LC-26

<400> SEQUENCE: 253
cagtctgtgc tgactcagcc accctcagcg tctgggaccc ccgggcagag ggtcacgata      60
tcctgttctg gaagcagctc caacatcgga ataatgctg taaactggta tcagcagctc     120
ccaggaacgg cccccaaact cctcatctat gccagtaaca tgagacgctt aggggtccct     180
gaccgattct ctggctccaa gtctggcacc tcagcctccc tggccatcag tgggctccgg     240
tccgaggatg aggctgatta ttactgtgca gcatgggatg acagcagaa ggctgttgtt     300
ttcggcggag gaaccaagct tacggtccta ggtcaaccca aggccgctcc cagcgtgacc     360
ctgttccccc ccagcagcga ggagctgcag gccaacaagg ccaccctggt gtgtctgatc     420
agcgacttct acccaggcgc cgtgaccgtg gcctggaagg ccgacagcag ccccgtgaag     480
gccggcgtgg agaccaccac ccccagcaag cagagcaaca caagtacgc cgccagcagc     540
tacctgagcc tgaccccaga gcagtggaag agccacagga gctacagctg ccaggtcacc     600
cacgagggca gcaccgtgga aaagaccgtg gccccaaccg agtgctcc               648

<210> SEQ ID NO 254
<211> LENGTH: 1338
<212> TYPE: DNA
<213> ORGANISM: Artificial Sequence
<220> FEATURE:
<223> OTHER INFORMATION: N-HC-1

<400> SEQUENCE: 254
gaggtgcagc tgttggagtc tgggggaggc ttggtacagc ctgggggtc cctgagactc      60
tcctgtgcag cctctggatt caccttcagt gactactaca tgaactgggt ccgccaggct     120
ccagggaagg ggctggagtg gtctctcatcc attagtcggt atagtagtta catatactac     180
gcagactcag tgaagggccg attcaccatc tccagagaca attccaagaa cacgctgtat     240
ctgcaaatga acagcctgag agccgaggac actgccgtgt attactgtgc gagagatatt     300
ggcggtatgg acgtctgggg ccaaggtaca ctggtcaccg tgagcagcgc cagcaccaag     360
ggcccaagcg tgttcccct ggcccccagc agcaagagca ccagcggcgg cacagccgcc     420
ctgggctgcc tggtgaagga ctacttcccc gagcccgtga ccgtgtcctg aacagcgga     480
gccctgacct ccggcgtgca caccttcccc gccgtgctgc agagcagcgg cctgtacagc     540
ctgagcagcg tggtgaccgt gcccagcagc agcctgggca cccagaccta catctgtaac     600
gtgaaccaca agcccagcaa caccaaggtg gacaagaagg tggagcccaa gagctgtgac     660
aagacccaca cctgcccccc ctgcccagcc ccgagctgtg ggcggacc cagcgtgttc     720
ctgttccccc ccaagcccaa ggacaccctg atgatcagca gaaccccga ggtgacctgt     780
gtggtggtgg acgtgtccca cgaggaccca gaggtgaagt tcaactggta cgtggacggc     840
gtggaggtgc acaacgccaa gaccaagccc agagaggagc agtacaacag cacctacagg     900
gtggtgtccg tgctgaccgt gctgcaccag gactggctga acggcaagga gtacaagtgt     960
aaggtgtcca acaaggccct gccagcccca atcgaaaaga ccatcagcaa ggccaagggc    1020
cagccaagag agccccaggt gtacaccctg ccacccagca gggacgagct gaccaagaac    1080

| | |
|---|---|
| caggtgtccc tgacctgtct ggtgaagggc ttctacccaa gcgacatcgc cgtggagtgg | 1140 |
| gagagcaacg gccagcccga gaacaactac aagaccaccc ccccagtgct ggacagcgac | 1200 |
| ggcagcttct tcctgtacag caagctgacc gtggacaaga gcagatggca gcagggcaac | 1260 |
| gtgttcagct gctccgtgat gcacgaggcc ctgcacaacc actacaccca gaagagcctg | 1320 |
| agcctgtccc caggcaag | 1338 |

<210> SEQ ID NO 255
<211> LENGTH: 1338
<212> TYPE: DNA
<213> ORGANISM: Artificial Sequence
<220> FEATURE:
<223> OTHER INFORMATION: N-HC-2

<400> SEQUENCE: 255

| | |
|---|---|
| gaggtgcagc tgttggagtc tgggggaggc ttggtacagc ctggggggtc cctgagactc | 60 |
| tcctgtgcag cctctggatt caccttcagt gactactaca tgaactgggt ccgccaggct | 120 |
| ccagggaagg gctggagtg gtctcatcc attagtcggt atagtggcta cgtttactac | 180 |
| gcagactcag tgaagggccg attcaccatc tccagagaca attccaagaa cacgctgtat | 240 |
| ctgcaaatga acagcctgag agccgaggac actgccgtgt attactgtgc gagagatatt | 300 |
| ggcggtatgg acgtctgggg ccaaggtaca ctggtcaccg tgagcagcgc cagcaccaag | 360 |
| ggcccaagcg tgttcccccct ggcccccagc agcaagagca ccagcggcgg cacagccgcc | 420 |
| ctgggctgcc tggtgaagga ctacttcccc gagcccgtga ccgtgtcctg gaacagcgga | 480 |
| gccctgacct ccggcgtgca caccttcccc gccgtgctgc agagcagcgg cctgtacagc | 540 |
| ctgagcagcg tggtgaccgt gcccagcagc agcctgggca cccagaccta catctgtaac | 600 |
| gtgaaccaca agcccagcaa caccaaggtg gacaagaagg tggagcccaa gagctgtgac | 660 |
| aagacccaca cctgcccccc ctgcccagcc cccgagctgc tgggcggacc cagcgtgttc | 720 |
| ctgttccccc ccaagcccaa ggacaccctg atgatcagca gaacccccga ggtgacctgt | 780 |
| gtggtggtgg acgtgtccca cgaggaccca gaggtgaagt tcaactggta cgtggacggc | 840 |
| gtggaggtgc acaacgccaa gaccaagccc agagaggagc agtacaacag cacctacagg | 900 |
| gtggtgtccg tgctgaccgt gctgcaccag gactggctga acggcaagga gtacaagtgt | 960 |
| aaggtgtcca acaaggccct gccagcccca atcgaaaaga ccatcagcaa ggccaagggc | 1020 |
| cagccaagag agccccaggt gtacaccctg ccacccagca gggacgagct gaccaagaac | 1080 |
| caggtgtccc tgacctgtct ggtgaagggc ttctacccaa gcgacatcgc cgtggagtgg | 1140 |
| gagagcaacg gccagcccga gaacaactac aagaccaccc ccccagtgct ggacagcgac | 1200 |
| ggcagcttct tcctgtacag caagctgacc gtggacaaga gcagatggca gcagggcaac | 1260 |
| gtgttcagct gctccgtgat gcacgaggcc ctgcacaacc actacaccca gaagagcctg | 1320 |
| agcctgtccc caggcaag | 1338 |

<210> SEQ ID NO 256
<211> LENGTH: 1338
<212> TYPE: DNA
<213> ORGANISM: Artificial Sequence
<220> FEATURE:
<223> OTHER INFORMATION: N-HC-3

<400> SEQUENCE: 256

| | |
|---|---|
| gaggtgcagc tgttggagtc tgggggaggc ttggtacagc ctggggggtc cctgagactc | 60 |

| | |
|---|---|
| tcctgtgcag cctctggatt caccttcagt gactactaca tggactgggt ccgccaggct | 120 |
| ccagggaagg ggctggagtg ggtctcatcc attagtcggt atagtggcta cgtttactac | 180 |
| gcagactcag tgaagggccg attcaccatc tccagagaca attccaagaa cacgctgtat | 240 |
| ctgcaaatga acagcctgag agccgaggac actgccgtgt attactgtgc gagagatatt | 300 |
| ggcggtatgg acgtctgggg ccaaggtaca ctggtcaccg tgagcagcgc cagcaccaag | 360 |
| ggcccaagcg tgttccccct ggcccccagc agcaagagca ccagcggcgg cacagccgcc | 420 |
| ctgggctgcc tggtgaagga ctacttcccc gagcccgtga ccgtgtcctg aacagcgga | 480 |
| gccctgacct ccggcgtgca caccttcccc gccgtgctgc agagcagcgg cctgtacagc | 540 |
| ctgagcagcg tggtgaccgt gcccagcagc agcctgggca cccagaccta catctgtaac | 600 |
| gtgaaccaca agcccagcaa caccaaggtg gacaagaagg tggagcccaa gagctgtgac | 660 |
| aagacccaca cctgcccccc ctgcccagcc cccgagctgc tgggcggacc cagcgtgttc | 720 |
| ctgttccccc ccaagcccaa ggacaccctg atgatcagca gaaccccga ggtgacctgt | 780 |
| gtggtggtgg acgtgtccca cgaggaccca gaggtgaagt tcaactggta cgtggacggc | 840 |
| gtggaggtgc acaacgccaa gaccaagccc agagaggagc agtacaacag cacctacagg | 900 |
| gtggtgtccg tgctgaccgt gctgcaccag gactggctga acggcaagga gtacaagtgt | 960 |
| aaggtgtcca acaaggccct gccagcccca atcgaaaaga ccatcagcaa ggccaagggc | 1020 |
| cagccaagag agcccaggt gtacaccctg ccacccagca gggacgagct gaccaagaac | 1080 |
| caggtgtccc tgacctgtct ggtgaagggc ttctacccaa gcgacatcgc cgtggagtgg | 1140 |
| gagagcaacg gccagcccga gaacaactac aagaccaccc ccccagtgct ggacagcgac | 1200 |
| ggcagcttct tcctgtacag caagctgacc gtggacaaga gcagatggca gcagggcaac | 1260 |
| gtgttcagct gctccgtgat gcacgaggcc ctgcacaacc actacacccca gaagagcctg | 1320 |
| agcctgtccc caggcaag | 1338 |

<210> SEQ ID NO 257
<211> LENGTH: 1338
<212> TYPE: DNA
<213> ORGANISM: Artificial Sequence
<220> FEATURE:
<223> OTHER INFORMATION: N-HC-4

<400> SEQUENCE: 257

| | |
|---|---|
| gaggtgcagc tgttggagtc tgggggaggc ttggtacagc ctggggggtc cctgagactc | 60 |
| tcctgtgcag cctctggatt caccttcagt gactactaca tggactgggt ccgccaggct | 120 |
| ccagggaagg ggctggagtg ggtctcatcc attagtcggg ctagtagcta cgtttactac | 180 |
| gcagactcag tgaagggccg attcaccatc tccagagaca attccaagaa cacgctgtat | 240 |
| ctgcaaatga acagcctgag agccgaggac actgccgtgt attactgtgc gagagatatt | 300 |
| ggcggtatgg acgtctgggg ccaaggtaca ctggtcaccg tgagcagcgc cagcaccaag | 360 |
| ggcccaagcg tgttcccccct ggcccccagc agcaagagca ccagcggcgg cacagccgcc | 420 |
| ctgggctgcc tggtgaagga ctacttcccc gagcccgtga ccgtgtcctg aacagcgga | 480 |
| gccctgacct ccggcgtgca caccttcccc gccgtgctgc agagcagcgg cctgtacagc | 540 |
| ctgagcagcg tggtgaccgt gcccagcagc agcctgggca cccagaccta catctgtaac | 600 |
| gtgaaccaca agcccagcaa caccaaggtg gacaagaagg tggagcccaa gagctgtgac | 660 |
| aagacccaca cctgcccccc ctgcccagcc cccgagctgc tgggcggacc cagcgtgttc | 720 |
| ctgttccccc ccaagcccaa ggacaccctg atgatcagca gaaccccga ggtgacctgt | 780 |

```
gtggtggtgg acgtgtccca cgaggaccca gaggtgaagt tcaactggta cgtggacggc    840
gtggaggtgc acaacgccaa gaccaagccc agagaggagc agtacaacag cacctacagg    900
gtggtgtccg tgctgaccgt gctgcaccag gactggctga acggcaagga gtacaagtgt    960
aaggtgtcca acaaggccct gccagcccca atcgaaaaga ccatcagcaa ggccaagggc   1020
cagccaagag agccccaggt gtacaccctg ccacccagca gggacgagct gaccaagaac   1080
caggtgtccc tgacctgtct ggtgaagggc ttctacccaa gcgacatcgc cgtggagtgg   1140
gagagcaacg gccagcccga gaacaactac aagaccaccc cccagtgctg gacagcgac    1200 ggcagcttct tcctgtacag caagctgacc gtggacaaga gcagatggca gcagggcaac   1260
gtgttcagct gctccgtgat gcacgaggcc ctgcacaacc actacaccca gaagagcctg   1320
agcctgtccc caggcaag                                                 1338
```

<210> SEQ ID NO 258
<211> LENGTH: 1338
<212> TYPE: DNA
<213> ORGANISM: Artificial Sequence
<220> FEATURE:
<223> OTHER INFORMATION: N-HC-5

<400> SEQUENCE: 258

```
gaggtgcagc tgttggagtc tggggggaggc ttggtacagc ctgggggtc cctgagactc     60 tcctgtgcag cctctggatt caccttcagt gactactaca tgaactgggt ccgccaggct    120
ccagggaagg ggctggagtg ggtctcatcc attagtcggt atagtggcta catatactac    180
gcagactcag tgaagggccg attcaccatc tccagagaca attccaagaa cacgctgtat    240
ctgcaaatga acagcctgag agccgaggac actgccgtgt attactgtgc gagagatatt    300
ggcggtatgg acgtctgggg ccaaggtaca ctggtcaccg tgagcagcgc cagcaccaag    360
ggcccaagcg tgttcccct ggcccccagc agcaagagca ccagcggcgg cacagccgcc    420
ctgggctgcc tggtgaagga ctacttcccc gagcccgtga ccgtgtcctg aacagcgga    480 gccctgacct ccggcgtgca caccttcccc gccgtgctgc agagcagcgg cctgtacagc    540
ctgagcagcg tggtgaccgt gcccagcagc agcctgggca cccagaccta catctgtaac    600
gtgaaccaca agcccagcaa caccaaggtg gacaagaagg tggagcccaa gagctgtgac    660
aagacccaca cctgccccc ctgcccagcc ccgagctgtg ggcggacc cagcgtgttc    720 ctgttccccc caagcccaa ggacaccctg atgatcagca gaacccccga ggtgacctgt    780
gtggtggtgg acgtgtccca cgaggaccca gaggtgaagt tcaactggta cgtggacggc    840
gtggaggtgc acaacgccaa gaccaagccc agagaggagc agtacaacag cacctacagg    900
gtggtgtccg tgctgaccgt gctgcaccag gactggctga acggcaagga gtacaagtgt    960
aaggtgtcca acaaggccct gccagcccca atcgaaaaga ccatcagcaa ggccaagggc   1020
cagccaagag agccccaggt gtacaccctg ccacccagca gggacgagct gaccaagaac   1080
caggtgtccc tgacctgtct ggtgaagggc ttctacccaa gcgacatcgc cgtggagtgg   1140
gagagcaacg gccagcccga gaacaactac aagaccaccc cccagtgctg gacagcgac    1200 ggcagcttct tcctgtacag caagctgacc gtggacaaga gcagatggca gcagggcaac   1260
gtgttcagct gctccgtgat gcacgaggcc ctgcacaacc actacaccca gaagagcctg   1320
agcctgtccc caggcaag                                                 1338
```

<210> SEQ ID NO 259

<211> LENGTH: 1338
<212> TYPE: DNA
<213> ORGANISM: Artificial Sequence
<220> FEATURE:
<223> OTHER INFORMATION: N-HC-6

<400> SEQUENCE: 259

| | |
|---|---|
| gaggtgcagc tgttggagtc tgggggaggc ttggtacagc ctggggggtc cctgagactc | 60 |
| tcctgtgcag cctcgggatt caccttcagt gtctactaca tgaactgggt ccgccaggct | 120 |
| ccagggaagg ggctggagtg ggtctcatcc attagtcggt atagtggcta cgtttactac | 180 |
| gcagactcag tgaagggccg attcaccatc tccagagaca attccaagaa cacgctgtat | 240 |
| ctgcaaatga acagcctgag agccgaggac actgccgtgt attactgtgc gagagatatt | 300 |
| ggcggtatgg acgtctgggg ccaaggtaca ctggtcaccg tgagcagcgc cagcaccaag | 360 |
| ggcccaagcg tgttccccct ggccccagc agcaagagca ccagcggcgg cacagccgcc | 420 |
| ctgggctgcc tggtgaagga ctacttcccc gagcccgtga ccgtgtcctg aacagcgga | 480 |
| gccctgacct ccggcgtgca caccttcccc gccgtgctgc agagcagcgg cctgtacagc | 540 |
| ctgagcagcg tggtgaccgt gcccagcagc agcctgggca cccagaccta catctgtaac | 600 |
| gtgaaccaca agcccagcaa caccaaggtg gacaagaagg tggagcccaa gagctgtgac | 660 |
| aagacccaca cctgcccccc ctgcccagcc ccgagctgc tgggcggacc cagcgtgttc | 720 |
| ctgttccccc ccaagcccaa ggacaccctg atgatcagca gaacccccga ggtgacctgt | 780 |
| gtggtggtgg acgtgtccca cgaggaccca gaggtgaagt tcaactggta cgtggacggc | 840 |
| gtggaggtgc acaacgccaa gaccaagccc agagaggagc agtacaacag cacctacagg | 900 |
| gtggtgtccg tgctgaccgt gctgcaccag gactggctga acggcaagga gtacaagtgt | 960 |
| aaggtgtcca acaaggccct gccagcccca atcgaaaaga ccatcagcaa ggccaagggc | 1020 |
| cagccaagag agcccaggt gtacaccctg ccacccagca gggacgagct gaccaagaac | 1080 |
| caggtgtccc tgacctgtct ggtgaagggc ttctacccaa gcgacatcgc cgtggagtgg | 1140 |
| gagagcaacg gccagcccga gaacaactac aagaccaccc cccagtgct ggacagcgac | 1200 |
| ggcagcttct tcctgtacag caagctgacc gtggacaaga gcagatggca gcagggcaac | 1260 |
| gtgttcagct gctccgtgat gcacgaggcc ctgcacaacc actacaccca aagagcctg | 1320 |
| agcctgtccc caggcaag | 1338 |

<210> SEQ ID NO 260
<211> LENGTH: 1338
<212> TYPE: DNA
<213> ORGANISM: Artificial Sequence
<220> FEATURE:
<223> OTHER INFORMATION: N-HC-7

<400> SEQUENCE: 260

| | |
|---|---|
| gaggtgcagc tgttggagtc tgggggaggc ttggtacagc ctggggggtc cctgagactc | 60 |
| tcctgtgcag cctctggatt caccttcagt gactactacg tgaactgggt ccgccaggct | 120 |
| ccagggaagg ggctggagtg ggtctcatcc attagtcggt atagtggcta cgtttactac | 180 |
| gcagactcag tgaagggccg attcaccatc tccagagaca attccaagaa cacgctgtat | 240 |
| ctgcaaatga acagcctgag agccgaggac actgccgtgt attactgtgc gagagatatt | 300 |
| ggcggtatgg acgtctgggg ccaaggtaca ctggtcaccg tgagcagcgc cagcaccaag | 360 |
| ggcccaagcg tgttccccct ggccccagc agcaagagca ccagcggcgg cacagccgcc | 420 |
| ctgggctgcc tggtgaagga ctacttcccc gagcccgtga ccgtgtcctg aacagcgga | 480 |

```
gccctgacct ccggcgtgca ccttcccc gccgtgctgc agagcagcgg cctgtacagc      540
ctgagcagcg tggtgaccgt gcccagcagc agcctgggca cccagaccta catctgtaac   600
gtgaaccaca agcccagcaa caccaaggtg gacaagaagg tggagcccaa gagctgtgac   660
aagacccaca cctgccccc ctgcccagcc ccgagctgc tgggcggacc cagcgtgttc     720
ctgttccccc ccaagcccaa ggacaccctg atgatcagca gaaccccga ggtgacctgt    780 gtggtggtgg acgtgtccca cgaggaccca gaggtgaagt tcaactggta cgtggacggc   840
gtggaggtgc acaacgccaa gaccaagccc agagaggagc agtacaacag cacctacagg   900
gtggtgtccg tgctgaccgt gctgcaccag gactggctga acggcaagga gtacaagtgt   960
aaggtgtcca acaaggccct gccagcccca tcgaaaaga ccatcagcaa ggccaagggc   1020
cagccaagag agcccaggt gtacaccctg ccacccagca gggacgagct gaccaagaac   1080
caggtgtccc tgacctgtct ggtgaagggc ttctacccaa gcgacatcgc cgtggagtgg   1140
gagagcaacg gccagcccga gaacaactac aagaccaccc ccccagtgct ggacagcgac   1200
ggcagcttct tcctgtacag caagctgacc gtggacaaga gcagatggca gcagggcaac   1260
gtgttcagct gctccgtgat gcacgaggcc ctgcacaacc actacaccca gaagagcctg   1320
agcctgtccc caggcaag                                                1338
```

<210> SEQ ID NO 261
<211> LENGTH: 1347
<212> TYPE: DNA
<213> ORGANISM: Artificial Sequence
<220> FEATURE:
<223> OTHER INFORMATION: N-HC-8

<400> SEQUENCE: 261

```
gaggtgcagc tgttggagtc tgggggaggc ttggtacagc ctggggggaag cttgagactc     60 tcctgtgcag cctctggatt caccttcagt aattactaca tgcactgggt ccgccaagct   120
ccagggaagg gctggagtg ggtctcatcc attagtgcta ggagtcgtta ccactactac    180
gcagactcag tgaagggccg attcaccatc tccagagaca attccaagaa cacgctgtat   240
ctgcaaatga acagcctgag agccgaggac actgccgtgt attactgtgc gagacttgct   300
acgaggcata atgcttttga tatctggggc cagggtacac tggtcaccgt gagctcagcc   360
agcaccaagg gcccaagcgt gttccccctg gcccccagca gcaagagcac cagcggcggc   420
acagccgccc tgggctgcct ggtgaaggac tacttccccg agcccgtgac cgtgtcctgg   480
aacagcggag ccctgacctc cggcgtgcac accttcccg ccgtgctgca gagcagcggc    540
ctgtacagcc tgagcagcgt ggtgaccgtg cccagcagca gcctgggcac ccagacctac   600
atctgtaacg tgaaccacaa gcccagcaac accaaggtgg acaagaaggt ggagcccaag   660
agctgtgaca agacccacac ctgcccccc tgcccagccc ccgagctgct gggcggaccc    720
agcgtgttcc tgttccccc caagcccaag gacaccctga tgatcagcag aaccccgag    780 gtgacctgtg tggtggtgga cgtgtcccac gaggacccag aggtgaagtt caactggtac   840
gtggacggcg tggaggtgca caacgccaag accaagccca gagaggagca gtacaacagc   900
acctacaggg tggtgtccgt gctgaccgtg ctgcaccagg actggctgaa cggcaaggag   960
tacaagtgta aggtgtccaa caaggccctg ccagcccaa tcgaaaagac catcagcaag   1020
gccaagggcc agccaagaga gccccaggtg tacaccctgc cacccagcag ggacgagctg   1080
accaagaacc aggtgtccct gacctgtctg gtgaagggct tctacccaag cgacatcgcc   1140
```

| | |
|---|---|
| gtggagtggg agagcaacgg ccagcccgag aacaactaca agaccacccc cccagtgctg | 1200 |
| gacagcgacg gcagcttctt cctgtacagc aagctgaccg tggacaagag cagatggcag | 1260 |
| cagggcaacg tgttcagctg ctccgtgatg cacgaggccc tgcacaacca ctacacccag | 1320 |
| aagagcctga gcctgtcccc aggcaag | 1347 |

<210> SEQ ID NO 262
<211> LENGTH: 1347
<212> TYPE: DNA
<213> ORGANISM: Artificial Sequence
<220> FEATURE:
<223> OTHER INFORMATION: N-HC-9

<400> SEQUENCE: 262

| | |
|---|---|
| gaggtgcagc tgttggagtc tggggggaggc ttggtacagc ctgggggaag cttgagactc | 60 |
| tcctgtgcag catctggatt caccttcagt aattactaca tgcactgggt ccgccaagct | 120 |
| ccagggaagg ggctggagtg ggtctcatcc attagtgctc gtagtagtta catatactac | 180 |
| gcagactcag tgaagggccg attcaccatc tccagagaca attccaagaa cacgctgtat | 240 |
| ctgcaaatga acagcctgag agccgaggac actgccgtgt attactgtgc gagacttgct | 300 |
| acgaggaata atgcttttga tatctggggc cagggtacac tggtcaccgt gagctcagcc | 360 |
| agcaccaagg gcccaagcgt gttccccctg gcccccagca gcaagagcac cagcggcggc | 420 |
| acagccgccc tgggctgcct ggtgaaggac tacttccccg agcccgtgac cgtgtcctgg | 480 |
| aacagcggag ccctgacctc cggcgtgcac accttccccg ccgtgctgca gagcagcggc | 540 |
| ctgtacagcc tgagcagcgt ggtgaccgtg cccagcagca gcctgggcac ccagacctac | 600 |
| atctgtaacg tgaaccacaa gcccagcaac accaaggtgg acaagaaggt ggagcccaag | 660 |
| agctgtgaca gacccacac ctgcccccc tgcccagccc cgagctgct gggcggaccc | 720 |
| agcgtgttcc tgttcccccc caagcccaag gacaccctga tgatcagcag aacccccgag | 780 |
| gtgacctgtg tggtggtgga cgtgtcccac gaggacccag aggtgaagtt caactggtac | 840 |
| gtggacggcg tggaggtgca caacgccaag accaagccca gagaggagca gtacaacagc | 900 |
| acctacaggg tggtgtccgt gctgaccgtg ctgcaccagg actggctgaa cggcaaggag | 960 |
| tacaagtgta aggtgtccaa caaggccctg ccagcccaa tcgaaaagac catcagcaag | 1020 |
| gccaagggcc agccaagaga gccccaggtg tacccctgc cacccagcag ggacgagctg | 1080 |
| accaagaacc aggtgtccct gacctgtctg gtgaagggct ctacccaag cgacatcgcc | 1140 |
| gtggagtggg agagcaacgg ccagcccgag aacaactaca agaccacccc cccagtgctg | 1200 |
| gacagcgacg gcagcttctt cctgtacagc aagctgaccg tggacaagag cagatggcag | 1260 |
| cagggcaacg tgttcagctg ctccgtgatg cacgaggccc tgcacaacca ctacacccag | 1320 |
| aagagcctga gcctgtcccc aggcaag | 1347 |

<210> SEQ ID NO 263
<211> LENGTH: 1347
<212> TYPE: DNA
<213> ORGANISM: Artificial Sequence
<220> FEATURE:
<223> OTHER INFORMATION: N-HC-10

<400> SEQUENCE: 263

| | |
|---|---|
| gaggtgcagc tgttggagtc tggggggaggc ttggtacaac ctgggggaag cttgagactc | 60 |
| tcctgtgcag cctctggatt caccttcagt cattactaca tgcactgggt ccgccaagct | 120 |
| ccagggaagg ggctggagtg ggtctcatcc attagtgctc ttagtagtta catatactac | 180 |

```
gcagactcag tgaggggccg attcaccatc tccagagaca attccaagaa cacgctgtat    240
ctgcaaatga acagcctgag agccgaggac actgccgtgt attactgtgc gagacttgct    300
acgaggcgtg atgctttga tatctggggc cagggtacac tggtcaccgt gagctcagcc    360
agcaccaagg gcccaagcgt gttccccctg gcccccagca gcaagagcac cagcggcggc    420
acagccgccc tgggctgcct ggtgaaggac tacttccccg agccgtgac cgtgtcctgg    480 aacagcggag ccctgacctc cggcgtgcac accttccccg ccgtgctgca gagcagcggc    540
ctgtacagcc tgagcagcgt ggtgaccgtg cccagcagca gcctgggcac ccagacctac    600
atctgtaacg tgaaccacaa gcccagcaac accaaggtgg acaagaaggt ggagcccaag    660
agctgtgaca agacccacac ctgccccccc tgcccagccc ccgagctgct gggcggaccc    720
agcgtgttcc tgttcccccc caagcccaag gacaccctga tgatcagcag aaccccgag    780 gtgacctgtg tggtggtgga cgtgtcccac gaggacccag aggtgaagtt caactggtac    840
gtggacggcg tggaggtgca caacgccaag accaagccca gaggagca gtacaacagc    900 acctacaggg tggtgtccgt gctgaccgtg ctgcaccagg actggctgaa cggcaaggag    960
tacaagtgta aggtgtccaa caaggccctg ccagccccaa tcgaaagac catcagcaag   1020 gccaagggcc agccaagaga gccccaggtg tacaccctgc acccagcag ggacgagctg   1080 accaagaacc aggtgtccct gacctgtctg gtgaagggct tctacccaag cgacatcgcc   1140
gtggagtggg agagcaacgg ccagcccgag aacaactaca agaccacccc cccagtgctg   1200
gacagcgacg gcagcttctt cctgtacagc aagctgaccg tggacaagag cagatggcag   1260
cagggcaacg tgttcagctg ctccgtgatg cacgaggccc tgcacaacca ctacacccag   1320
aagagcctga gcctgtcccc aggcaag                                       1347

<210> SEQ ID NO 264
<211> LENGTH: 1347
<212> TYPE: DNA
<213> ORGANISM: Artificial Sequence
<220> FEATURE:
<223> OTHER INFORMATION: N-HC-11

<400> SEQUENCE: 264
gaggtgcagc tgttggagtc tgggggaggc ttggtacagc ctgggggaag cttgagactc     60
tcctgtgcag cctctggatt caccttcagt cgttactaca tgcactgggt ccgccaagct    120
ccagggaagg ggctggagtg ggtctcatcc attagtgctc agagtagtca catatactac    180
gcagactcag tgaggggccg attcaccatc tccagagaca attccaagaa cacgctgtat    240
ctgcaaatga acagcctgag agccgaggac actgccgtgt attactgtgc gagacttgct    300
acgaggcaaa acgcttttga tatctggggc cagggtacac tggtcaccgt gagctcagcc    360
agcaccaagg gcccaagcgt gttccccctg gcccccagca gcaagagcac cagcggcggc    420
acagccgccc tgggctgcct ggtgaaggac tacttccccg agccgtgac cgtgtcctgg    480 aacagcggag ccctgacctc cggcgtgcac accttccccg ccgtgctgca gagcagcggc    540
ctgtacagcc tgagcagcgt ggtgaccgtg cccagcagca gcctgggcac ccagacctac    600
atctgtaacg tgaaccacaa gcccagcaac accaaggtgg acaagaaggt ggagcccaag    660
agctgtgaca agacccacac ctgccccccc tgcccagccc ccgagctgct gggcggaccc    720
agcgtgttcc tgttcccccc caagcccaag gacaccctga tgatcagcag aaccccgag    780 gtgacctgtg tggtggtgga cgtgtcccac gaggacccag aggtgaagtt caactggtac    840
```

| | |
|---|---|
| gtggacggcg tggaggtgca caacgccaag accaagccca gagaggagca gtacaacagc | 900 |
| acctacaggg tggtgtccgt gctgaccgtg ctgcaccagg actggctgaa cggcaaggag | 960 |
| tacaagtgta aggtgtccaa caaggccctg ccagccccaa tcgaaaagac catcagcaag | 1020 |
| gccaagggcc agccaagaga gccccaggtg tacaccctgc cacccagcag ggacgagctg | 1080 |
| accaagaacc aggtgtccct gacctgtctg gtgaagggct tctacccaag cgacatcgcc | 1140 |
| gtggagtggg agagcaacgg ccagcccgag aacaactaca agaccacccc cccagtgctg | 1200 |
| gacagcgacg gcagcttctt cctgtacagc aagctgaccg tggacaagag cagatggcag | 1260 |
| cagggcaacg tgttcagctg ctccgtgatg cacgaggccc tgcacaacca ctacacccag | 1320 |
| aagagcctga gcctgtcccc aggcaag | 1347 |

<210> SEQ ID NO 265
<211> LENGTH: 1347
<212> TYPE: DNA
<213> ORGANISM: Artificial Sequence
<220> FEATURE:
<223> OTHER INFORMATION: N-HC-12

<400> SEQUENCE: 265

| | |
|---|---|
| gaggtgcagc tgttggagtc tgggggaggc ttggtacagc ctgggggaag cttgagactc | 60 |
| tcctgtgcag cctctggatt caccttcagt aattactaca tgcactgggt ccgccaagct | 120 |
| ccagggaagg gctggagtg gtctcatcc attagtgctc ggagtagcta cctatactac | 180 |
| gcagactcag tgaagggccg attcaccatc tccagagaca attccaagaa cacgctgtat | 240 |
| ctgcaaatga acagcctgag agccgaggac actgccgtgt attactgtgc gagacttgct | 300 |
| accaggcatg tcgcttttga tatctggggc cagggtacac tggtcaccgt gagctcagcc | 360 |
| agcaccaagg gcccaagcgt gttcccctg gcccccagca gcaagagcac cagcggcggc | 420 |
| acagccgccc tgggctgcct ggtgaaggac tacttccccg agcccgtgac cgtgtcctgg | 480 |
| aacagcggag ccctgacctc cggcgtgcac accttccccg ccgtgctgca gagcagcggc | 540 |
| ctgtacagcc tgagcagcgt ggtgaccgtg cccagcagca gcctgggcac ccagacctac | 600 |
| atctgtaacg tgaaccacaa gcccagcaac accaaggtgg acaagaaggt ggagcccaag | 660 |
| agctgtgaca agacccacac ctgcccccc tgcccagccc ccgagctgct gggcggaccc | 720 |
| agcgtgttcc tgttcccccc caagcccaag gacaccctga tgatcagcag aacccccgag | 780 |
| gtgacctgtg tggtggtgga cgtgtcccac gaggacccag aggtgaagtt caactggtac | 840 |
| gtggacggcg tggaggtgca caacgccaag accaagccca gagaggagca gtacaacagc | 900 |
| acctacaggg tggtgtccgt gctgaccgtg ctgcaccagg actggctgaa cggcaaggag | 960 |
| tacaagtgta aggtgtccaa caaggccctg ccagccccaa tcgaaaagac catcagcaag | 1020 |
| gccaagggcc agccaagaga gccccaggtg tacaccctgc cacccagcag ggacgagctg | 1080 |
| accaagaacc aggtgtccct gacctgtctg gtgaagggct tctacccaag cgacatcgcc | 1140 |
| gtggagtggg agagcaacgg ccagcccgag aacaactaca agaccacccc cccagtgctg | 1200 |
| gacagcgacg gcagcttctt cctgtacagc aagctgaccg tggacaagag cagatggcag | 1260 |
| cagggcaacg tgttcagctg ctccgtgatg cacgaggccc tgcacaacca ctacacccag | 1320 |
| aagagcctga gcctgtcccc aggcaag | 1347 |

<210> SEQ ID NO 266
<211> LENGTH: 1347
<212> TYPE: DNA
<213> ORGANISM: Artificial Sequence

<220> FEATURE:
<223> OTHER INFORMATION: N-HC-13

<400> SEQUENCE: 266

| | | |
|---|---|---|
| gaggtgcagc tgttggagtc tgggggaggc ttggtacagc ctgggggaag cttgagactc | 60 |
| tcctgtgcag cctctggatt caccttcagt aattactaca tgcactgggt ccgccaagct | 120 |
| ccagggaagg gctggagtg gtctcatcc attagtgctc ggagtagcta catatactac | 180 |
| gcagactcag tgaagggccg attcaccatc tccagagaca attccaagaa cacgctgtat | 240 |
| ctgcaaatga acagcctgag agccgaggac actgccgtgt attactgtgc gagacttgct | 300 |
| accaggcatg gcgcttttga tatctggggc cagggtacac tggtcaccgt gagctcagcc | 360 |
| agcaccaagg gcccaagcgt gttccccctg gccccagca gcaagagcac cagcggcggc | 420 |
| acagccgccc tgggctgcct ggtgaaggac tacttccccg agcccgtgac cgtgtcctgg | 480 |
| aacagcggag ccctgaccct cggcgtgcac accttccccg ccgtgctgca gagcagcggc | 540 |
| ctgtacagcc tgagcagcgt ggtgaccgtg cccagcagca gcctgggcac ccagacctac | 600 |
| atctgtaacg tgaaccacaa gcccagcaac accaaggtgg acaagaaggt ggagcccaag | 660 |
| agctgtgaca gacccacac ctgccccccc tgcccagccc cgagctgct gggcggaccc | 720 |
| agcgtgttcc tgttcccccc caagcccaag gacaccctga tgatcagcag aaccccgag | 780 |
| gtgacctgtg tggtggtgga cgtgtcccac gaggacccag aggtgaagtt caactggtac | 840 |
| gtggacggcg tggaggtgca caacgccaag accaagccca gagaggagca gtacaacagc | 900 |
| acctacaggg tggtgtccgt gctgaccgtg ctgcaccagg actggctgaa cggcaaggag | 960 |
| tacaagtgta aggtgtccaa caaggccctg ccagccccaa tcgaaaagac catcagcaag | 1020 |
| gccaagggcc agccaagaga gccccaggtg tacaccctgc cacccagcag ggacgagctg | 1080 |
| accaagaacc aggtgtccct gacctgtctg gtgaagggct ctacccaag cgacatcgcc | 1140 |
| gtggagtggg agagcaacgg ccagcccgag aacaactaca agaccacccc cccagtgctg | 1200 |
| gacagcgacg gcagcttctt cctgtacagc aagctgaccg tggacaagag cagatggcag | 1260 |
| cagggcaacg tgttcagctg ctccgtgatg cacgaggccc tgcacaacca ctacacccag | 1320 |
| aagagcctga gcctgtcccc aggcaag | 1347 |

<210> SEQ ID NO 267
<211> LENGTH: 1347
<212> TYPE: DNA
<213> ORGANISM: Artificial Sequence
<220> FEATURE:
<223> OTHER INFORMATION: N-HC-14

<400> SEQUENCE: 267

| | | |
|---|---|---|
| gaggtgcagc tgttggagtc tgggggaggc ttggtacagc ctgggggaag cttgagactc | 60 |
| tcctgtgcag cctctggatt caccttcagt aattactaca tgcactgggt ccgccaagct | 120 |
| ccagggaagg gctggagtg gtctcatcc attagtgctc ggagtagcta catatactac | 180 |
| gcagactcag tgaagggccg attcaccatc tccagagaca attccaagaa cacgctgtat | 240 |
| ctgcaaatga acagcctgag agccgaggac actgccgtgt attactgtgc gagacttgct | 300 |
| accaggcata cgcttttga tatctggggc cagggtacac tggtcaccgt gagctcagcc | 360 |
| agcaccaagg gcccaagcgt gttccccctg gccccagca gcaagagcac cagcggcggc | 420 |
| acagccgccc tgggctgcct ggtgaaggac tacttccccg agcccgtgac cgtgtcctgg | 480 |
| aacagcggag ccctgaccct cggcgtgcac accttccccg ccgtgctgca gagcagcggc | 540 |

```
ctgtacagcc tgagcagcgt ggtgaccgtg cccagcagca gcctgggcac ccagacctac      600
atctgtaacg tgaaccacaa gcccagcaac accaaggtgg acaagaaggt ggagcccaag      660
agctgtgaca agacccacac ctgcccccc tgcccagccc ccgagctgct gggcggaccc       720
agcgtgttcc tgttcccccc caagcccaag gacaccctga tgatcagcag aaccccgag       780 gtgacctgtg tggtggtgga cgtgtcccac gaggacccag aggtgaagtt caactggtac      840
gtggacggcg tggaggtgca caacgccaag accaagccca gaggagca gtacaacagc        900 acctacaggg tggtgtccgt gctgaccgtg ctgcaccagg actggctgaa cggcaaggag      960
tacaagtgta aggtgtccaa caaggccctg ccagccccaa tcgaaaagac catcagcaag     1020
gccaagggcc agccaagaga gccccaggtg tacaccctgc cacccagcag ggacgagctg     1080
accaagaacc aggtgtccct gacctgtctg gtgaagggct tctacccaag cgacatcgcc     1140
gtggagtggg agagcaacgg ccagcccgag aacaactaca agaccacccc cccagtgctg     1200
gacagcgacg gcagcttctt cctgtacagc aagctgaccg tggacaagag cagatggcag     1260
cagggcaacg tgttcagctg ctccgtgatg cacgaggccc tgcacaacca ctacacccag     1320
aagagcctga gcctgtcccc aggcaag                                         1347
```

<210> SEQ ID NO 268
<211> LENGTH: 1347
<212> TYPE: DNA
<213> ORGANISM: Artificial Sequence
<220> FEATURE:
<223> OTHER INFORMATION: N-HC-15

<400> SEQUENCE: 268

```
gaggtgcagc tgttggagtc tgggggaggc ttggtacagc ctggggggaag cttgagactc      60 tcctgtgcag cctctggatt caccttcagt aattactaca tgcactgggt ccgccaagct     120
ccagggaagg gctggagtg gtctcatcc attagtgctc gcagtagcta ccgctactac       180
gcagactcag tgaagggccg attcaccatc tccagagaca attccaagaa cacgctgtat     240
ctgcaaatga acagcctgag agccgaggac actgccgtgt attactgtgc gagacttgct     300
accaggcatc tcgcttttga tatctggggc cagggtacac tggtcaccgt gagctcagcc     360
agcaccaagg gcccaagcgt gttccccctg gccccagca gcaagagcac cagcggcggc     420
acagccgccc tgggctgcct ggtgaaggac tacttccccg agcccgtgac cgtgtcctgg     480
aacagcggag ccctgacctc cggcgtgcac accttccccg ccgtgctgca gagcagcggc     540
ctgtacagcc tgagcagcgt ggtgaccgtg cccagcagca gcctgggcac ccagacctac      600
atctgtaacg tgaaccacaa gcccagcaac accaaggtgg acaagaaggt ggagcccaag      660
agctgtgaca agacccacac ctgcccccc tgcccagccc ccgagctgct gggcggaccc       720
agcgtgttcc tgttcccccc caagcccaag gacaccctga tgatcagcag aaccccgag       780 gtgacctgtg tggtggtgga cgtgtcccac gaggacccag aggtgaagtt caactggtac      840
gtggacggcg tggaggtgca caacgccaag accaagccca gaggagca gtacaacagc        900 acctacaggg tggtgtccgt gctgaccgtg ctgcaccagg actggctgaa cggcaaggag      960
tacaagtgta aggtgtccaa caaggccctg ccagccccaa tcgaaaagac catcagcaag     1020
gccaagggcc agccaagaga gccccaggtg tacaccctgc cacccagcag ggacgagctg     1080
accaagaacc aggtgtccct gacctgtctg gtgaagggct tctacccaag cgacatcgcc     1140
gtggagtggg agagcaacgg ccagcccgag aacaactaca agaccacccc cccagtgctg     1200
gacagcgacg gcagcttctt cctgtacagc aagctgaccg tggacaagag cagatggcag     1260
``` caggg caacg tgttcagctg ctccgtgatg cacgaggccc tgcacaacca ctacacccag    1320
aagagcctga gcctgtcccc aggcaag    1347

<210> SEQ ID NO 269
<211> LENGTH: 1347
<212> TYPE: DNA
<213> ORGANISM: Artificial Sequence
<220> FEATURE:
<223> OTHER INFORMATION: N-HC-16

<400> SEQUENCE: 269
gaggtgcagc tgttggagtc tgggggaggc ttggtacagc ctgggggaag cttgagactc     60
tcctgtgcag cctctggatt caccttcagt aattactaca tgcactgggt ccgccaagct    120
ccagggaagg ggctggagtg ggtctcatcc attagtgctc ggagtagcta catatactac    180
gcagactcag tgaagggccg attcaccatc tccagagaca attccaagaa cacgctgtat    240
ctgcaaatga acagcctgag agccgaggac actgccgtgt attactgtgc gagacttgct    300
accaggcata gcgcttttga tatctggggc cagggtacac tggtcaccgt gagctcagcc    360
agcaccaagg gcccaagcgt gttccccctg gccccagca gcaagagcac cagcggcggc    420
acagccgccc tgggctgcct ggtgaaggac tacttccccg agcccgtgac cgtgtcctgg    480
aacagcggag ccctgacctc cggcgtgcac accttccccg ccgtgctgca gagcagcggc    540
ctgtacagcc tgagcagcgt ggtgaccgtg cccagcagca gcctgggcac ccagacctac    600
atctgtaacg tgaaccacaa gcccagcaac accaaggtgg acaagaaggt ggagcccaag    660
agctgtgaca gacccacac ctgccccccc tgcccagccc cgagctgct gggcggaccc    720 agcgtgttcc tgttcccccc caagcccaag gacaccctga tgatcagcag aacccccgag    780
gtgacctgtg tggtggtgga cgtgtcccac gaggacccag aggtgaagtt caactggtac    840
gtggacggcg tggaggtgca caacgccaag accaagccca gagaggagca gtacaacagc    900
acctacaggg tggtgtccgt gctgaccgtg ctgcaccagg actggctgaa cggcaaggag    960
tacaagtgta aggtgtccaa caaggccctg ccagccccaa tcgaaaagac catcagcaag   1020
gccaagggcc agccaagaga gccccaggtg tacaccctgc cacccagcag ggacgagctg   1080
accaagaacc aggtgtccct gacctgtctg gtgaagggct tctacccaag cgacatcgcc   1140
gtggagtggg agagcaacgg ccagcccgag aacaactaca agaccacccc cccagtgctg   1200
gacagcgacg gcagcttctt cctgtacagc aagctgaccg tggacaagag cagatggcag   1260
cagggcaacg tgttcagctg ctccgtgatg cacgaggccc tgcacaacca ctacacccag   1320
aagagcctga gcctgtcccc aggcaag    1347

<210> SEQ ID NO 270
<211> LENGTH: 1347
<212> TYPE: DNA
<213> ORGANISM: Artificial Sequence
<220> FEATURE:
<223> OTHER INFORMATION: N-HC-17

<400> SEQUENCE: 270
gaggtgcagc tgttggagtc tgggggaggc ttggtacagc ctgggggaag cttgagactc     60
tcctgtgcag cctctggatt caccttcagt cgctactaca tgcactgggt ccgccaagct    120
ccagggaagg ggctggagtg ggtctcatcc attagtgctc ggagtagcta catctactac    180
gcagattcag tgaagggccg attcaccatc tccagagaca attccaagaa cacgctgtat    240

```
ctgcaaatga acagcctgag agccgaggac actgccgtgt attactgtgc gagacttgct    300
accaggcgcg acgcttttga tatctggggc cagggtacac tggtcaccgt gagctcagcc    360
agcaccaagg gcccaagcgt gttccccctg gccccagca gcaagagcac cagcggcggc     420
acagccgccc tgggctgcct ggtgaaggac tacttccccg agcccgtgac cgtgtcctgg    480
aacagcggag ccctgaccct cggcgtgcac accttccccg ccgtgctgca gagcagcggc    540
ctgtacagcc tgagcagcgt ggtgaccgtg cccagcagca gcctgggcac ccagacctac    600
atctgtaacg tgaaccacaa gcccagcaac accaaggtgg acaagaaggt ggagcccaag    660
agctgtgaca gacccacac ctgccccccc tgcccagccc ccgagctgct gggcggaccc     720
agcgtgttcc tgttcccccc caagcccaag gacaccctga tgatcagcag aacccccgag   780
gtgacctgtg tggtggtgga cgtgtcccac gaggacccag aggtgaagtt caactggtac    840
gtggacggcg tggaggtgca caacgccaag accaagccca gaggagca gtacaacagc      900 acctacaggg tggtgtccgt gctgaccgtg ctgcaccagg actggctgaa cggcaaggag    960
tacaagtgta aggtgtccaa caaggccctg ccagccccaa tcgaaaagac catcagcaag   1020
gccaagggcc agccaagaga gccccaggtg tacaccctgc cacccagcag ggacgagctg    1080
accaagaacc aggtgtccct gacctgtctg gtgaagggct tctacccaag cgacatcgcc    1140
gtggagtggg agagcaacgg ccagcccgag aacaactaca agaccacccc cccagtgctg   1200
gacagcgacg gcagcttctt cctgtacagc aagctgaccg tggacaagag cagatggcag    1260
cagggcaacg tgttcagctg ctccgtgatg cacgaggccc tgcacaacca ctacacccag    1320
aagagcctga gcctgtcccc aggcaag                                         1347

<210> SEQ ID NO 271
<211> LENGTH: 1347
<212> TYPE: DNA
<213> ORGANISM: Artificial Sequence
<220> FEATURE:
<223> OTHER INFORMATION: N-HC-18

<400> SEQUENCE: 271
gaggtgcagc tgttggagtc tgggggaggc ttggtacagc ctgggggaag cttgagactc     60
tcctgtgcag cctctggatt caccttcagt aactactaca tgcactgggt ccgccaagct   120
ccagggaagg ggctggagtg ggtctcatcc attagtgctc ggagtagcta ccgctactac    180
gcagattcag tgaagggccg attcaccatc tccagagaca attccaagaa cacgctgtat    240
ctgcaaatga acagcctgag agccgaggac actgccgtgt attactgtgc gagacttgct   300
accaggcaca gcgcttttga tatctggggc cagggtacac tggtcaccgt gagctcagcc    360
agcaccaagg gcccaagcgt gttccccctg gccccagca gcaagagcac cagcggcggc     420
acagccgccc tgggctgcct ggtgaaggac tacttccccg agcccgtgac cgtgtcctgg    480
aacagcggag ccctgaccct cggcgtgcac accttccccg ccgtgctgca gagcagcggc    540
ctgtacagcc tgagcagcgt ggtgaccgtg cccagcagca gcctgggcac ccagacctac    600
atctgtaacg tgaaccacaa gcccagcaac accaaggtgg acaagaaggt ggagcccaag    660
agctgtgaca gacccacac ctgccccccc tgcccagccc ccgagctgct gggcggaccc     720
agcgtgttcc tgttcccccc caagcccaag gacaccctga tgatcagcag aacccccgag   780
gtgacctgtg tggtggtgga cgtgtcccac gaggacccag aggtgaagtt caactggtac    840
gtggacggcg tggaggtgca caacgccaag accaagccca gaggagca gtacaacagc      900 acctacaggg tggtgtccgt gctgaccgtg ctgcaccagg actggctgaa cggcaaggag    960
```

| | |
|---|---|
| tacaagtgta aggtgtccaa caaggccctg ccagccccaa tcgaaaagac catcagcaag | 1020 |
| gccaagggcc agccaagaga gccccaggtg tacaccctgc cacccagcag ggacgagctg | 1080 |
| accaagaacc aggtgtccct gacctgtctg gtgaagggct tctacccaag cgacatcgcc | 1140 |
| gtggagtggg agagcaacgg ccagcccgag aacaactaca agaccacccc cccagtgctg | 1200 |
| gacagcgacg gcagcttctt cctgtacagc aagctgaccg tggacaagag cagatggcag | 1260 |
| cagggcaacg tgttcagctg ctccgtgatg cacgaggccc tgcacaacca ctacacccag | 1320 |
| aagagcctga gcctgtcccc aggcaag | 1347 |

<210> SEQ ID NO 272
<211> LENGTH: 1347
<212> TYPE: DNA
<213> ORGANISM: Artificial Sequence
<220> FEATURE:
<223> OTHER INFORMATION: N-HC-19

<400> SEQUENCE: 272

| | |
|---|---|
| gaggtgcagc tgttggagtc tgggggaggc ttggtacagc ctggggggaag cttgagactc | 60 |
| tcctgtgcag cctctggatt caccttcagt aactactaca tgcactgggt ccgccaagct | 120 |
| ccagggaagg ggctggagtg ggtctcatcc attagtgctc ggagtagcta catctactac | 180 |
| gcaggttcag tgaagggccg attcaccatc tccagagaca attccaagaa cacgctgtat | 240 |
| ctgcaaatga acagcctgag agccgaggac actgccgtgt attactgtgc gagacttggt | 300 |
| accaggcgcg tcgcttttga tatctggggc cagggtacac tggtcaccgt gagctcagcc | 360 |
| agcaccaagg gcccaagcgt gttcccctg gcccccagca gcaagagcac cagcggcggc | 420 |
| acagccgccc tgggctgcct ggtgaaggac tacttccccg agcccgtgac cgtgtcctgg | 480 |
| aacagcggag ccctgacctc cggcgtgcac accttccccg ccgtgctgca gagcagcggc | 540 |
| ctgtacagcc tgagcagcgt ggtgaccgtg cccagcagca gcctgggcac ccagacctac | 600 |
| atctgtaacg tgaaccacaa gcccagcaac accaaggtgg acaagaaggt ggagcccaag | 660 |
| agctgtgaca gacccacac ctgccccccc tgcccagccc ccgagctgct gggcggaccc | 720 |
| agcgtgttcc tgttcccccc caagcccaag gacaccctga tgatcagcag aacccccgag | 780 |
| gtgacctgtg tggtggtgga cgtgtcccac gaggacccag aggtgaagtt caactggtac | 840 |
| gtggacggcg tggaggtgca caacgccaag accaagccca gagaggagca gtacaacagc | 900 |
| acctacaggg tggtgtccgt gctgaccgtg ctgcaccagg actggctgaa cggcaaggag | 960 |
| tacaagtgta aggtgtccaa caaggccctg ccagccccaa tcgaaaagac catcagcaag | 1020 |
| gccaagggcc agccaagaga gccccaggtg tacaccctgc cacccagcag ggacgagctg | 1080 |
| accaagaacc aggtgtccct gacctgtctg gtgaagggct tctacccaag cgacatcgcc | 1140 |
| gtggagtggg agagcaacgg ccagcccgag aacaactaca agaccacccc cccagtgctg | 1200 |
| gacagcgacg gcagcttctt cctgtacagc aagctgaccg tggacaagag cagatggcag | 1260 |
| cagggcaacg tgttcagctg ctccgtgatg cacgaggccc tgcacaacca ctacacccag | 1320 |
| aagagcctga gcctgtcccc aggcaag | 1347 |

<210> SEQ ID NO 273
<211> LENGTH: 1347
<212> TYPE: DNA
<213> ORGANISM: Artificial Sequence
<220> FEATURE:
<223> OTHER INFORMATION: N-HC-20

<400> SEQUENCE: 273

```
gaggtgcagc tgttggagtc tgggggaggc ttggtacagc ctgggggaag cttgagactc    60
tcctgtgcag cctctggatt caccttcagt aactactaca tgcactgggt ccgccaagct   120
ccagggaagg ggctggagtg ggtctcatcc attagttcta ggagtagcca ccaatactac   180
gcaggttcag tgaagggccg attcaccatc tccagagaca attccaagaa cacgctgtat   240
ctgcaaatga acagcctgag agccgaggac actgccgtgt attactgtgc gagacttggt   300
ctcaggcacg acgcttttga tatctggggc cagggtacac tggtcaccgt gagctcagcc   360
agcaccaagg gcccaagcgt gttcccctg gcccccagca gcagagcac cagcggcggc     420
acagccgccc tgggctgcct ggtgaaggac tacttccccg agcccgtgac cgtgtcctgg   480
aacagcggag ccctgacctc cggcgtgcac accttccccg ccgtgctgca gagcagcggc   540
ctgtacagcc tgagcagcgt ggtgaccgtg cccagcagca gcctgggcac ccagacctac   600
atctgtaacg tgaaccacaa gcccagcaac accaaggtgg acaagaaggt ggagcccaag   660
agctgtgaca gacccacac ctgccccccc tgcccagccc cgagctgct gggcggaccc      720
agcgtgttcc tgttccccc caagcccaag gacaccctga tgatcagcag aaccccgag     780
gtgacctgtg tggtggtgga cgtgtcccac gaggacccag aggtgaagtt caactggtac   840
gtggacggcg tggaggtgca caacgccaag accaagccca gaggagca gtacaacagc      900
acctacaggg tggtgtccgt gctgaccgtg ctgcaccagg actggctgaa cggcaaggag   960
tacaagtgta aggtgtccaa caaggccctg ccagcccaa tcgaaaagac catcagcaag   1020
gccaagggcc agccaagaga gccccaggtg tacaccctgc cacccagcag ggacgagctg   1080
accaagaacc aggtgtccct gacctgtctg gtgaagggct tctacccaag cgacatcgcc   1140
gtggagtggg agagcaacgg ccagcccgag aacaactaca agaccacccc cccagtgctg   1200
gacagcgacg gcagcttctt cctgtacagc aagctgaccg tggacaagag cagatggcag   1260
cagggcaacg tgttcagctg ctccgtgatg cacgaggccc tgcacaacca ctacacccag   1320
aagagcctga gcctgtcccc aggcaag                                      1347
```

<210> SEQ ID NO 274
<211> LENGTH: 1347
<212> TYPE: DNA
<213> ORGANISM: Artificial Sequence
<220> FEATURE:
<223> OTHER INFORMATION: N-HC-21

<400> SEQUENCE: 274

```
gaggtgcagc tgttggagtc tgggggaggc ttggtacagc ctgggggaag cttgagactc    60
tcctgtgcag cctctggatt caccttcagt agctactaca tgcactgggt ccgccaagct   120
ccagggaagg ggctggagtg ggtctcatcc attagtgcta ggagtagcta catctactac   180
gcagattcag tgaagggccg attcaccatc tccagagaca attccaagaa cacgctgtat   240
ctgcaaatga acagcctgag agccgaggac actgccgtgt attactgtgc gagacttgct   300
accaggcgca tcgcttttga tatctggggc cagggtacac tggtcaccgt gagctcagcc   360
agcaccaagg gcccaagcgt gttcccctg gcccccagca gcagagcac cagcggcggc     420
acagccgccc tgggctgcct ggtgaaggac tacttccccg agcccgtgac cgtgtcctgg   480
aacagcggag ccctgacctc cggcgtgcac accttccccg ccgtgctgca gagcagcggc   540
ctgtacagcc tgagcagcgt ggtgaccgtg cccagcagca gcctgggcac ccagacctac   600
atctgtaacg tgaaccacaa gcccagcaac accaaggtgg acaagaaggt ggagcccaag   660
```

| | |
|---|---|
| agctgtgaca agacccacac ctgcccccc tgcccagccc ccgagctgct gggcggaccc | 720 |
| agcgtgttcc tgttcccccc caagcccaag gacaccctga tgatcagcag aaccccgag | 780 |
| gtgacctgtg tggtggtgga cgtgtcccac gaggacccag aggtgaagtt caactggtac | 840 |
| gtggacggcg tggaggtgca caacgccaag accaagccca gagaggagca gtacaacagc | 900 |
| acctacaggg tggtgtccgt gctgaccgtg ctgcaccagg actggctgaa cggcaaggag | 960 |
| tacaagtgta aggtgtccaa caaggccctg ccagccccaa tcgaaaagac catcagcaag | 1020 |
| gccaagggcc agccaagaga gccccaggtg tacaccctgc cacccagcag ggacgagctg | 1080 |
| accaagaacc aggtgtccct gacctgtctg gtgaagggct tctacccaag cgacatcgcc | 1140 |
| gtggagtggg agagcaacgg ccagcccgag aacaactaca agaccacccc cccagtgctg | 1200 |
| gacagcgacg gcagcttctt cctgtacagc aagctgaccg tggacaagag cagatggcag | 1260 |
| cagggcaacg tgttcagctg ctccgtgatg cacgaggccc tgcacaacca ctacacccag | 1320 |
| aagagcctga gcctgtcccc aggcaag | 1347 |

<210> SEQ ID NO 275
<211> LENGTH: 1347
<212> TYPE: DNA
<213> ORGANISM: Artificial Sequence
<220> FEATURE:
<223> OTHER INFORMATION: N-HC-22

<400> SEQUENCE: 275

| | |
|---|---|
| gaggtgcagc tgttggagtc tgggggaggc ttggtacagc ctgggggaag cttgagactc | 60 |
| tcctgtgcag cctctggatt caccttcagt aattactaca tgcactgggt ccgccaagct | 120 |
| ccagggaagg gctggagtg gtctcatcc attagtgctc tgagtagcta ccgatactac | 180 |
| gcagattcag tgaagggccg attcaccatc tccagagaca attccaagaa cacgctgtat | 240 |
| ctgcaaatga acagcctgag agccgaggac actgccgtgt attactgtgc gagacttgct | 300 |
| accaggcgcg tcgcttttga tatctggggc cagggtacac tggtcaccgt gagctcagcc | 360 |
| agcaccaagg gcccaagcgt gttcccctg gccccagca gcaagagcac cagcggcggc | 420 |
| acagccgccc tgggctgcct ggtgaaggac tacttccccg agcccgtgac cgtgtcctgg | 480 |
| aacagcggag ccctgacctc cggcgtgcac accttccccg ccgtgctgca gagcagcggc | 540 |
| ctgtacagcc tgagcagcgt ggtgaccgtg cccagcagca gcctgggcac ccagacctac | 600 |
| atctgtaacg tgaaccacaa gcccagcaac accaaggtgg acaagaaggt ggagcccaag | 660 |
| agctgtgaca agacccacac ctgccccccc tgcccagccc ccgagctgct gggcggaccc | 720 |
| agcgtgttcc tgttcccccc caagcccaag gacaccctga tgatcagcag aaccccgag | 780 |
| gtgacctgtg tggtggtgga cgtgtcccac gaggacccag aggtgaagtt caactggtac | 840 |
| gtggacggcg tggaggtgca caacgccaag accaagccca gagaggagca gtacaacagc | 900 |
| acctacaggg tggtgtccgt gctgaccgtg ctgcaccagg actggctgaa cggcaaggag | 960 |
| tacaagtgta aggtgtccaa caaggccctg ccagccccaa tcgaaaagac catcagcaag | 1020 |
| gccaagggcc agccaagaga gccccaggtg tacaccctgc cacccagcag ggacgagctg | 1080 |
| accaagaacc aggtgtccct gacctgtctg gtgaagggct tctacccaag cgacatcgcc | 1140 |
| gtggagtggg agagcaacgg ccagcccgag aacaactaca agaccacccc cccagtgctg | 1200 |
| gacagcgacg gcagcttctt cctgtacagc aagctgaccg tggacaagag cagatggcag | 1260 |
| cagggcaacg tgttcagctg ctccgtgatg cacgaggccc tgcacaacca ctacacccag | 1320 | aagagcctga gcctgtcccc aggcaag                                          1347

<210> SEQ ID NO 276
<211> LENGTH: 1338
<212> TYPE: DNA
<213> ORGANISM: Artificial Sequence
<220> FEATURE:
<223> OTHER INFORMATION: N-HC-23

<400> SEQUENCE: 276
gaggtgcagc tgttggagtc tgggggaggc ttggtacagc ctggggggtc cctgagactc         60
tcctgtgcag cctctggatt caccttcagt gactactaca tgaactgggt ccgccaggct        120
ccagggaagg ggctggagtg ggtctcatcc attagtagta gtagtagtta catatactac        180
gcagactcag tgaagggccg attcaccatc tccagagaca attccaagaa cacgctgtat        240
ctgcaaatga acagcctgag agccgaggac actgccgtgt attactgtgc gagagatatt        300
ggcggtatgg acgtctgggg ccaaggtaca ctggtcaccg tgagcagcgc cagcaccaag        360
ggcccaagcg tgttcccccct ggccccccagc agcaagagca ccagcggcgg cacagccgcc        420
ctgggctgcc tggtgaagga ctacttcccc gagcccgtga ccgtgtcctg aacagcgga        480
gccctgacct ccggcgtgca caccttcccc gccgtgctgc agagcagcgg cctgtacagc        540
ctgagcagcg tggtgaccgt gcccagcagc agcctgggca cccagaccta catctgtaac        600
gtgaaccaca agcccagcaa caccaaggtg gacaagaagg tggagcccaa gagctgtgac        660
aagacccaca cctgcccccc ctgcccagcc ccgagctgc tgggcggacc cagcgtgttc        720
ctgttccccc ccaagcccaa ggacaccctg atgatcagca gaaccccga ggtgacctgt        780
gtggtggtgg acgtgtccca cgaggaccca gaggtgaagt tcaactggta cgtggacggc        840
gtggaggtgc acaacgccaa gaccaagccc agagaggagc agtacaacag cacctacagg        900
gtggtgtccg tgctgaccgt gctgcaccag gactggctga acggcaagga gtacaagtgt        960
aaggtgtcca acaaggccct gccagcccca atcgaaaaga ccatcagcaa ggccaagggc       1020
cagccaagag agccccaggt gtacaccctg ccacccagca gggacgagct gaccaagaac       1080
caggtgtccc tgacctgtct ggtgaagggc ttctacccaa gcgacatcgc cgtggagtgg       1140
gagagcaacg gccagcccga gaacaactac aagaccaccc cccagtgct ggacagcgac       1200
ggcagcttct tcctgtacag caagctgacc gtggacaaga gcagatggca gcagggcaac       1260
gtgttcagct gctccgtgat gcacgaggcc ctgcacaacc actacaccca gaagagcctg       1320
agcctgtccc caggcaag                                                     1338

<210> SEQ ID NO 277
<211> LENGTH: 1347
<212> TYPE: DNA
<213> ORGANISM: Artificial Sequence
<220> FEATURE:
<223> OTHER INFORMATION: N-HC-24

<400> SEQUENCE: 277
gaggtgcagc tgttggagtc tgggggaggc ttggtacagc ctgggggaag cttgagactc         60
tcctgtgcag cctctggatt caccttcagt aattactaca tgcactgggt ccgccaagct        120
ccagggaagg ggctggagtg ggtctcatcc attagtagta gtagtagtta catatactac        180
gcagactcag tgaagggccg attcaccatc tccagagaca attccaagaa cacgctgtat        240
ctgcaaatga acagcctgag agccgaggac actgccgtgt attactgtgc gagacttggt        300
acgaggcatg atgctttga tatctggggc cagggtacac tggtcaccgt gagctcagcc        360

```
agcaccaagg gcccaagcgt gttccccctg gccccagca gcaagagcac cagcggcggc    420
acagccgccc tgggctgcct ggtgaaggac tacttccccg agcccgtgac cgtgtcctgg    480
aacagcggag ccctgacctc cggcgtgcac accttccccg ccgtgctgca gagcagcggc    540
ctgtacagcc tgagcagcgt ggtgaccgtg cccagcagca gcctgggcac ccagacctac    600
atctgtaacg tgaaccacaa gcccagcaac accaaggtgg acaagaaggt ggagcccaag    660
agctgtgaca gacccacac ctgccccccc tgcccagccc ccgagctgct gggcggaccc    720
agcgtgttcc tgttcccccc caagcccaag gacaccctga tgatcagcag aaccccgag    780 gtgacctgtg tggtggtgga cgtgtcccac gaggacccag aggtgaagtt caactggtac    840
gtggacggcg tggaggtgca caacgccaag accaagccca gagaggagca gtacaacagc    900
acctacaggg tggtgtccgt gctgaccgtg ctgcaccagg actggctgaa cggcaaggag    960
tacaagtgta aggtgtccaa caaggccctg ccagccccaa tcgaaaagac catcagcaag    1020
gccaagggcc agccaagaga gccccaggtg tacaccctgc cacccagcag ggacgagctg    1080
accaagaacc aggtgtccct gacctgtctg gtgaagggct tctacccaag cgacatcgcc    1140
gtggagtggg agagcaacgg ccagcccgag aacaactaca agaccacccc cccagtgctg    1200
gacagcgacg gcagcttctt cctgtacagc aagctgaccg tggacaagag cagatggcag    1260
cagggcaacg tgttcagctg ctccgtgatg cacgaggccc tgcacaacca ctacacccag    1320
aagagcctga gcctgtcccc aggcaag                                        1347

<210> SEQ ID NO 278
<211> LENGTH: 95
<212> TYPE: PRT
<213> ORGANISM: Homo sapiens

<400> SEQUENCE: 278

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Ser
                85                  90                  95

<210> SEQ ID NO 279
<211> LENGTH: 95
<212> TYPE: PRT
<213> ORGANISM: Homo sapiens

<400> SEQUENCE: 279

Ala Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
```

```
                50              55              60
Ser Gly Ser Gly Thr Asp Phe Thr Leu Thr Ile Ser Ser Leu Gln Pro
 65                  70                  75                  80

Glu Asp Phe Ala Thr Tyr Tyr Cys Leu Gln Asp Tyr Asn Tyr Pro
                 85                  90                  95
```

<210> SEQ ID NO 280
<211> LENGTH: 95
<212> TYPE: PRT
<213> ORGANISM: Homo sapiens

<400> SEQUENCE: 280

```
Ala Ile Arg Met Thr Gln Ser Pro Ser Ser Phe Ser Ala Ser Thr Gly
 1               5                  10                  15

Asp Arg Val Thr Ile Thr Cys Arg Ala Ser Gln Gly Ile Ser Ser Tyr
                 20                  25                  30

Leu Ala Trp Tyr Gln Gln Lys Pro Gly Lys Ala Pro Lys Leu Leu Ile
             35                  40                  45

Tyr Ala Ala Ser Thr Leu Gln Ser Gly Val Pro Ser Arg Phe Ser Gly
 50                  55                  60

Ser Gly Ser Gly Thr Asp Phe Thr Leu Thr Ile Ser Cys Leu Gln Ser
 65                  70                  75                  80

Glu Asp Phe Ala Thr Tyr Tyr Cys Gln Gln Tyr Tyr Ser Tyr Pro
                 85                  90                  95
```

<210> SEQ ID NO 281
<211> LENGTH: 95
<212> TYPE: PRT
<213> ORGANISM: Homo sapiens

<400> SEQUENCE: 281

```
Asp Ile Gln Leu Thr Gln Ser Pro Ser Phe Leu Ser Ala Ser Val Gly
 1               5                  10                  15

Asp Arg Val Thr Ile Thr Cys Arg Ala Ser Gln Gly Ile Ser Ser Tyr
                 20                  25                  30

Leu Ala Trp Tyr Gln Gln Lys Pro Gly Lys Ala Pro Lys Leu Leu Ile
             35                  40                  45

Tyr Ala Ala Ser Thr Leu Gln Ser Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Gln Gln Leu Asn Ser Tyr Pro
                 85                  90                  95
```

<210> SEQ ID NO 282
<211> LENGTH: 95
<212> TYPE: PRT
<213> ORGANISM: Homo sapiens

<400> SEQUENCE: 282

```
Asp Ile Gln Met Thr Gln Ser Pro Ser Ser Val Ser Ala Ser Val Gly
 1               5                  10                  15

Asp Arg Val Thr Ile Thr Cys Arg Ala Ser Gln Gly Ile Ser Ser Trp
                 20                  25                  30

Leu Ala Trp Tyr Gln Gln Lys Pro Gly Lys Ala Pro Lys Leu Leu Ile
             35                  40                  45

Tyr Ala Ala Ser Ser Leu Gln Ser Gly Val Pro Ser Arg Phe Ser Gly
 50                  55                  60
```

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro
                85                  90                  95

<210> SEQ ID NO 283
<211> LENGTH: 95
<212> TYPE: PRT
<213> ORGANISM: Homo sapiens

<400> SEQUENCE: 283

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Phe Gln Gln Lys Pro Gly Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro
                85                  90                  95

<210> SEQ ID NO 284
<211> LENGTH: 95
<212> TYPE: PRT
<213> ORGANISM: Homo sapiens

<400> SEQUENCE: 284

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro
                85                  90                  95

<210> SEQ ID NO 285
<211> LENGTH: 95
<212> TYPE: PRT
<213> ORGANISM: Homo sapiens

<400> SEQUENCE: 285

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Tyr Gln Gln Lys Pro Gly Lys Val Pro Lys Leu Leu Ile
        35                  40                  45

Tyr Ala Ala Ser Thr Leu Gln Ser Gly Val Pro Ser Arg Phe Ser Gly
    50                  55                  60

```
Ser Gly Ser Gly Thr Asp Phe Thr Leu Thr Ile Ser Ser Leu Gln Pro
 65                  70                  75                  80

Glu Asp Val Ala Thr Tyr Tyr Cys Gln Lys Tyr Asn Ser Ala Pro
                 85                  90                  95
```

<210> SEQ ID NO 286
<211> LENGTH: 95
<212> TYPE: PRT
<213> ORGANISM: Homo sapiens

<400> SEQUENCE: 286

```
Asp Ile Gln Met Thr Gln Ser Pro Ser Ser Leu Ser Ala Ser Val Gly
  1               5                  10                  15

Asp Arg Val Thr Ile Thr Cys Gln Ala Ser Gln Asp Ile Ser Asn Tyr
                 20                  25                  30

Leu Asn Trp Tyr Gln Gln Lys Pro Gly Lys Ala Pro Lys Leu Leu Ile
             35                  40                  45

Tyr Asp Ala Ser Asn Leu Glu Thr Gly Val Pro Ser Arg Phe Ser Gly
 50                  55                  60

Ser Gly Ser Gly Thr Asp Phe Thr Phe Thr Ile Ser Ser Leu Gln Pro
 65                  70                  75                  80

Glu Asp Ile Ala Thr Tyr Tyr Cys Gln Gln Tyr Asp Asn Leu Pro
                 85                  90                  95
```

<210> SEQ ID NO 287
<211> LENGTH: 95
<212> TYPE: PRT
<213> ORGANISM: Homo sapiens

<400> SEQUENCE: 287

```
Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Ser Ile Ser Ser Tyr
                 20                  25                  30

Leu Asn Trp Tyr Gln Gln Lys Pro Gly Lys Ala Pro Lys Leu Leu Ile
             35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Ser Thr Pro
                 85                  90                  95
```

<210> SEQ ID NO 288
<211> LENGTH: 95
<212> TYPE: PRT
<213> ORGANISM: Homo sapiens

<400> SEQUENCE: 288

```
Val Ile Trp Met Thr Gln Ser Pro Ser Leu Leu Ser Ala Ser Thr Gly
  1               5                  10                  15

Asp Arg Val Thr Ile Ser Cys Arg Met Ser Gln Gly Ile Ser Ser Tyr
                 20                  25                  30

Leu Ala Trp Tyr Gln Gln Lys Pro Gly Lys Ala Pro Glu Leu Leu Ile
             35                  40                  45

Tyr Ala Ala Ser Thr Leu Gln Ser Gly Val Pro Ser Arg Phe Ser Gly
 50                  55                  60

Ser Gly Ser Gly Thr Asp Phe Thr Leu Thr Ile Ser Cys Leu Gln Ser
```

```
                65                  70                  75                  80
Glu Asp Phe Ala Thr Tyr Tyr Cys Gln Gln Tyr Tyr Ser Phe Pro
                85                  90                  95

<210> SEQ ID NO 289
<211> LENGTH: 95
<212> TYPE: PRT
<213> ORGANISM: Homo sapiens

<400> SEQUENCE: 289

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
                20                  25                  30

Leu Ala Trp Tyr Gln Gln Lys Pro Gly Lys Ala Pro Lys Leu Leu Ile
            35                  40                  45

Tyr Asp Ala Ser Ser Leu Glu Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Asn Tyr Pro
                85                  90                  95

<210> SEQ ID NO 290
<211> LENGTH: 95
<212> TYPE: PRT
<213> ORGANISM: Homo sapiens

<400> SEQUENCE: 290

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
                20                  25                  30

Leu Ala Trp Tyr Gln Gln Lys Pro Glu Lys Ala Pro Lys Ser Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro
                85                  90                  95

<210> SEQ ID NO 291
<211> LENGTH: 95
<212> TYPE: PRT
<213> ORGANISM: Homo sapiens

<400> SEQUENCE: 291

Asn Ile Gln Met Thr Gln Ser Pro Ser Ala Met Ser Ala Ser Val Gly
1               5                   10                  15

Asp Arg Val Thr Ile Thr Cys Arg Ala Arg Gln Gly Ile Ser Asn Tyr
                20                  25                  30

Leu Ala Trp Phe Gln Gln Lys Pro Gly Lys Val Pro Lys His Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Glu Phe Thr Leu Thr Ile Ser Ser Leu Gln Pro
65                  70                  75                  80
```

-continued

Glu Asp Phe Ala Thr Tyr Tyr Cys Leu Gln His Asn Ser Tyr Pro
                85                  90                  95

<210> SEQ ID NO 292
<211> LENGTH: 95
<212> TYPE: PRT
<213> ORGANISM: Homo sapiens

<400> SEQUENCE: 292

Ala Ile Arg Met Thr Gln Ser Pro Phe Ser Leu Ser Ala Ser Val Gly
1               5                   10                  15

Asp Arg Val Thr Ile Thr Cys Trp Ala Ser Gln Gly Ile Ser Ser Tyr
            20                  25                  30

Leu Ala Trp Tyr Gln Gln Lys Pro Ala Lys Ala Pro Lys Leu Phe Ile
        35                  40                  45

Tyr Tyr Ala Ser Ser Leu Gln Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Tyr Tyr Ser Thr Pro
                85                  90                  95

<210> SEQ ID NO 293
<211> LENGTH: 95
<212> TYPE: PRT
<213> ORGANISM: Homo sapiens

<400> SEQUENCE: 293

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Ser
            20                  25                  30

Leu Ala Trp Tyr Gln Gln Lys Pro Gly Lys Ala Pro Lys Leu Leu Leu
        35                  40                  45

Tyr Ala Ala Ser Arg Leu Glu Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Tyr Tyr Ser Thr Pro
                85                  90                  95

<210> SEQ ID NO 294
<211> LENGTH: 100
<212> TYPE: PRT
<213> ORGANISM: Homo sapiens

<400> SEQUENCE: 294

Asp Ile Val Met Thr Gln Thr Pro Leu Ser Ser Pro Val Thr Leu Gly
1               5                   10                  15

Gln Pro Ala Ser Ile Ser Cys Arg Ser Ser Gln Ser Leu Val His Ser
            20                  25                  30

Asp Gly Asn Thr Tyr Leu Ser Trp Leu Gln Gln Arg Pro Gly Gln Pro
        35                  40                  45

Pro Arg Leu Leu Ile Tyr Lys Ile Ser Asn Arg Phe Ser Gly Val Pro
    50                  55                  60

Asp Arg Phe Ser Gly Ser Gly Ala Gly Thr Asp Phe Thr Leu Lys Ile
65                  70                  75                  80

```
Ser Arg Val Glu Ala Glu Asp Val Gly Val Tyr Tyr Cys Met Gln Ala
                85                  90                  95

Thr Gln Phe Pro
            100

<210> SEQ ID NO 295
<211> LENGTH: 100
<212> TYPE: PRT
<213> ORGANISM: Homo sapiens

<400> SEQUENCE: 295

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro
            100

<210> SEQ ID NO 296
<211> LENGTH: 100
<212> TYPE: PRT
<213> ORGANISM: Homo sapiens

<400> SEQUENCE: 296

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val Tyr Ser
            20                  25                  30

Asp Gly Asn Thr Tyr Leu Asn Trp Phe Gln Gln Arg Pro Gly Gln Ser
        35                  40                  45

Pro Arg Arg Leu Ile Tyr Lys Val Ser Asn Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr His Trp Pro
            100

<210> SEQ ID NO 297
<211> LENGTH: 101
<212> TYPE: PRT
<213> ORGANISM: Homo sapiens

<400> SEQUENCE: 297

Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Leu Asp Ser
            20                  25                  30

Asp Asp Gly Asn Thr Tyr Leu Asp Trp Tyr Leu Gln Lys Pro Gly Gln
```

```
                35                  40                  45
Ser Pro Gln Leu Leu Ile Tyr Thr Leu Ser Tyr Arg Ala Ser Gly Val
 50                  55                  60

Pro Asp Arg Phe Ser Gly Ser Gly Ser Gly Thr Asp Phe Thr Leu Lys
 65                  70                  75                  80

Ile Ser Arg Val Glu Ala Glu Asp Val Gly Val Tyr Tyr Cys Met Gln
                 85                  90                  95

Arg Ile Glu Phe Pro
                100

<210> SEQ ID NO 298
<211> LENGTH: 100
<212> TYPE: PRT
<213> ORGANISM: Homo sapiens

<400> SEQUENCE: 298

Glu Ile Val Met Thr Gln Thr Pro Leu Ser Leu Ser Ile Thr Pro Gly
 1               5                  10                  15

Glu Gln Ala Ser Ile Ser Cys Arg Ser Ser Gln Ser Leu Leu His Ser
                 20                  25                  30

Asp Gly Tyr Thr Tyr Leu Tyr Trp Phe Leu Gln Lys Ala Arg Pro Val
                 35                  40                  45

Ser Thr Leu Leu Ile Tyr Glu Val Ser Asn Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Phe Gly Val Tyr Tyr Cys Met Gln Asp
                 85                  90                  95

Ala Gln Asp Pro
                100

<210> SEQ ID NO 299
<211> LENGTH: 100
<212> TYPE: PRT
<213> ORGANISM: Homo sapiens

<400> SEQUENCE: 299

Asp Ile Val Met Thr Gln Thr Pro Leu Ser Leu Ser Val Thr Pro Gly
 1               5                  10                  15

Gln Pro Ala Ser Ile Ser Cys Lys Ser Ser Gln Ser Leu Leu His Ser
                 20                  25                  30

Asp Gly Lys Thr Tyr Leu Tyr Trp Tyr Leu Gln Lys Pro Gly Gln Pro
                 35                  40                  45

Pro Gln Leu Leu Ile Tyr Glu Val Ser Asn Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Ser
                 85                  90                  95

Ile Gln Leu Pro
                100

<210> SEQ ID NO 300
<211> LENGTH: 100
<212> TYPE: PRT
<213> ORGANISM: Homo sapiens

<400> SEQUENCE: 300
```

```
Asp Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val Tyr Ser
            20                  25                  30

Asp Gly Asn Thr Tyr Leu Asn Trp Phe Gln Gln Arg Pro Gly Gln Ser
        35                  40                  45

Pro Arg Arg Leu Ile Tyr Lys Val Ser Asn Trp Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr His Trp Pro
            100
```

<210> SEQ ID NO 301
<211> LENGTH: 95
<212> TYPE: PRT
<213> ORGANISM: Homo sapiens

<400> SEQUENCE: 301

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro
                85                  90                  95
```

<210> SEQ ID NO 302
<211> LENGTH: 95
<212> TYPE: PRT
<213> ORGANISM: Homo sapiens

<400> SEQUENCE: 302

```
Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro
                85                  90                  95
```

<210> SEQ ID NO 303
<211> LENGTH: 96
<212> TYPE: PRT
<213> ORGANISM: Homo sapiens

<400> SEQUENCE: 303

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

<210> SEQ ID NO 304
<211> LENGTH: 96
<212> TYPE: PRT
<213> ORGANISM: Homo sapiens

<400> SEQUENCE: 304

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ser Trp Tyr Gln Gln Lys Pro Gly Gln Ala Pro Arg Leu Leu
        35                  40                  45

Ile Tyr Gly Ala Ser Thr Arg Ala Thr Gly Ile Pro Ala Arg Phe Ser
50                  55                  60

Gly Ser Gly Ser Gly Thr Asp Phe Thr Leu Thr Ile Ser Ser Leu Gln
65                  70                  75                  80

Pro Glu Asp Phe Ala Val Tyr Tyr Cys Gln Gln Asp Tyr Asn Leu Pro
                85                  90                  95

<210> SEQ ID NO 305
<211> LENGTH: 95
<212> TYPE: PRT
<213> ORGANISM: Homo sapiens

<400> SEQUENCE: 305

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Gly Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
50                  55                  60

Ser Gly Pro Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp His
                85                  90                  95

<210> SEQ ID NO 306
<211> LENGTH: 96
<212> TYPE: PRT
<213> ORGANISM: Homo sapiens

<400> SEQUENCE: 306

Glu Ile Val Leu Thr Gln Ser Pro Ala Thr Leu Ser Leu Ser Pro Gly
1               5                   10                  15

Glu Arg Ala Thr Leu Ser Cys Gly Ala Ser Gln Ser Val Ser Ser Ser
                20                  25                  30

Tyr Leu Ala Trp Tyr Gln Gln Lys Pro Gly Leu Ala Pro Arg Leu Leu
            35                  40                  45

Ile Tyr Asp Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

<210> SEQ ID NO 307
<211> LENGTH: 89
<212> TYPE: PRT
<213> ORGANISM: Homo sapiens

<400> SEQUENCE: 307

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
                20                  25                  30

Leu Ala Trp Tyr Gln Gln Lys Pro Gly Gln Ala Pro Arg Leu Leu Ile
            35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln
                85

<210> SEQ ID NO 308
<211> LENGTH: 89
<212> TYPE: PRT
<213> ORGANISM: Homo sapiens

<400> SEQUENCE: 308

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Gly Val Ser Ser Tyr
                20                  25                  30

Leu Ala Trp Tyr Gln Gln Lys Pro Gly Gln Ala Pro Arg Leu Leu Ile
            35                  40                  45

Tyr Asp Ala Ser Ser Arg Ala Thr Gly Ile Pro Ala Arg Phe Ser Gly
    50                  55                  60

Ser Gly Pro Gly Thr Asp Phe Thr Leu Thr Ile Ser Ser Leu Glu Pro
65                  70                  75                  80

Glu Asp Phe Ala Val Tyr Tyr Cys Gln
                85

<210> SEQ ID NO 309
<211> LENGTH: 90
<212> TYPE: PRT
<213> ORGANISM: Homo sapiens

<400> SEQUENCE: 309

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Leu Ala Pro Arg Leu Leu
        35                  40                  45

Ile Tyr Gly Ala Ser Thr Arg Ala Thr Gly Ile Pro Ala Arg Phe Ser
50                  55                  60

Gly Ser Gly Ser Gly Thr Glu Phe Thr Leu Thr Ile Ser Arg Leu Gln
65                  70                  75                  80

Ser Glu Asp Phe Ala Val Tyr Tyr Cys Gln
            85                  90

<210> SEQ ID NO 310
<211> LENGTH: 95
<212> TYPE: PRT
<213> ORGANISM: Homo sapiens

<400> SEQUENCE: 310

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Gly Val Ser Ser Asn
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
50                  55                  60

Ser Gly Pro Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp His
            85                  90                  95

<210> SEQ ID NO 311
<211> LENGTH: 96
<212> TYPE: PRT
<213> ORGANISM: Homo sapiens

<400> SEQUENCE: 311

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Asp Ala Ser Ser Arg Ala Thr Gly Ile Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Arg Ser Asn Trp His
            85                  90                  95

<210> SEQ ID NO 312
<211> LENGTH: 101
<212> TYPE: PRT
<213> ORGANISM: Homo sapiens

<400> SEQUENCE: 312

```
Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro
            100

<210> SEQ ID NO 313
<211> LENGTH: 95
<212> TYPE: PRT
<213> ORGANISM: Homo sapiens

<400> SEQUENCE: 313

Glu Thr Thr Leu Thr Gln Ser Pro Ala Phe Met Ser Ala Thr Pro Gly
1               5                   10                  15

Asp Lys Val Asn Ile Ser Cys Lys Ala Ser Gln Asp Ile Asp Asp Asp
            20                  25                  30

Met Asn Trp Tyr Gln Gln Lys Pro Gly Glu Ala Ala Ile Phe Ile Ile
        35                  40                  45

Gln Glu Ala Thr Thr Leu Val Pro Gly Ile Pro Pro Arg Phe Ser Gly
50                  55                  60

Ser Gly Tyr Gly Thr Asp Phe Thr Leu Thr Ile Asn Asn Ile Glu Ser
65                  70                  75                  80

Glu Asp Ala Ala Tyr Tyr Phe Cys Leu Gln His Asp Asn Phe Pro
                85                  90                  95

<210> SEQ ID NO 314
<211> LENGTH: 98
<212> TYPE: PRT
<213> ORGANISM: Homo sapiens

<400> SEQUENCE: 314

Gln Ser Val Leu Thr Gln Pro Pro Ser Val Ser Glu Ala Pro Arg Gln
1               5                   10                  15

Arg Val Thr Ile Ser Cys Ser Gly Ser Ser Ser Asn Ile Gly Asn Asn
            20                  25                  30

Ala Val Asn Trp Tyr Gln Gln Leu Pro Gly Lys Ala Pro Lys Leu Leu
        35                  40                  45

Ile Tyr Tyr Asp Asp Leu Leu Pro Ser Gly Val Ser Asp Arg Phe Ser
50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly

<210> SEQ ID NO 315
<211> LENGTH: 99
<212> TYPE: PRT
```

<213> ORGANISM: Homo sapiens

<400> SEQUENCE: 315

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Ser Gly

<210> SEQ ID NO 316
<211> LENGTH: 98
<212> TYPE: PRT
<213> ORGANISM: Homo sapiens

<400> SEQUENCE: 316

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Thr Val Asn Trp Tyr Gln Gln Leu Pro Gly Thr Ala Pro Lys Leu Leu
        35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly

<210> SEQ ID NO 317
<211> LENGTH: 98
<212> TYPE: PRT
<213> ORGANISM: Homo sapiens

<400> SEQUENCE: 317

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Tyr Val Tyr Trp Tyr Gln Gln Leu Pro Gly Thr Ala Pro Lys Leu Leu
        35                  40                  45

Ile Tyr Arg Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Leu
                85                  90                  95

Ser Gly

<210> SEQ ID NO 318
<211> LENGTH: 98
<212> TYPE: PRT
<213> ORGANISM: Homo sapiens

<400> SEQUENCE: 318

Gln Ser Val Leu Thr Gln Pro Pro Ser Val Ala Ala Pro Gly Gln
1               5                   10                  15

Lys Val Thr Ile Ser Cys Ser Gly Ser Ser Asn Ile Gly Asn Asn
                20                  25                  30

Tyr Val Ser Trp Tyr Gln Gln Leu Pro Gly Thr Ala Pro Lys Leu Leu
            35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Ala

<210> SEQ ID NO 319
<211> LENGTH: 99
<212> TYPE: PRT
<213> ORGANISM: Homo sapiens

<400> SEQUENCE: 319

Gln Ser Ala Leu Thr Gln Pro Pro Ser Ala Ser Gly Ser Pro Gly Gln
1               5                   10                  15

Ser Val Thr Ile Ser Cys Thr Gly Thr Ser Ser Asp Val Gly Gly Tyr
                20                  25                  30

Asn Tyr Val Ser Trp Tyr Gln Gln His Pro Gly Lys Ala Pro Lys Leu
            35                  40                  45

Met Ile Tyr Glu Val Ser Lys Arg Pro Ser Gly Val Pro Asp Arg Phe
    50                  55                  60

Ser Gly Ser Lys Ser Gly Asn Thr Ala Ser Leu Thr Val Ser Gly Leu
65                  70                  75                  80

Gln Ala Glu Asp Glu Ala Asp Tyr Tyr Cys Ser Ser Tyr Ala Gly Ser
                85                  90                  95

Asn Asn Phe

<210> SEQ ID NO 320
<211> LENGTH: 99
<212> TYPE: PRT
<213> ORGANISM: Homo sapiens

<400> SEQUENCE: 320

Gln Ser Ala Leu Thr Gln Pro Arg Ser Val Ser Gly Ser Pro Gly Gln
1               5                   10                  15

Ser Val Thr Ile Ser Cys Thr Gly Thr Ser Ser Asp Val Gly Gly Tyr
                20                  25                  30

Asn Tyr Val Ser Trp Tyr Gln Gln His Pro Gly Lys Ala Pro Lys Leu
            35                  40                  45

Met Ile Tyr Asp Val Ser Lys Arg Pro Ser Gly Val Pro Asp Arg Phe
    50                  55                  60

Ser Gly Ser Lys Ser Gly Asn Thr Ala Ser Leu Thr Ile Ser Gly Leu
65                  70                  75                  80

```
Gln Ala Glu Asp Glu Ala Asp Tyr Tyr Cys Cys Ser Tyr Ala Gly Ser
                85                  90                  95

Tyr Thr Phe

<210> SEQ ID NO 321
<211> LENGTH: 99
<212> TYPE: PRT
<213> ORGANISM: Homo sapiens

<400> SEQUENCE: 321

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
                20                  25                  30

Asn Tyr Val Ser Trp Tyr Gln Gln His Pro Gly Lys Ala Pro Lys Leu
            35                  40                  45

Met Ile Tyr Glu Val Ser Asn Arg Pro Ser Gly Val Ser Asn Arg Phe
        50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Leu

<210> SEQ ID NO 322
<211> LENGTH: 99
<212> TYPE: PRT
<213> ORGANISM: Homo sapiens

<400> SEQUENCE: 322

Gln Ser Ala Leu Thr Gln Pro Pro Ser Val Ser Gly Ser Pro Gly Gln
1               5                   10                  15

Ser Val Thr Ile Ser Cys Thr Gly Thr Ser Ser Asp Val Gly Ser Tyr
                20                  25                  30

Asn Arg Val Ser Trp Tyr Gln Gln Pro Pro Gly Thr Ala Pro Lys Leu
            35                  40                  45

Met Ile Tyr Glu Val Ser Asn Arg Pro Ser Gly Val Pro Asp Arg Phe
        50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Leu Tyr Thr Ser Ser
                85                  90                  95

Ser Thr Phe

<210> SEQ ID NO 323
<211> LENGTH: 99
<212> TYPE: PRT
<213> ORGANISM: Homo sapiens

<400> SEQUENCE: 323

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Ser Tyr
                20                  25                  30

Asn Leu Val Ser Trp Tyr Gln Gln His Pro Gly Lys Ala Pro Lys Leu
            35                  40                  45
```

```
Met Ile Tyr Glu Gly Ser Lys Arg Pro Ser Gly Val Ser Asn Arg Phe
    50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Cys Ser Tyr Ala Gly Ser
                 85                  90                  95

Ser Thr Leu

<210> SEQ ID NO 324
<211> LENGTH: 95
<212> TYPE: PRT
<213> ORGANISM: Homo sapiens

<400> SEQUENCE: 324

Ser Tyr Glu Leu Thr Gln Pro Pro Ser Val Ser Val Ser Pro Gly Gln
  1               5                  10                  15

Thr Ala Ser Ile Thr Cys Ser Gly Asp Lys Leu Gly Asp Lys Tyr Ala
                 20                  25                  30

Cys Trp Tyr Gln Gln Lys Pro Gly Gln Ser Pro Val Leu Val Ile Tyr
             35                  40                  45

Gln Asp Ser Lys Arg Pro Ser Gly Ile Pro Glu Arg Phe Ser Gly Ser
 50                  55                  60

Asn Ser Gly Asn Thr Ala Thr Leu Thr Ile Ser Gly Thr Gln Ala Met
 65                  70                  75                  80

Asp Glu Ala Asp Tyr Tyr Cys Gln Ala Trp Asp Ser Ser Thr Ala
                 85                  90                  95

<210> SEQ ID NO 325
<211> LENGTH: 95
<212> TYPE: PRT
<213> ORGANISM: Homo sapiens

<400> SEQUENCE: 325

Ser Tyr Glu Leu Thr Gln Pro Leu Ser Val Ser Val Ala Leu Gly Gln
  1               5                  10                  15

Thr Ala Arg Ile Thr Cys Gly Gly Asn Asn Ile Gly Ser Lys Asn Val
                 20                  25                  30

His Trp Tyr Gln Gln Lys Pro Gly Gln Ala Pro Val Leu Val Ile Tyr
             35                  40                  45

Arg Asp Ser Asn Arg Pro Ser Gly Ile Pro Glu Arg Phe Ser Gly Ser
 50                  55                  60

Asn Ser Gly Asn Thr Ala Thr Leu Thr Ile Ser Arg Ala Gln Ala Gly
 65                  70                  75                  80

Asp Glu Ala Asp Tyr Tyr Cys Gln Val Trp Asp Ser Ser Thr Ala
                 85                  90                  95

<210> SEQ ID NO 326
<211> LENGTH: 96
<212> TYPE: PRT
<213> ORGANISM: Homo sapiens

<400> SEQUENCE: 326

Ser Tyr Glu Leu Thr Gln Pro Pro Ser Val Ser Val Ser Pro Gly Gln
  1               5                  10                  15

Thr Ala Arg Ile Thr Cys Ser Gly Asp Ala Leu Pro Lys Lys Tyr Ala
                 20                  25                  30

Tyr Trp Tyr Gln Gln Lys Ser Gly Gln Ala Pro Val Leu Val Ile Tyr
             35                  40                  45
```

-continued

```
Glu Asp Ser Lys Arg Pro Ser Ile Pro Glu Arg Phe Ser Gly Ser
    50                  55                  60
Ser Ser Gly Thr Met Ala Thr Leu Thr Ile Ser Gly Ala Gln Val Glu
65                  70                  75                  80
Asp Glu Ala Asp Tyr Tyr Cys Tyr Ser Thr Asp Ser Ser Gly Asn His
                85                  90                  95

<210> SEQ ID NO 327
<211> LENGTH: 96
<212> TYPE: PRT
<213> ORGANISM: Homo sapiens

<400> SEQUENCE: 327

Ser Tyr Glu Leu Thr Gln Pro His Ser Val Ser Val Ala Thr Ala Gln
1               5                   10                  15
Met Ala Arg Ile Thr Cys Gly Gly Asn Asn Ile Gly Ser Lys Ala Val
                20                  25                  30
His Trp Tyr Gln Gln Lys Pro Gly Gln Asp Pro Val Leu Val Ile Tyr
            35                  40                  45
Ser Asp Ser Asn Arg Pro Ser Gly Ile Pro Glu Arg Phe Ser Gly Ser
    50                  55                  60
Asn Pro Gly Asn Thr Thr Thr Leu Thr Ile Ser Arg Ile Glu Ala Gly
65                  70                  75                  80
Asp Glu Ala Asp Tyr Tyr Cys Gln Val Trp Asp Ser Ser Asp His
                85                  90                  95

<210> SEQ ID NO 328
<211> LENGTH: 96
<212> TYPE: PRT
<213> ORGANISM: Homo sapiens

<400> SEQUENCE: 328

Ser Tyr Glu Leu Thr Gln Pro Pro Ser Val Ser Val Ser Leu Gly Gln
1               5                   10                  15
Met Ala Arg Ile Thr Cys Ser Gly Glu Ala Leu Pro Lys Lys Tyr Ala
                20                  25                  30
Tyr Trp Tyr Gln Gln Lys Pro Gly Gln Phe Pro Val Leu Val Ile Tyr
            35                  40                  45
Lys Asp Ser Glu Arg Pro Ser Gly Ile Pro Glu Arg Phe Ser Gly Ser
    50                  55                  60
Ser Ser Gly Thr Ile Val Thr Leu Thr Ile Ser Gly Val Gln Ala Glu
65                  70                  75                  80
Asp Glu Ala Asp Tyr Tyr Cys Leu Ser Ala Asp Ser Ser Gly Thr Tyr
                85                  90                  95

<210> SEQ ID NO 329
<211> LENGTH: 96
<212> TYPE: PRT
<213> ORGANISM: Homo sapiens

<400> SEQUENCE: 329

Ser Ser Glu Leu Thr Gln Asp Pro Ala Val Ser Val Ala Leu Gly Gln
1               5                   10                  15
Thr Val Arg Ile Thr Cys Gln Gly Asp Ser Leu Arg Ser Tyr Tyr Ala
                20                  25                  30
Ser Trp Tyr Gln Gln Lys Pro Gly Gln Ala Pro Val Leu Val Ile Tyr
            35                  40                  45
```

-continued

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Ser Ser Gly Asn His
                85                  90                  95

<210> SEQ ID NO 330
<211> LENGTH: 96
<212> TYPE: PRT
<213> ORGANISM: Homo sapiens

<400> SEQUENCE: 330

Ser Tyr Val Leu Thr Gln Pro Pro Ser Val Ser Val Ala Pro Gly Lys
1               5                   10                  15

Thr Ala Arg Ile Thr Cys Gly Gly Asn Asn Ile Gly Ser Lys Ser Val
                20                  25                  30

His Trp Tyr Gln Gln Lys Pro Gly Gln Ala Pro Val Leu Val Ile Tyr
            35                  40                  45

Tyr Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

<210> SEQ ID NO 331
<211> LENGTH: 94
<212> TYPE: PRT
<213> ORGANISM: Homo sapiens

<400> SEQUENCE: 331

Ser Tyr Glu Leu Thr Gln Leu Pro Ser Val Ser Val Ser Pro Gly Gln
1               5                   10                  15

Thr Ala Arg Ile Thr Cys Ser Gly Asp Val Leu Gly Glu Asn Tyr Ala
                20                  25                  30

Asp Trp Tyr Gln Gln Lys Pro Gly Gln Ala Pro Glu Leu Val Ile Tyr
            35                  40                  45

Glu Asp Ser Glu Arg Tyr Pro Gly Ile Pro Glu Arg Phe Ser Gly Ser
    50                  55                  60

Thr Ser Gly Asn Thr Thr Thr Leu Thr Ile Ser Arg Val Leu Thr Glu
65                  70                  75                  80

Asp Glu Ala Asp Tyr Tyr Cys Leu Ser Gly Asp Glu Asp Asn
                85                  90

<210> SEQ ID NO 332
<211> LENGTH: 96
<212> TYPE: PRT
<213> ORGANISM: Homo sapiens

<400> SEQUENCE: 332

Ser Tyr Glu Leu Met Gln Pro Pro Ser Val Ser Val Ser Pro Gly Gln
1               5                   10                  15

Thr Ala Arg Ile Thr Cys Ser Gly Asp Ala Leu Pro Lys Gln Tyr Ala
                20                  25                  30

Tyr Trp Tyr Gln Gln Lys Pro Gly Gln Ala Pro Val Leu Val Ile Tyr
            35                  40                  45

Lys Asp Ser Glu Arg Pro Ser Gly Ile Pro Glu Arg Phe Ser Gly Ser

```
                 50                  55                  60

Ser Ser Gly Thr Thr Val Thr Leu Thr Ile Ser Gly Val Gln Ala Glu
 65                  70                  75                  80

Asp Glu Ala Asp Tyr Tyr Cys Gln Ser Ala Asp Ser Ser Gly Thr Tyr
                 85                  90                  95
```

<210> SEQ ID NO 333
<211> LENGTH: 94
<212> TYPE: PRT
<213> ORGANISM: Homo sapiens

<400> SEQUENCE: 333

```
Ser Tyr Glu Leu Thr Gln Pro Ser Ser Val Ser Val Ser Pro Gly Gln
  1               5                  10                  15

Thr Ala Arg Ile Thr Cys Ser Gly Asp Val Leu Ala Lys Lys Tyr Ala
                 20                  25                  30

Arg Trp Phe Gln Gln Lys Pro Gly Gln Ala Pro Val Leu Val Ile Tyr
                 35                  40                  45

Lys Asp Ser Glu Arg Pro Ser Gly Ile Pro Glu Arg Phe Ser Gly Ser
                 50                  55                  60

Ser Ser Gly Thr Thr Val Thr Leu Thr Ile Ser Gly Ala Gln Val Glu
 65                  70                  75                  80

Asp Glu Ala Asp Tyr Tyr Cys Tyr Ser Ala Ala Asp Asn Asn
                 85                  90
```

<210> SEQ ID NO 334
<211> LENGTH: 103
<212> TYPE: PRT
<213> ORGANISM: Homo sapiens

<400> SEQUENCE: 334

```
Leu Pro Val Leu Thr Gln Pro Pro Ser Ala Ser Ala Leu Leu Gly Ala
  1               5                  10                  15

Ser Ile Lys Leu Thr Cys Thr Leu Ser Ser Glu His Ser Thr Tyr Thr
                 20                  25                  30

Ile Glu Trp Tyr Gln Gln Arg Pro Gly Arg Ser Pro Gln Tyr Ile Met
                 35                  40                  45

Lys Val Lys Ser Asp Gly Ser His Ser Lys Gly Asp Gly Ile Pro Asp
                 50                  55                  60

Arg Phe Met Gly Ser Ser Ser Gly Ala Asp Arg Tyr Leu Thr Phe Ser
 65                  70                  75                  80

Asn Leu Gln Ser Asp Asp Glu Ala Glu Tyr His Cys Gly Glu Ser His
                 85                  90                  95

Thr Ile Asp Gly Gln Val Gly
                100
```

<210> SEQ ID NO 335
<211> LENGTH: 99
<212> TYPE: PRT
<213> ORGANISM: Homo sapiens

<400> SEQUENCE: 335

```
Gln Pro Val Leu Thr Gln Ser Ser Ala Ser Ala Ser Leu Gly Ser
  1               5                  10                  15

Ser Val Lys Leu Thr Cys Thr Leu Ser Ser Gly His Ser Ser Tyr Ile
                 20                  25                  30

Ile Ala Trp His Gln Gln Gln Pro Gly Lys Ala Pro Arg Tyr Leu Met
                 35                  40                  45
```

```
Lys Leu Glu Gly Ser Gly Ser Tyr Asn Lys Gly Ser Gly Val Pro Asp
         50                  55                  60

Arg Phe Ser Gly Ser Ser Ser Gly Ala Asp Arg Tyr Leu Thr Ile Ser
 65                  70                  75                  80

Asn Leu Gln Leu Glu Asp Glu Ala Asp Tyr Tyr Cys Glu Thr Trp Asp
                 85                  90                  95

Ser Asn Thr

<210> SEQ ID NO 336
<211> LENGTH: 99
<212> TYPE: PRT
<213> ORGANISM: Homo sapiens

<400> SEQUENCE: 336

Gln Leu Val Leu Thr Gln Ser Pro Ser Ala Ser Ala Ser Leu Gly Ala
 1               5                  10                  15

Ser Val Lys Leu Thr Cys Thr Leu Ser Ser Gly His Ser Ser Tyr Ala
                 20                  25                  30

Ile Ala Trp His Gln Gln Pro Glu Lys Gly Pro Arg Tyr Leu Met
                 35                  40                  45

Lys Leu Asn Ser Asp Gly Ser His Ser Lys Gly Asp Gly Ile Pro Asp
         50                  55                  60

Arg Phe Ser Gly Ser Ser Ser Gly Ala Glu Arg Tyr Leu Thr Ile Ser
 65                  70                  75                  80

Ser Leu Gln Ser Glu Asp Glu Ala Asp Tyr Tyr Cys Gln Thr Trp Gly
                 85                  90                  95

Thr Gly Ile

<210> SEQ ID NO 337
<211> LENGTH: 104
<212> TYPE: PRT
<213> ORGANISM: Homo sapiens

<400> SEQUENCE: 337

Gln Pro Val Leu Thr Gln Pro Pro Ser Ser Ser Ala Ser Pro Gly Glu
 1               5                  10                  15

Ser Ala Arg Leu Thr Cys Thr Leu Pro Ser Asp Ile Asn Val Gly Ser
                 20                  25                  30

Tyr Asn Ile Tyr Trp Tyr Gln Gln Lys Pro Gly Ser Pro Arg Tyr
                 35                  40                  45

Leu Leu Tyr Tyr Tyr Ser Asp Ser Asp Lys Gly Gln Gly Ser Gly Val
         50                  55                  60

Pro Ser Arg Phe Ser Gly Ser Lys Asp Ala Ser Ala Asn Thr Gly Ile
 65                  70                  75                  80

Leu Leu Ile Ser Gly Leu Gln Ser Glu Asp Glu Ala Asp Tyr Tyr Cys
                 85                  90                  95

Met Ile Trp Pro Ser Asn Ala Ser
            100

<210> SEQ ID NO 338
<211> LENGTH: 104
<212> TYPE: PRT
<213> ORGANISM: Homo sapiens

<400> SEQUENCE: 338

Gln Pro Val Leu Thr Gln Pro Thr Ser Leu Ser Ala Ser Pro Gly Ala
 1               5                  10                  15
```

-continued

```
Ser Ala Arg Phe Thr Cys Thr Leu Arg Ser Gly Ile Asn Val Gly Thr
            20                  25                  30

Tyr Arg Ile Tyr Trp Tyr Gln Gln Lys Pro Gly Ser Leu Pro Arg Tyr
        35                  40                  45

Leu Leu Arg Tyr Lys Ser Asp Ser Asp Lys Gln Gly Ser Gly Val
50                  55                  60

Pro Ser Arg Phe Ser Gly Ser Lys Asp Ala Ser Thr Asn Ala Gly Leu
65                  70                  75                  80

Leu Leu Ile Ser Gly Leu Gln Ser Glu Asp Glu Ala Asp Tyr Tyr Cys
                85                  90                  95

Ala Ile Trp Tyr Ser Ser Thr Ser
            100
```

<210> SEQ ID NO 339
<211> LENGTH: 104
<212> TYPE: PRT
<213> ORGANISM: Homo sapiens

<400> SEQUENCE: 339

```
Gln Ala Val Leu Thr Gln Pro Ala Ser Leu Ser Ala Ser Pro Gly Ala
1               5                   10                  15

Ser Ala Ser Leu Thr Cys Thr Leu Arg Ser Gly Ile Asn Val Gly Thr
            20                  25                  30

Tyr Arg Ile Tyr Trp Tyr Gln Gln Lys Pro Gly Ser Pro Pro Gln Tyr
        35                  40                  45

Leu Leu Arg Tyr Lys Ser Asp Ser Asp Lys Gln Gly Ser Gly Val
50                  55                  60

Pro Ser Arg Phe Ser Gly Ser Lys Asp Ala Ser Ala Asn Ala Gly Ile
65                  70                  75                  80

Leu Leu Ile Ser Gly Leu Gln Ser Glu Asp Glu Ala Asp Tyr Tyr Cys
                85                  90                  95

Met Ile Trp His Ser Ser Ala Ser
            100
```

<210> SEQ ID NO 340
<211> LENGTH: 105
<212> TYPE: PRT
<213> ORGANISM: Homo sapiens

<400> SEQUENCE: 340

```
Gln Pro Val Leu Thr Gln Pro Ser Ser His Ser Ala Ser Ser Gly Ala
1               5                   10                  15

Ser Val Arg Leu Thr Cys Met Leu Ser Ser Gly Phe Ser Val Gly Asp
            20                  25                  30

Phe Trp Ile Arg Trp Tyr Gln Gln Lys Pro Gly Asn Pro Pro Arg Tyr
        35                  40                  45

Leu Leu Tyr Tyr His Ser Asp Ser Asn Lys Gly Gln Gly Ser Gly Val
50                  55                  60

Pro Ser Arg Phe Ser Gly Ser Asn Asp Ala Ser Ala Asn Ala Gly Ile
65                  70                  75                  80

Leu Arg Ile Ser Gly Leu Gln Pro Glu Asp Glu Ala Asp Tyr Tyr Cys
                85                  90                  95

Gly Thr Trp His Ser Asn Ser Lys Thr
            100                 105
```

<210> SEQ ID NO 341

```
<211> LENGTH: 98
<212> TYPE: PRT
<213> ORGANISM: Homo sapiens

<400> SEQUENCE: 341

Asn Phe Met Leu Thr Gln Pro His Ser Val Ser Glu Ser Pro Gly Lys
1               5                   10                  15

Thr Val Thr Ile Ser Cys Thr Arg Ser Ser Gly Ser Ile Ala Ser Asn
            20                  25                  30

Tyr Val Gln Trp Tyr Gln Gln Arg Pro Gly Ser Ser Pro Thr Thr Val
        35                  40                  45

Ile Tyr Glu Asp Asn Gln Arg Pro Ser Gly Val Pro Asp Arg Phe Ser
50                  55                  60

Gly Ser Ile Asp Ser Ser Ser Asn Ser Ala Ser Leu Thr Ile Ser Gly
65                  70                  75                  80

Leu Lys Thr Glu Asp Glu Ala Asp Tyr Tyr Cys Gln Ser Tyr Asp Ser
                85                  90                  95

Ser Asn

<210> SEQ ID NO 342
<211> LENGTH: 98
<212> TYPE: PRT
<213> ORGANISM: Homo sapiens

<400> SEQUENCE: 342

Gln Thr Val Val Thr Gln Glu Pro Ser Leu Thr Val Ser Pro Gly Gly
1               5                   10                  15

Thr Val Thr Leu Thr Cys Ala Ser Ser Thr Gly Ala Val Thr Ser Gly
            20                  25                  30

Tyr Tyr Pro Asn Trp Phe Gln Gln Lys Pro Gly Gln Ala Pro Arg Ala
        35                  40                  45

Leu Ile Tyr Ser Thr Ser Asn Lys His Ser Trp Thr Pro Ala Arg Phe
50                  55                  60

Ser Gly Ser Leu Leu Gly Gly Lys Ala Ala Leu Thr Leu Ser Gly Val
65                  70                  75                  80

Gln Pro Glu Asp Glu Ala Glu Tyr Tyr Cys Leu Leu Tyr Tyr Gly Gly
                85                  90                  95

Ala Gln

<210> SEQ ID NO 343
<211> LENGTH: 98
<212> TYPE: PRT
<213> ORGANISM: Homo sapiens

<400> SEQUENCE: 343

Gln Ala Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Ser Gly
            20                  25                  30

His Tyr Pro Tyr Trp Phe Gln Gln Lys Pro Gly Gln Ala Pro Arg Thr
        35                  40                  45

Leu Ile Tyr Asp Thr Ser Asn Lys His Ser Trp Thr Pro Ala Arg Phe
50                  55                  60

Ser Gly Ser Leu Leu Gly Gly Lys Ala Ala Leu Thr Leu Ser Gly Ala
65                  70                  75                  80

Gln Pro Glu Asp Glu Ala Glu Tyr Tyr Cys Leu Leu Ser Tyr Ser Gly
                85                  90                  95
```

Ala Arg

<210> SEQ ID NO 344
<211> LENGTH: 98
<212> TYPE: PRT
<213> ORGANISM: Homo sapiens

<400> SEQUENCE: 344

Gln Thr Val Val Thr Gln Glu Pro Ser Phe Ser Val Ser Pro Gly Gly
1               5                   10                  15

Thr Val Thr Leu Thr Cys Gly Leu Ser Ser Gly Ser Val Ser Thr Ser
            20                  25                  30

Tyr Tyr Pro Ser Trp Tyr Gln Gln Thr Pro Gly Gln Ala Pro Arg Thr
        35                  40                  45

Leu Ile Tyr Ser Thr Asn Thr Arg Ser Ser Gly Val Pro Asp Arg Phe
50                  55                  60

Ser Gly Ser Ile Leu Gly Asn Lys Ala Ala Leu Thr Ile Thr Gly Ala
65                  70                  75                  80

Gln Ala Asp Asp Glu Ser Asp Tyr Tyr Cys Val Leu Tyr Met Gly Ser
                85                  90                  95

Gly Ile

<210> SEQ ID NO 345
<211> LENGTH: 104
<212> TYPE: PRT
<213> ORGANISM: Homo sapiens

<400> SEQUENCE: 345

Gln Pro Val Leu Thr Gln Pro Pro Ser Ala Ser Ala Ser Leu Gly Ala
1               5                   10                  15

Ser Val Thr Leu Thr Cys Thr Leu Ser Ser Gly Tyr Ser Asn Tyr Lys
            20                  25                  30

Val Asp Trp Tyr Gln Gln Arg Pro Gly Lys Gly Pro Arg Phe Val Met
        35                  40                  45

Arg Val Gly Thr Gly Gly Ile Val Gly Ser Lys Gly Asp Gly Ile Pro
50                  55                  60

Asp Arg Phe Ser Val Leu Gly Ser Gly Leu Asn Arg Tyr Leu Thr Ile
65                  70                  75                  80

Lys Asn Ile Gln Glu Glu Asp Glu Ser Asp Tyr His Cys Gly Ala Asp
                85                  90                  95

His Gly Ser Gly Ser Asn Phe Val
            100

<210> SEQ ID NO 346
<211> LENGTH: 98
<212> TYPE: PRT
<213> ORGANISM: Homo sapiens

<400> SEQUENCE: 346

Gln Ala Gly Leu Thr Gln Pro Pro Ser Val Ser Lys Gly Leu Arg Gln
1               5                   10                  15

Thr Ala Thr Leu Thr Cys Thr Gly Asn Ser Asn Asn Val Gly Asn Gln
            20                  25                  30

Gly Ala Ala Trp Leu Gln Gln His Gln Gly His Pro Pro Lys Leu Leu
        35                  40                  45

Ser Tyr Arg Asn Asn Asn Arg Pro Ser Gly Ile Ser Glu Arg Leu Ser
50                  55                  60

-continued

```
Ala Ser Arg Ser Gly Asn Thr Ala Ser Leu Thr Ile Thr Gly Leu Gln
 65                  70                  75                  80

Pro Glu Asp Glu Ala Asp Tyr Tyr Cys Ser Ala Trp Asp Ser Ser Leu
                 85                  90                  95

Ser Ala

<210> SEQ ID NO 347
<211> LENGTH: 98
<212> TYPE: PRT
<213> ORGANISM: Homo sapiens

<400> SEQUENCE: 347

Gln Val Gln Leu Val Gln Ser Gly Ala Glu Val Lys Lys Pro Gly Ala
  1               5                  10                  15

Ser Val Lys Val Ser Cys Lys Ala Ser Gly Tyr Thr Phe Thr Gly Tyr
                 20                  25                  30

Tyr Met His Trp Val Arg Gln Ala Pro Gly Gln Gly Leu Glu Trp Met
             35                  40                  45

Gly Arg Ile Asn Pro Asn Ser Gly Gly Thr Asn Tyr Ala Gln Lys Phe
         50                  55                  60

Gln Gly Arg Val Thr Ser Thr Arg Asp Thr Ser Ile Ser Thr Ala Tyr
 65                  70                  75                  80

Met Glu Leu Ser Arg Leu Arg Ser Asp Asp Thr Val Val Tyr Tyr Cys
                 85                  90                  95

Ala Arg

<210> SEQ ID NO 348
<211> LENGTH: 98
<212> TYPE: PRT
<213> ORGANISM: Homo sapiens

<400> SEQUENCE: 348

Gln Val Gln Leu Val Gln Ser Gly Ala Glu Val Lys Lys Pro Gly Ala
  1               5                  10                  15

Ser Val Lys Val Ser Cys Lys Ala Ser Gly Tyr Thr Phe Thr Ser Tyr
                 20                  25                  30

Ala Met His Trp Val Arg Gln Ala Pro Gly Gln Arg Leu Glu Trp Met
             35                  40                  45

Gly Trp Ile Asn Ala Gly Asn Gly Asn Thr Lys Tyr Ser Gln Lys Phe
         50                  55                  60

Gln Gly Arg Val Thr Ile Thr Arg Asp Thr Ser Ala Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg

<210> SEQ ID NO 349
<211> LENGTH: 98
<212> TYPE: PRT
<213> ORGANISM: Homo sapiens

<400> SEQUENCE: 349

Gln Val Gln Leu Val Gln Ser Gly Ala Glu Val Lys Lys Pro Gly Ala
  1               5                  10                  15

Ser Val Lys Val Ser Cys Lys Ala Ser Gly Tyr Thr Phe Thr Ser Tyr
                 20                  25                  30
```

Asp Ile Asn Trp Val Arg Gln Ala Thr Gly Gln Gly Leu Glu Trp Met
            35                  40                  45

Gly Trp Met Asn Pro Asn Ser Gly Asn Thr Gly Tyr Ala Gln Lys Phe
 50                  55                  60

Gln Gly Arg Val Thr Met Thr Arg Asn Thr Ser Ile Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg

<210> SEQ ID NO 350
<211> LENGTH: 98
<212> TYPE: PRT
<213> ORGANISM: Homo sapiens

<400> SEQUENCE: 350

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser Tyr
                 20                  25                  30

Gly Ile Ser Trp Val Arg Gln Ala Pro Gly Gln Gly Leu Glu Trp Met
            35                  40                  45

Gly Trp Ile Ser Ala Tyr Asn Gly Asn Thr Asn Tyr Ala Gln Lys Leu
 50                  55                  60

Gln Gly Arg Val Thr Met Thr Thr Asp Thr Ser Thr Ser Thr Ala Tyr
 65                  70                  75                  80

Met Glu Leu Arg Ser Leu Arg Ser Asp Asp Thr Ala Val Tyr Tyr Cys
                 85                  90                  95

Ala Arg

<210> SEQ ID NO 351
<211> LENGTH: 98
<212> TYPE: PRT
<213> ORGANISM: Homo sapiens

<400> SEQUENCE: 351

Gln Val Gln Leu Val Gln Ser Gly Ala Glu Val Lys Lys Pro Gly Ala
 1               5                  10                  15

Ser Val Lys Val Ser Cys Lys Val Ser Gly Tyr Thr Leu Thr Glu Leu
                 20                  25                  30

Ser Met His Trp Val Arg Gln Ala Pro Gly Lys Gly Leu Glu Trp Met
            35                  40                  45

Gly Gly Phe Asp Pro Glu Asp Gly Glu Thr Ile Tyr Ala Gln Lys Phe
 50                  55                  60

Gln Gly Arg Val Thr Met Thr Glu Asp Thr Ser Thr Asp Thr Ala Tyr
 65                  70                  75                  80

Met Glu Leu Ser Ser Leu Arg Ser Glu Asp Thr Ala Val Tyr Tyr Cys
                 85                  90                  95

Ala Thr

<210> SEQ ID NO 352
<211> LENGTH: 98
<212> TYPE: PRT
<213> ORGANISM: Homo sapiens

<400> SEQUENCE: 352

Gln Met Gln Leu Val Gln Ser Gly Ala Glu Val Lys Lys Thr Gly Ser

-continued

```
                 1               5                  10                 15
            Ser Val Lys Val Ser Cys Lys Ala Ser Gly Tyr Thr Phe Thr Tyr Arg
                             20                 25                 30

Tyr Leu His Trp Val Arg Gln Ala Pro Gly Gln Ala Leu Glu Trp Met
                         35                 40                 45

Gly Trp Ile Thr Pro Phe Asn Gly Asn Thr Asn Tyr Ala Gln Lys Phe
                     50                 55                 60

Gln Asp Arg Val Thr Ile Thr Arg Asp Arg Ser Met Ser Thr Ala Tyr
            65                 70                 75                 80

Met Glu Leu Ser Ser Leu Arg Ser Glu Asp Thr Ala Met Tyr Tyr Cys
                             85                 90                 95

Ala Arg

<210> SEQ ID NO 353
<211> LENGTH: 98
<212> TYPE: PRT
<213> ORGANISM: Homo sapiens

<400> SEQUENCE: 353

Gln Val Gln Leu Val Gln Ser Gly Ala Glu Val Lys Lys Pro Gly Ala
            1               5                  10                 15

Ser Val Lys Val Ser Cys Lys Ala Ser Gly Tyr Thr Phe Thr Ser Tyr
                             20                 25                 30

Tyr Met His Trp Val Arg Gln Ala Pro Gly Gln Gly Leu Glu Trp Met
                         35                 40                 45

Gly Ile Ile Asn Pro Ser Gly Gly Ser Thr Ser Tyr Ala Gln Lys Phe
                     50                 55                 60

Gln Gly Arg Val Thr Met Thr Arg Asp Thr Ser Thr Ser Thr Val Tyr
            65                 70                 75                 80

Met Glu Leu Ser Ser Leu Arg Ser Glu Asp Thr Ala Val Tyr Tyr Cys
                             85                 90                 95

Ala Arg

<210> SEQ ID NO 354
<211> LENGTH: 98
<212> TYPE: PRT
<213> ORGANISM: Homo sapiens

<400> SEQUENCE: 354

Gln Met Gln Leu Val Gln Ser Gly Pro Glu Val Lys Lys Pro Gly Thr
            1               5                  10                 15

Ser Val Lys Val Ser Cys Lys Ala Ser Gly Phe Thr Phe Thr Ser Ser
                             20                 25                 30

Ala Val Gln Trp Val Arg Gln Ala Arg Gly Gln Arg Leu Glu Trp Ile
                         35                 40                 45

Gly Trp Ile Val Gly Ser Gly Asn Thr Asn Tyr Ala Gln Lys Phe
                     50                 55                 60

Gln Glu Arg Val Thr Ile Thr Arg Asp Met Ser Thr Ser Thr Ala Tyr
            65                 70                 75                 80

Met Glu Leu Ser Ser Leu Arg Ser Glu Asp Thr Ala Val Tyr Tyr Cys
                             85                 90                 95

Ala Ala

<210> SEQ ID NO 355
<211> LENGTH: 98
<212> TYPE: PRT
```

<213> ORGANISM: Homo sapiens

<400> SEQUENCE: 355

Glu Val Gln Leu Val Gln Ser Gly Ala Glu Val Lys Lys Pro Gly Ala
1               5                   10                  15
Thr Val Lys Ile Ser Cys Lys Val Ser Gly Tyr Thr Phe Thr Asp Tyr
            20                  25                  30
Tyr Met His Trp Val Gln Gln Ala Pro Gly Lys Gly Leu Glu Trp Met
        35                  40                  45
Gly Leu Val Asp Pro Glu Asp Gly Glu Thr Ile Tyr Ala Glu Lys Phe
    50                  55                  60
Gln Gly Arg Val Thr Ile Thr Ala Asp Thr Ser Thr Asp Thr Ala Tyr
65                  70                  75                  80
Met Glu Leu Ser Ser Leu Arg Ser Glu Asp Thr Ala Val Tyr Tyr Cys
                85                  90                  95
Ala Thr

<210> SEQ ID NO 356
<211> LENGTH: 98
<212> TYPE: PRT
<213> ORGANISM: Homo sapiens

<400> SEQUENCE: 356

Gln Val Gln Leu Val Gln Ser Gly Ala Glu Val Lys Lys Pro Gly Ser
1               5                   10                  15
Ser Val Lys Val Ser Cys Lys Ala Ser Gly Gly Thr Phe Ser Ser Tyr
            20                  25                  30
Ala Ile Ser Trp Val Arg Gln Ala Pro Gly Gln Gly Leu Glu Trp Met
        35                  40                  45
Gly Gly Ile Ile Pro Ile Phe Gly Thr Ala Asn Tyr Ala Gln Lys Phe
    50                  55                  60
Gln Gly Arg Val Thr Ile Thr Ala Asp Glu Ser Thr Ser Thr Ala Tyr
65                  70                  75                  80
Met Glu Leu Ser Ser Leu Arg Ser Glu Asp Thr Ala Val Tyr Tyr Cys
                85                  90                  95
Ala Arg

<210> SEQ ID NO 357
<211> LENGTH: 100
<212> TYPE: PRT
<213> ORGANISM: Homo sapiens

<400> SEQUENCE: 357

Gln Ile Thr Leu Lys Glu Ser Gly Pro Thr Leu Val Lys Pro Thr Gln
1               5                   10                  15
Thr Leu Thr Leu Thr Cys Thr Phe Ser Gly Phe Ser Leu Ser Thr Ser
            20                  25                  30
Gly Val Gly Val Gly Trp Ile Arg Gln Pro Pro Gly Lys Ala Leu Glu
        35                  40                  45
Trp Leu Ala Leu Ile Tyr Trp Asn Asp Asp Lys Arg Tyr Ser Pro Ser
    50                  55                  60
Leu Lys Ser Arg Leu Thr Ile Thr Lys Asp Thr Ser Lys Asn Gln Val
65                  70                  75                  80
Val Leu Thr Met Thr Asn Met Asp Pro Val Asp Thr Ala Thr Tyr Tyr
                85                  90                  95
Cys Ala His Arg

```
<210> SEQ ID NO 358
<211> LENGTH: 100
<212> TYPE: PRT
<213> ORGANISM: Homo sapiens

<400> SEQUENCE: 358
```

| Gln | Val | Thr | Leu | Lys | Glu | Ser | Gly | Pro | Val | Leu | Val | Lys | Pro | Thr | Glu |
|---|---|---|---|---|---|---|---|---|---|---|---|---|---|---|---|
| 1 | | | | 5 | | | | | 10 | | | | | 15 | |

| Thr | Leu | Thr | Leu | Thr | Cys | Thr | Val | Ser | Gly | Phe | Ser | Leu | Ser | Asn | Ala |
|---|---|---|---|---|---|---|---|---|---|---|---|---|---|---|---|
| | | | 20 | | | | | 25 | | | | | 30 | | |

| Arg | Met | Gly | Val | Ser | Trp | Ile | Arg | Gln | Pro | Pro | Gly | Lys | Ala | Leu | Glu |
|---|---|---|---|---|---|---|---|---|---|---|---|---|---|---|---|
| | | 35 | | | | | 40 | | | | | 45 | | | |

| Trp | Leu | Ala | His | Ile | Phe | Ser | Asn | Asp | Glu | Lys | Ser | Tyr | Ser | Thr | Ser |
|---|---|---|---|---|---|---|---|---|---|---|---|---|---|---|---|
| | 50 | | | | | 55 | | | | | 60 | | | | |

| Leu | Lys | Ser | Arg | Leu | Thr | Ile | Ser | Lys | Asp | Thr | Ser | Lys | Ser | Gln | Val |
|---|---|---|---|---|---|---|---|---|---|---|---|---|---|---|---|
| 65 | | | | | 70 | | | | | 75 | | | | | 80 |

| Val | Leu | Thr | Met | Thr | Asn | Met | Asp | Pro | Val | Asp | Thr | Ala | Thr | Tyr | Tyr |
|---|---|---|---|---|---|---|---|---|---|---|---|---|---|---|---|
| | | | | 85 | | | | | 90 | | | | | 95 | |

| Cys | Ala | Arg | Ile |
|---|---|---|---|
| | | | 100 |

```
<210> SEQ ID NO 359
<211> LENGTH: 100
<212> TYPE: PRT
<213> ORGANISM: Homo sapiens

<400> SEQUENCE: 359
```

| Gln | Val | Thr | Leu | Arg | Glu | Ser | Gly | Pro | Ala | Leu | Val | Lys | Pro | Thr | Gln |
|---|---|---|---|---|---|---|---|---|---|---|---|---|---|---|---|
| 1 | | | | 5 | | | | | 10 | | | | | 15 | |

| Thr | Leu | Thr | Leu | Thr | Cys | Thr | Phe | Ser | Gly | Phe | Ser | Leu | Ser | Thr | Ser |
|---|---|---|---|---|---|---|---|---|---|---|---|---|---|---|---|
| | | | 20 | | | | | 25 | | | | | 30 | | |

| Gly | Met | Cys | Val | Ser | Trp | Ile | Arg | Gln | Pro | Pro | Gly | Lys | Ala | Leu | Glu |
|---|---|---|---|---|---|---|---|---|---|---|---|---|---|---|---|
| | | 35 | | | | | 40 | | | | | 45 | | | |

| Trp | Leu | Ala | Leu | Ile | Asp | Trp | Asp | Asp | Asp | Lys | Tyr | Tyr | Ser | Thr | Ser |
|---|---|---|---|---|---|---|---|---|---|---|---|---|---|---|---|
| | 50 | | | | | 55 | | | | | 60 | | | | |

| Leu | Lys | Thr | Arg | Leu | Thr | Ile | Ser | Lys | Asp | Thr | Ser | Lys | Asn | Gln | Val |
|---|---|---|---|---|---|---|---|---|---|---|---|---|---|---|---|
| 65 | | | | | 70 | | | | | 75 | | | | | 80 |

| Val | Leu | Thr | Met | Thr | Asn | Met | Asp | Pro | Val | Asp | Thr | Ala | Thr | Tyr | Tyr |
|---|---|---|---|---|---|---|---|---|---|---|---|---|---|---|---|
| | | | | 85 | | | | | 90 | | | | | 95 | |

| Cys | Ala | Arg | Ile |
|---|---|---|---|
| | | | 100 |

```
<210> SEQ ID NO 360
<211> LENGTH: 98
<212> TYPE: PRT
<213> ORGANISM: Homo sapiens

<400> SEQUENCE: 360
```

| Glu | Val | Gln | Leu | Val | Glu | Ser | Gly | Gly | Gly | Leu | Val | Gln | Pro | Gly | Gly |
|---|---|---|---|---|---|---|---|---|---|---|---|---|---|---|---|
| 1 | | | | 5 | | | | | 10 | | | | | 15 | |

| Ser | Leu | Arg | Leu | Ser | Cys | Ala | Ala | Ser | Gly | Phe | Thr | Phe | Ser | Ser | Tyr |
|---|---|---|---|---|---|---|---|---|---|---|---|---|---|---|---|
| | | | 20 | | | | | 25 | | | | | 30 | | |

| Trp | Met | Ser | Trp | Val | Arg | Gln | Ala | Pro | Gly | Lys | Gly | Leu | Glu | Trp | Val |
|---|---|---|---|---|---|---|---|---|---|---|---|---|---|---|---|
| | | 35 | | | | | 40 | | | | | 45 | | | |

| Ala | Asn | Ile | Lys | Gln | Asp | Gly | Ser | Glu | Lys | Tyr | Tyr | Val | Asp | Ser | Val |
|---|---|---|---|---|---|---|---|---|---|---|---|---|---|---|---|
| | 50 | | | | | 55 | | | | | 60 | | | | |

```
Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg

<210> SEQ ID NO 361
<211> LENGTH: 99
<212> TYPE: PRT
<213> ORGANISM: Homo sapiens

<400> SEQUENCE: 361

Glu Val Gln Leu Val Glu Ser Gly Gly Gly Leu Val Gln Pro Gly Arg
 1               5                  10                  15

Ser Leu Arg Leu Ser Cys Ala Ala Ser Gly Phe Thr Phe Asp Asp Tyr
                20                  25                  30

Ala Met His Trp Val Arg Gln Ala Pro Gly Lys Gly Leu Glu Trp Val
             35                  40                  45

Ser Gly Ile Ser Trp Asn Ser Gly Ser Ile Gly Tyr Ala Asp Ser Val
         50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Leu Tyr Tyr Cys
                 85                  90                  95

Ala Lys Asp

<210> SEQ ID NO 362
<211> LENGTH: 98
<212> TYPE: PRT
<213> ORGANISM: Homo sapiens

<400> SEQUENCE: 362

Gln Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Asp Tyr
                20                  25                  30

Tyr Met Ser Trp Ile Arg Gln Ala Pro Gly Lys Gly Leu Glu Trp Val
             35                  40                  45

Ser Tyr Ile Ser Ser Ser Gly Ser Thr Ile Tyr Tyr Ala Asp Ser Val
         50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg

<210> SEQ ID NO 363
<211> LENGTH: 97
<212> TYPE: PRT
<213> ORGANISM: Homo sapiens

<400> SEQUENCE: 363

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
                20                  25                  30
```

```
Asp Met His Trp Val Arg Gln Ala Thr Gly Lys Gly Leu Glu Trp Val
         35                  40                  45

Ser Ala Ile Gly Thr Ala Gly Asp Thr Tyr Tyr Pro Gly Ser Val Lys
 50                  55                  60

Gly Arg Phe Thr Ile Ser Arg Glu Asn Ala Lys Asn Ser Leu Tyr Leu
 65                  70                  75                  80

Gln Met Asn Ser Leu Arg Ala Gly Asp Thr Ala Val Tyr Tyr Cys Ala
                 85                  90                  95

Arg
```

<210> SEQ ID NO 364
<211> LENGTH: 100
<212> TYPE: PRT
<213> ORGANISM: Homo sapiens

<400> SEQUENCE: 364

```
Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Asn Ala
                 20                  25                  30

Trp Met Ser Trp Val Arg Gln Ala Pro Gly Lys Gly Leu Glu Trp Val
         35                  40                  45

Gly Arg Ile Lys Ser Lys Thr Asp Gly Gly Thr Thr Asp Tyr Ala Ala
 50                  55                  60

Pro Val Lys Gly Arg Phe Thr Ile Ser Arg Asp Asp Ser Lys Asn Thr
 65                  70                  75                  80

Leu Tyr Leu Gln Met Asn Ser Leu Lys Thr Glu Asp Thr Ala Val Tyr
                 85                  90                  95

Tyr Cys Thr Thr
            100
```

<210> SEQ ID NO 365
<211> LENGTH: 98
<212> TYPE: PRT
<213> ORGANISM: Homo sapiens

<400> SEQUENCE: 365

```
Glu Val Gln Leu Val Glu Ser Gly Gly Gly Val Val Arg Pro Gly Gly
 1               5                  10                  15

Ser Leu Arg Leu Ser Cys Ala Ala Ser Gly Phe Thr Phe Asp Asp Tyr
                 20                  25                  30

Gly Met Ser Trp Val Arg Gln Ala Pro Gly Lys Gly Leu Glu Trp Val
         35                  40                  45

Ser Gly Ile Asn Trp Asn Gly Gly Ser Thr Gly Tyr Ala Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Leu Tyr His Cys
                 85                  90                  95

Ala Arg
```

<210> SEQ ID NO 366
<211> LENGTH: 98
<212> TYPE: PRT
<213> ORGANISM: Homo sapiens

<400> SEQUENCE: 366

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 367
<211> LENGTH: 98
<212> TYPE: PRT
<213> ORGANISM: Homo sapiens

<400> SEQUENCE: 367

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys

<210> SEQ ID NO 368
<211> LENGTH: 98
<212> TYPE: PRT
<213> ORGANISM: Homo sapiens

<400> SEQUENCE: 368

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 369
<211> LENGTH: 98

```
<212> TYPE: PRT
<213> ORGANISM: Homo sapiens

<400> SEQUENCE: 369

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 370
<211> LENGTH: 99
<212> TYPE: PRT
<213> ORGANISM: Homo sapiens

<400> SEQUENCE: 370

Glu Val Gln Leu Val Glu Ser Gly Gly Val Val Gln Pro Gly Gly
1               5                   10                  15

Ser Leu Arg Leu Ser Cys Ala Ala Ser Gly Phe Thr Phe Asp Asp Tyr
            20                  25                  30

Thr Met His Trp Val Arg Gln Ala Pro Gly Lys Gly Leu Glu Trp Val
        35                  40                  45

Ser Leu Ile Ser Trp Asp Gly Gly Ser Thr Tyr Tyr Ala Asp Ser Val
    50                  55                  60

Lys Gly Arg Phe Thr Ile Ser Arg Asp Asn Ser Lys Asn Ser Leu Tyr
65                  70                  75                  80

Leu Gln Met Asn Ser Leu Arg Thr Glu Asp Thr Ala Leu Tyr Tyr Cys
                85                  90                  95

Ala Lys Asp

<210> SEQ ID NO 371
<211> LENGTH: 98
<212> TYPE: PRT
<213> ORGANISM: Homo sapiens

<400> SEQUENCE: 371

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Tyr Ile Ser Ser Ser Ser Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95
```

Ala Arg

<210> SEQ ID NO 372
<211> LENGTH: 100
<212> TYPE: PRT
<213> ORGANISM: Homo sapiens

<400> SEQUENCE: 372

Glu Val Gln Leu Val Glu Ser Gly Gly Gly Leu Val Gln Pro Gly Arg
1               5                   10                  15

Ser Leu Arg Leu Ser Cys Thr Ala Ser Gly Phe Thr Phe Gly Asp Tyr
            20                  25                  30

Ala Met Ser Trp Phe Arg Gln Ala Pro Gly Lys Gly Leu Glu Trp Val
        35                  40                  45

Gly Phe Ile Arg Ser Lys Ala Tyr Gly Gly Thr Thr Glu Tyr Thr Ala
    50                  55                  60

Ser Val Lys Gly Arg Phe Thr Ile Ser Arg Asp Gly Ser Lys Ser Ile
65                  70                  75                  80

Ala Tyr Leu Gln Met Asn Ser Leu Lys Thr Glu Asp Thr Ala Val Tyr
                85                  90                  95

Tyr Cys Thr Arg
            100

<210> SEQ ID NO 373
<211> LENGTH: 97
<212> TYPE: PRT
<213> ORGANISM: Homo sapiens

<400> SEQUENCE: 373

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Thr Val Ser Ser Asn
            20                  25                  30

Tyr Met Ser Trp Val Arg Gln Ala Pro Gly Lys Gly Leu Glu Trp Val
        35                  40                  45

Ser Val Ile Tyr Ser Gly Gly Ser Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg

<210> SEQ ID NO 374
<211> LENGTH: 98
<212> TYPE: PRT
<213> ORGANISM: Homo sapiens

<400> SEQUENCE: 374

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Tyr Val
        35                  40                  45

Ser Ala Ile Ser Ser Asn Gly Ser Thr Tyr Tyr Ala Asn Ser Val
    50                  55                  60

Lys Gly Arg Phe Thr Ile Ser Arg Asp Asn Ser Lys Asn Thr Leu Tyr
65                  70                  75                  80

Leu Gln Met Gly Ser Leu Arg Ala Glu Asp Met Ala Val Tyr Tyr Cys
            85                  90                  95

Ala Arg

<210> SEQ ID NO 375
<211> LENGTH: 97
<212> TYPE: PRT
<213> ORGANISM: Homo sapiens

<400> SEQUENCE: 375

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Val Ser Ser Asn
            20                  25                  30

Tyr Met Ser Trp Val Arg Gln Ala Pro Gly Lys Gly Leu Glu Trp Val
        35                  40                  45

Ser Val Ile Tyr Ser Gly Gly Ser Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
            85                  90                  95

Arg

<210> SEQ ID NO 376
<211> LENGTH: 100
<212> TYPE: PRT
<213> ORGANISM: Homo sapiens

<400> SEQUENCE: 376

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp His
            20                  25                  30

Tyr Met Asp Trp Val Arg Gln Ala Pro Gly Lys Gly Leu Glu Trp Val
        35                  40                  45

Gly Arg Thr Arg Asn Lys Ala Asn Ser Tyr Thr Thr Glu Tyr Ala Ala
    50                  55                  60

Ser Val Lys Gly Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
            85                  90                  95

Tyr Cys Ala Arg
            100

<210> SEQ ID NO 377
<211> LENGTH: 100
<212> TYPE: PRT
<213> ORGANISM: Homo sapiens

<400> SEQUENCE: 377

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Gly Ser
            20                  25                  30

Ala Met His Trp Val Arg Gln Ala Ser Gly Lys Gly Leu Glu Trp Val
            35                  40                  45

Gly Arg Ile Arg Ser Lys Ala Asn Ser Tyr Ala Thr Ala Tyr Ala Ala
 50                  55                  60

Ser Val Lys Gly Arg Phe Thr Ile Ser Arg Asp Asp Ser Lys Asn Thr
 65                  70                  75                  80

Ala Tyr Leu Gln Met Asn Ser Leu Lys Thr Glu Asp Thr Ala Val Tyr
                 85                  90                  95

Tyr Cys Thr Arg
            100

<210> SEQ ID NO 378
<211> LENGTH: 98
<212> TYPE: PRT
<213> ORGANISM: Homo sapiens

<400> SEQUENCE: 378

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
                 20                  25                  30

Trp Met His Trp Val Arg Gln Ala Pro Gly Lys Gly Leu Val Trp Val
            35                  40                  45

Ser Arg Ile Asn Ser Asp Gly Ser Ser Thr Ser Tyr Ala Asp Ser Val
 50                  55                  60

Lys Gly Arg Phe Thr Ile Ser Arg Asp Asn Ala Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg

<210> SEQ ID NO 379
<211> LENGTH: 96
<212> TYPE: PRT
<213> ORGANISM: Homo sapiens

<400> SEQUENCE: 379

Glu Val Gln Leu Val Glu Ser Arg Gly Val Leu Val Gln Pro Gly Gly
 1               5                  10                  15

Ser Leu Arg Leu Ser Cys Ala Ala Ser Gly Phe Thr Val Ser Ser Asn
                 20                  25                  30

Glu Met Ser Trp Val Arg Gln Ala Pro Gly Lys Gly Leu Glu Trp Val
            35                  40                  45

Ser Ser Ile Ser Gly Gly Ser Thr Tyr Tyr Ala Asp Ser Arg Lys Gly
 50                  55                  60

Arg Phe Thr Ile Ser Arg Asp Asn Ser Lys Asn Thr Leu His Leu Gln
 65                  70                  75                  80

Met Asn Ser Leu Arg Ala Glu Asp Thr Ala Val Tyr Tyr Cys Lys Lys
                 85                  90                  95

<210> SEQ ID NO 380
<211> LENGTH: 98
<212> TYPE: PRT
<213> ORGANISM: Homo sapiens

<400> SEQUENCE: 380

Gln Val Gln Leu Val Glu Ser Gly Gly Gly Val Val Gln Pro Gly Gly
 1               5                  10                  15

```
Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ser Val Ile Tyr Ser Gly Gly Ser Thr Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys

<210> SEQ ID NO 381
<211> LENGTH: 98
<212> TYPE: PRT
<213> ORGANISM: Homo sapiens

<400> SEQUENCE: 381

Gln Val Gln Leu Gln Glu Ser Gly Pro Gly Leu Val Lys Pro Pro Gly
1               5                   10                  15

Thr Leu Ser Leu Thr Cys Ala Val Ser Gly Gly Ser Ile Ser Ser Ser
            20                  25                  30

Asn Trp Trp Ser Trp Val Arg Gln Pro Pro Gly Lys Gly Leu Glu Trp
        35                  40                  45

Ile Gly Glu Ile Tyr His Ser Gly Ser Thr Asn Tyr Asn Pro Ser Leu
    50                  55                  60

Lys Ser Arg Val Thr Ile Ser Val Asp Lys Ser Lys Asn Gln Phe Ser
65                  70                  75                  80

Leu Lys Leu Ser Ser Val Thr Ala Ala Asp Thr Ala Val Tyr Cys Cys
                85                  90                  95

Ala Arg

<210> SEQ ID NO 382
<211> LENGTH: 98
<212> TYPE: PRT
<213> ORGANISM: Homo sapiens

<400> SEQUENCE: 382

Gln Val Gln Leu Gln Glu Ser Gly Pro Gly Leu Val Lys Pro Ser Asp
1               5                   10                  15

Thr Leu Ser Leu Thr Cys Ala Val Ser Gly Tyr Ser Ile Ser Ser Ser
            20                  25                  30

Asn Trp Trp Gly Trp Ile Arg Gln Pro Pro Gly Lys Gly Leu Glu Trp
        35                  40                  45

Ile Gly Tyr Ile Tyr Tyr Ser Gly Ser Thr Tyr Tyr Asn Pro Ser Leu
    50                  55                  60

Lys Ser Arg Val Thr Met Ser Val Asp Thr Ser Lys Asn Gln Phe Ser
65                  70                  75                  80

Leu Lys Leu Ser Ser Val Thr Ala Val Asp Thr Ala Val Tyr Tyr Cys
                85                  90                  95

Ala Arg

<210> SEQ ID NO 383
<211> LENGTH: 99
<212> TYPE: PRT
<213> ORGANISM: Homo sapiens
```

<400> SEQUENCE: 383

Gln Leu Gln Leu Gln Glu Ser Gly Ser Gly Leu Val Lys Pro Ser Gln
1               5                   10                  15

Thr Leu Ser Leu Thr Cys Ala Val Ser Gly Gly Ser Ile Ser Ser Gly
            20                  25                  30

Gly Tyr Ser Trp Ser Trp Ile Arg Gln Pro Pro Gly Lys Gly Leu Glu
        35                  40                  45

Trp Ile Gly Tyr Ile Tyr His Ser Gly Ser Thr Tyr Tyr Asn Pro Ser
50                  55                  60

Leu Lys Ser Arg Val Thr Ile Ser Val Asp Arg Ser Lys Asn Gln Phe
65                  70                  75                  80

Ser Leu Lys Leu Ser Ser Val Thr Ala Ala Asp Thr Ala Val Tyr Tyr
            85                  90                  95

Cys Ala Arg

<210> SEQ ID NO 384
<211> LENGTH: 99
<212> TYPE: PRT
<213> ORGANISM: Homo sapiens

<400> SEQUENCE: 384

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Asp Tyr Tyr Trp Ser Trp Ile Arg Gln Pro Pro Gly Lys Gly Leu Glu
        35                  40                  45

Trp Ile Gly Tyr Ile Tyr Tyr Ser Gly Ser Thr Tyr Tyr Asn Pro Ser
50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
            85                  90                  95

Cys Ala Arg

<210> SEQ ID NO 385
<211> LENGTH: 99
<212> TYPE: PRT
<213> ORGANISM: Homo sapiens

<400> SEQUENCE: 385

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Gly Tyr Tyr Trp Ser Trp Ile Arg Gln His Pro Gly Lys Gly Leu Glu
        35                  40                  45

Trp Ile Gly Tyr Ile Tyr Tyr Ser Gly Ser Thr Tyr Tyr Asn Pro Ser
50                  55                  60

Leu Lys Ser Leu Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
            85                  90                  95

Cys Ala Arg

<210> SEQ ID NO 386
<211> LENGTH: 97
<212> TYPE: PRT
<213> ORGANISM: Homo sapiens

<400> SEQUENCE: 386

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg

<210> SEQ ID NO 387
<211> LENGTH: 99
<212> TYPE: PRT
<213> ORGANISM: Homo sapiens

<400> SEQUENCE: 387

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly Ser Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg

<210> SEQ ID NO 388
<211> LENGTH: 97
<212> TYPE: PRT
<213> ORGANISM: Homo sapiens

<400> SEQUENCE: 388

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

```
Lys Leu Ser Ser Val Thr Ala Ala Asp Thr Ala Val Tyr Tyr Cys Ala
                85                  90                  95
Arg

<210> SEQ ID NO 389
<211> LENGTH: 98
<212> TYPE: PRT
<213> ORGANISM: Homo sapiens

<400> SEQUENCE: 389

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Ser Gly
                20                  25                  30

Tyr Tyr Trp Gly Trp Ile Arg Gln Pro Pro Gly Lys Gly Leu Glu Trp
            35                  40                  45

Ile Gly Ser Ile Tyr His Ser Gly Ser Thr Tyr Tyr Asn Pro Ser Leu
        50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg

<210> SEQ ID NO 390
<211> LENGTH: 99
<212> TYPE: PRT
<213> ORGANISM: Homo sapiens

<400> SEQUENCE: 390

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Val Ser Ser Gly
                20                  25                  30

Ser Tyr Tyr Trp Ser Trp Ile Arg Gln Pro Pro Gly Lys Gly Leu Glu
            35                  40                  45

Trp Ile Gly Tyr Ile Tyr Tyr Ser Gly Ser Thr Asn Tyr Asn Pro Ser
        50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg

<210> SEQ ID NO 391
<211> LENGTH: 98
<212> TYPE: PRT
<213> ORGANISM: Homo sapiens

<400> SEQUENCE: 391

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Thr Ser Tyr
                20                  25                  30

Trp Ile Ser Trp Val Arg Gln Met Pro Gly Lys Gly Leu Glu Trp Met
            35                  40                  45

Gly Arg Ile Asp Pro Ser Asp Ser Tyr Thr Asn Tyr Ser Pro Ser Phe
```

```
            50                  55                  60
Gln Gly His Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                 85                  90                  95

Ala Arg

<210> SEQ ID NO 392
<211> LENGTH: 98
<212> TYPE: PRT
<213> ORGANISM: Homo sapiens

<400> SEQUENCE: 392

Glu Val Gln Leu Val Gln Ser Gly Ala Glu Val Lys Lys Pro Gly Glu
 1               5                  10                  15

Ser Leu Lys Ile Ser Cys Lys Gly Ser Gly Tyr Ser Phe Thr Ser Tyr
                 20                  25                  30

Trp Ile Gly Trp Val Arg Gln Met Pro Gly Lys Gly Leu Glu Trp Met
             35                  40                  45

Gly Ile Ile Tyr Pro Gly Asp Ser Asp Thr Arg Tyr Ser Pro Ser Phe
         50                  55                  60

Gln Gly Gln Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                 85                  90                  95

Ala Arg

<210> SEQ ID NO 393
<211> LENGTH: 101
<212> TYPE: PRT
<213> ORGANISM: Homo sapiens

<400> SEQUENCE: 393

Gln Val Gln Leu Gln Gln Ser Gly Pro Gly Leu Val Lys Pro Ser Gln
 1               5                  10                  15

Thr Leu Ser Leu Thr Cys Ala Ile Ser Gly Asp Ser Val Ser Ser Asn
                 20                  25                  30

Ser Ala Ala Trp Asn Trp Ile Arg Gln Ser Pro Ser Arg Gly Leu Glu
             35                  40                  45

Trp Leu Gly Arg Thr Tyr Tyr Arg Ser Lys Trp Tyr Asn Asp Tyr Ala
         50                  55                  60

Val Ser Val Lys Ser Arg Ile Thr Ile Asn Pro Asp Thr Ser Lys Asn
 65                  70                  75                  80

Gln Phe Ser Leu Gln Leu Asn Ser Val Thr Pro Glu Asp Thr Ala Val
                 85                  90                  95

Tyr Tyr Cys Ala Arg
            100

<210> SEQ ID NO 394
<211> LENGTH: 98
<212> TYPE: PRT
<213> ORGANISM: Homo sapiens

<400> SEQUENCE: 394

Gln Val Gln Leu Val Gln Ser Gly Ser Glu Leu Lys Lys Pro Gly Ala
 1               5                  10                  15

Ser Val Lys Val Ser Cys Lys Ala Ser Gly Tyr Thr Phe Thr Ser Tyr
```

```
                    20                  25                  30
Ala Met Asn Trp Val Arg Gln Ala Pro Gly Gln Gly Leu Glu Trp Met
            35                  40                  45

Gly Trp Ile Asn Thr Asn Thr Gly Asn Pro Thr Tyr Ala Gln Gly Phe
        50                  55                  60

Thr Gly Arg Phe Val Phe Ser Leu Asp Thr Ser Val Ser Thr Ala Tyr
 65                  70                  75                  80

Leu Gln Ile Cys Ser Leu Lys Ala Glu Asp Thr Ala Val Tyr Tyr Cys
                85                  90                  95

Ala Arg

<210> SEQ ID NO 395
<211> LENGTH: 12
<212> TYPE: PRT
<213> ORGANISM: Homo sapiens

<400> SEQUENCE: 395

Trp Thr Phe Gly Gln Gly Thr Lys Val Glu Ile Lys
 1               5                  10

<210> SEQ ID NO 396
<211> LENGTH: 12
<212> TYPE: PRT
<213> ORGANISM: Homo sapiens

<400> SEQUENCE: 396

Tyr Thr Phe Gly Gln Gly Thr Lys Leu Glu Ile Lys
 1               5                  10

<210> SEQ ID NO 397
<211> LENGTH: 12
<212> TYPE: PRT
<213> ORGANISM: Homo sapiens

<400> SEQUENCE: 397

Phe Thr Phe Gly Pro Gly Thr Lys Val Asp Ile Lys
 1               5                  10

<210> SEQ ID NO 398
<211> LENGTH: 12
<212> TYPE: PRT
<213> ORGANISM: Homo sapiens

<400> SEQUENCE: 398

Leu Thr Phe Gly Gly Gly Thr Lys Val Glu Ile Lys
 1               5                  10

<210> SEQ ID NO 399
<211> LENGTH: 12
<212> TYPE: PRT
<213> ORGANISM: Homo sapiens

<400> SEQUENCE: 399

Ile Thr Phe Gly Gln Gly Thr Arg Leu Glu Ile Lys
 1               5                  10

<210> SEQ ID NO 400
<211> LENGTH: 12
<212> TYPE: PRT
<213> ORGANISM: Homo sapiens

<400> SEQUENCE: 400
```

Tyr Val Phe Gly Thr Gly Thr Lys Val Thr Val Leu
1               5                   10

<210> SEQ ID NO 401
<211> LENGTH: 12
<212> TYPE: PRT
<213> ORGANISM: Homo sapiens

<400> SEQUENCE: 401

Val Val Phe Gly Gly Gly Thr Lys Leu Thr Val Leu
1               5                   10

<210> SEQ ID NO 402
<211> LENGTH: 12
<212> TYPE: PRT
<213> ORGANISM: Homo sapiens

<400> SEQUENCE: 402

Asn Val Phe Gly Ser Gly Thr Lys Val Thr Val Leu
1               5                   10

<210> SEQ ID NO 403
<211> LENGTH: 12
<212> TYPE: PRT
<213> ORGANISM: Homo sapiens

<400> SEQUENCE: 403

Ala Val Phe Gly Gly Gly Thr Gln Leu Thr Val Leu
1               5                   10

<210> SEQ ID NO 404
<211> LENGTH: 17
<212> TYPE: PRT
<213> ORGANISM: Homo sapiens

<400> SEQUENCE: 404

Ala Glu Tyr Phe Gln His Trp Gly Gln Gly Thr Leu Val Thr Val Ser
1               5                   10                  15

Ser

<210> SEQ ID NO 405
<211> LENGTH: 17
<212> TYPE: PRT
<213> ORGANISM: Homo sapiens

<400> SEQUENCE: 405

Tyr Trp Tyr Phe Asp Leu Trp Gly Arg Gly Thr Leu Val Thr Val Ser
1               5                   10                  15

Ser

<210> SEQ ID NO 406
<211> LENGTH: 16
<212> TYPE: PRT
<213> ORGANISM: Homo sapiens

<400> SEQUENCE: 406

Asp Ala Phe Asp Val Trp Gly Gln Gly Thr Met Val Thr Val Ser Ser
1               5                   10                  15

<210> SEQ ID NO 407
<211> LENGTH: 15
<212> TYPE: PRT
<213> ORGANISM: Homo sapiens

```
<400> SEQUENCE: 407

Tyr Phe Asp Tyr Trp Gly Gln Gly Thr Leu Val Thr Val Ser Ser
1               5                   10                  15

<210> SEQ ID NO 408
<211> LENGTH: 16
<212> TYPE: PRT
<213> ORGANISM: Homo sapiens

<400> SEQUENCE: 408

Asn Trp Phe Asp Ser Trp Gly Gln Gly Thr Leu Val Thr Val Ser Ser
1               5                   10                  15

<210> SEQ ID NO 409
<211> LENGTH: 20
<212> TYPE: PRT
<213> ORGANISM: Homo sapiens

<400> SEQUENCE: 409

Tyr Tyr Tyr Tyr Tyr Gly Met Asp Val Trp Gly Gln Gly Thr Thr Val
1               5                   10                  15

Thr Val Ser Ser
            20

<210> SEQ ID NO 410
<211> LENGTH: 20
<212> TYPE: PRT
<213> ORGANISM: Homo sapiens

<400> SEQUENCE: 410

Val Gln Lys Tyr Thr Arg Ala Leu His Asp Ser Ser Ile Thr Gly Ile
1               5                   10                  15

Ser Pro Ile Thr
            20

<210> SEQ ID NO 411
<211> LENGTH: 20
<212> TYPE: PRT
<213> ORGANISM: Homo sapiens

<400> SEQUENCE: 411

Ser Ser Ile Thr Gly Ile Ser Pro Ile Thr Glu Tyr Leu Ala Ser Leu
1               5                   10                  15

Ser Thr Tyr Asn
            20

<210> SEQ ID NO 412
<211> LENGTH: 20
<212> TYPE: PRT
<213> ORGANISM: Homo sapiens

<400> SEQUENCE: 412

Glu Tyr Leu Ala Ser Leu Ser Thr Tyr Asn Asp Gln Ser Ile Thr Phe
1               5                   10                  15

Ala Leu Glu Asp
            20

<210> SEQ ID NO 413
<211> LENGTH: 20
<212> TYPE: PRT
<213> ORGANISM: Homo sapiens

<400> SEQUENCE: 413
```

```
Asp Gln Ser Ile Thr Phe Ala Leu Glu Asp Glu Ser Tyr Glu Ile Tyr
1               5                   10                  15

Val Glu Asp Leu
            20

<210> SEQ ID NO 414
<211> LENGTH: 20
<212> TYPE: PRT
<213> ORGANISM: Homo sapiens

<400> SEQUENCE: 414

Glu Ser Tyr Glu Ile Tyr Val Glu Asp Leu Lys Lys Asp Glu Lys Lys
1               5                   10                  15

Asp Lys Val Leu
            20

<210> SEQ ID NO 415
<211> LENGTH: 20
<212> TYPE: PRT
<213> ORGANISM: Homo sapiens

<400> SEQUENCE: 415

Lys Lys Asp Glu Lys Lys Asp Lys Val Leu Leu Ser Tyr Tyr Glu Ser
1               5                   10                  15

Gln His Pro Ser
            20

<210> SEQ ID NO 416
<211> LENGTH: 20
<212> TYPE: PRT
<213> ORGANISM: Homo sapiens

<400> SEQUENCE: 416

Leu Ser Tyr Tyr Glu Ser Gln His Pro Ser Asn Glu Ser Gly Asp Gly
1               5                   10                  15

Val Asp Gly Lys
            20

<210> SEQ ID NO 417
<211> LENGTH: 20
<212> TYPE: PRT
<213> ORGANISM: Homo sapiens

<400> SEQUENCE: 417

Asn Glu Ser Gly Asp Gly Val Asp Gly Lys Met Leu Met Val Thr Leu
1               5                   10                  15

Ser Pro Thr Lys
            20

<210> SEQ ID NO 418
<211> LENGTH: 20
<212> TYPE: PRT
<213> ORGANISM: Homo sapiens

<400> SEQUENCE: 418

Met Leu Met Val Thr Leu Ser Pro Thr Lys Asp Phe Trp Leu His Ala
1               5                   10                  15

Asn Asn Lys Glu
            20

<210> SEQ ID NO 419
```

```
<211> LENGTH: 20
<212> TYPE: PRT
<213> ORGANISM: Homo sapiens

<400> SEQUENCE: 419

Asp Phe Trp Leu His Ala Asn Asn Lys Glu His Ser Val Glu Leu His
1               5                   10                  15

Lys Cys Glu Lys
            20

<210> SEQ ID NO 420
<211> LENGTH: 20
<212> TYPE: PRT
<213> ORGANISM: Homo sapiens

<400> SEQUENCE: 420

His Ser Val Glu Leu His Lys Cys Glu Lys Pro Leu Pro Asp Gln Ala
1               5                   10                  15

Phe Phe Val Leu
            20

<210> SEQ ID NO 421
<211> LENGTH: 20
<212> TYPE: PRT
<213> ORGANISM: Homo sapiens

<400> SEQUENCE: 421

Pro Leu Pro Asp Gln Ala Phe Phe Val Leu His Asn Met His Ser Asn
1               5                   10                  15

Cys Val Ser Phe
            20

<210> SEQ ID NO 422
<211> LENGTH: 20
<212> TYPE: PRT
<213> ORGANISM: Homo sapiens

<400> SEQUENCE: 422

His Asn Met His Ser Asn Cys Val Ser Phe Glu Cys Lys Thr Asp Pro
1               5                   10                  15

Gly Val Phe Ile
            20

<210> SEQ ID NO 423
<211> LENGTH: 20
<212> TYPE: PRT
<213> ORGANISM: Homo sapiens

<400> SEQUENCE: 423

Glu Cys Lys Thr Asp Pro Gly Val Phe Ile Gly Val Lys Asp Asn His
1               5                   10                  15

Leu Ala Leu Ile
            20

<210> SEQ ID NO 424
<211> LENGTH: 20
<212> TYPE: PRT
<213> ORGANISM: Homo sapiens

<400> SEQUENCE: 424

Gly Val Lys Asp Asn His Leu Ala Leu Ile Lys Val Asp Ser Ser Glu
1               5                   10                  15
```

```
Asn Leu Cys Thr
            20

<210> SEQ ID NO 425
<211> LENGTH: 20
<212> TYPE: PRT
<213> ORGANISM: Homo sapiens

<400> SEQUENCE: 425

Lys Val Asp Ser Ser Glu Asn Leu Cys Thr Glu Asn Ile Leu Phe Lys
1               5                   10                  15

Leu Ser Glu Thr
            20

<210> SEQ ID NO 426
<211> LENGTH: 10
<212> TYPE: PRT
<213> ORGANISM: Homo sapiens

<400> SEQUENCE: 426

Leu Glu Asp Glu Ser Tyr Glu Ile Tyr Val
1               5                   10

<210> SEQ ID NO 427
<211> LENGTH: 9
<212> TYPE: PRT
<213> ORGANISM: Homo sapiens

<400> SEQUENCE: 427

Glu Asp Glu Ser Tyr Glu Ile Tyr Val
1               5
```